(12) United States Patent
Tang et al.

(10) Patent No.: US 9,279,806 B2
(45) Date of Patent: *Mar. 8, 2016

(54) WATER-SOLUBLE AIE LUMINOGENS FOR MONITORING AND RETARDATION OF FIBRILLATION OF AMYLOID PROTEINS

(71) Applicant: THE HONG KONG UNIVERSITY OF SCIENCE AND TECHNOLOGY, Kowloon, Hong Kong (CN)

(72) Inventors: Benzhong Tang, Hong Kong (CN); Yuning Hong, Hong Kong (CN); Sijie Chen, Hong Kong (CN); Tsz Kin Ryan Kwok, Hong Kong (CN); Wai Tung Leung, Hong Kong (CN)

(73) Assignee: THE HONG KONG UNIVERSITY OF SCIENCE AND TECHNOLOGY, Clear Water Bay Kowloon, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/171,957

(22) Filed: Feb. 4, 2014

(65) Prior Publication Data

US 2015/0031607 A1    Jan. 29, 2015

Related U.S. Application Data

(63) Continuation-in-part of application No. 13/359,514, filed on Jan. 27, 2012, now Pat. No. 8,679,738, and a
(Continued)

(51) Int. Cl.
*C12Q 1/00* (2006.01)
*G01N 33/53* (2006.01)
(Continued)

(52) U.S. Cl.
CPC ...... *G01N 33/542* (2013.01); *G01N 2021/6432* (2013.01); *G01N 2021/7786* (2013.01); *G01N 2333/4709* (2013.01); *G01N 2333/62* (2013.01)

(58) Field of Classification Search
CPC ..................................... G01N 33/542
USPC ................................ 435/4, 7.1, 174; 436/518
See application file for complete search history.

(56) References Cited

U.S. PATENT DOCUMENTS 6,607,758 B2   8/2003   Castillo et al.
7,311,893 B2   12/2007  Gervais et al.
(Continued)

OTHER PUBLICATIONS

Chang, Cheng-Chung et al., "A Fluorescent Carbazole Derivative: High Sensitivity for Quadruplex DNA", Anal. Chem., 2003, pp. 6177-6183, vol. 75, No. 22, American Chemical Society.
(Continued)

*Primary Examiner* — Jezia Riley
(74) *Attorney, Agent, or Firm* — Nath, Goldberg & Meyer; Joshua Goldberg

(57) ABSTRACT

Compounds that exhibit aggregation induced emission (AIE), and more particularly to water-soluble conjugated polyene compounds that exhibit aggregation induced emission. The conjugated polyene compounds can be used as bioprobes for DNA detection, G-quadruplex identification, and potassium-ion sensing. The polyenes also can be utilized as an external fluorescent marker to study conformational structures, to monitor folding processes of label-free oligonucleotides with G-rich strand sequences, and to visualize DNA bands in PAGE assay. The polyenes have applications in high-throughput anticancer drug screening and are useful for the development of efficient anti-cancer drugs. Furthermore, the present subject matter can also be used to monitor fibrillation of amyloid proteins and to facilitate the storage and delivery thereof.

15 Claims, 91 Drawing Sheets

Related U.S. Application Data continuation-in-part of application No. 12/453,892, filed on May 26, 2009, now Pat. No. 8,129,111, which is a continuation-in-part of application No. 12/000,130, filed on Dec. 10, 2007, now Pat. No. 7,939,613, and a continuation-in-part of application No. 11/408,846, filed on Apr. 21, 2006, now Pat. No. 8,263,018.

(60) Provisional application No. 61/457,207, filed on Jan. 31, 2011, provisional application No. 60/873,431, filed on Dec. 8, 2006, provisional application No. 60/929,364, filed on Jun. 25, 2007, provisional application No. 61/071,928, filed on May 27, 2008, provisional application No. 60/673,562, filed on Apr. 22, 2005.

(51) Int. Cl.
  *G01N 33/543* (2006.01)
  *G01N 33/542* (2006.01)
  *G01N 21/64* (2006.01)
  *G01N 21/77* (2006.01)

(56) References Cited

U.S. PATENT DOCUMENTS 7,595,199 B1   9/2009   Wanker et al.
8,679,738 B2 *  3/2014   Tang et al. .................. 435/4

OTHER PUBLICATIONS

Dixon, Isabel M. et al., "A G-Quadruplex Ligand with 10000-Fold Selectively over Duplex DNA", J. Am. Chem. Soc., 2007, pp. 1502-1503, vol. 129, American Chemical Society.

Moyzis, Robert K. et al., "A highly conserved repetitive DNA sequence, (TTAGGG)n, present at the telomeres of human chromosomes", Proc. Natl. Aca. Sci: USA, 1988, pp. 6622-6626, vol. 85.

Walmsley, Judity A. et al., "A New Model for the K+-induced Macromolecular Structure of Guanosine 5'-Monophosphate in Solution", Biochemistry, 1999, pp. 14063-14068, vol. 38, America Chemical Society.

Xie, Zengqi Xie et al., "A Class of Nonplanar Conjugated Compounds with Aggregation-Induced Emission: Structural and Optical Properties of 2,5-Dephen1-1,4-distyrylbenzene Derivatives with All Cis Double Bonds", J. Phys. Chem. B, 2006, pp. 20993-21000, vol. 110, American Chemical Society.

Dong, Yongqiang et al., "Aggregation-induced and crystallization-enhanced emission of 1,2-diphenyl-3,4-bis (diphenylmethylene)-1-cyclobutene", Chem. Commun., 2007, pp. 3255-3257, The Royal Society of Chemistry.

Luo, Jingdong et al., "Aggregation-induced and crystallization-enhanced emission of 1-methyl-1,2,3,4,5- pentaphenyisilole", Chem. Commun., 2001, pp. 1740-1741, The Royal Society of Chemistry.

Dong, Yongqiang et al., "Aggregation-induced emissions of tetraphenylethene derivatives and their utilities as chemical vapor sensors and in organic light-emitting diodes", Applied Physics Letters, 2007, vol. 91, American Institute of Physics.

Zhao, Qiang et al., "Aggregation-induced phosphorescent emission (AIPE) of iridium(III) complexes", Chem. Commun., 2008, pp. 685-687, The Royal Society of Chemistry.

Phan, Anh Tuan et al., "An interlocked dimeric parallel-stranded DNA quadruplex: A potent inhibitor of HIV-1 integrase", PNAS, 2005, pp. 634-639, vol. 102, No. 3, The National Academy of Sciences of the USA.

Ueyama, Hiroyuki et al., "A Novel Potassium Sensing in Aqueous Media with a Synthetic Oligonucleotide Derivative, Fluorescence Resonance Energy Transfer Associated with Guanine Quartet—Potassium Ion Complex Formation", J. Am. Chem. Soc., 2002, pp. 14286-14287, vol. 124, The American Chemical Society.

McMurray, John E., "Carbonyl-Coupling Reactions Using Low-Valent Titanium", Chem. Rev., 1989, pp. 1513-1524, vol. 89, American Chemical Society.

Wheelhouse, Richard T. et al., "Cationic Porphyrins as Telomerase Inhibitors: the Interaction of Tetra-(N-methyl-4-pyridyl)porphine with Quadruplex DNA", J. Am. Chem. Soc., 1998, pp. 3261-3262, vol. 120, American Chemical Society.

Parkinson, Gary N. et al., "Crystal structure of parallel quadruplexes from human telomeric DNA", Nature, 2002, pp. 876-880, vol. 417, Nature Publishing Group.

Zhao, Yong et al., "Determining the Folding and Unfolding Rate Constants of Nucleic Acids by Biosensor. Application to Telomere G-Quadruplex", J. Am. Chem. Soc., 2004, pp. 13255-13264, vol. 126, American Chemical Society.

Simonsson, Tomas, "DNA Tetraplex Formation Studied with Fluorescence Resonance Energy Transfer", The Journal of Biological Chemistry, 1999, pp. 17379-17383, vol. 274, No. 24, The American Society for Biochemistry and Molecular Biology, Inc.

Jayanty, S. et al., "Enhanced Fluorescence of Remote Functionalized Diaminodicyonaquinodimethanes in the Solid State and Fluorescence Switching in a Doped Polymer by Solvent Vapors", Chem. Eur. J., 2004, pp. 791-797, vol. 10, Wiley-VCH Verlag GmbH & Co. KGaA, Weinheim, Germany.

An, Byeong-Kwan et al., "Enhanced Emission and its Switching in Fluorescent Organic Nanoparticles", J. Am. Chem. Soc., 2002, pp. 14410-14415, vol. 124, American Chemical Society.

Mergny, Jean-Louis, "Fluorescence Energy Transfer as a Probe for Tetraplex Formation: The 1-Motif", Biochemistry, 1999, pp. 1573-1581, vol. 38, American Chemical Society.

Han, Mina R. et al., "Fluorescence Enhancement from Self-Assembled Aggregates: Substituent Effects on Self-Assemby of Azobenzenes", Chem. Mater., 2006, pp. 2784-2786, vol. 18, American Chemical Society.

Zeng, Qi et al., "Fluorescence enhancements of benzene-cored luminophors by restricted intramolecular rotations: AIE and AIEE effects", Chem Commun., 2007, pp. 70-72, The Royal Society of Chemistry.

Mergny, Jean-Louis et al., "Fluorescence Resonance Energy Transfer as a Probe for G-Quartet Formation by a Telomeric Repeat", Chembiochem, 2001, pp. 124-132, vol. 2, Wiley-VCH-Verlag GmbH, Weinheim, Germany.

He, Fang et al., "Fluorescent Amplifying Recognition for DNA G-Quadruplex Folding with a Cationic Conjugated Polymer: A Platform for Homogeneous Potassium Detection", J. Am. Chem. Soc., 2005, pp. 12343-12346, vol. 127, American Chemical Society.

Tong, Hui et al., "Fluorescent 'light-up' bioprobes based on tetraphenylethylene derivatives with aggregation-induced emission characteristics", Chem. Commun., 2006, pp. 3705-3707, The Royal Society of Chemistry.

Ambrus, Attila et al., "Human telomeric sequence forms a hybrid-type intramolecular G-quadruplex structure with mixed parallel/antiparallel strands in potassium solution", Nucleic Acids Research, 2006, pp. 2723-2735, vol. 34, No. 9, Oxford University Press.

Haq, Ihtshamul et al., "Intercalative G-Tetraplex Stabilization of Telomeric DNA by a Cationic Porphyrin", J. Am. Chem. Soc., 1999, pp. 1768-1779, vol. 121, American Chemical Society.

Chang, Cheng-Chung et al., "Kinetic Stability of Intermolecular DNA Quadruplexes", Biophysical Journal, 2005, pp. 365-373, vol. 89, Biophysical Society.

Merkina, Elena E. et al., "Kinetic Stability of Intermolecular DNA Quadruplexes", Biophysical Journal 2005, pp. 365-373, vol. 89, Biophycial Society.

Green, Jeremy J. et al., "Kinetics of Unfolding the Human Telomeric DNA Quadruplex Using a PNA Trap", J. Am. Chem. Soc., 2003, pp. 3763-3767, vol. 125, American Chemical Society.

Toal, Sarah J. et al., "Luminescent Silote Nanoparticles as Chemoselective Sensors for Cr(VI)", J. Am. Chem. Soc., 2005, pp. 11661-11665, vol. 127, American Chemical Society.

Collins, Kathleen, "Mammalian telomeres and telomerase", Current Opinion in Cell Biology, 2000, pp. 378-383, vol. 12, Elsevier Science Ltd.

(56) References Cited

OTHER PUBLICATIONS

Gilbert, Dara E. et al., Multistranded DNA structures, Current Opinion in Structural Biology, 1999, pp. 305-314, vol. 9, Elsevier Science Ltd.

Mergny, Jean-Louis et al., "Natural and pharmacological regulation of telomerase", Nucleic Acids Research, 2002, pp. 839-865, vol. 30, No. 4, Oxford University Press.

Ho, Hoang-Anh et al., "Optical Sensors Based on Hybrid Aptamer/Conjugated Polymer Complexes", J. Am. Chem. Soc., 2004, pp. 1384-1387, vol. 126, American Chemical Society.

Venczel, Eduard A. et al., "Parallel and Antiparallel G-DNA Structures from a Complex Telomeric Sequence", Biochemistry, 1993, pp. 6220-6228, vol. 32, American Chemical Society.

Tong, Hui et al., "Protein Detection and Quantitation by Tetraphenylethene-Based Fluorescent Probes with Aggregation-Induced Emission Characteristics", J. Phys. Chem. B, 2007, pp. 11817-11823, vol. 111, American Chemical Society.

Bourdoncle, A et al., "Quadruplex-Based Molecular Beacons as Tunable DNA Probes", J. Am. Chem. Soc., 2006, pp. 11094-11105, vol. 128, American Chemical Society.

He, Fang et al., "Quadruplex-to-Duplex Transition of G-Rich Oligonucleotides Probed by Cationic Water-Soluble Conjugated Polyelectrolytes", J. Am. Chem. Soc., 2006, pp. 6764-6765, vol. 128, American Chemical Society.

Yeh, Hsiu-Chih et al., "Readily synthesized arylamino fumaronitrile for non-dopes red organic light-emitting diodes", Chem. Commun., 2003, pp. 2632-2633, The Royal Society of Chemistry.

Xu, Qiuwei et al., "Selective Localization and Rotational Immobilization of Univalent Cations on Quadruplex DNA", Biochemistry, 1993, pp. 13130-13137, vol. 32, American Chemical Society.

LV, Wei et al., "Shape-Specific Detection Based on Fluorescence Resonance Energy Transfer Using a Flexible Water-Soluble Conjugated Polymer", J. Am. Chem. Soc., 2006, pp. 10281-10287, vol. 128, American Chemical Society.

Dai, Jixun et al., "Structure of the intramolecular human telomeric G-quadruplex in potassium solution: a novel adenine triple formation", Nuctelo Acids Research, 2007, pp. 2440-2450, vol. 35, No. 7.

Furstenberg, Alexandre et al., "Structure-Fluorescence Contrast Relationship in Cyanine DNA Intercalators: Toward Rational Dye Design", Chem. Eur. J., 2007, pp. 8600-8609, vol. 13, Wiley-VCH Verlag GmbH & Co. KGaA, Weinheim, Germany.

Yu, Gui et al., "Structures, Electronic States, Photoluminescence, and Carrier Transport Properties of 1,1-Disubstituted 2,3,4,5-Tetraphenylsiloles", J. Am. Chem. Soc., 2005, pp. 6335-6346, vol. 127, American Chemical Society.

Dong, Yongqiang et al., "Switching the light emission of (4-biphenylyl)phenyldibenzofulvene by morphological modulation: crystallization-induced emission enhancement", Chem. Commun. 2007, pp. 40-42, The Royal Society of Chemistry.

Chen, Juwu et al., "Synthesis, Light Emission, Nanoaggregation, and Restriction Intramolecular Rotation of 1,1-Substituted 2,3,4,5-Tetraphenylsiloles", Chem. Mater, 2003, pp. 1535-1546, vol. 15, American Chemical Society.

Yuan, Chun-Xue et al., "Synthesis, Structure and Aggregation-Induced Emission of a Novel Lamda-Shaped Pyridinium Salt based on Troger's Base", J. Phy. Chem. C, 2007, pp. 12811-12816, vol. 111, American Chemical Society.

Peng, Qian et al., "Toward Quantitative Prediction of Molecular Fluorescence Quantum Efficiency: Role of Duschinsky Rotation", J. Am. Chem. Soc., 2007, pp. 9333-9339, vol. 129, American Chemical Society.

Tong, Hui et al., "Tunable aggregation-induced emission of diphenyldibenzofulvenes", Chem. Commun., 2006, pp. 1133-1135, The Royal Society of Chemistry.

Hardin, Charles C. et al., "Monovalent Cation Induced Structural Transitions in Telomeric DNAs: G-DNA Folding Intermediates", Biochemistry, 1991, pp. 4460-4472, vol. 30, American Chemical Society.

White, Elizabeth W., "Structure-specific recognition of quadruplex DNA by organic cations: Influence of Shape Substituents and charge", Biophysical Chemistry, 2007, pp. 140-153, vol. 126. Elsevier B.V.

Giger, Katie et al., "Suppression of Insulin Aggregation by Heparin", Biomacromolecules, 2008, 9, 2338-2344.

Lindorff-Larsen, Kresten et al., "Protein folding and the organization of the protein topology universe", Trends in Biochemical Sciences, vol. 30, No. 1, 2005 Elsevier.

Ivanova, Magdalena I et al., "Molecular basis for insulin fibril assembly", PNAS early edition, 2009.

Muchowski, Paul, "Protein misfolding, amyloid formation and neurodegeneration: A critical role for molecular chaperones", Neuron, 2002, vol. 35, pp. 9-12.

Dobson, Christopher M, "Protein folding and misfolding", Nature, 2003, vol. 426, pp. 884-890.

Wilelm, K.R. et al., "Immune reactivity towards insulin, its amyloid and protein S100B in blood sera of Parkinson's disease patients", European Journal of Neurology, 2007, vol. 14, pp. 327-334.

Blundell, T.L. et al., "Proceedings of the biochemical society", Biochem. J. 1971, 125, 50P-51P.

Nielsen, Lizza et al., "Effect of environmeal factors on the kinetics of insulin fibril formation: Elucidation of the molecular mechanism", Biochemistry, 2001, vol. 40, pp. 6036-6046.

Skora, Lukasz et al., "Molten globule precursor states are conformationally correlated to amyloid fibrils of human beta-2-microglobulin", 2010, J. Am, Chem. Soc., vol. 132, pp. 9223-9225, American Chemical Society.

Rubin, Noa et al., "Chiralty of amyloid suprastructures", J. Am. Chem. Soc., 2008, vol. 130, pp. 4602-4603, American Chemical Society.

Mauro, Manno et al., "Kinetics of different processes in human insulin amyloid formation", J. Mol. Biol., 2007, vol. 366, pp. 258-274, Elsevier.

Dzwolak, Wojciech et al., "Hydration and structure—the two sides of the insulin aggregation process", Phys. Chem., 2004, vol. 6, pp. 1938-1943.

Herland, Anna et al., "Synthesis of a regioregular zwitterionic conjugated oligoelectrolyte, usable as an optical for detection of amyloid fibril formation of acidic pH", J. Am. Chem. Soc. 2005, vol. 127, pp. 2317-2323, American Chemical Society.

Domike, Kristin R et al., "Thermal dependence of thermally induced protein spherulite formation and growth: kinetics of beta-lactoglobulin and insulin", Biomacromolecules, 2007, vol. 8, pp. 3930-3937, American Chemical Society.

Bose, Parth Pratim et al., "Effects of congo red on Abeta 1-40 fibril formation process and morphology", ACS Chem. Neurosci., 2010, vol. 1, pp. 315-324, American Chemical Society.

Bekard, Innocent B et al., "Tyrosine autofluorescence as a measure of bovine insulin fibrillation", Biophysical Journal, 2009, vol. 97, pp. 2531-2532. The Biophysical Society.

LeVine, Harry III, "Thioflavine T interaction with synthetic Alzheimer's disease beta-amyloid peptides: detection of amyloid aggregation in solution", Protein Science, 1993, vol. 2, pp. 404-410, The Protein Society.

Liang, Yan et al., "Direct Observation of nucleation and growth in amyloid self-assembly", J. Am. Chem. Soc., 2010, vol. 132, pp. 6306-6308, American Chemical Society.

Hong, Yuning et al., "Aggregation-induced emission: phenomenon, mechanism and applications", Chem Comm. 2009, pp. 4332-4353, The Royal Society of Chemistry.

Cabaleiro-Lago, C et al., Inhibition of IAPP and IAPP (20-29) fibrillation by polymeric nanoparticles:, Langmuir, 2010, vol. 26(5), pp. 3453-3461. American Chemical Society.

Hong, Yuning et al., "Quantitation, visualization and monitoring of conformational transitions of human serum albumin by tetraphenyletheme derivative with aggregation-induced emission characteristics", Anal. Chem., 2010, vol. 82, pp. 7035-7043, American Chemical Society.

Wang, Ming et al., "Fluorescence biolchemoschensors based on silole and teraphenylethene luminogens with aggregation-induced emission feature", J. Mater. Chem., 2010, vol. 20, pp. 1858-1867, The Royal Society of Chemistry.

(56) References Cited

OTHER PUBLICATIONS

Brange, Jens et al., "Toward understanding insulin fibrillation", Journal of Pharmaceutical Sciences, 1997, vol. 88, pp. 517-525, American Chemical Society and American Pharmaceutical Association.

Dische, F.F. et al., "Insulin as an amyloid-fibril protein at sites of repeated insulin injections in a diabetic patient", Diabetologiz, 1988, vol. 31, pp. 158-161.

Frokjaer, Sven et al., "Protein drug stability: a formulation challenge", Nature, 2005, vol. 4, pp. 298-306.

Rodrigues-Rodriguez, Cristina et al., "Crystal structure of thioflavin-T and its binding to amyloid fibrils: insight at the molecular level", Chem. Comm., 2010, vol. 46, pp. 1156-1158, The Royal Society of Chemistry.

Hong, Yuning et al., "Label-Free fluorescence probing of G-quadruplex formation and real-time monitoring of DNA folding by a quaternized tetraphenylethene salt with aggregation-induced emission characteristics", Chem. Eur. J., 2008, vol. 14, pp. 6428-6437.

Hong, Yuning et al., "Fluorescence bioprobes: structural matching in the docking processes of aggregation-induced emission fluorogens on DNA surfaces", Chem. Eur. J. 2010, vol. 16, pp. 1232-1245.

Cabaleiro-Lago, Celia et al., "Inhibition of Amyloid beta protein fibrillation by polymeric nanoparticles", J. Am. Chem. Soc., 2008, vol. 130, pp. 15437-15443, American Chemical Society.

\* cited by examiner

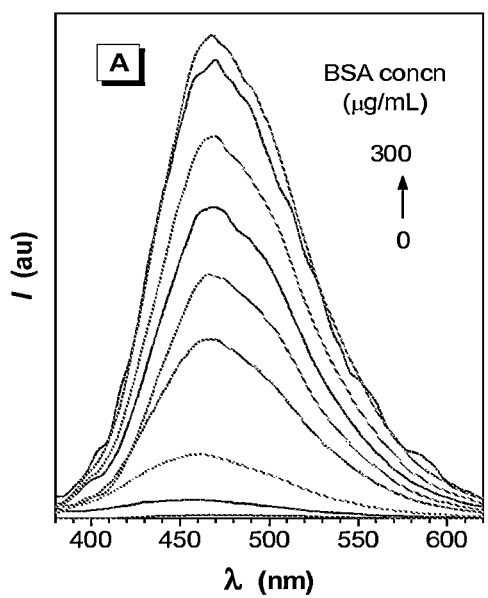
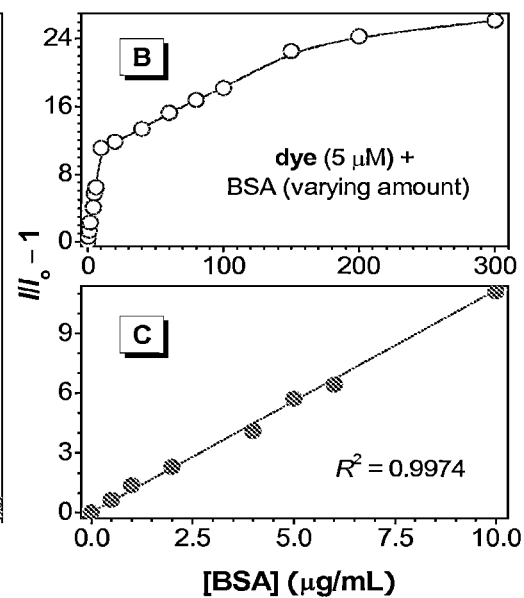
FIG. 2A
FIG. 2B
FIG. 2C

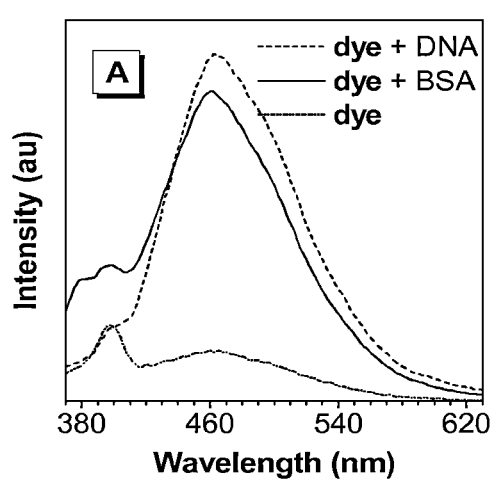
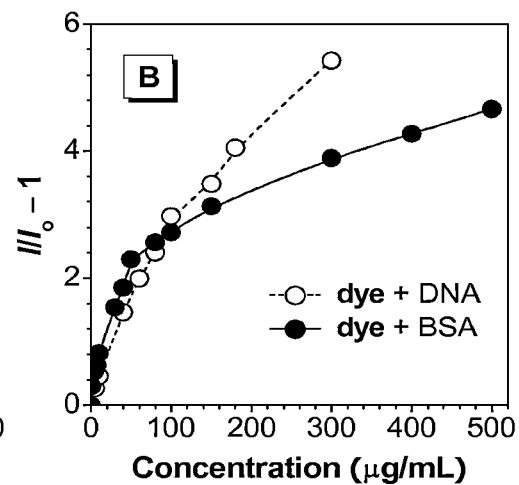
FIG. 5A                                    FIG. 5B

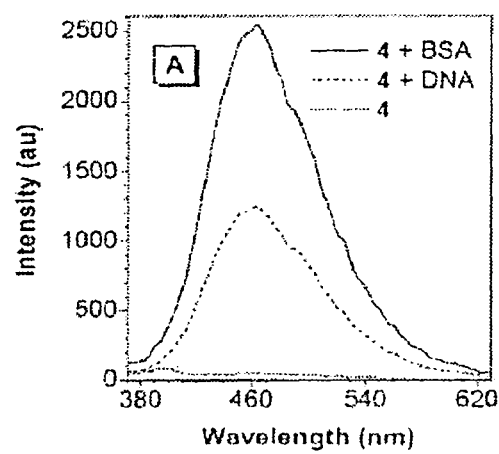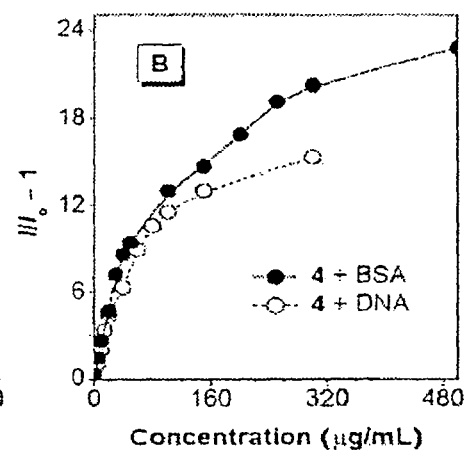
FIG. 12A  FIG. 12B

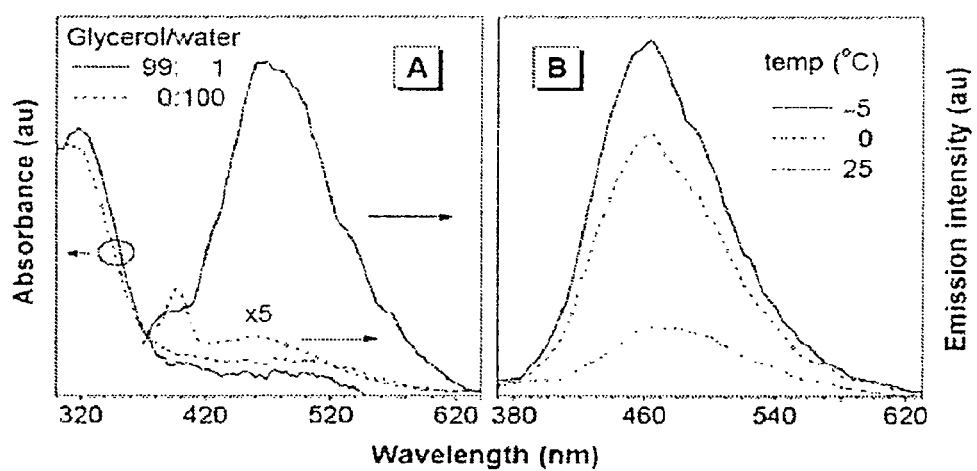
FIG. 13A  FIG. 13B

FIG. 16A and B (inset)

FIG. 19A
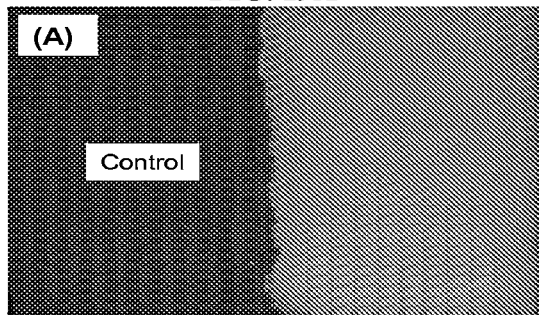
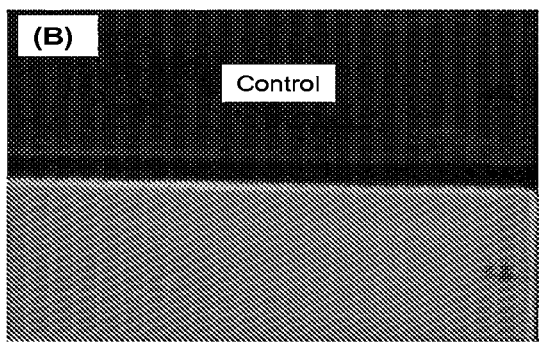
FIG. 19B

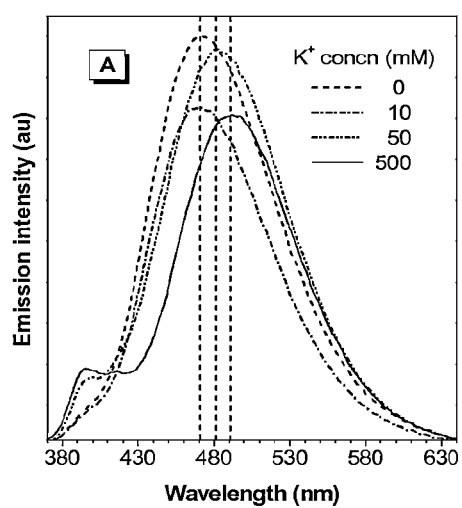
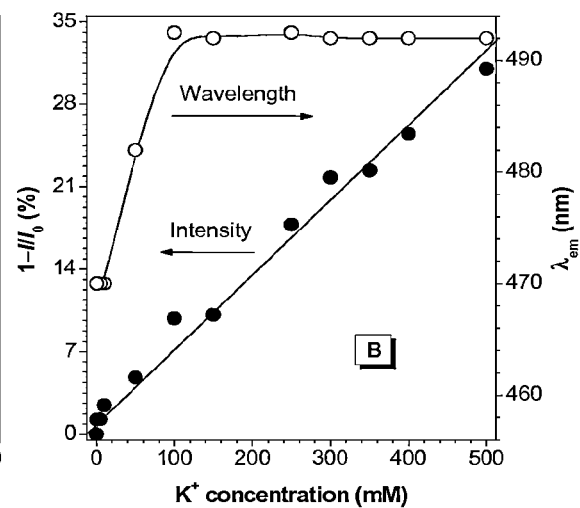
FIG. 32A  FIG. 32B

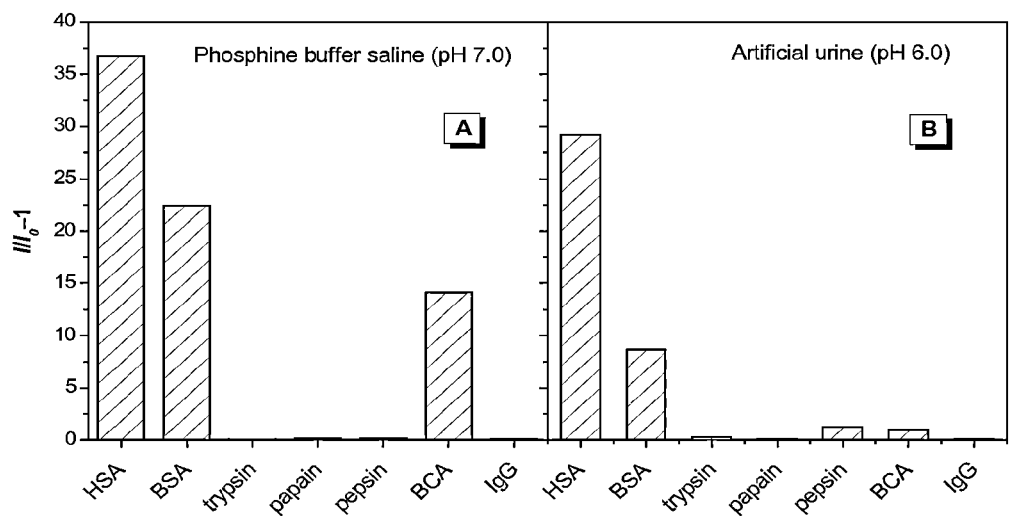
FIG. 47A  FIG. 47B

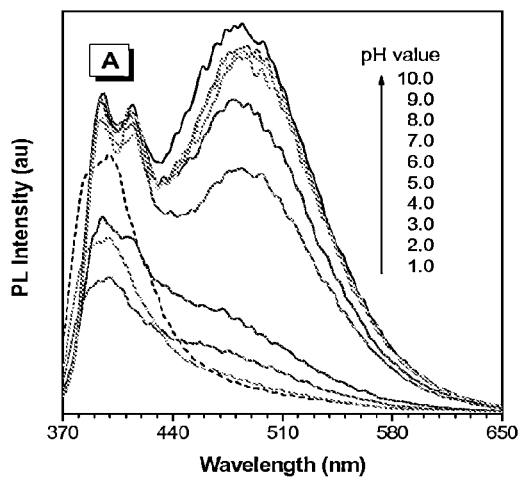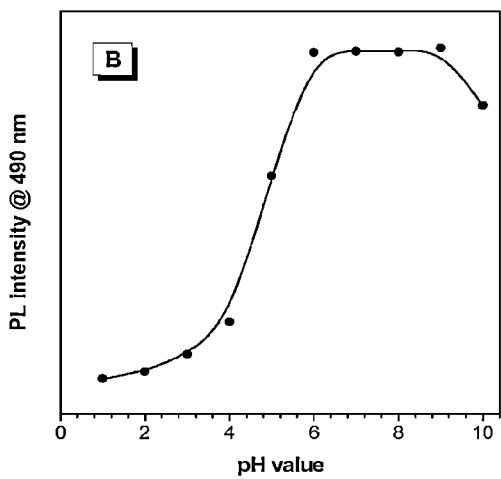
FIG. 62A                    FIG. 62B

Pre-stained    Post-stained

FIG. 69A
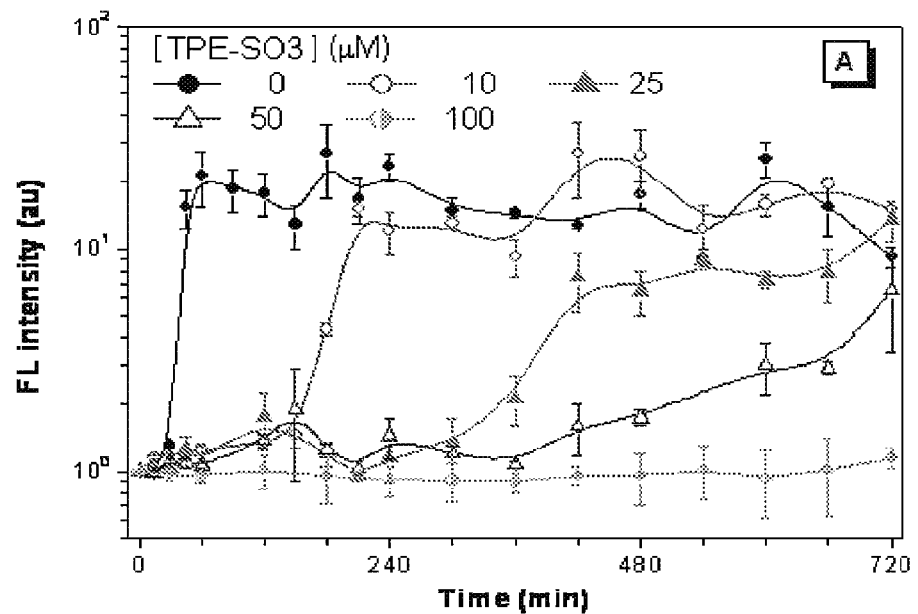
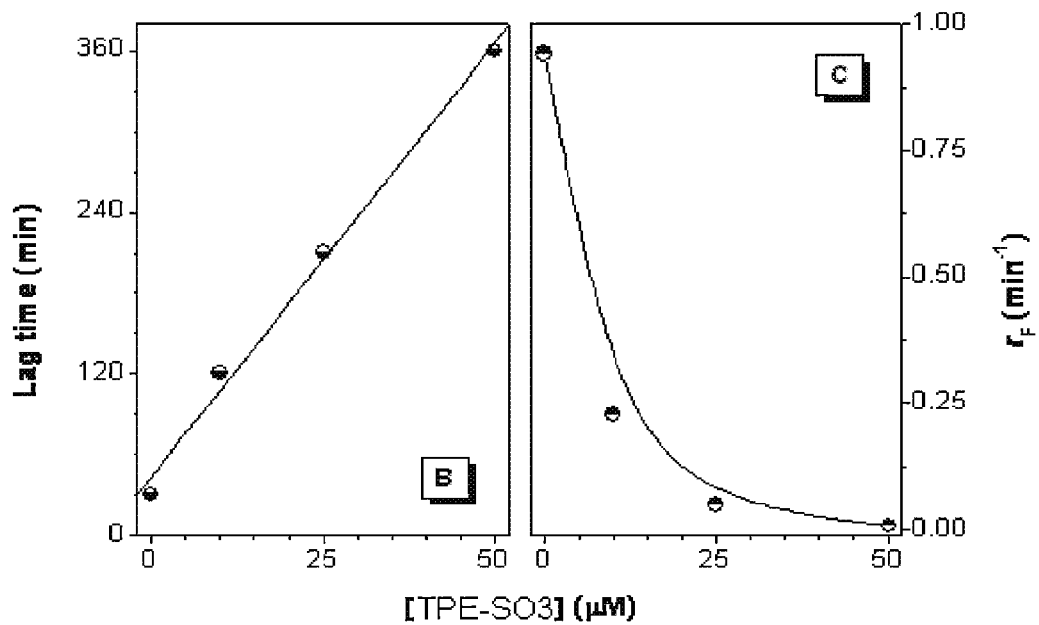
FIG. 69B            FIG. 69C

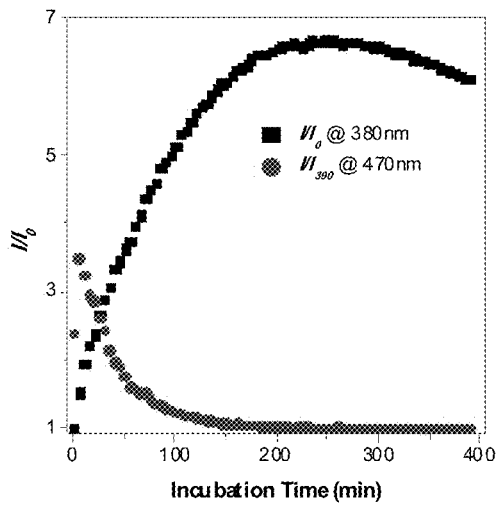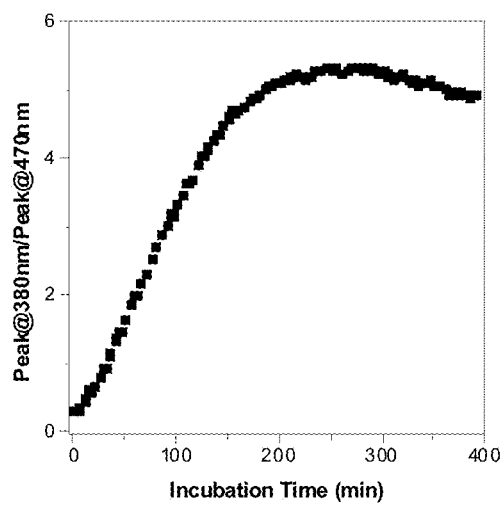
FIG. 86A  FIG. 86B
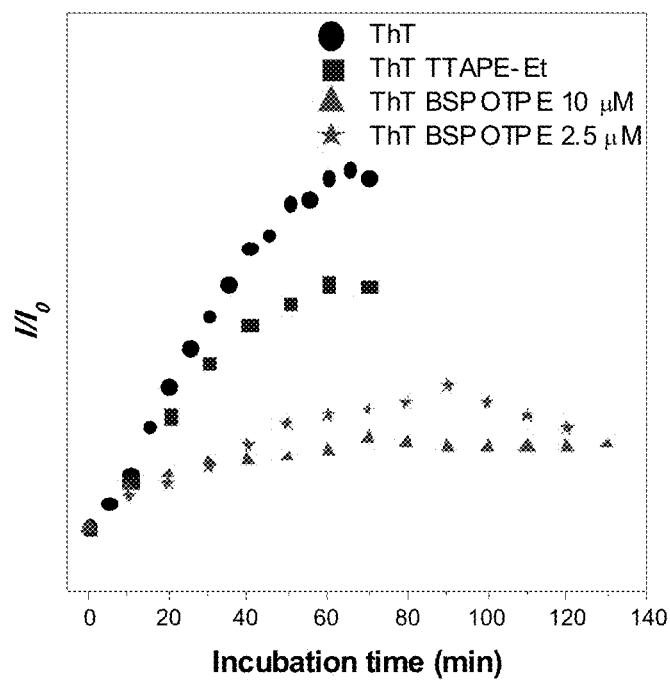
FIG. 87

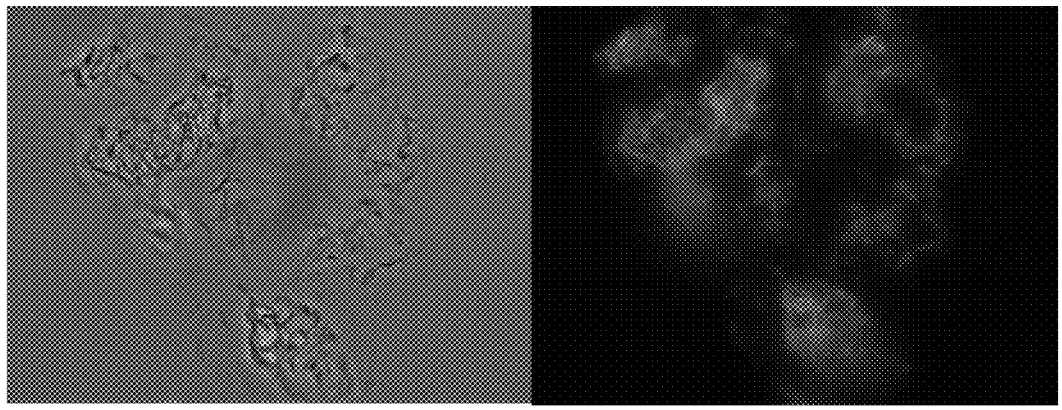
FIG. 90A  FIG. 90B
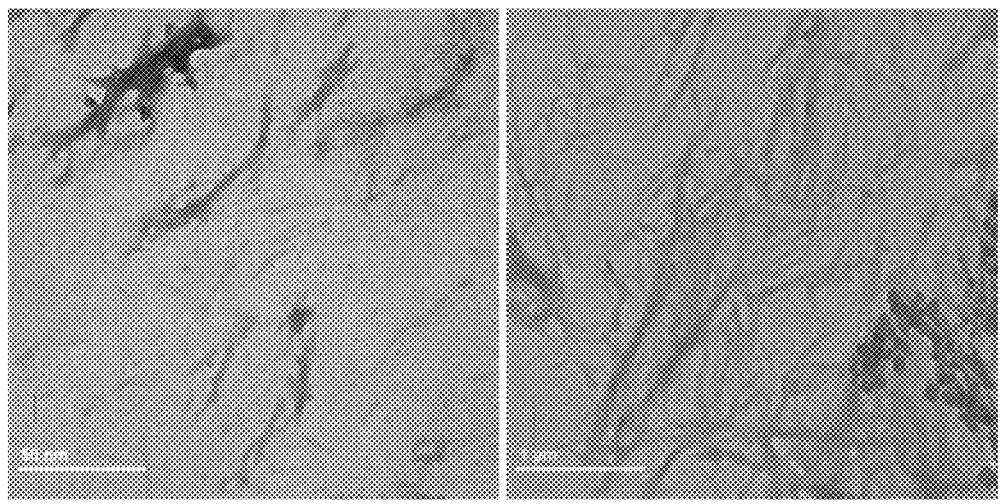
FIG. 91

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide G1 mimicking human telomeric
      repeat sequence

<400> SEQUENCE: 1
gggttagggt tagggttagg g                                             21

<210> SEQ ID NO 2
<211> LENGTH: 21
<212> TYPE: DNA
<213> ORGANISM: Artificial Sequence
<220> FEATURE:
<223> OTHER INFORMATION: Complimentary ssDNA of G1 (C1)

<400> SEQUENCE: 2
ccctaaccct aaccctaacc c                                             21

<210> SEQ ID NO 3
<211> LENGTH: 21
<212> TYPE: DNA
<213> ORGANISM: Artificial Sequence
<220> FEATURE:
<223> OTHER INFORMATION: Non-complimentary ssDNA of G1 (C2)

<400> SEQUENCE: 3
cccaatccca atcccaatcc c                                             21
```

WATER-SOLUBLE AIE LUMINOGENS FOR MONITORING AND RETARDATION OF FIBRILLATION OF AMYLOID PROTEINS

CROSS REFERENCE TO RELATED APPLICATIONS

This application is a Continuation-in-Part Application of U.S. patent application Ser. No. 13/359,514, which was filed on Jan. 27, 2012 and which claims the benefit of Provisional Application No. 61/457,207 filed on Jan. 31, 2011, and is also a Continuation-in-Part Application of U.S. patent application Ser. No. 12/453,892, which was filed on May 26, 2009, which claims the benefit of Provisional Application No. 60/873,431 filed on Dec. 8, 2006, and to Provisional Application No. 60/929,364 filed on Jun. 25, 2007, and to Provisional Application No. 61/071,928 filed on May 27, 2008, and which is also a Continuation-in-Part Application of U.S. patent application Ser. No. 12/000,130, which was filed on Dec. 10, 2007, now U.S. Pat. No. 7,939,613, and which is also a Continuation-in-Part Application of U.S. patent application Ser. No. 11/408,846, which was filed on Apr. 21, 2006 and claims priority to U.S. Provisional Application No. 60/673,562 filed on Apr. 22, 2005. All of these applications are hereby incorporated by reference in their entirety.

TECHNICAL FIELD

The presently described subject matter relates generally to compounds that exhibit aggregation induced emission (AIE), and more particularly to water-soluble conjugated polyene compounds that exhibit aggregation induced emission. The conjugated polyene compounds can be used as bioprobes for DNA detection, G-quadruplex identification, and potassium-ion sensing. The polyenes also can be utilized as an external fluorescent marker to study conformational structures, to monitor folding processes of label-free oligonucleotides with G-rich strand sequences, and to visualize DNA bands in PAGE assay. The polyenes have applications in high-throughput anticancer drug screening and are useful for the development of efficient anti-cancer drugs. Furthermore, the present subject matter can also be used to monitor fibrillation of amyloid proteins and to facilitate the storage and delivery thereof.

BACKGROUND

Fluorescence (FL) techniques have emerged as a mainstream research and development area in science and engineering, particularly in the field of biochemical and biological science. Currently, fluorescent molecules are used as probes for DNA sequencing, fluorescence-activated cell sorting, high-throughput screening, and clinical diagnostics.

Fluorescence-based techniques offer high sensitivity, low background noise and broad dynamic ranges. A great number of fluorescent probes have been investigated and are already widely used in biotechnology. Many of them show favorable spectral properties of visible absorption and emission wavelength, high extinction coefficients, and reasonable quantum yields. Upon complexation with proteins and DNA, the fluorescence of the bioprobes can be enhanced/quenched and/or red/blue-shifted, thus enabling visual observation of the biomacromolecular species. Among these, the most useful probes are those that act as "turn-on" sensors, whose fluorescence is activated by the analytes.

Several probes for DNA detection based on fluorescent enhancement have been developed such as phenanthridine and acridine derivatives. Middendorf et al. have reported on ethidium bromide (EB), a well-known phenanthridine derivative, which has already been widely used for DNA sequencing (See, for example, U.S. Pat. No. 4,729,947, U.S. Pat. No. 5,346,603, U.S. Pat. No. 6,143,151, and U.S. Pat. No. 6,143,153). FL enhancement induced by proteins can be attributed to the interaction with hydrophobic regions of proteins, such as NanoOrange (Molecular Probes, Inc., U.S. Pat. No. 6,818,642) and Nile red (U.S. Pat. No. 6,897,297, U.S. Pat. No. 6,465,208), or reaction with amine groups of proteins in the presence of cyanide or thiols, such as fluorescamine (U.S. Pat. No. 4,203,967) and o-phthaldialdehyde (U.S. Pat. No. 6,969,615, U.S. Pat. No. 6,607,918). The FL of cyanine dyes has been found to increase dramatically upon complexation with DNA and proteins. (U.S. Pat. No. 5,627,027, U.S. Pat. No. 5,410,030). Haugland et al. have reported unsymmetrical cyanine dyes, which possess superior fluorescent characteristics when complexed with nucleic acids (U.S. Pat. No. 5,436,134). The SYPRO® dyes are merocyanine dyes that are essentially non-fluorescent when free in solution but become intensely fluorescent in hydrophobic environments (e.g. SYPRO® Red and SYPRO® Orange dyes of Molecular Probes, Inc., U.S. Pat. No. 6,914,250, U.S. Pat. No. 6,316,267). Water-soluble cyanine dyes, such as Cy3 and Cy5, are commonly used in labeling of DNA or RNA for microarray (Y. R. Iyer et al., Science, 1999, 283, 83). Cy3 and Cy5 have merits of high fluorescence intensity and emission even in the solid state; however, they are quite unstable and show insufficient detection sensitivity (U.S. Pat. No. 7,015,002).

As described in U.S. Pat. No. 7,109,314, a good fluorescent dye should possess a high fluorescent quantum yield and molecular absorption coefficient, as well as good solubility in aqueous media and stability under ambient conditions. However, most of the dyes discussed above are lipophilic, which are, at best, only dispersible in aqueous media. For example, Nile Red, a dye used to stain proteins, should be first dissolved in acetone and then mixed rapidly with water immediately prior to use (J. R. Daban et al., Anal. Biochem, 1991, 199, 169).

Additionally, substantially all of the above-described fluorescent dyes suffer from the problem of aggregation-caused quenching (ACQ). Due to their lipophilic character, these fluorescent dyes are prone to aggregate when dispersed in aqueous media or when bound to biological macromolecules. The close proximity of the chromophores often induces a non-radiative energy transfer mechanism that results in self-quenching of the luminescence. This self-quenching drastically reduces the dyes' fluorescent signal thereby prohibiting their use as efficient bioprobes or biosensors.

Substantial effort has been made to mitigate aggregate formation of these dyes (J. R. Lakowicz, et al. Anal Biochem, 2003, 320, 13). However, only a small number of researchers have focused on the design and synthesis of novel organic molecules or polymers that do not suffer from fluorescent quenching, and moreover, even display enhanced light emission upon aggregation.

Recently, some non-emissive dyes have been induced to emit efficiently by aggregate formation, the exact opposite of ACQ. AIE molecules with a high quantum yield $\Phi_F$ (up to 0.85) and various emission colors (blue, green, yellow and red) have been reported. While the AIE dyes have been used for the construction of efficient optical and photonic devices, the possibility of employing them as bioprobes for detecting biopolymers has been virtually unexplored. Accordingly, there remains a great need for water-soluble "light-up" compounds and probes, for example, for the detection of biomacromolecules such as DNA and proteins.

Many known fluorescent materials accomplish the detection of saccharides by the competing intramolecular interaction of an amine functionality with a boronic acid pendant. Less effort has been spent on the detection of other biological compounds. Furthermore, vapor-sensing compounds and devices are often manufactured from expensive platinum salts and complexes and/or in combination with palladium. They are based mainly on a color shift from dark-red to light-red, making it difficult to visually sense the color shift. Sensors exhibiting an on-off change in their luminescent color rather than a color shift will be thus not only advantageous but also more sensitive. To date, the only known "on-off" example was shown by Kato (U.S. Pat. No. 6,822,096), who utilized the luminescence change from the invisible near-infrared to the visible red of binuclear platinum (II) complexes. However, these complexes only shift the emitted wavelength out of the visible spectrum.

Fluorescent materials, including inorganic semiconductor quantum dots, organic and metallorganic dyes, dye-doped silica or polymer particles, have currently attracted great attention in a wide variety of high-technology applications such as high-throughput screening, ultra-sensitive assays, optoelectronics, and living cell imaging. Colloidal quantum dots (hundreds to thousands of atoms) are traditionally made from crystals of IIA-VIA or IIIB-VB elements (PbS, CdSe, etc.) or other semiconductors. The heavy metals therein are intrinsically toxic to the researchers and the experimental systems (e.g., living cells), as well as generating a toxic waste stream into the environment. Organic and metallorganic dyes generally consist of α-conjugated ring structures such as xanthenes, pyrenes or cyanines, with emissions across the spectrum from UV to the near infrared (~300-900 nm) and may be fine tuned to particular wavelengths or applications by changing the chemistry of their substituent groups. The size of individual dye molecules is very small (~1 nm), which causes non-specific labeling and high background signals as dyes diffuse away from their intended targets. Spectrally, organic dyes tend to have fairly wide absorption and emission spectra (FWHM~0.50 nm), which can lead to spectral overlap and re-absorption when using multiple dye species simultaneously. In normal use, dye molecules are exposed to a variety of harsh environments and often suffer from photobleaching and quenching due to the interactions with solvent molecules and reactive species such as oxygen or ions dissolved in solution.

In order to create more robust emitters with enhanced brightness and stability, composite nano- and micro-particles consisting of dye molecules and silica or polymer matrix have been developed. Thus the encapsulated dye molecules can be protected from external perturbations, with reduced stochastic blinking, photobleaching, and quenching. Dye-loaded polymer particles are superior to their silica counterparts in terms of the versatile chemical compositions, tunable surface chemistry suited for biocompatibility and bioconjugation, *facile* preparation, and easy control of the particle size and size distribution.

Gao et al. have incorporated pyrene dyes into polystyrene particles using a normal microemulsion approach, leading to a 40-fold increase in emission intensity with respect to the pure dye at the identical concentration (H. Gao et al., Colloid Polym. Sci. 2002, 280, 653). Dinsmore et al. swelled poly(methyl methacrylate) particles and absorbed a rhodamine dye into them for usage in a confocal microscopic study of colloidal dispersions (A. D. Dinsmore et al., Appl. Opt. 2001, 40, 4152). U.S. Pat. No. 5,716,855 discloses fluorescent particles containing anthracene- or naphthacene-derived dyes aiming to the application as biological markers.

Up to now, most of the organic dyes commercially available, including the above mentioned dyes as well as ethidium, Nile red, fluorescamine, o-phthaldialdehyde, cyanine dyes, etc. are emissive only in their solution state, whereas emission is quenched in aggregation states (e.g., high dye concentration state, film state, solid state, etc.). This is attributed to the mechanism of non-radiative energy transfer between the closely packed chromophores, thus resulting in self-quenching of the fluorescence. Thus, the loading concentration of dyes in the polymer particles cannot be sufficiently high and accordingly the intensity of fluorescence is considerably limited.

With respect to polymers for dye encapsulation, the currently available species are mainly hydrophobic polystyrene and less hydrophobic poly(methyl methacrylate), as mentioned hereinabove. The hydrophobic nature of these particles commonly leads to clustering and non-specific binding of biological materials, which considerably limits their application in the aqueous environment of biology and other fields. Additionally, these particles are prepared and dispersed in an organic solvent. For example, Hu et al. prepared poly(methyl methacrylate) fluorescent particles through dispersion polymerization in a mixture of hexane and ethanol (H. Hu et al., Langmuir 2004, 20, 7436). The solvent-dispersible polymer particles are difficult to disperse stably in aqueous media.

Recent studies on biomacromolecules aid the understanding of pathogenesis of numerous diseases as well as development of effective therapeutic agents. For example, fibrillation of amyloid proteins is recognized as a pathological hallmark of many neurodegenerative diseases, including Alzheimer's disease, Parkinson's disease, Prion disease, and Huntington's disease. Insulin is a well-established model of amyloid fibrillation and its amyloid fibrils are found at frequent injection sites of diabetic patients and have been suggested as indicative of Parkinson's disease. Therefore, monitoring insulin aggregation and/or other amyloid proteins facilitates the understanding of pathogenesis of many neurodegenerative diseases or other diseases associated therewith, thereby developing effective diagnostic tools and therapeutic agents.

Amyloid fibril formation of insulin has been studied by a variety of spectroscopy and microscopy techniques including transmission electron microscopy (TEM), atomic force microscopy (APM), real-time light scattering, stopped-flow turbidimetry, X-ray diffraction, fluorescence, circular dichroism (CD), and NMR spectroscopy. Among them, fluorescence technique is the most commonly used method on intrinsic fluorescence of proteins. For example, Thioflavin T (ThT) is a standard fluorescence probe for amyloid assay. Despite its widespread use, it suffers from a number of drawbacks, such as small stokes shift, low specificity, poor sensitivity, false-positive response, poor reliability, incapability of catching oligomeric intermediates, and unsuitability for kinetic study. Many of the other fluorophores for amyloid detection also contain electron donors and acceptors, between which intramolecular charge transfer occurs. Such fluorophores are sensitive to the hydrophobicity of the environment and their emissions are intensified upon binding to hydrophobic regions of amyloids rich in n-sheet structure. However, when multiple fluorophore molecules are accumulated in a hydrophobic patch of protein, π-π interaction between their stacked aromatic rings occurs, which promotes the formation of such detrimental species as excimers and exciplexes. This can lead to severe emission self-quenching, making the fluorophores unsuitable for quantitative analysis.

In addition to the problems in monitoring, insulin fibril formation has been a nuisance in delivery and long-term storage for treatment of diabetes because insulin can form amyloid fibrils in vitro under certain destabilizing conditions, such as elevated temperature, low pH, increased ionic strength and exposure to hydrophobic surfaces. It is also generally believed that dissociation of the native associated states of insulin (i.e., dimers, tetramers and hexamers) into monomers is a prerequisite for fibril formulation. The monomers undergo partial unfolding into intermediate states, in which they re-associate into stable and fibrous amyloid aggregates. These destabilizing conditions lead to an early maturity of amyloid fibrils, which does not favor the long-term storage and delivery of insulin. Therefore, inhibitors for protein aggregation are also of great significance in developing effective therapeutic agents for diabetes or for diseases treatable by similar biomolecules.

Functional kidneys are capable of removing wastes from the body, regulating electrolyte balance and blood pressure, and stimulating red blood cell production. Kidney diseases are a major cause of health problems world-wide. E.g. >20 million Americans-1 of 9-adults have chronic kidney disease (CKD). Another 20 million more Americans are at increased risk (US National Kidney Foundation). Each year in the United States, more than 100,000 people are diagnosed with kidney failure (ESRD: End-Stage Renal Disease). The high-risk groups for kidney disease include diabetes and hypertension patient. Most kidney diseases do not cause noticeable symptoms until very late. Nearly 50% of people with an advanced form of kidney disease even don't know. However, certain changes in the urine can be seen earlier, which may suggest problems with kidneys or urinary tract. There are over a hundred different types of proteins in the blood and the kidneys are very good at keeping them from entering the urine. Most of the proteins that make it into the urine are reabsorbed, chewed up and returned to the blood. As a result, less than 150 mg (30 mg/L) of protein is normal lost in the urine per day. A higher level of protein loss in the urine is called proteinuria and may mean there is a kidney disease. Determination of urinary protein is of major clinical importance because it readily reflects kidney functionality.

Accordingly, there is a need in the art for new sensors useful for detecting/sensing a wide variety of biomacromolecules. Sensors based on detecting fluorescence of an analyte such as a biomacromolecule are highly sensitive, thereby lowering detection limits. Sensors that have the capability to quantitatively analyze kinetics of biomacromolecules are desired. Notably, fluorescent markers that enable the monitoring of amyloid fibrillation and compounds that inhibit fibrillation are most desired.

SUMMARY

The presently described subject matter is directed to water-soluble conjugated polyenes which exhibit aggregation induced emission (AIE) and are useful as bioprobes and for manufacturing sensors. The emission color of these water-soluble conjugated polyenes ranges from blue to red arising from the different chromophoric structures. They exhibit AIE (i.e., increased fluorescence) upon addition of a non-aqueous solvent. Their luminescent behavior features the AIE phenomenon, which turns the dyes (water-soluble conjugated polyenes) from faint-emitters when molecularly dissolved in an aqueous solvent, i.e., water, into strong luminophors when aggregated or in the solid state. Stated differently, when the compounds are dissolved in aqueous solvents, they are substantially non-emissive ("off") while when a non-aqueous solvent is added, they aggregate and emit intensely ("on"). The quantum efficiency increases when the amount of non-aqueous solvent is increased. The presently described water-soluble conjugated polyene compounds are useful as "turn-on" fluorescence sensors. In addition, the presently described subject matter is directed to water-dispersible fluorescent polymer particles, i.e., micro-particles and/or nanoparticles, comprising the described water-soluble conjugated polyenes, for example, a tetraphenylethylene ("TPE").

In an embodiment, the present subject matter relates to a water-soluble conjugated polyene compound comprising a backbone structure of a formula selected from:

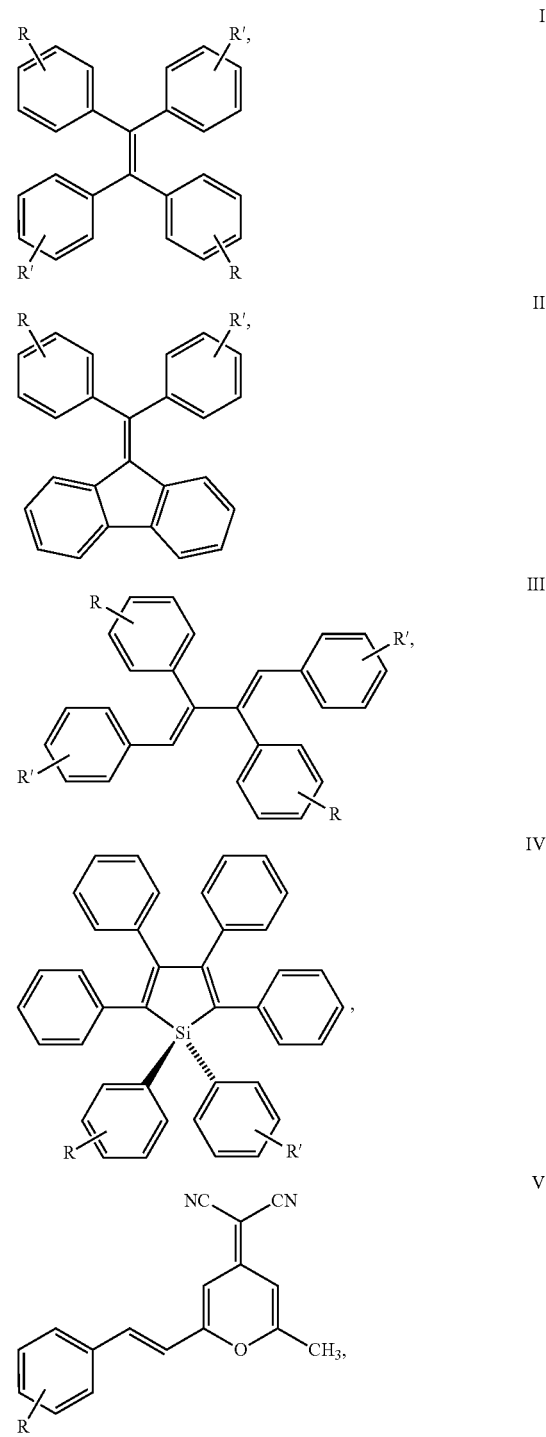

-continued

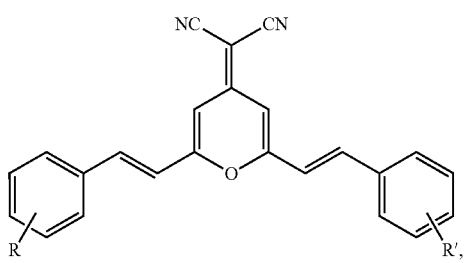

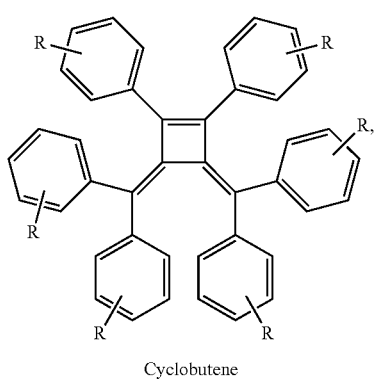
Cyclobutene

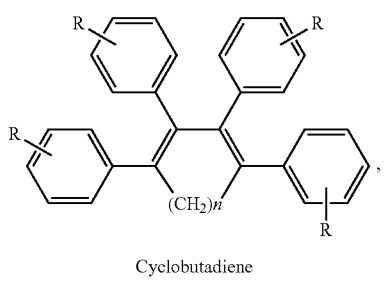
Cyclobutadiene

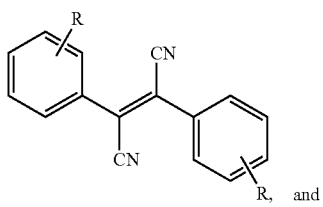

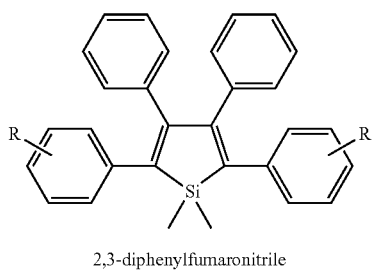
2,3-diphenylfumaronitrile wherein
R and R' are independently selected from H, X, B(OH)$_2$, $(X)_n$COOR", $(X)_n$COOH, $(X)_n$NH$_2$, $(X)_n$NHR", $(X)_n$NR"$_2$, $(X)_n$N$^+$R"$_3$Br$^-$, $(X)_n$OH, $(X)_n$SH, $(X)_n$SO$_3^-$Na$^+$, $(CH_2)_n$—P$^+$R"$_3$Br$^-$,

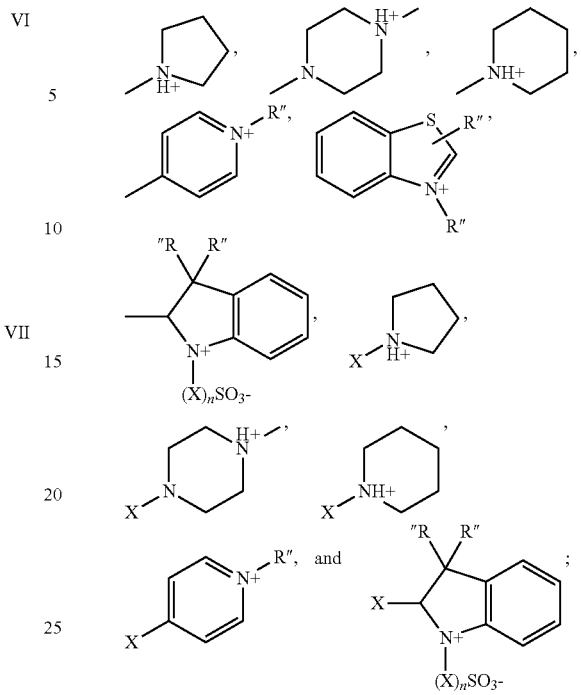

X is selected from $(CH_2)_n$, $O(CH_2)_n$, $NH(CH_2)_n$, $N[(CH_2)_n]_2$, $(CH=CH)_n$ and $(OCH_2CH_2)_n$; and R" is selected from R, R', $(CH_2)_n CH_3$, CONH—X—, COO—X—, $C_6H_5$—R, —CH$_2$—C$_6$H$_5$, and C$_6$H$_5$; n=0 to 20, and salts thereof, and wherein the compound is water-soluble and exhibits aggregation induced emission.

In an embodiment, the present subject matter relates to a water-soluble conjugated polyene compound, wherein the compound does not exhibit aggregation induced quenching.

In an additional embodiment, the present subject matter relates to a method for detecting the presence or absence of a target biomacromolecule in a biological sample, comprising contacting the biological sample with the water-soluble conjugated polyene compound, and detecting luminescence.

In a further embodiment, the present subject matter relates to a method for detecting the presence or absence of a target biomacromolecule in a biological sample, wherein the biological sample is selected from the group consisting of a tissue sample, a cell sample, blood, saliva, spinal fluid, lymph fluid, vaginal fluid, seminal fluid, and urine.

In an embodiment, the present subject matter relates to a sensor device for detecting the presence or absence of a target biomacromolecule, comprising a holder and a detecting molecule comprising the water-soluble conjugated polyene compound, the detecting molecule being held in place by the holder and being accessible to the target molecule or substance.

In a further embodiment, the present subject matter relates to a sensor device, wherein the luminance of the detecting molecule increases upon contact with the target biomacromolecule.

In another embodiment, the present subject matter relates to a sensor device, wherein the holder is a container and the detecting molecule is disposed inside the container; the container having one or more openings or orifices to allow access to the detecting molecule by the target molecule.

In yet another embodiment, the present subject matter relates to a sensor device, wherein the holder is a surface on which the detecting molecule is coated in a thin film.

In an embodiment, the present subject matter relates to water-dispersible, fluorescent polymeric particles, comprising or consisting of a water-soluble conjugated polyene compound of any of formulae I-X; and a polymer comprising one or more ethylenically unsaturated monomers.

In an embodiment, the present subject matter relates to a method of detecting G-quadruplex formation, DNA, or protein and protein levels in a biological sample comprising contacting the biological sample with the water-soluble conjugated polyene compound and detecting luminescence.

In another embodiment, the present subject matter relates to a method of detecting G-quadruplex formation, DNA, or protein and protein levels wherein the conjugated polyene compound forms a complex with G-rich strand sequences of the biological sample which activates the fluorescence of the polyene.

In a further embodiment, the present subject matter relates to a method of detecting G-quadruplex formation, DNA, or protein and protein levels wherein a cation is added to the biological sample and polyene mixture.

In another embodiment, the present subject matter relates to a method of detecting G-quadruplex formation fluorescence emission intensity is monitored for any spectral shifts signaling the presence of a G-quadruplex conformation in the folded oligonucleotide.

In a further embodiment, the present subject matter relates to a method of detecting G-quadruplex formation, DNA, or protein and protein levels in a biological sample wherein the biological sample is selected from the group consisting of a tissue sample, cell sample, blood, saliva, spinal fluid, lymph fluid, vaginal fluid, seminal fluid, and urine.

In another embodiment, the present subject matter relates to a method of detecting G-quadruplex formation, DNA, or protein and protein levels in a biological sample wherein the biological sample is urine.

In another embodiment, the present subject matter relates to a method of detecting G-quadruplex formation, DNA, or protein and protein levels in a biological sample wherein the protein being detected in the biological sample is human serum albumin.

In another embodiment, the present subject matter relates to a method of diagnosing a kidney disorder comprising contacting a biological sample with a water-soluble conjugated polyene compound and detecting luminescence.

In another embodiment, the present subject matter relates to a method of diagnosing a kidney disorder wherein the conjugated polyene compound forms a complex with proteins in the biological sample thereby causing the conjugated polyene compound to fluoresce wherein the huninescence levels indicate the levels of protein present in the biological sample.

In yet another embodiment, the present subject matter relates to a method of diagnosing a kidney disorder wherein the protein being detected in the biological sample is human serum albumin.

In a further embodiment, the present subject matter relates to a method of detecting guanine (G)-rich repeat sequences in a biological sample comprising running the biological sample through a poly(acrylamide) gel electrophoresis (PAGE) assay, staining the PAGE assay with a water-soluble conjugated polyene compound, and detecting luminescence.

In an exemplary embodiment, the present subject matter relates to a method of screening a potential anti-cancer drug for activity including contacting said anti-cancer drug with a biological sample having a G-rich DNA sequence that is capable of forming a particular G-quadruplex conformer to form a reaction mixture, adding a water-soluble conjugated polyene compound to the reaction mixture of said anti-cancer drug and said G-rich DNA, and detecting luminescence. In another embodiment, the water-soluble conjugated polyene is added to the biological sample before the anti-cancer drug is mixed with the biological sample to form the reaction mixture. The potential anti-cancer drug, biological sample and water-soluble conjugated polyene can be added in any order and such will not affect the determination of the activity of the screened potential anti-cancer drug.

In another embodiment, the present subject matter relates to a method of screening a potential anti-cancer drug for activity further including comparing the detected luminescence from said water-soluble conjugated polyene compound in the reaction mixture of said biological sample having the G-rich DNA sequence and said anti-cancer rug with a luminescence detected from said water-soluble conjugated polyene compound in said biological sample having the G-rich DNA sequence alone, wherein said comparing further includes observing a bathochromic shift as an indicator of the formation of the particular G-quadruplex conformer in the biological sample.

In a further embodiment, the present subject matter relates to a method of screening a potential anti-cancer drug for activity, further comprising comparing the detected luminescence from said water-soluble conjugated polyene compound in the reaction mixture of said biological sample having the G-rich DNA sequence and said anti-cancer drug with a luminescence detected from said water-soluble conjugated polyene compound in a mixture of said biological sample having the G-rich DNA sequence and $K^+$ ions, wherein the fluorescence emission profiles between the biological sample with said anti-cancer drug and the biological sample with $K^+$ ions are similar. The G-quadruplex-inducing ability of the screened anti-cancer drug relative to the known G-quadruplex inducer, $K^+$ ions can be determined by the fluorescence intensities thereof at a specific wavelength, e.g. at 492 nm. In yet another embodiment, the water-soluble conjugated polyene compound is 1,1,2,2-tetrakis[4-(2-triethylammonioethoxy)phenyl]ethene tetrabromide (TTAPE).

In an embodiment, the present subject matter relates to an anti-cancer pharmaceutical composition comprises a water-soluble conjugated polyene compound. In another embodiment, said compound is conjugated with a G-quadruplex targeting motif, wherein the G-quadruplex targeting motif is capable of targeting a DNA sequence that is induced by said motif to form a particular G-quadruplex conformer over other G-quadruplex structures or duplex structures. The G-quadruplex targeting motif may be isolated from an anticancer drug being screened by the present. In a further embodiment, said compound is a chemically modified TPE. In another embodiment, said compound is a chemically modified TTAPE. In yet another embodiment, one or more of the triethylamine groups of the TTAPE are substituted with other positively charged groups including piperidine, pyrazole, piperazine and imidazole so as to obtain a chemically modified TTAPE. The chemically modified TTAPE may also act as a lead compound in said pharmaceutical composition because TTAPE itself has been shown to have a low efficiency of inducing the formation of G-quadruplex at certain conditions such as at room temperature.

The presently described series of linear and cyclic π-conjugated organic compounds (hereinafter polyenes) have been designed and synthesized with different chromophores including tetraphenylethylene, siloles, fulvene, butadienes, and 4H-pyrans. The emission color of these new polyenes ranges from blue to red arising from the different chromophoric structures. Their fluorescent behavior features the AIE phenomenon, which turns the dyes from faint-emitters when molecularly dissolved into strong luminophors when aggregated or in the solid state. The presently described AIE-active-molecules are highly specific to amyloid proteins and exhibit retardation effect on amyloid protein fibrillation. The excellent water solubility of the AIE-active-molecules allow background luminescence to be ignored. All these features make the presently described ME-active molecules excellent candidates for use as bioprobes for DNA detection, G-quadruplex identification and potassium-ion sensing as well as in polymeric particles, sensors and detection devices. The AIE-active-molecules can also be used to study conformational structures and folding processes, as fluorescent markers to visualize DNA bands in assays and to screen anti-cancer drug as well as for use in anti-cancer therapy. In addition, the presently described AIE-active-molecule's dual capability to discriminate native and fibrillar forms of amyloid proteins under physiological condition and to retard fibrillation, serve its use as an external tool for quantitative and kinetic analysis of amyloid fibrillation and as an antiamyloid agent for long-term storage and delivery of amyloid, such as pharmaceutical insulin.

In an embodiment, the present subject matter relates to a method of monitoring amyloid protein fibrillation in a biological sample. The method includes the use of a water-soluble conjugated polyene compound to contact with the biological sample and detecting luminescence from the compound induced by aggregation when contacting the biological sample, and wherein an increase of luminescence indicates fibrillogencsis. In a preferred embodiment, the conjugated polyene compound for monitoring amyloid protein fibrillation in a biological sample includes a chemical structure of the following formula:

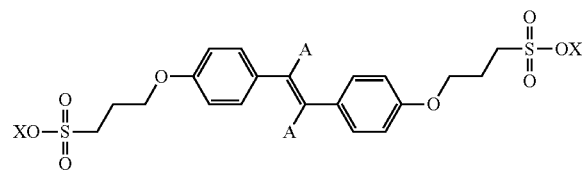

wherein A is selected from a cyanide or any aromatic group; and X is a cation. In a preferred embodiment, A is a substituted or unsubstituted aromatic moiety. In a more preferred embodiment, A is a phenyl. In another preferred embodiment, X is selected from the group consisting of $K^+$, $Li^+$, $Na^+$, $Mg^{2+}$, $NH_4^+$ and $Ca^{2+}$. In a further preferred embodiment, the conjugated polyene compound for monitoring amyloid protein is sodium 1,2-bis[4-(3-sulfonatopropoxyl)phenyl]-1,2-diphenylethene (TPE-SO3)

In another embodiment, the amyloid protein being monitored by the method of the present subject matter is selected from the group consisting of insulin, amyloid beta-peptide, tau, alpha-Synuclein, PrP and polyglutamine-containing peptides, such as human islet amyloid polypeptide (hIAPP).

In a further embodiment, the present subject matter relates to a method of retarding fibrillation of an amyloid protein for long-term storage and the delivery thereof, comprising storing said amyloid protein with a water-soluble conjugated polyene compound. In yet another embodiment, the fibrillation of the amyloid protein being retarded by the method of the present subject matter is selected from the group consisting of insulin, amyloid beta-peptide, tau, alpha-Synuclein, PrP and polyglutamine-containing peptides, such as hIAPP. In a preferred embodiment, the amyloid protein is insulin. In a more preferred embodiment, the amyloid protein is pharmaceutical insulin for treatment of diabetes.

BRIEF DESCRIPTION OF DRAWINGS

FIG. 1A-C shows that the three TPE derivatives are practically non-emissive when dissolved but highly emissive when aggregated.

FIG. 2A illustrates the change of fluorescence spectrum of TPE-OHNa$_2$ (5 μM) with addition of BSA in aqueous phosphate buffer (pH=7.0).

FIG. 2B illustrates a plot of fluorescence intensity at 476 nm versus BSA concentration.

FIG. 2C illustrates the linear region of the binding isotherm of TPE-OH to BSA. The FL of TPE-OH is turned on in the presence of BSA (FIG. 2). Its intensity increased with increasing BSA concentration, and in the BSA concentration range of 0-10 μg/ml exhibited a linear relationship with a $R^2$ value of 0.9974.

FIG. 5A illustrates the emission spectra of TPE-C2N$^+$ (2.5 μM) in an aqueous phosphate buffer (pH=7) and in the buffers containing 300 μg/ml BSA.

FIG. 5B illustrates a plot of fluorescence intensities of buffer solutions of TPE-C2N$^+$ at 462 nm versus concentrations of DNA and BSA.

FIGS. 5 and 6 illustrate that the FL of cationic TPE derivatives in aqueous solution can is turned on in the presence of BSA or DNA. TPE-C2N$^+$ exhibits better affinity to ctDNA than BSA while TPE-C4N$^+$ gives the opposite result.

FIG. 9 illustrates that N+C2-TPE-C2N$^+$ has larger affinity to DNA than to RNA and proteins.

FIG. 12A illustrates the emission spectra of derivative 4 (2.5 µM) in an aqueous phosphate buffer (pH=7) and in the buffers containing 300 µml$^{-1}$ ct DNA and 500 µml$^{-1}$ BSA.

FIG. 12B illustrates plots of fluorescence intensities of buffer solutions of derivative 4 at 463 nm vs. concentrations of ct DNA and BSA.

FIG. 13A illustrates the absorption and emission spectra of derivative 4 (2.5 µM) in water and a glycerol-water mixture at 25° C.

FIG. 13B illustrates the emission spectra of derivative 4 (2.5 µM)

FIG. 19A is a photograph of the coating film of Example 32 formed by the polymer nanoparticle dispersion with and without (controls) TPE-COOH fluorophores. The photos were taken under 365 nm irradiation from a UV lamp.

FIG. 19B is a photograph of the flexible thin sheets of Example 33 formed by the polymer nanoparticle dispersion with and without (controls) TPE-COOH fluorophores. The photos were taken under 365 nm irradiation from a UV lamp.

FIG. 32A shows the emission spectra of TTAPE in a Tris-HCl buffer in the presence of G1 and K$^+$.

FIG. 32B shows the effects of [K$^+$] on emission intensity at 470 nm and peak wavelength ($\lambda_{em}$) of the TTAPE/G1 solution. [TTAPE]=4.5 μM, [G1]=9 μM; $\lambda_{ex}$=350 nm.

FIG. 47A shows the dependence of FL intensity of SATPE at 476 nm on different proteins in phosphate buffer solution. [SATPE]=5 [protein]=100 μg/ml. Excitation wavelength: 350 nm.

FIG. 47B shows the dependence of FL intensity of SATPE at 476 nm on different proteins in artificial urine. [SATPE]=5 [protein]=100 μg/ml. Excitation wavelength: 350 nm.

FIG. 62A shows the emission spectra of TTAPE/H21 containing $K^+$ under environments of different pH value. [TTAPE]=4.5 μM; [DNA]=4.5 μM, [$K^+$]=0.5 M. Excitation wavelength: 350 nm.

FIG. 62B shows the effect of pH value on the PL intensity at 490 nm of TTAPE/H21 in the presence of $K^+$. [TTAPE]=4.5 μM; [DNA]=4.5 μM, [$K^+$]=0.5 M. Excitation wavelength: 350 nm.

FIG. 66B inset illustrates the FL intensity of TPE-SO3 in an insulin mixture with different molar fractions of fibrillar insulin ($f_f$), where total protein concentration (5 μM) is kept constant at each run. $I_0$=FL intensity in the absence of insulin; [TPE-SO3] is 5 μM; $\lambda_{ex}$=350 nm.

FIG. 69A shows effect of incubating insulin with different concentrations of TPE-SO3 on insulin fibrillation.

FIG. 69B shows the change in duration of lag phase when incubating insulin with increase in TPE-SO3 concentration.

FIG. 69C illustrates the change in fibrillation rate (rF) when incubating insulin with increase in TPE-SO3 concentration.

FIG. 84 shows peak intensity of BSPOTPE (50 μM) dyed hIAPP (0.1 mM) fibril at 470 nm.

FIG. 85 shows emission spectra of BSPOTPE (10 μM) monitoring the fibrillation of hIAPP (0.1 mM) with the presence of DOPC:DOPS (7:3) large unilamellar vesicles (0.9 mM), $\lambda_{ex}$=350 nm.

FIG. 86A shows a plot of $I/I_0$ of BSPOTPE (10 μM) monitoring hIAPP (0.1 mM) fibrillation at 380 and 470 nm with increasing incubation time at room temperature with LUVs.

FIG. 86B shows a plot of the ratio of peak intensity at 380 nm to peak intensity at 470 nm of BSPOTPE (10 μM) monitoring hIAPP (0.1 mM) fibrillation with LUVs at room temperature.

FIG. 87 shows emission spectra of ThT (10 μM) monitoring the fibrillation of hIAPP (0.1 mM) with the presence of DOPC:DOPS (7:3) large unilamellar vesicles (0.9 mM) and AIE luminogens, BSPOTPE and TTAPE-Et, $\lambda_{ex}$=430 nm.

FIG. 88 shows a plot of $(I-I_0)/(I_{max}-I_0)$ at 470 nm of BSPOTPE (10 μM) monitored β-amyloid (0.1 mg/mL) fibrillation with different incubation time.

FIG. 89 shows peak intensity at 470 nm of serial dilution of BSPOTPE (10 μM) monitored β-amyloid (0.1 mg/mL) fibrillation with different incubation time.

FIGS. 90A and 90B show images of β-amyloid fibril (Day 7) with BSPOTPE (50 μM) taken under daylight (A) and UV irradiation (B).

FIG. 91 shows TEM images of β-amyloid fibril at Day 7.

FIG. 92 shows the migration pathway of fluorescent nanoparticles into cells.

DETAILED DESCRIPTION OF PARTICULAR EMBODIMENTS

Definitions

Figures 1A, 1B, 1C:
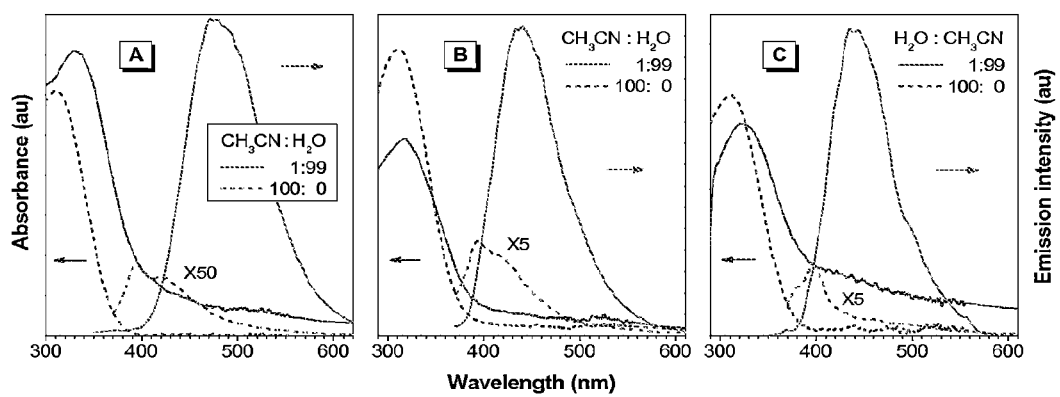
FIGS. 1A, 1B, and 1C illustrate absorption and emission spectra of (A) TPE-OMe (10 μM), (B) TPE-OH (10 μM), and (C) TPE-SO3 (5 μM) in pure acetonitrile, pure water, and mixtures of acetonitrile and water.
Figures 3A, 3B, 3C:
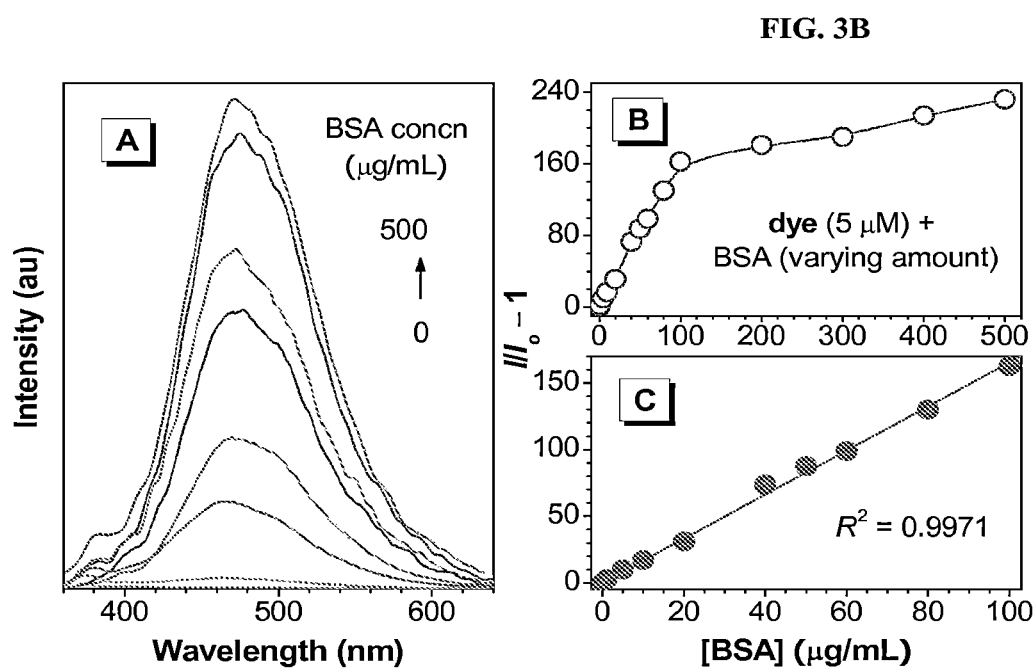
FIG. 3A illustrates the change of FL spectrum of TPE-SO3 with addition of BSA in an aqueous phosphate buffer.
FIG. 3B illustrates the plot of FL intensity at 472 nm versus BSA concentration.
FIG. 3C illustrates the linear region of the $(I/I_0-1)$-[BSA] plot in FIG. 3B. TPE-SO3 shows similar behavior as TPE-OH but better performance. The FL intensity increase up to 240 times upon binding with BSA. Linear range in the BSA concentration from 0 to 100 μg/ml is given with a $R^2$ value of 0.9971.
Figures 4A, 4B:
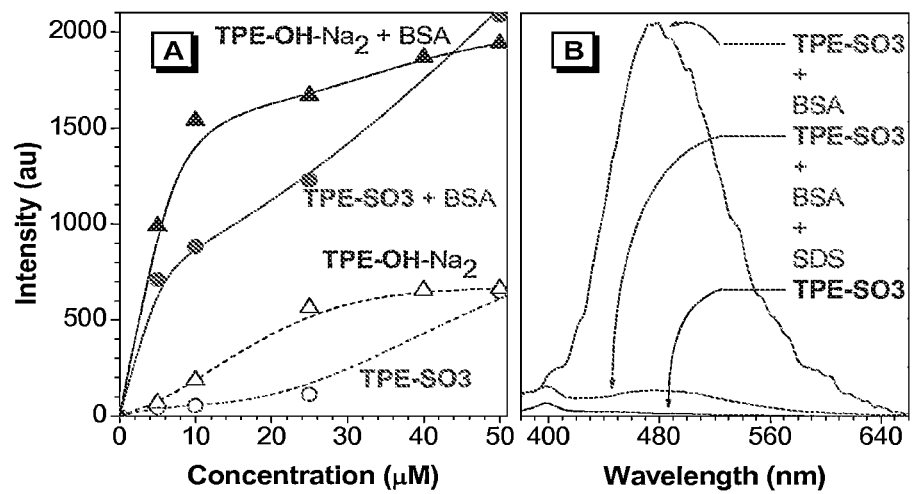
FIG. 4A illustrates the effect of dye concentration on the FL intensity of buffer solution of TPE-OHNa$_2$ at 467 nm or TPE-SO3 at 472 nm in the absence or presence of BSA (10 μg/ml).
FIG. 4B illustrates the effect of BSA (100 μg/ml) and/or SDS (1 mg/ml) on the FL spectrum of a buffer solution of TPE-SO3 (5 μM). Conventional fluorescent dyes suffer from self-quenching at high dye concentrations, whereas the FL of the AIE-active dyes is intensified with increasing dye concentration as illustrated in FIG. 4A. The FL of TPE-SO3 solution in the presence of BSA is diminished by adding surfactants such as sodium dodecyl sulphate (SDS) in high concentration (1 mg/ml) as illustrated in FIG. 4 B.
Figure 6A:
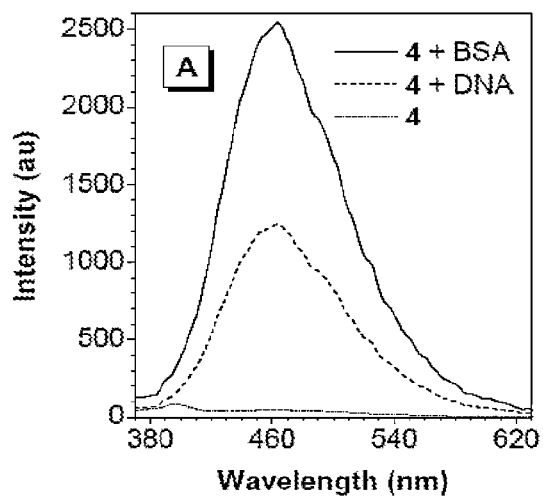
FIG. 6A illustrates the emission spectra of TPE-C4N$^+$ (4) (2.5 μM) in an aqueous phosphate buffer (pH=7) and in the buffers containing 300 μg/ml calf *thymus* DNA ("ctDNA") and 500 μg/ml BSA.
Figure 6B:
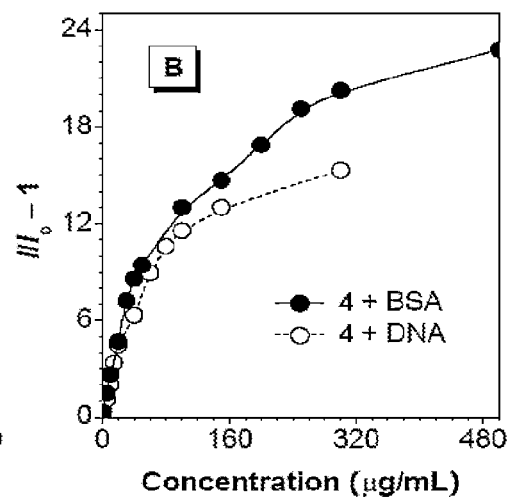
FIG. 6B illustrates plots of fluorescence intensities of buffer solutions of TPE-C4N$^+$ (4) at 463 nm versus concentrations of ct DNA and BSA.
Figure 7A:
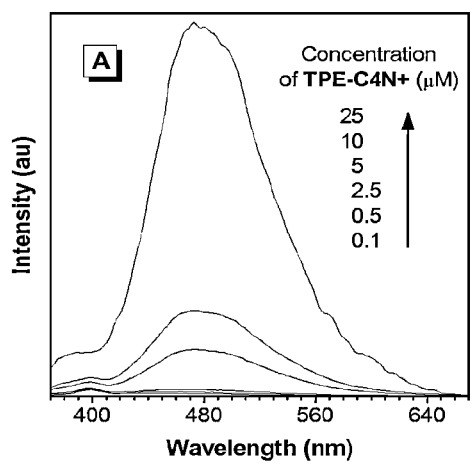
FIG. 7A illustrates the emission spectra of TPE-C4N$^+$ (2.5 μM) in an aqueous phosphate buffer (pH=7) and in buffers containing 300 μg/ml ctDNA and 500 μg/ml BSA.
Figure 7B:
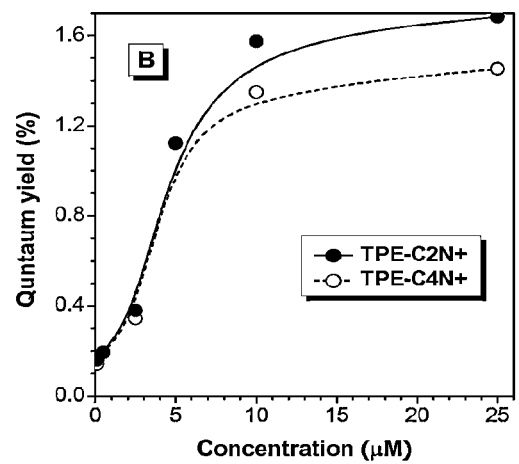
FIG. 7B illustrates plots of fluorescence intensities of buffer solutions of TPE-C4N$^+$ at 463 nm versus concentrations of ctDNA and BSA. The FL of TPE-C4N$^+$ and TPE-C2N$^+$ is intensified with increased dye concentration.
Figure 8:
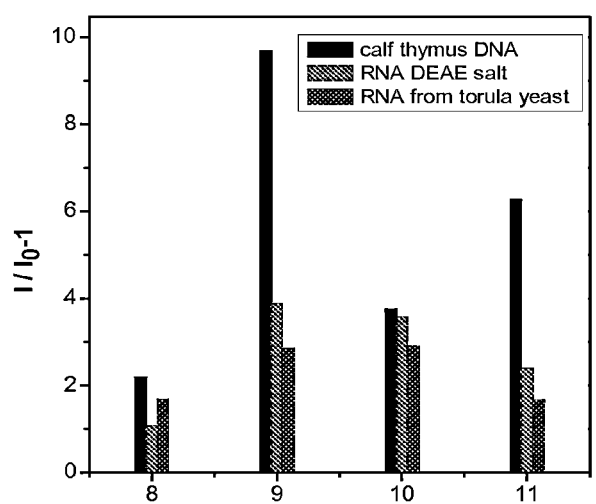
FIG. 8 illustrates increments of fluorescence of TPE-C2N$^+$ (8), N+C2-TPE-C2N$^+$ (9), TPE-C4N$^+$ (10), N+C4-TPE-C4N$^+$ (11) when binding with 10 µg/ml ctDNA/10 µg/ml RNA diethylaminoethanol (DEAE) salt from torula yeast/10 µg/ml RNA from torula yeast in buffer solution pH=7. Concentration of dyes: 5 µM; excitation wavelength: 350 nm. The four cationic TPE derivatives display larger FL enhancement in the presence of DNA than that of RNA. Meanwhile N+C2-TPE-C2N$^+$ and N+C4-TPE-C4N$^+$ show much larger variety of FL than that of TPE-C2N$^+$ and TPE-C4N$^+$ in the presence of DNA and RNA.
Figure 9:
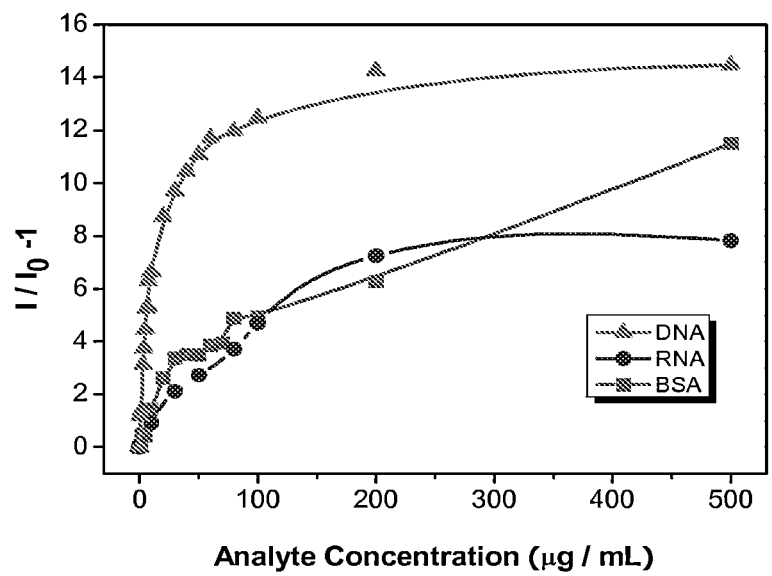
FIG. 9 illustrates the binding isotherm of N+C2-TPE-C2N$^+$ (5 µM) to ctDNA/RNA from torula yeast/BSA (plot of the fluorescence intensity at 470 nm for ctDNA/RNA, and at 467 nm for BSA) in aqueous phosphate buffer (pH=7.0).
Figure 10:
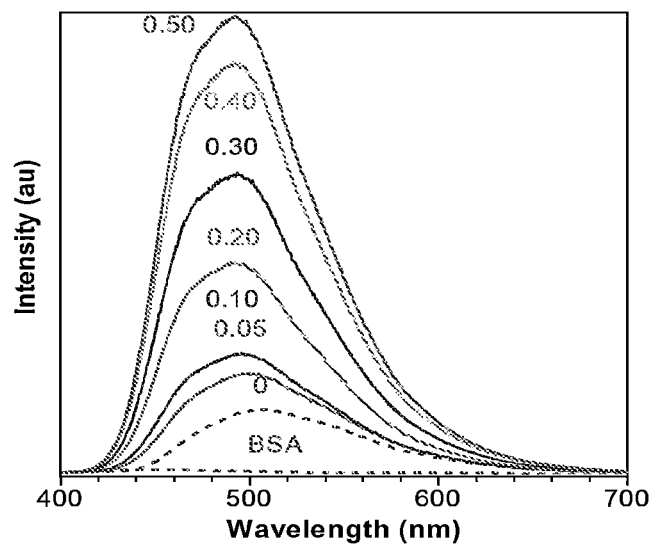
FIG. 10 illustrates the photoluminescence spectra of the water/methanol (6:4) solutions of a PPS-OH ($5.7 \times 10^{-5}$ M) in the presence of KOH ($8.4 \times 10^{-4}$ M) and BSA. The spectrum of a "pure" BSA solution (0.50 wt %) is shown for comparison. Excitation wavelength: 378 nm. Water-soluble silole derivatives also show this "turn-on" property when binding to BSA in aqueous solutions.

The following definitions are provided for the purpose of understanding the present subject matter and for constructing the appended patent claims.

It is noted that, as used in this specification and the appended claims, the singular forms "a," "an" and "the" include plural references unless the context clearly dictates otherwise.

"A chemically conjugated system" means a system of atoms covalently bonded with alternating single and double bonds in a molecule of an organic compound.

"A polyene" means a molecule of an organic compound containing more than one alkene. For example, a diene has two C=C; a triene has three C=C; etc.

"Target molecule" means the molecule whose changes in concentration in an environment are intended to be detected by a sensor. A target molecule can comprise or consist of a biomacromolecule. "Detecting molecule" means a molecule which, upon contacting with a target molecule in the environment, can provide a signal perceivable to human.

"Alkyl" means, unless otherwise specified, an aliphatic hydrocarbon group which may be straight or branched chain having about 1 to about 15 carbon atoms in the chain, optionally substituted by one or more halogen atoms. A particularly suitable alkyl group has from 1 to about 6 carbon atoms. The term "unsaturated" refers to the presence of one or more double and triple bonds between atoms of a radical group, for example.

"Heteroatom" means an atom selected from the group consisting nitrogen, oxygen, sulfur, phosphorus, boron and silicon.

"Heteroaryl" as a group or part of a group denotes an optionally substituted aromatic monocyclic or multicyclic organic moiety of about 5 to about 10 ring members in which at least one ring member is a heteroatom.

"Cycloalkyl" means an optionally substituted non-aromatic monocyclic or multicyclic ring system of about 3 to about 10 carbon atoms.

"Heterocycloalkyl" means a cycloalkyl group of about 3 to 7 ring members in which at least one ring member is a heteroatom.

"Aryl" or "aromatic group" means a group or part of a group denotes an optionally substituted monocyclic or multicyclic aromatic carbocyclic moiety of about 6 to about 14 carbon atoms, such as phenyl or naphthyl. Examples of substituents of aromatic moiety are those as disclosed herein as R.

"Heteroalkyl" refer to alkyl in which at least one carbon atom is replaced by a heteroatom.

"Biomacromolecule" means a high molecular biological weight substance comprising or consisting of one or more of nucleic acids, proteins and/or complex carbohydrates.

"Alkali metals ions" or "Alkaline earth metals ions" means metals selected from the group consisting of $K^+$, $Li^+$, $Na^+$, $Mg^{2+}$ and $Ca^{2+}$.

"Microparticle" means any microscopic particle or particle population having a mean diameter of less than about 10 microns (μm); less than about 5 μm; less than about 1 μm; or having a mean diameter in the range of from greater than or equal to 10 nm to less than 5 μm; of from greater than or equal to 40 nm to less than 3 μm; of from greater than or equal to 50 nm to less than 1 μm; of from greater than or equal to 60 nm to less than 750 nm; of from greater than or equal to 50 nm to less than 500 nm; of from greater than or equal to 60 nm to less than 300 nm; of from greater than or equal to 80 nm to less than or equal to 250 nm; of from greater than or equal to 1 μm to less than 10 μm; of from greater than or equal to 2.5 μm to less than 10 μm; of from greater than or equal to 5 μm to less than 10 μm; of from greater than or equal to 7.5 μm to less than 10 μm; of from greater than or equal to 2.5 μm to 7.5 μm; or having a mean diameter in the range of from greater than or equal to 5 μm to 7.5 μm. In an embodiment, greater than 99% of the microparticles of a microparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

"Nanoparticle" means any microscopic particle or particle population having a mean diameter of less than about 100 nanometers (nm); less than about 90 nm; less than about 80 nm; less than about 70 nm; less than about 60 nm; less than about 50 nm in diameter; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

"Aggregation-induced emission" or "AIE" means the fluorescence/phosphorescence is turned on upon aggregation formation or in the solid state. When molecularly dissolved, the material is non-emissive. However, the emission is turned on when the intramolecular rotation is restricted.

"Bathochromic shift" means a change of spectral band position in the absorption, reflectance, transmittance, or emission spectrum of a molecule to a longer wavelength (lower frequency) due to the influence of substitution or a change in environment. It is informally referred to as a red shift and is opposite to hypsochromic shift.

"Emission intensity" means the magnitude of fluorescence/phosphorescence normally obtained from fluorescence spectrometer, fluorescence microscopy measurement.

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Water-Soluble Conjugated Polyenes

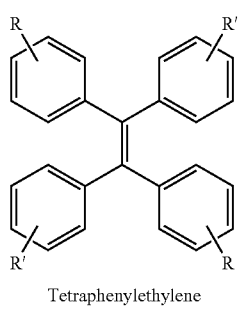
Tetraphenylethylene

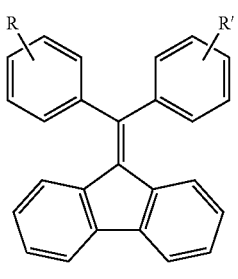
Fulvene

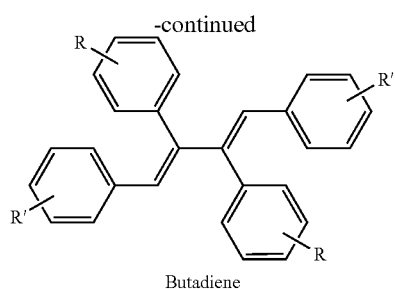
Butadiene

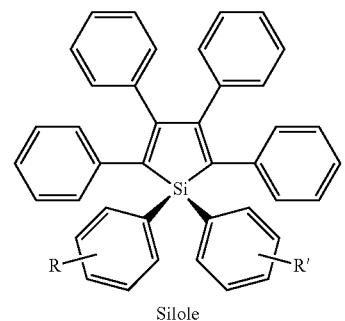
Silole

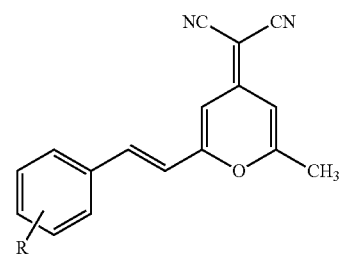

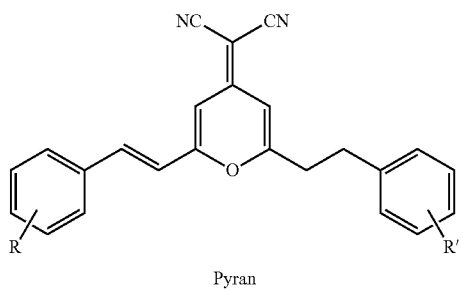
Pyran

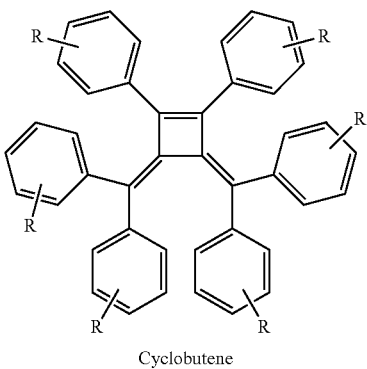
Cyclobutene

-continued

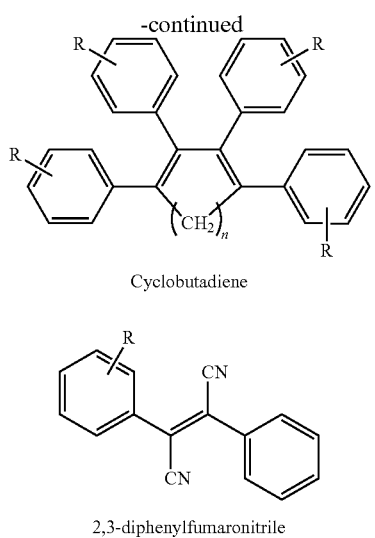

Cyclobutadiene 2,3-diphenylfumaronitrile

R, R' = —B(OH)$_2$
—(X)$_n$COOR''
—(X)$_n$COOH
—(X)$_n$NH$_2$
—(X)$_n$NHR''
—(X)$_n$NR''$_2$
—(X)$_n$N$^+$R''$_3$Br$^-$
—(X)$_n$OH
—(X)$_n$SH
—(X)$_n$SO$_3^-$Na$^+$

X = —(CH$_2$)$_n$—
—O(CH$_2$)$_n$—
—NH(CH$_2$)$_n$—
—N[(CH$_2$)$_n$]$_2$—
—(OCH$_2$CH$_2$)$_n$—

R'' = —R
—R'
—(CH$_2$)$_n$CH$_3$
—C(O)NH—X—
—C(O)O—X—
—C$_6$H$_4$—R
—CH$_2$—C$_6$H$_5$
—C$_6$H$_5$

R, R' =  pyrrolidinium, methylpiperazinium, piperidinium, methylpyridinium

R'' = —R
—R'
—(CH$_2$)$_n$CH$_3$
—C(O)NH—X—
—C(O)O—X—
—C$_6$H$_4$—R
—CH$_2$—C$_6$H$_5$
—C$_6$H$_5$

R, R' can also = pyrrolidinium, methylpiperazinium, piperidinium, methylpyridinium $n$ = 0-25

In an embodiment, the present subject matter relates to a water-soluble conjugated polyene compound comprising a backbone structure of a formula selected from the group consisting of:

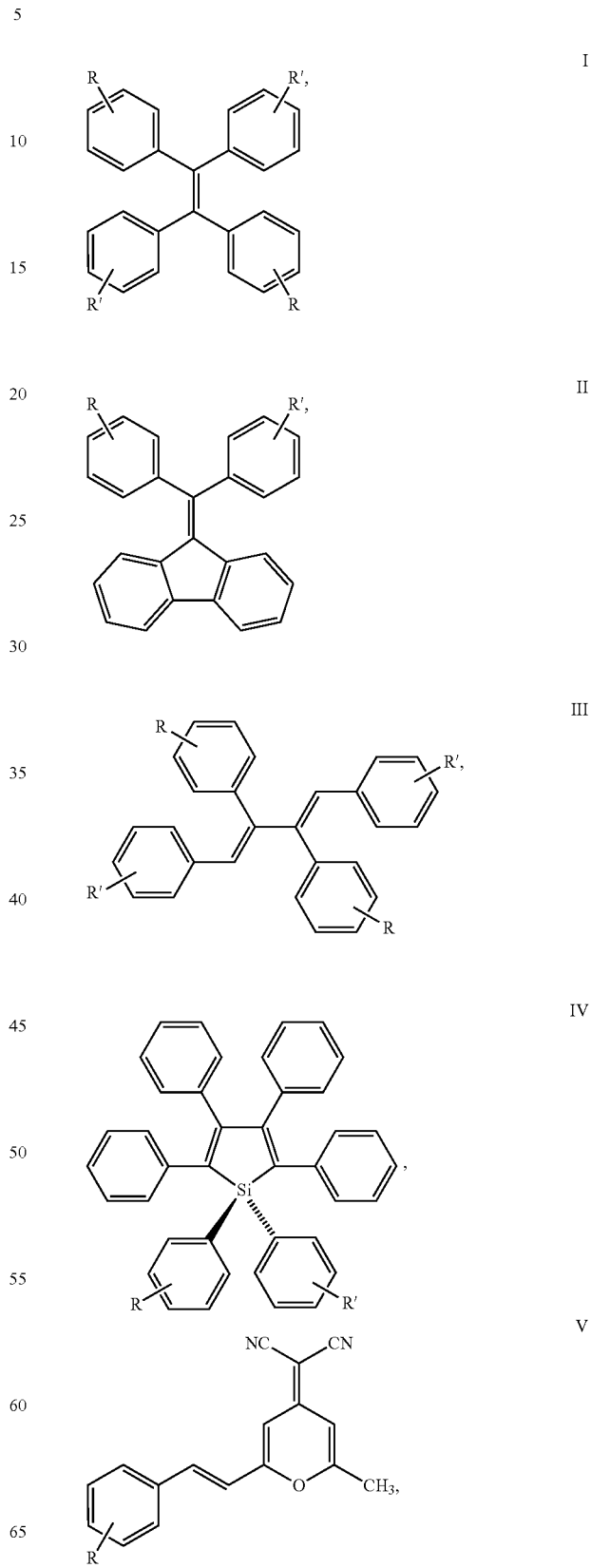

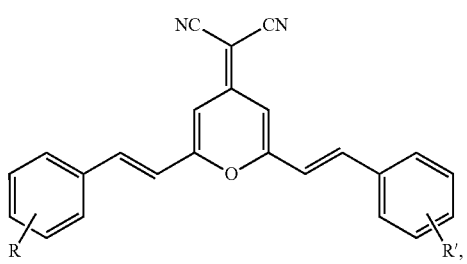

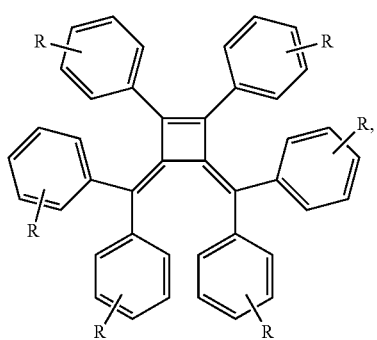

Cyclobutene

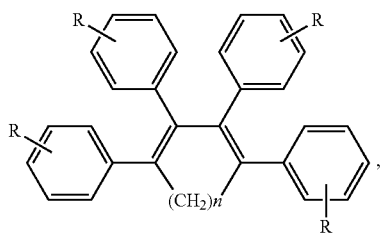

Cyclobutadiene

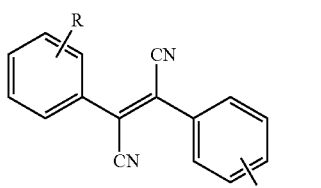

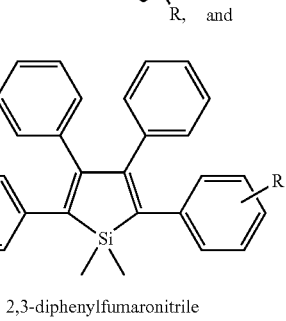

2,3-diphenylfumaronitrile 2,3- diphenylfumaronitrile
wherein
R and R' are independently selected from H, X, B(OH)$_2$, (X)$_n$COOR", (X)$_n$COOH, (X)$_n$NH$_2$, (X)$_n$NHR", (X)$_n$NR"$_2$, (X)$_n$N$^+$R"$_3$Br$^-$, (X)$_n$OH, (X)$_n$SH, (X)$_n$SO$_3$$^-$Na$^+$, (CH$_2$)—P$^+$R"$_3$Br$^-$, VI 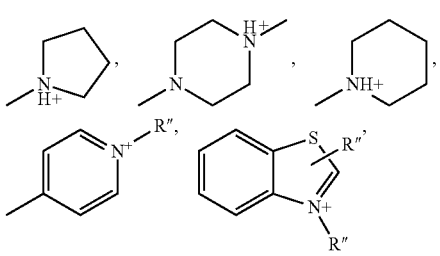

VII 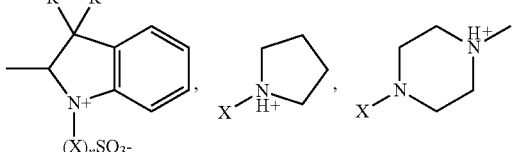

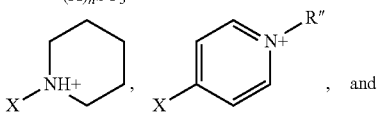, and

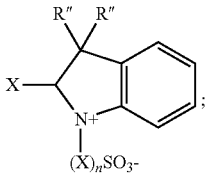;

VIII X is selected from (CH$_2$)$_n$, O(CH$_2$)$_n$, NH(CH$_2$)$_n$, N[(CH$_2$)$_n$]$_2$, (CH═CH)$_n$ and (OCH$_2$CH$_2$)$_n$; and R" is selected from R, R', (CH$_2$)$_n$CH$_3$, CONH—X—, COO—X—, C$_6$H$_5$—R, —CH$_2$—C$_6$H$_5$, and C$_6$H$_5$; n=0 to 20, and salts thereof, and wherein the compound is water-soluble and exhibits aggregation induced emission.

In another embodiment, the present subject matter relates to a water-soluble conjugated polyene compound, wherein the molecule has a backbone structure of formula I.

In an embodiment, the present subject matter relates to a water-soluble conjugated polyene compound of claim formula I, wherein R is H and R' is selected from the group consisting of H, OH, COOH, CH$_2$NH$_2$, B(OH)$_2$, O(CH$_2$)$_2$SO$_3$$^-$Na$^+$, O(CH$_2$)$_3$SO$_3$$^-$Na$^+$, O(CH$_2$)$_2$N$^+$(CH$_2$CH$_3$)$_3$Br$^-$, O(CH$_2$)$_2$N$^+$(CH$_3$)$_3$Br$^-$, O(CH$_2$)$_4$N$^+$(CH$_2$CH$_3$)$_3$Br$^-$, CH$_2$PPh$_3$$^+$Br$^-$,

IX

X 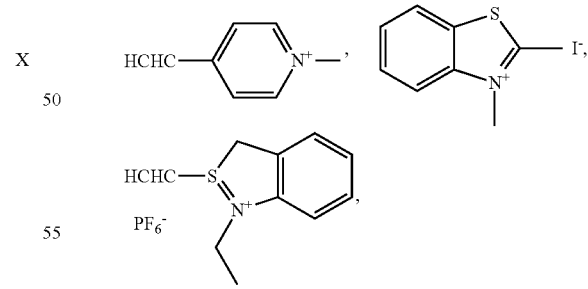

and N$^+$OCH$_3$.

In a further embodiment, the present subject matter relates to a water-soluble conjugated polyene compound of formula I, wherein R and R' are the same and are selected from the group consisting of OH, O(CH$_2$)$_2$N$^+$(CH$_2$CH$_3$)$_3$Br$^-$, and O(CH$_2$)$_4$N$^+$(CH$_2$CH$_3$)$_3$Br$^-$.

The presently described subject matter is also directed to a water-soluble conjugated polyene compound of formula I, selected from the group consisting of 1,2-Bis(4-hydroxyphenyl)-1,2-diphenylethylene;
1,2-Bis(4-methoxyphenyl)-1,2-diphenylethylene;
1,2-diphenyl-1,2-bis(4,4'(3-sulfonato)propoxyl)phenyleth-
  ylene;
N,N'-[1,2-diphenyl-1,2-bis(1,4-phenoxyethyl)vinyl]bis(tri-
  ethylammoniumbromide);
N,N'-[1,2-diphenyl-1,2-bis(1,4-phenoxybutyl)vinyl]bis(tri-
  ethylammoniumbromide);
1,1,2,2-tetrakis(4-hydroxyphenyl)ethylene;
N,N',N'',N'''-[1,2-tetrakis(1,4-phenoxybutyl)vinyl]tetrakis
  (triethylammoniumbromide);
N,N',N'',N'''-[1,2-tetrakis(1,4-phenoxyethyl)vinyl]tetrakis
  (triethylammoniumbromide);
4,4'-(1,2-diphenylvinyl)di(phenylboronic acid);
4,4'-(1,2-diphenylvinyl)di(phenylcarboxylic acid);
1,2-di[4-(aminomethyl)phenyl]-1,2-diphenylethylene;
1,2-Bis[4-(3-sulfonatopropoxy)phenyl]-1,2-diphenylethene
  sodium;
1,2-Bis[4-(3-triphenylphosphonium)phenyl]-1,2-diphe-
  nylethene bromide;
1-[4-(1-methyl-4-pyridine)ethene]-1,2,3-triphenylethene
  hexafluorophosphate;
1-[4-(1,2-dimethyl-5-benzothiazole)]-1,2,3-triphenylethene
  iodide;
N,N',N'',N'''-[1,2-tetrakis(1,4-phenoxyethyl)vinyl]tetrakis
  (trimethylammoniumbromide); and
1-[4-(1-ethyl-2-benzothiazole)ethene]-1,2,3-triph-
  enylethene hexafluorophosphate.

In another embodiment, the present subject matter relates to a water-soluble conjugated polyene compound wherein the molecule has a backbone structure of formula II.

In yet another embodiment, the present subject matter relates to a water-soluble conjugated polyene compound wherein the molecule has a backbone structure of formula III.

In a further embodiment, the present subject matter relates to a water-soluble conjugated polyene compound wherein the molecule has a backbone structure of formula IV.

In an embodiment, the present subject matter relates to a water-soluble conjugated polyene compound of formula IV, wherein R is H and R' is selected from the group consisting of $CH_2N^+(CH_2CH_3)_2Br^-$ and $CH_2N(CH_2CH_3)_2$.

In another embodiment, the present subject matter relates to a water-soluble conjugated polyene compound of formula IV, selected from the group consisting of
1,1'-Bis-[4-(N,N'-diethylaminomethyl)phenyl]-2,3,4,5-tet-
  raphenylsilole; and
N,N'-[1,1'-bis(1,4-benzylene)-2,3,4,5-tetraphenyl-silolyl)bis
  (triethylammoniumbromide).

In yet another embodiment, the present subject matter relates to a water-soluble conjugated polyene compound, wherein the molecule has a backbone structure of formula V.

In a further embodiment, the present subject matter relates to a water-soluble conjugated polyene compound, wherein the molecule has a backbone structure of formula VI.

In a further embodiment, the present subject matter relates to a water-soluble conjugated polyene compound, wherein the molecule has a backbone structure of formula VII.

In a further embodiment, the present subject matter relates to a water-soluble conjugated polyene compound, wherein the molecule has a backbone structure of formula VIII.

In a further embodiment, the present subject matter relates to a water-soluble conjugated polyene compound, wherein the molecule has a backbone structure of formula IX.

In a further embodiment, the present subject matter relates to a water-soluble conjugated polyene compound, wherein the molecule has a backbone structure of formula X.

In an embodiment, the present subject matter relates to a water-soluble conjugated polyene compound of claim formula X, wherein R is

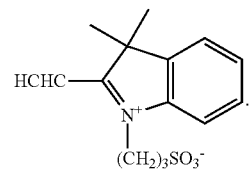

In another embodiment, the present subject matter relates to a water-soluble conjugated polyene compound of formula X, which is 1,1'-methyl-2,5-bis[4-(1-sulfonatopropyl-2-isoindole)ethenephenyl]-3,4-bisphenyl silole.

Synthesis of Water-Soluble Conjugated Polyenes

In one embodiment, the present subject matter relates to water-soluble conjugated polyenes useful as bioprobes and for manufacturing sensors. These polyenes can be prepared according to a variety of different methods. Non-limiting examples of such synthetic methods are discussed below.

Scheme 1a: Synthesis of TPE derivatives

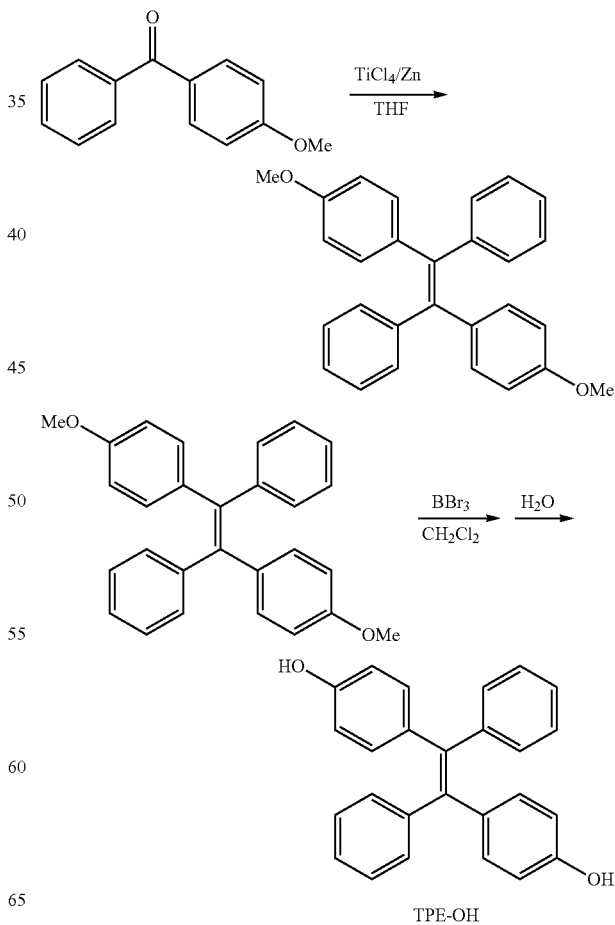

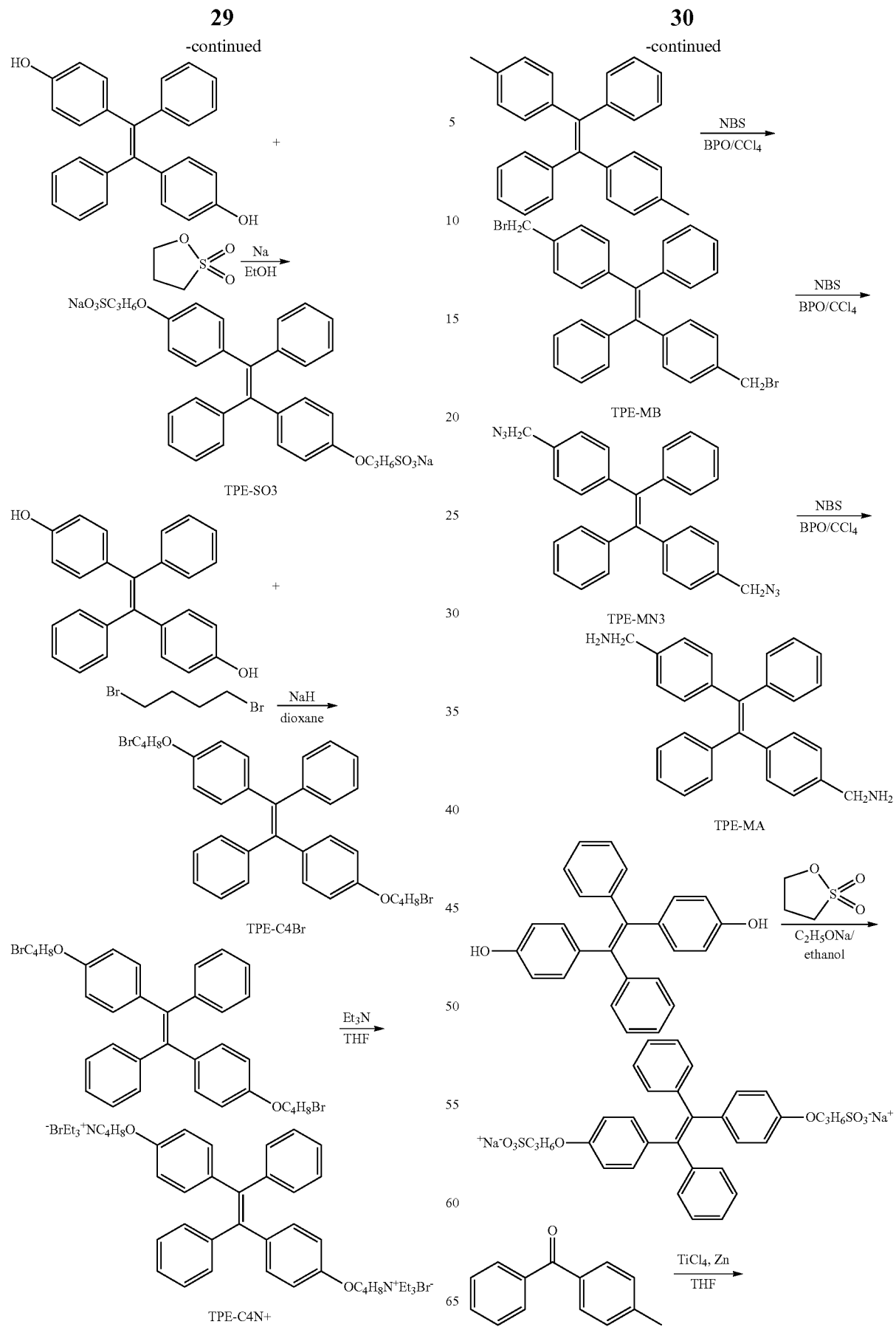

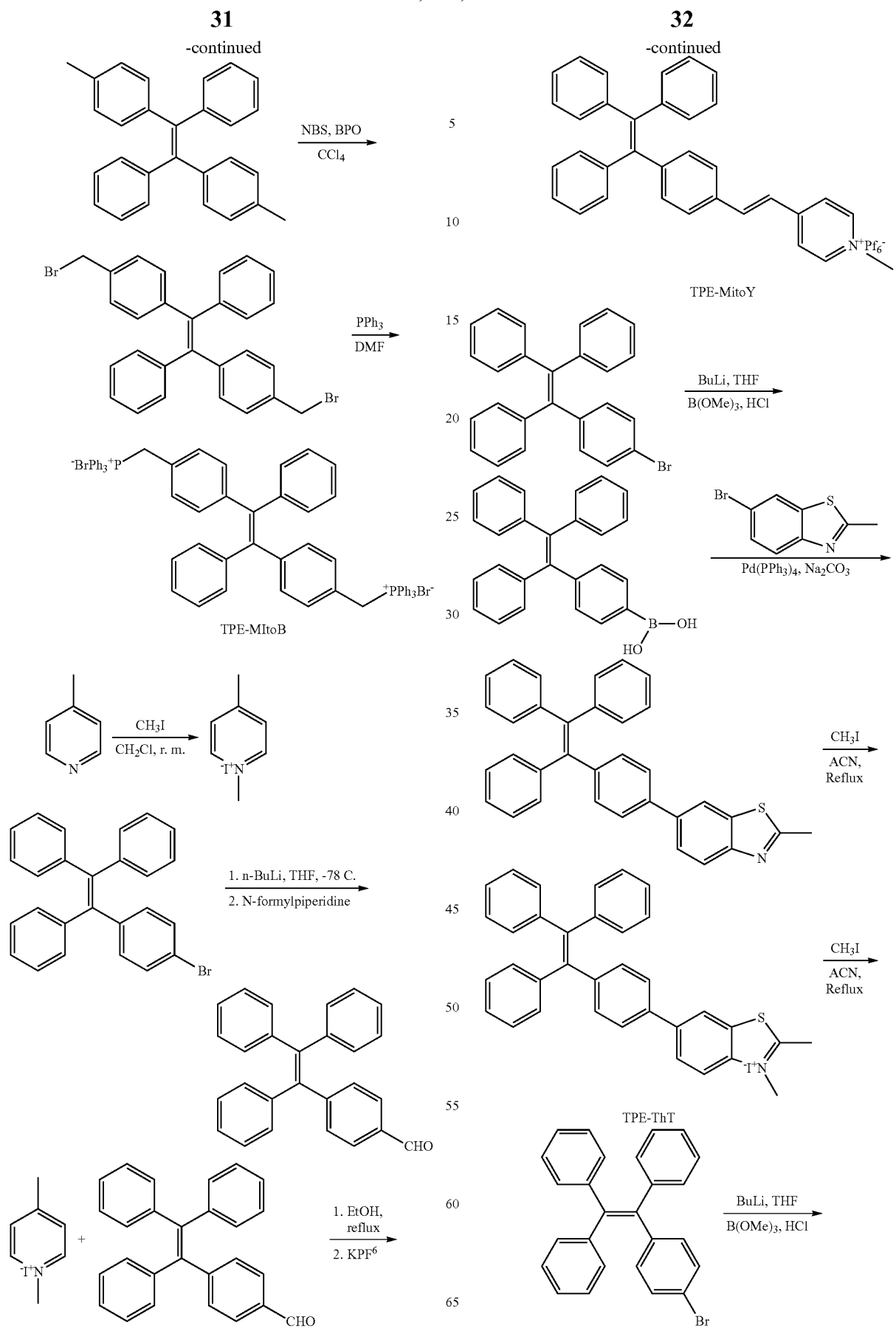

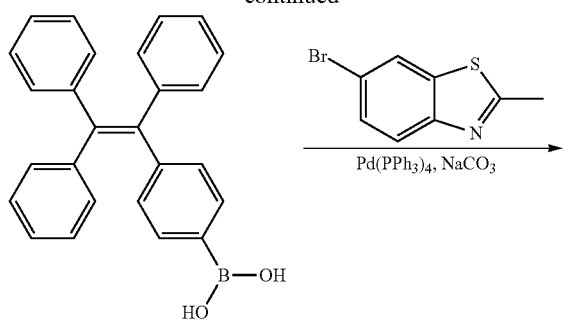
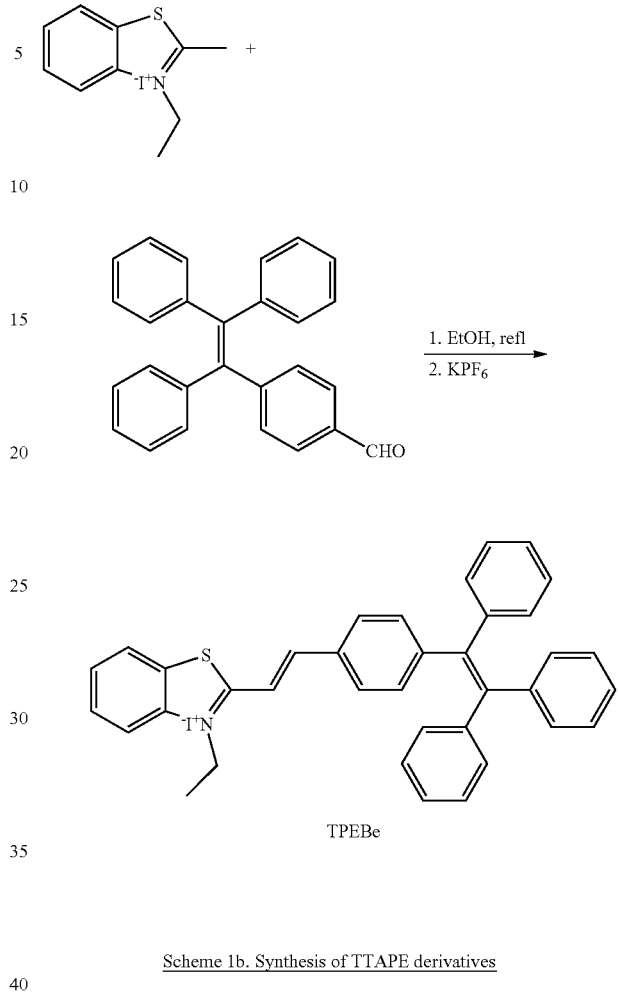
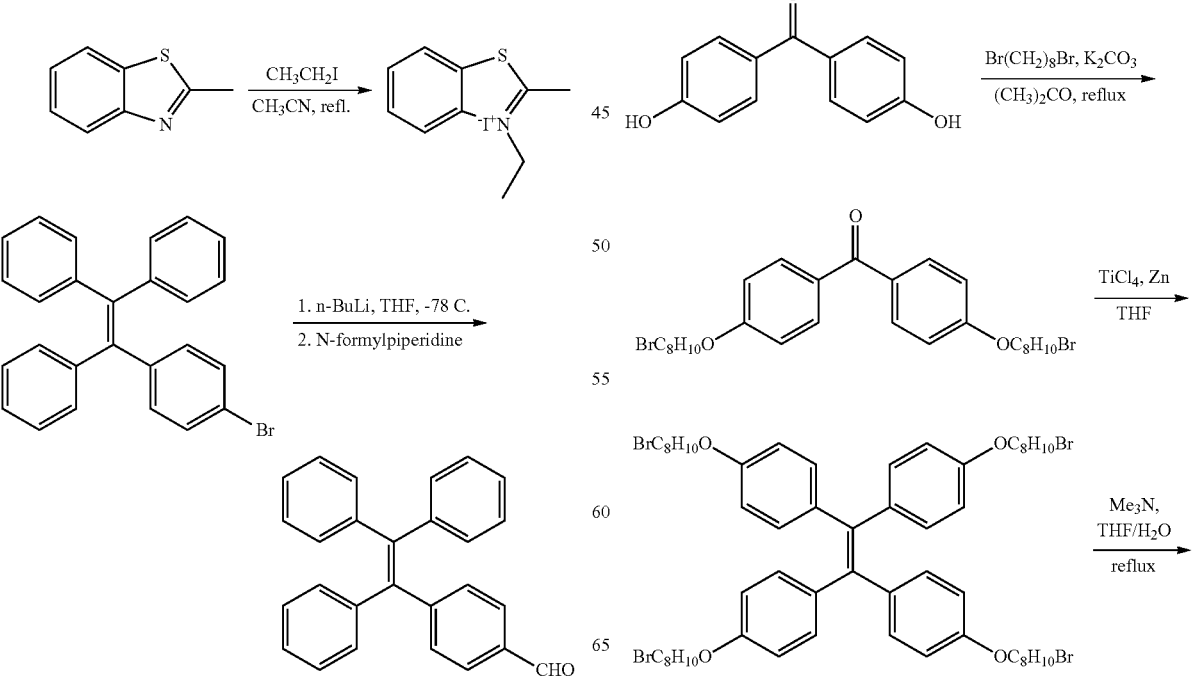
Scheme 1b. Synthesis of TTAPE derivatives

35
-continued
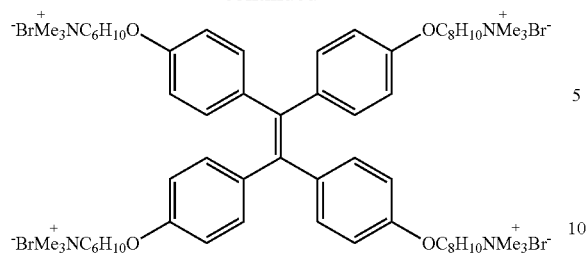
Scheme 2. Synthetic routes to the bromo-and carboxyl-substituted tetraphenylethylenes.
36
-continued
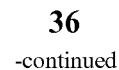
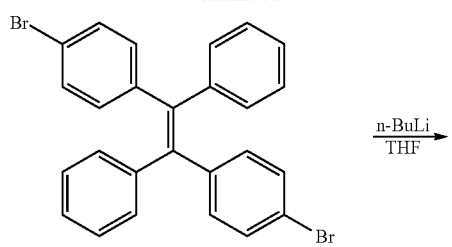
Scheme 2. Synthetic routes to the bromo-and carboxyl-substituted tetraphenylethlenes.
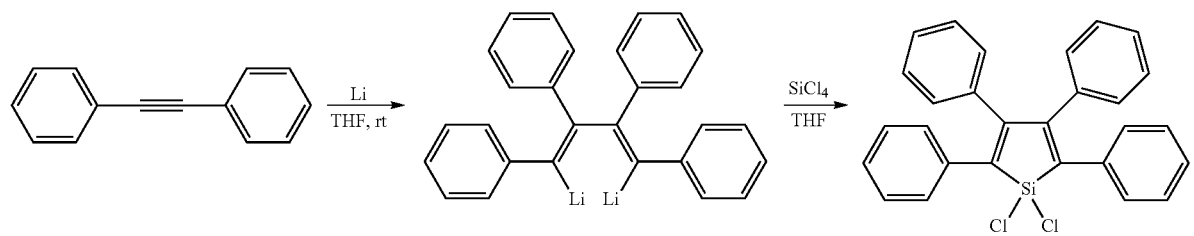
BBDA
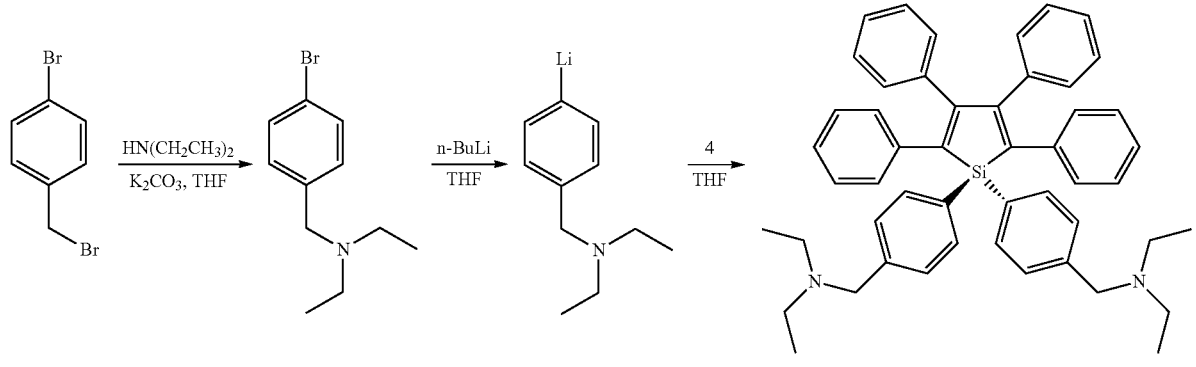
A₂-HPS
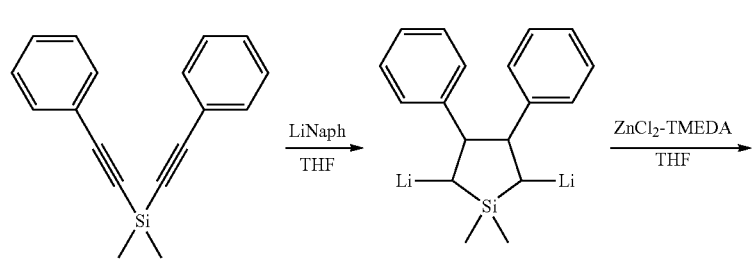

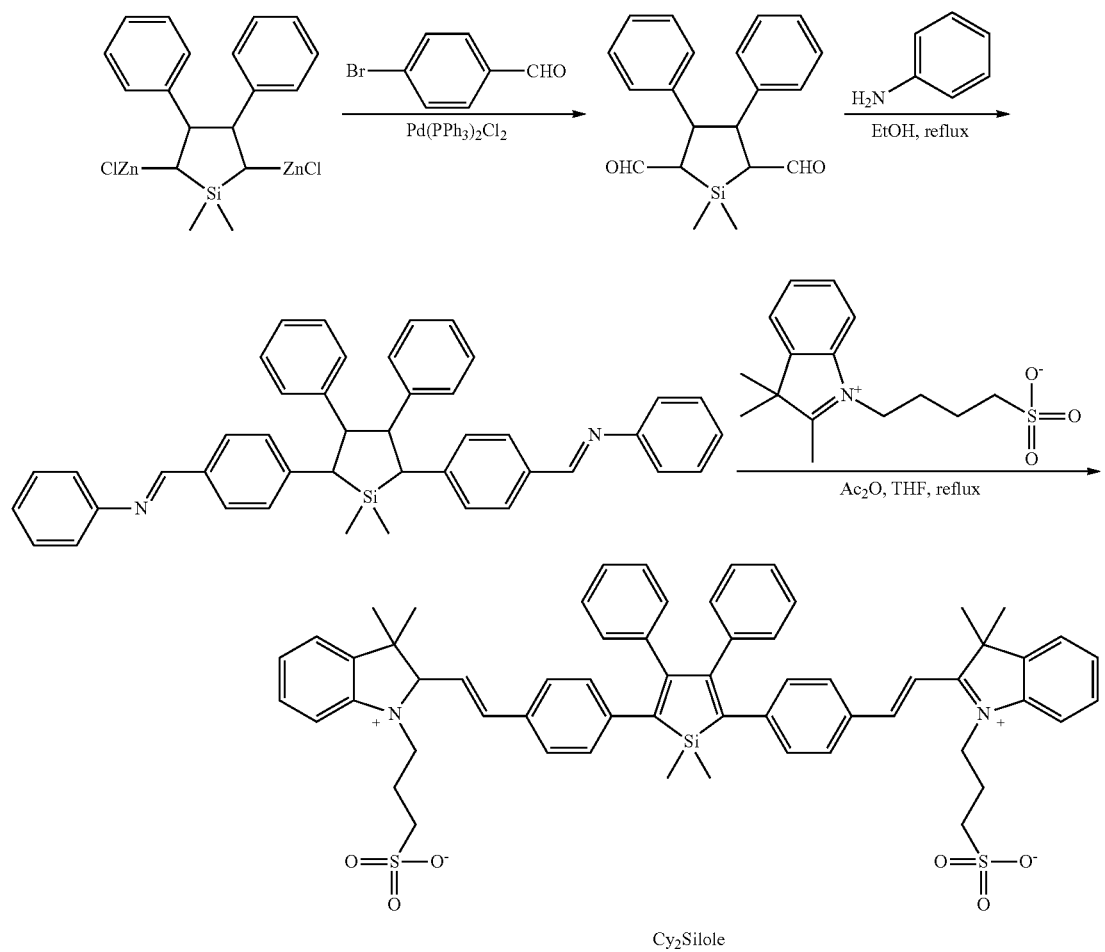
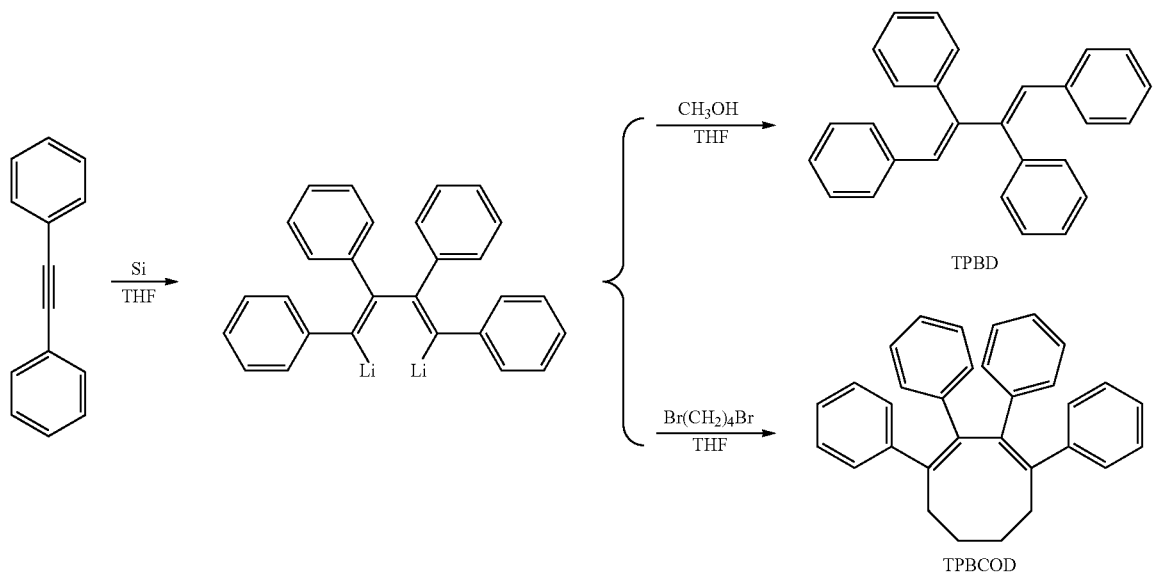
Scheme 4. Synthesis of Butadiene and Cyclobutadiene Derivatives

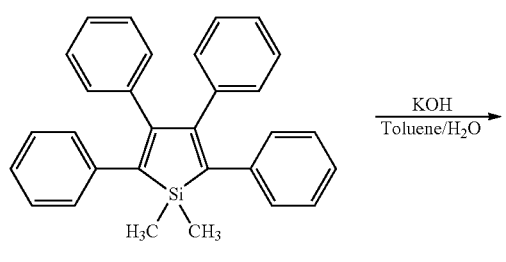 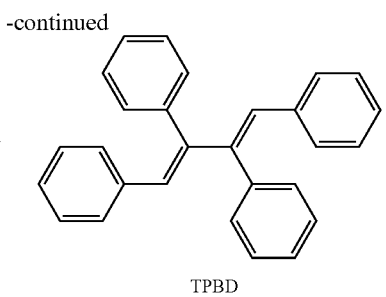

TPBD

Scheme 5. Synthesis of Fulvene Derivatives

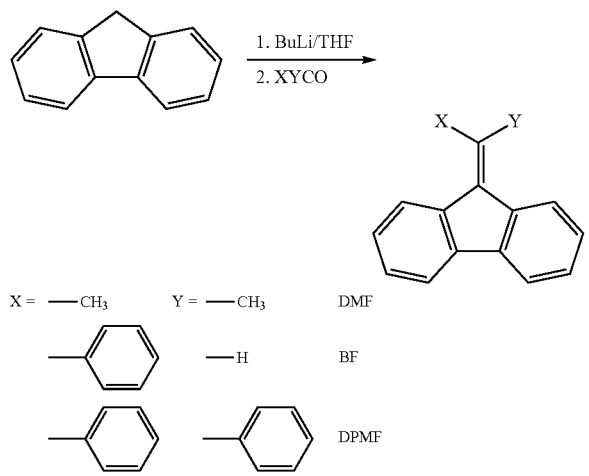

Scheme 6. Synthesis of Diphenylethylene Derivatives

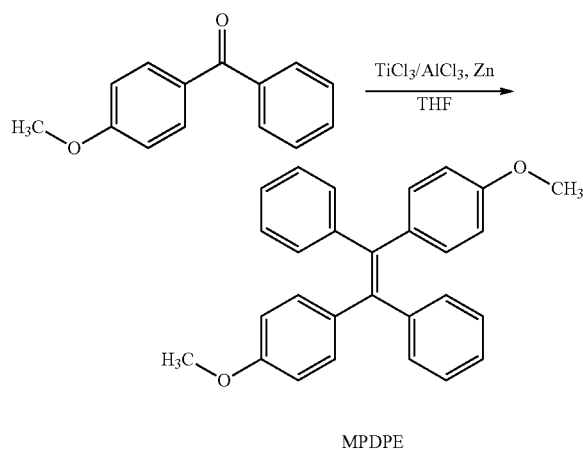

MPDPE

Appropriately substituted versions of the precursors illustrated in the above schemes can be readily selected and employed, by the person of ordinary skill in the art to which the presently described subject matter pertains, to synthesize corresponding substituted products without undue experimentation.

Fluorescent Polymer Particles

The presently described subject matter is directed to water-dispersible, fluorescent, polymeric particles, which comprise or consist of the presently described TPE-derived water-soluble conjugated polyenes ("TPE dyes") that exhibit ME, and a variety of polymer matrices having desirable hydrophilicity and chemical composition that can be designed to proved desirable characteristics.

Based on the proposed AIE mechanism, several of the presently described AIE-active dyes which exhibit fluorescent "turn-on" property when bound to biomacromolecules were investigated. A group of water-soluble AIE molecules were designed and synthesized. When the presently described water-soluble AIE molecules are dissolved in water or phosphate buffer saline (PBS), the solution is virtually non-emissive. However, the fluorescence increases significantly in the presence of proteins and DNA. There is a linear relationship between fluorescent intensity and the concentration of analytes in a certain range, which is of great importance in protein and DNA assays.

Furthermore, the presently described AIE water-soluble molecules are organic compounds, which make them easily accessible and much more economical compared to platinum or transition metal-containing counterparts. All of the presently described AIE-active water-soluble molecules are advantageous in that they can be synthesized in many structural forms and can be easily substituted with a variety of functional groups.

In addition, the presently described AIE-active water-soluble molecules are very stable. Virtually no change is observed in their photoluminescence spectra when they are stored under ambient temperature without any protection from light and air for more than two months. This is distinctly different from other dye molecules, which suffer from photobleaching when exposed to room illumination.

In one embodiment, the presently described TPE dyes have conjugated molecular structures which can be expressed by the following formula:

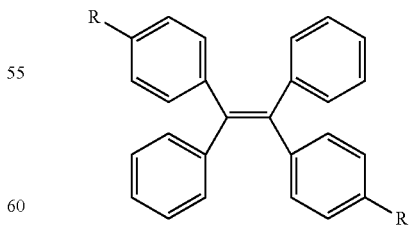

wherein R is selected from H, X, B(OH)$_2$, (X)$_n$COOR″, (X)$_n$COOH, (X)$_n$NH$_2$, (X)$_n$NHR″, (X)$_n$NR″$_2$, (X)$_n$N+R″$_3$Br$^-$, (X)$_n$OH, (X)$_n$SH, and (X)$_n$SO$_3^-$Na$^+$;

X is selected from (CH$_2$)$_n$, O(CH$_2$)$_n$, NH(CH$_2$)$_n$, N[(CH$_2$)$_n$]$_2$, and (OCH$_2$CH$_2$)—; and R" is selected from R, R', (CH$_2$)$_n$CH$_3$, CONH—X—, COO—X—, C$_6$H$_5$—R, —CH$_2$—C$_6$H$_5$, and C$_6$H$_5$; and
wherein n=0 to 20.

In an embodiment, R is selected from H, OH, COOH, and NH$_2$.

In a further embodiment, the present subject matter relates to water-dispersible, fluorescent, polymeric particles, wherein R is H and R' is selected from H, OH, COOH, and NH$_2$.

In yet a further embodiment, the present subject matter relates to water-dispersible, fluorescent, polymeric particles, wherein the water-soluble conjugated polyene compound is selected from the group consisting of
4,4'-(1,2-diphenylvinyl)di(phenylcarboxylic acid);
1,2-Bis(4-methoxyphenyl)-1,2-diphenylethylene; and
1,2-Bis(4-hydroxyphenyl)-1,2-diphenylethylene.

In another embodiment, the present subject matter relates to water-dispersible, fluorescent, polymeric particles, wherein the polymer is a homopolymer or a copolymer comprising one or more monomers selected from the group consisting of a vinylaromatic monomer, an ethylenic monomer, an alkanoic acid or ester or anhydride, and an ethylchic acid or ester, wherein one or more of the one or more monomers is optionally functionalized.

In a further embodiment, the present subject matter relates to water-dispersible, fluorescent, polymeric particles, comprising at least one functionalized monomer.

In another embodiment, the present subject matter relates to water-dispersible, fluorescent, polymeric particles, wherein the ethylenic monomer is selected from an ethylenic monomer of isoprene, 1,3-butadiene, vinylidene chloride, or acrylonitrile; the vinylaromatic monomer is selected from styrene, bromo-styrene, α-methylstyrene, ethylstyrene, vinyl-toluene, chlorostyrene, chloromethylstyrene, or vinyl-naphthalene; the alkanoic acid or ester or anhydride is selected from acrylic acid, methacrylic acid, an alkyl acrylate or an alkyl methacrylate in which the alkyl group possess from 3 to 10 carbon atoms; an hydroxyalkyl acrylate, acrylamide, ethylenic acid ester containing 4 or 5 carbon atoms; or a difunctional monomer selected from divinylbenzene or 2,2-dimethyl-1,3-propylene diacrylate.

In yet a further embodiment, the present subject matter relates to water-dispersible, fluorescent, polymeric particles, wherein the one or more monomers are selected from the group consisting of styrene, methyl methacrylate, ethyl acrylate, butyl acrylate, 2-hydroxyethyl methacrylate, acrylic acid, and acrylamide.

In an embodiment, the present subject matter relates to water-dispersible, fluorescent, polymeric particles, wherein the at least one functionalized monomer is selected from the group consisting of 2-hydroxyethyl methacrylate, 2-aminoethyl methacrylate, trimethylammoniumethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, and glutaraldehyde.

In a further embodiment, the present subject matter relates to water-dispersible, fluorescent, polymeric particles, wherein the one or more ethylenically unsaturated monomers comprise or consist of methyl methacrylate, butyl acrylate and 2-hydroxyethyl methacrylate.

In another embodiment, the present subject matter relates to water-dispersible, fluorescent, polymeric particles, wherein the methyl methacrylate, butyl acrylate, and 2-hydroxyethyl methacrylate are present in a ratio of from 4:5:1 to 5:4:1.

In yet another embodiment, the present subject matter relates to water-dispersible, fluorescent, polymeric particles, wherein the one or more ethylenically unsaturated monomers comprise or consist of methyl methacrylate, butyl acrylate, and acrylic acid and/or acrylamide.

In a further embodiment, the present subject matter relates to water-dispersible, fluorescent, polymeric particles, wherein the ratio of monomer to functionalized monomer is in the range of from about 3:1 to about 20:1.

In another embodiment, the present subject matter relates to water-dispersible, fluorescent, polymeric particles, wherein the ratio of monomer to functionalized monomer is in the range of from about 7:1 to about 11:1.

In yet another embodiment, the present subject matter relates to water-dispersible, fluorescent, polymeric particles, wherein the ratio of monomer to functionalized monomer is about 9:1.

In an embodiment, the present subject matter relates to water-dispersible, fluorescent, polymeric particles, having a glass transition temperature below room temperature.

In a further embodiment, the present subject matter relates to water-dispersible, fluorescent, polymeric particles, comprising microparticles.

In yet a further embodiment, the present subject matter relates to water-dispersible, fluorescent, polymeric particles, wherein the microparticles comprise a mean particle diameter in the range of from about 0.01 μm to about 5 μm.

In another embodiment, the present subject matter relates to water-dispersible, fluorescent, polymeric particles, wherein the microparticles comprise a mean particle diameter in the range of from about 10 nm to about 500 nm.

In an embodiment, the present subject matter relates to water-dispersible, fluorescent, polymeric particles, wherein greater than about 50% of the microparticles comprise a mean particle diameter in the range of from about 10 nm to about 500 nm.

In a further embodiment, the present subject matter relates to water-dispersible, fluorescent, polymeric particles, wherein greater than about 70% of the microparticles comprise a mean particle diameter in the range of from about 40 nm to about 400 nm.

In yet a further embodiment, the present subject matter relates to a method for making water-dispersible, fluorescent polymeric particles, comprising or consisting of: dissolving the water-soluble conjugated polyene compound in the one or more monomers to form a monomer solution; providing an aqueous composition comprising one or more members selected from the group consisting of a surfactant, a stabilizer and a cross-linking agent; adding the monomer solution dropwise to the aqueous composition to form a mixture; and polymerizing the mixture to produce the water-dispersible, fluorescent, polymeric particles.

In another embodiment, the present subject matter relates to the method for making water-dispersible, fluorescent, polymeric particles, wherein polymerizing comprises emulsion polymerization, microemulsion polymerization, suspension polymerization, or dispersion polymerization.

In another embodiment, the present subject matter relates to the method for making water-dispersible, fluorescent, polymeric particles, wherein the water-dispersible, fluorescent, polymeric particles are dispersed stably in the aqueous composition.

In a further embodiment, the present subject matter relates to the water-dispersible, fluorescent, polymeric particles, comprising a formulation selected from a bioprobe, a coating, a paint, a flexible free-standing film, a cosmetic, a fluidic tracer, or a marker. A fluidic tracer can be used to investigate capillary flow, to define neuronal cell connectivity and to study dye translocation through gap junctions, as well as to follow cell division, cell lysis or liposome fusion. A marker can be used as an indicator of a biologic state, for example, pH, polarity, and viscosity of the biological environment.

In another embodiment, the present subject matter relates to a flexible free-standing film comprising water-dispersible, fluorescent, polymeric particles.

The described TPE dyes possess unique characteristics, in that when molecularly dissolved in aqueous solutions, for example, water, emission is weak, whereas when aggregated in poor non-aqueous solvents or fabricated into thin films, emission is substantially increased.

The TPE dyes can be prepared according to the synthetic routes shown in Scheme 2 described herein. Bromo-substituted TPE (TPE-Br) can first be prepared by the McMurry coupling reaction of 4-bromobenzophenone using titanium (IV) chloride/zinc as catalyst. Then the bromo groups in TPE-Br can be transformed into other groups, e.g., carboxyl functionalities, by reaction with n-butyllithium followed by dry ice.

The polymers for encapsulation of the presently described TPE dyes are obtained by polymerization of ethylenically unsaturated monomers. Such a polymer can be a homopolymer or copolymer containing units derived from vinylaromatic or ethylenic monomers, or from alkanoic or ethyl chic acids or esters, which are optionally functionalized. This type of polymer is readily accessible to any person skilled in the art and it will be sufficient to mention only a few such polymers below, in a non-limiting manlier. Such polymers can comprise or consist of one or more of the following: ethylenic monomers of isoprene, 1,3-butadiene, vinylidene chloride or acrylonitrile type; vinylaromatic monomers such as styrene, bromo-styrene, alpha-methyl styrene, ethylstyrene, vinyltoluene, chlorostyrene or chloromethylstyrene, or vinylnaphthalene; alkanoic acids, esters or anhydrides such as acrylic acid, methacrylic acid, alkyl acrylates and alkyl methacrylates in which the alkyl group possesses 3 to 10 carbon atoms; hydroxyalkyl acrylates, acrylamides, ethylenic acid esters containing 4 or 5 carbon atoms; and difunctional monomers such as divinylbenzene or 2,2-dimethyl-1,3-propylene diacrylate and/or other copolymerizable monomers. Suitable monomers can comprise or consist of styrene, methyl methacrylate, ethyl acrylate, butyl acrylate, 2-hyroxyethyl methacrylate, acrylic acid, and acrylamide. These monomers are used alone or mixed with each other in any proportion, or alternatively mixed with another copolymerizable monomer selected from those described above. The functional groups can be incorporated onto the surface of the fluorescent particles by, for example, using a mixture of monomer and functionalized monomer during the polymerization. The functionalized monomer used can comprise or consist of one or more of the following: 2-hyroxyethyl methacrylate, 2-aminoethyl methacrylate, trimethylammonium-ethyl methacrylate methosulfate, dimethylaminoethyl methacrylate, methacrylic acid, undecylenic acid, methyl propene sulfonic acid, undecylenyl alcohol, oleyl amine, glycidyl methacrylate, acrolein, glutaraldehyde and the like.

The polymer particles may be formed by the use of appropriate polymerization techniques such as conventional emulsion polymerization, microemulsion polymerization, suspension polymerization or other means of polymerization with or without a crosslinking agent such as divinyl benzene or the like. These techniques and agents are well known to those of ordinary skill in the art to which the present subject matter pertains. The skilled artisan can readily select and employ such techniques and agents without undue experimentation.

The described TPE dyes are dissolved in the monomers prior to polymerization, then incorporated into the polymer matrices through the particle formation process. TPE dyes are organic in nature, which makes them readily soluble in the monomers used. TPE dyes can also withstand common polymerization conditions. Further, TPE dyes, for example, having various peripheral substituent groups on the aromatic rings, have an affinity towards the interior of the particles. That is, they are chemically compatible with the polymers constituting the latex particles. This compatibility is important during the formation of the corresponding fluorescent polymer particles.

The fluorescent polymer particles prepared according to the present subject matter are stable aqueous dispersions whose size is as described herein and is generally between 0.01 micron and 5 microns, for example, less than 1 micron in diameter, regardless of the polymer composition. The aqueous dispersions have a content of polymer particles from 0.1% to 50% by weight relative to the total weight of the dispersion, for example, from 10% to 30% by weight.

The special characteristics of these fluorescent particles can be varied by incorporating different TPE dyes. The fluorescent intensity of these polymer particles can be adjusted by varying the load concentration of the TPE dyes. The maximum TPE dye content in the polymer particles depends on the nature of the fluorochromes, the encapsulation technique used, the nature of the polymer constituting the particles and the size of these particles. Load concentration can depend on the functionalization density (the number of functional groups per particle) and the interaction (covalent or non-covalent) between the dye and the particles. The functionalization density depends on the size of the particles and the nature of the polymer (the polymer chain bearing functional groups), while the interaction depends on the nature of the fluorophores, the nature of the polymer, and the encapsulation technique used. The nature of the fluorophores depends on the kinds of functional groups they are facilitated. The maximum TPE dye content in the polymer particles may thus vary considerably and reach values of several million fluorochrome molecules per latex particle. The dye content of the presently described fluorescent polymer particles can be much higher in comparison to the conventional particles, owing to the absence of self-quenching of the TPE dyes. On the contrary, the fluorescence of the present TPE dyes can be remarkably enhanced at high concentrations, resulting from the AIE effect of TPE dyes.

By using the processes of the present subject matter, fluorescent polymer particles can be optimized in terms of size, polymer composition, surface chemistry, and/or spectral characteristics. The fluorescent polymer particles according to the present subject matter may be used in all the conventional applications of polymer particles which are well known to those skilled in the art (paint, coating, cosmetic, marker, fluidic tracer, etc.). Dye fluorescent polymer particles according to the present subject matter are more particularly intended for direct or indirect involvement in biological analyses.

Use of the Conjugated Polyenes

While biosensing processes such as molecular beacons require non-trivial effort to covalently label or mark biomolecules, presently described herein is a label-free DNA assay system using a simple dye with AIE characteristics as the fluorescent bioprobe. Telomerase is an enzyme that catalyzes the lengthening of telomeres which in turn enables cells to proliferate. Telomerase is active in 90% of cancer cells and activity thereof is needed for indefinite proliferation. G-quadruplex, a secondary structure of DNA, has been identified in human telomere DNA and such structure is believed to inhibit the activity of telomerase, thereby affects gene expression and controls cancel cell proliferation. TTAPE is non-emissive in solution but becomes highly emissive when aggregated. When TTAPE is bound to DNA via electrostatic attraction, its emission is turned on. This process can be reversible. When a competitive cation is added to the DNA solution, TTAPE is released and its emission is turned off. TTAPE works as a sensitive post-staining agent for electrophoresis gel visualization of DNA. The dye is highly affinitive to a secondary structure of G-quadruplex. The bathochromic shift involved in the folding process allows spectral discrimination of the G-quadruplex from other DNA structures. The strong affinity of TTAPE dye to G-quadruplex structure is associated with a geometric fit aided by the electrostatic attraction. The distinct AIE feature of TTAPE enables real-time monitoring of folding process of G1 in the absence of any pre-attached fluorogenic labels on the DNA strand, TTAPE can be used as a $K^+$ biosensor because its specificity to $K^+$-induced and stabilized quadruplex structure. On the other hand, TPE-SO3, the counterpart of TTAPE, can serve as a probe for protein detection in aqueous media. TPE-SO3 shows higher affinity to human serum albumin (HSA), the main protein in human urine. A higher level of protein loss in the urine, called proteinuria, may mean there is a kidney disease. Thus, TPE-SO3 can be potential used for urinary protein detection.

Figure 23:
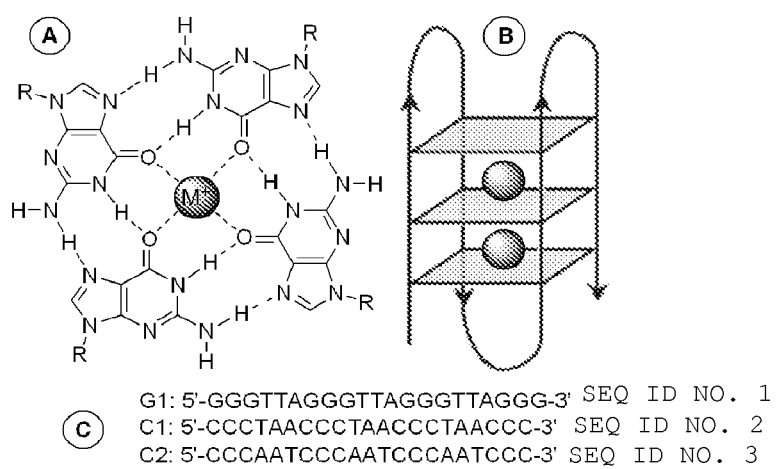
FIG. 23A shows the structure of a G-quartet showing hydrogen bonds between G units and interaction with a cation (M).
FIG. 23B shows a G-quadruplex folded by a human telomeric DNA strand.
FIG. 23C shows the sequences of G1 (SEQ ID 1) and its complementary (C1) (SEQ ID 2) and non-complementary (C2) (SEQ ID 3) strands.
Figure 24:
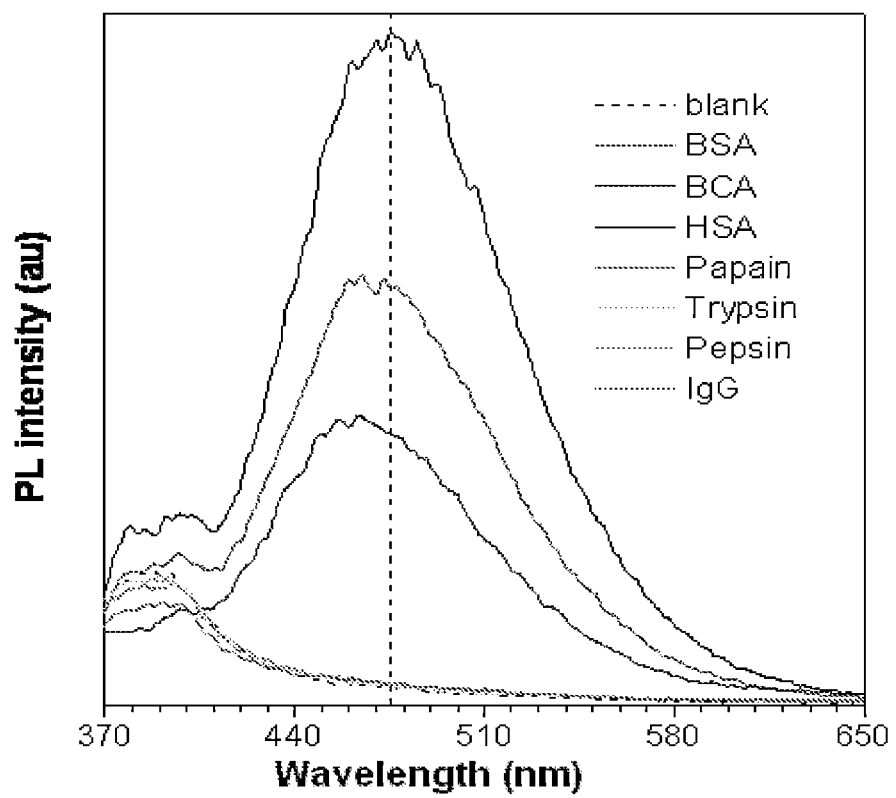
FIG. 24 shows the FL spectrum of TPE-SO3 with addition of different proteins in phosphate buffer saline (pH=7.0). [TPE-SO3]=5 µM. Excitation wavelength: 350 nm.

A single-stranded (ss) DNA with guanine (G)-rich repeat sequences can assume a square planar arrangement of the G units stabilized by Hoogsteen hydrogen bonds (FIG. 23A). An array of these G-quartets can stack on top of each other to form a secondary structure named G-quadruplex (FIG. 23B). This structure is further stabilized by the monovalent cations (e.g., $K^+$) located in the centers of G-tetrads. It is predicted that thousands of DNA sequences sprinkled over the human genome are potential quadruplex forming sites, making the tetrad structure one of the most prevalent regulatory motifs in the body. Much effort has been devoted to the studies on the biology of genomic and telomeric G-quadruplexes. It has been found, for example, that quadruplex formation can affect gene expression and inhibit telomerase activity in cancer cells. It has been envisioned that quadruplex-targeting drugs may enable artificial regulation of gene expression and control of cancel cell proliferation. Clearly, efficient formation and stabilization of G-quadruplex structures is a prerequisite to the rational design of quartet specific medication and telomere-aimed anticancer therapy.

A variety of techniques, including nuclear magnetic resonance (NMR), mass spectroscopy, circular dichroism (CD), UV melting profile analysis, poly(acrylamide) gel electrophoresis (PAGE), and surface plasmon resonance, have been used to study G-quadruplex formation. These methods, however, require large quantities of DNA samples because of their poor sensitivities. Fluorescence (FL)-based probe system, on the other hand, offers superb sensitivity, low background noise, and wide dynamic working range. A few FL sensors based on "molecular beacons" and fluorescent resonance energy transfer processes have been developed, which prove to be powerful in studying conformational transitions of quadruplexes. These processes, however, require pre-labeling of oligonucleotides by fuorophores or dual tagging on a single DNA strand by chemical reactions. Precise synthesis of a DNA-dye conjugate is a nontrivial job, and product isolation and purification is often painstaking. In addition, structural changes caused by the chemical modifications may affect conformations of the G-quadruplexes and interfere with their folding kinetics.

Biological processes are undertaking in physiological fluids and accordingly biological assays are commonly conducted in aqueous buffer solutions. The working units in the FL probes, however, are hydrophobic aromatic rings and other π-conjugated chromophores. The FL dyes tend to aggregate when absorbed onto strand surfaces or after entering hydrophobic pockets of folded strands, due to the incompatibility of tile dyes with the hydrophilic media and the π-π stacking interaction between their π-conjugated chromophores. The aggregate formation normally quenches light emissions of the dyes, which poses a thorny obstacle to the development of efficient FL probes. Various approaches have been taken in an effort to impede aggregate formation, such as using long spacers to separate chromophoric units. Obviously, it is nicer and more desirable to have sensitive and selective G-quadruplex probes that do not require pre-modifications of tile DNA strands and that do not suffer from aggregation-caused emission quenching.

A series of non-emissive dyes, such as siloles, butadienes, pyrans, fulvenes, biaryls and TPEs, are induced to luminesce by aggregate formation. The AIE dyes are not only excellent emitters for the fabrication of efficient light-emitting diodes but also sensitive probes for the detection of biomolecules. Among them, the TPE-based dyes have received much attention because of their *facile* synthesis, ready functionalization, good photostability, and high FL quantum yields ($\phi_F$).

TTAPE is potentially useful as a G-quadruplex probe, using an oligonucleotide of 5'-GGGTTAGGG-TTAGGGT-TAGGG-3' or $[dG_3(T_2AG_3)_3]$ (G1) as a model DNA that mimics the $T_2AG_3$ repeat sequences in the single-stranded region of a human telomere (FIG. 23C). Other examples of G-rich repeal sequences which are capable of forming G-quadruplex structures are disclosed in Hong et al., Chem. Eur. 1. 2010, 16, 1232-1245, which is incorporated herein by reference in its entirety. In an aqueous buffer, the non-emissive TTAPE dye becomes highly luminescent upon its binding to G1 via electrostatic attraction, thanks to its multiple positive charges. When G1 folds into G-quadruplex structure, emission peak ($\lambda_{em}$) of the AIE dye undergoes a noticeable bathochromic shift, allowing easy differentiation of the G-quadruplex from other DNA structures. The folding processes of G1 can be followed by the time-dependent FL measurement of the AIE dye.

In another embodiment, the present subject matter relates to a method of detecting G-quadruplex formation, DNA, or protein and protein levels wherein the cation added to the biological sample and polyene mixture is selected from the group consisting of $K^+$, $Li^+$, $Na^+$, $NH_4^+$, $Mg^{2+}$, and $Ca^{2+}$. In a particular embodiment, the cation added to the biological sample and polyene mixture is K. In another particular embodiment, the water-soluble conjugated polyene compound is a TPE, or other compound, as described herein. In this regard, by way of non-limiting example the TPE is selected from the group consisting of TPE-SO3 and TTAPE. In another embodiment, the TPE is TTAPE.

In an embodiment, the present subject matter relates to a method of diagnosing a kidney disorder comprising contacting a biological sample with a water-soluble conjugated polyene compound and detecting luminescence. In a particular embodiment, the biological sample is selected from the group consisting of a tissue sample, cell sample, blood, saliva, spinal fluid, lymph fluid, vaginal fluid, seminal fluid, and urine. In another particular embodiment, the biological sample is urine. In a further embodiment, the water-soluble conjugated polyene compound is a TPE, or other compound, as described herein. In this regard, by way of non-limiting example the TPE is selected from the group consisting of TPE-SO3 and TTAPE. In another embodiment, the TPE is TPE-SO3.

In an embodiment, the present subject matter relates to a method of screening a potential anti-cancer drug for activity including contacting said anti-cancer drug with a biological sample having a G-rich DNA sequence that is capable of forming a particular G-quadruplex conformer to form a reaction mixture, adding a water-soluble conjugated polyene compound to the reaction mixture of said anti-cancer drug and said biological sample having the G-rich DNA, and detecting luminescence. In another embodiment, the water soluble conjugated polyene compound is added to the biological sample before the anti-cancer drug is mixed with the biological sample to form the reaction mixture.

In another embodiment, the present subject matter relates to a method of screening a potential anti-cancer drug for activity, further comprising comparing the detected luminescence from said water-soluble conjugated polyene compound in said reaction mixture of said biological sample and said anti-cancer drug with a luminescence detected from said water-soluble conjugated polyene compound in said biological sample having the G-rich DNA sequence alone, wherein a bathochromic shift is observed in the emission spectrum of said reaction mixture having said anti-cancer drug and said biological sample to identify the G-quadruplex-inducing ability of the anti-cancer drug.

In a similar embodiment, luminescence is compared with that detected in a biological sample having the G-rich DNA sequence and $K^+$ ions alone, wherein the luminescence pattern of said G-rich DNA in the presence of said anti-cancer drug or $K^+$ ions are similar. In yet another embodiment, the water-soluble conjugated polyene compound is TTAPE.

In an embodiment, the present subject matter relates to an anti-cancer pharmaceutical composition comprises a water-soluble conjugated polyene compound. In another embodiment, said compound is conjugated with a G-quadruplex targeting motif. In a further embodiment, said compound is a chemically modified TPE. In another embodiment, said compound is a chemically modified TTAPE. In yet another embodiment, one or more of the triethylamine groups of the TTAPE are substituted with other positively charged groups including, piperidine, pyrazole, piperazine and imidazole. The G-quadruplex motif is specific to a DNA sequence which is capable of forming a particular G-quadruplex conformer in the presence of said motif. In one embodiment, the G-quadruplex motif in the anti-cancer pharmaceutical composition is isolated from an anti-cancer drug, which is screened by the present. In another embodiment, the G-quadruplex motif is any of the water-soluble conjugated polyene compounds disclosed herein which is capable of inducing the formation of the particular G-quadruplex conformer.

At certain conditions such as at room temperature, TTAPE also acts as a lead compound in an anti-cancer pharmaceutical composition. In one embodiment, the TTAPE induces the formation of a particular G-quadruplex when contacting with a biological sample having a DNA sequence that is capable of forming a particular G-quadruplex conformer, wherein said contacting is carried out at about 25° C. or more.

The present subject matter provides a highly water-soluble ME-active molecule capable of discriminating native and fibrillar forms of amyloid proteins and method of use thereof as an external tool for monitoring amyloid fibrillation.

In an embodiment, the present subject matter relates to a method of monitoring fibrillation of amyloid protein comprising contacting a biological sample with a water-soluble conjugated polyene compound and detecting luminescence. In one embodiment, the water-soluble conjugated polyene compound is TPE-SO3. In a further embodiment, the contacting is carried out at a pH value equal to or lower than pH 5.6.

In another embodiment, the present subject matter relates to a method of monitoring fibrillation of amyloid protein, wherein the biological sample contains amyloid protein which is selected from the group consisting of insulin, amyloid beta-peptide, tau, alpha-Synuclein, PrP and polyglutamine-containing proteins or peptides, such as human islet amyloid polypeptide (hIAPP). In yet another embodiment, the amyloid protein is insulin.

The present subject matter further relates to a method of using the water-soluble conjugated polyene compound in retarding amyloid fibrillation.

In one embodiment, the present subject matter relates to a method of retarding amyloid fibrillation for storing and delivery of amyloid protein comprises storing the amyloid protein with a water-soluble conjugated polyene. In an embodiment, the amyloid protein is stored with the water-soluble conjugated polyene under a pH of lower or equal to pH 5.6. In another embodiment, the amyloid protein is selected from the group consisting of insulin, amyloid betapeptide, tau, alpha-Synuclein, PrP and polyglutamine-containing proteins or peptides, such as hIAPP. In a further embodiment, the amyloid protein is insulin. In yet another embodiment, the insulin stored is for diabetes treatment.

In another embodiment, the present subject matter relates to a method of retarding amyloid fibrillation for storing and delivery of amyloid protein, wherein the water-soluble conjugated polyene is TPE-SO3.

Dye Synthesis

Figure 49:
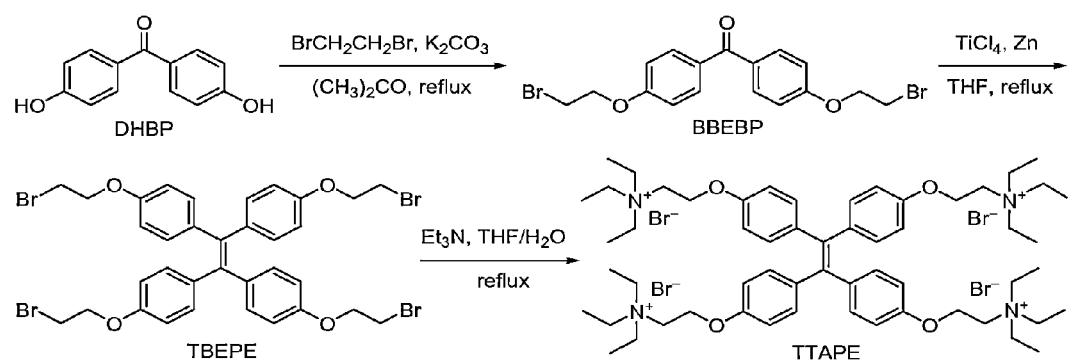
FIG. 49 is the Synthesis of 1,1,2,2-tetrakis[4-(2-triethylammonioethoxy)phenyl]ethene tetrabromide (TTAPE).
Figure 50:
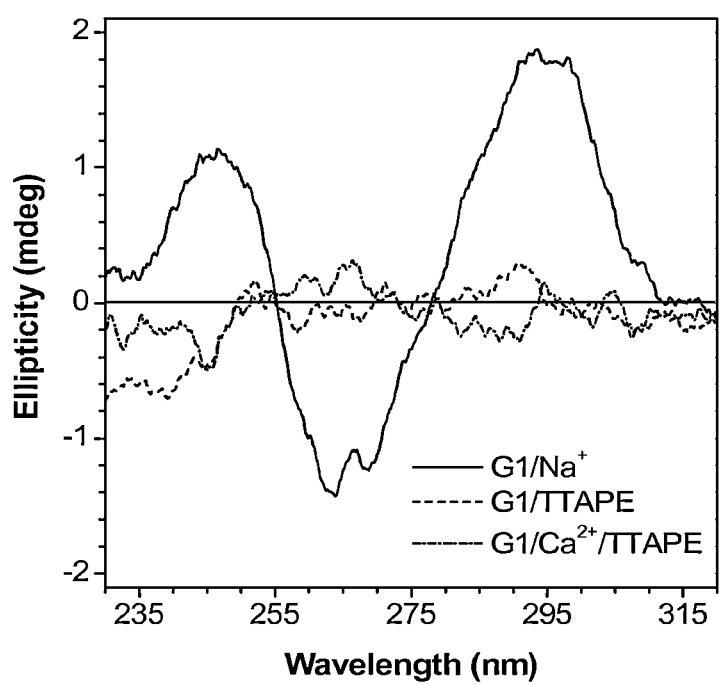
FIG. 50 shows the CD spectra of G1 in a Tris-HCl buffer in the presence or absence of a metal ion and/or TTAPE at 20° C. [G1]=9 μM, [ion]=0.5 M, [TTAPE]=4.5 μM.
Figure 51:
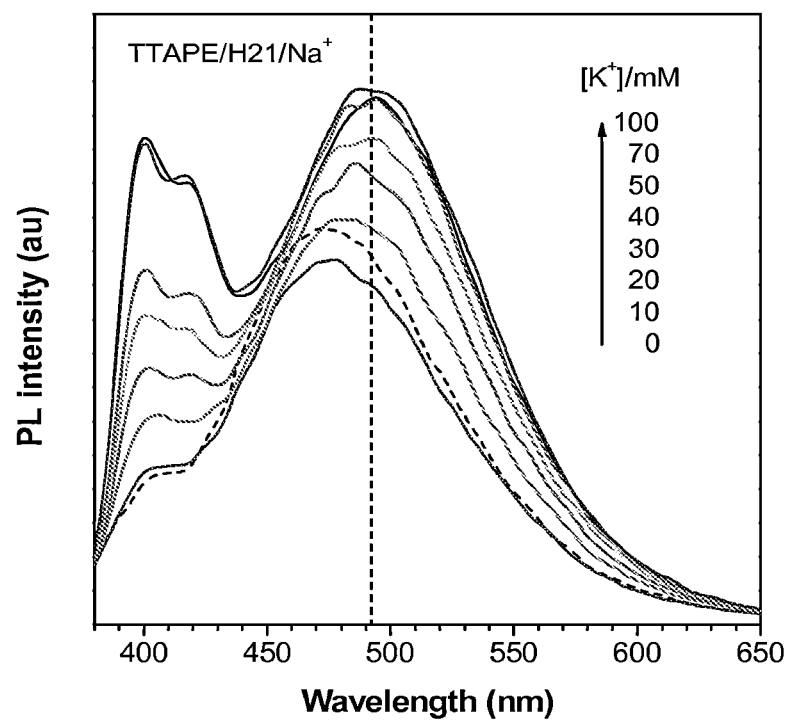
FIG. 51 shows the emission spectra of TTAPE/H21 in Na$^+$ solution (100 mM) upon K$^+$ titration in buffer solutions (pH=7.5). The final concentration of Na$^+$ is kept at 100 mM. [TTAPE]=4.5 [1-121]=4.5 μM. Excitation wavelength: 350 nm.
Figure 52:
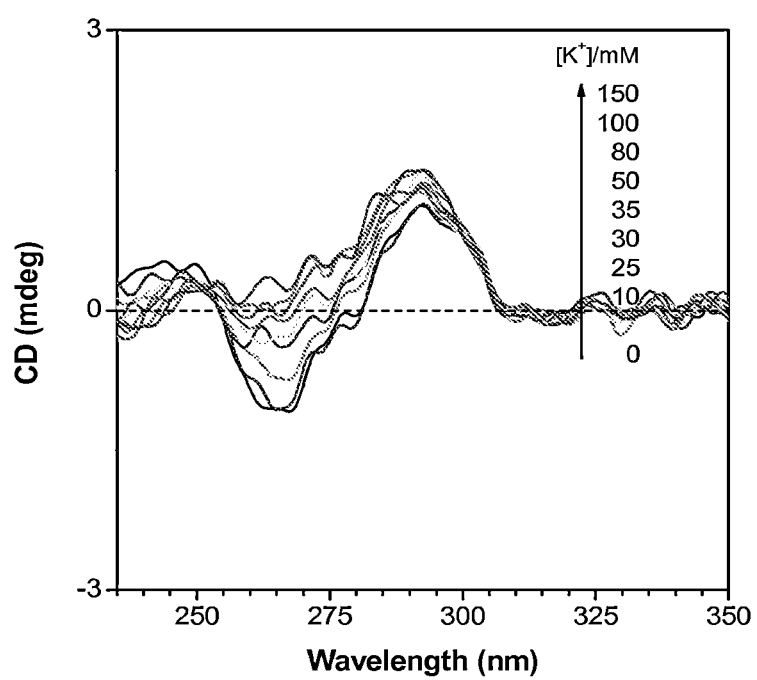
FIG. 52 shows the CD spectra of H21 (5 μM) in Na$^+$ solution (100 mM) upon K$^+$ titration in 5 mM Tris-HCl (pH=7.50).
Figure 53:
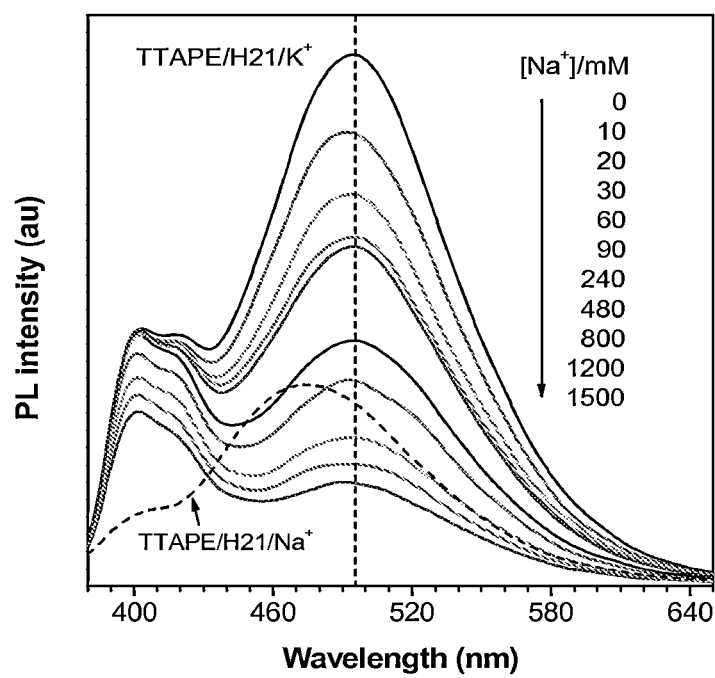
FIG. 53 shows the emission spectra of buffer solutions (pH=7.5) of TTAPE/G1 containing K$^+$ and Na$^+$ ions. The final concentration of K$^+$ is kept at 100 mM. [TTAPE]=4.5 μM, [DNA]=4.5 μM. Excitation wavelength: 350 nm.
Figure 54:
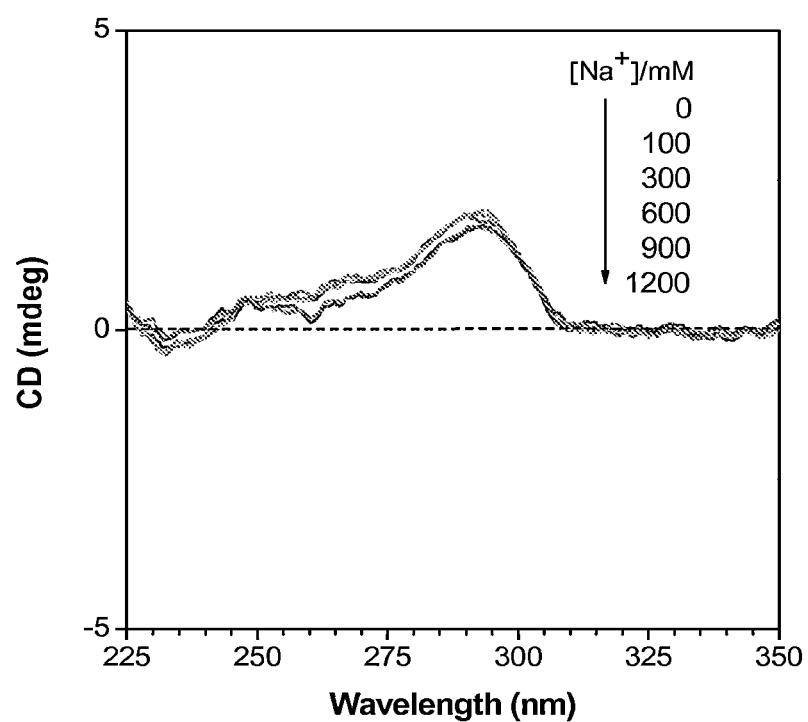
FIG. 54 shows the CD spectra of buffer solutions (pH=7.50) of TTAPE/G1 containing K$^+$/Na$^+$ ions. The final concentration of K$^+$ is kept at 100 mM. [TTAPE]=4.5 μM, [DNA]=9 μM. Excitation wavelength: 350 nm.
Figure 55:
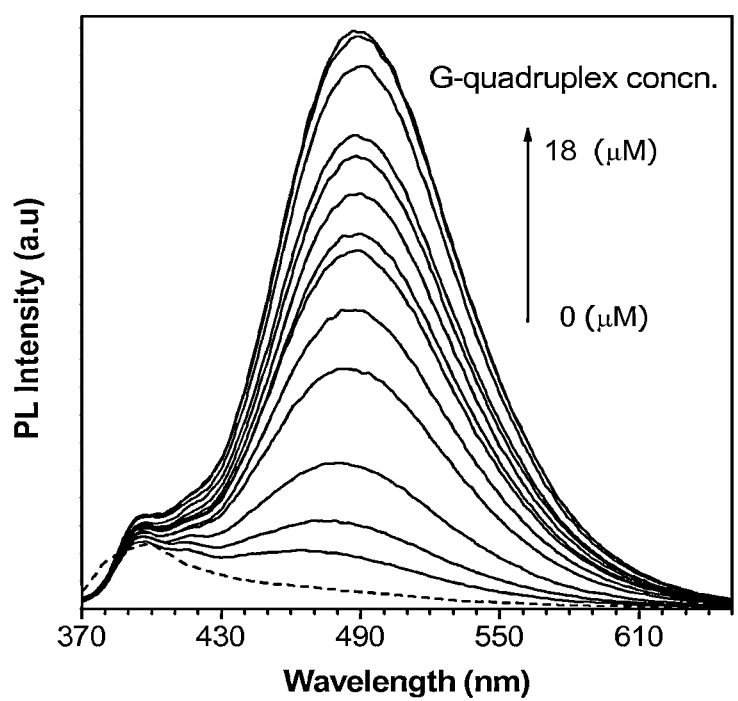
FIG. 55 shows the PL spectra of TTAPE (4.5 μM) in the presence of different concentrations of G-quadruplex DNA (G1 in 150 mM K$^+$) in 5 mM Tris-HCl buffer (pH=7.5). Excitation wavelength: 350 nm.
Figure 56:
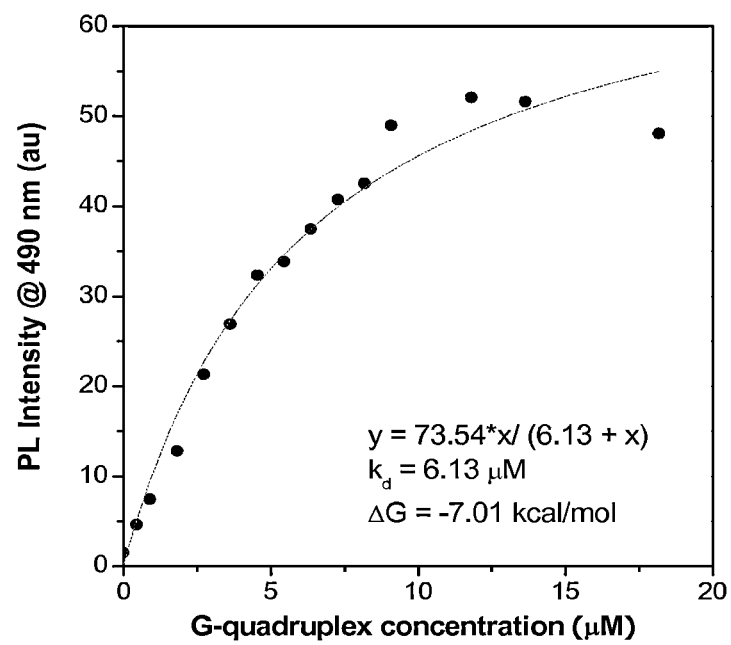
FIG. 56 shows the fluorometric titration of G-quadruplex DNA (plot of the fluorescence intensity at 470 nm) to the solution with TTAPE (4.5 μM) in 5 mM Tris-HCl buffer (pH=7.5) and its fitting curve to OneSiteBind mode. Excitation wavelength: 350 μm.
Figure 57:
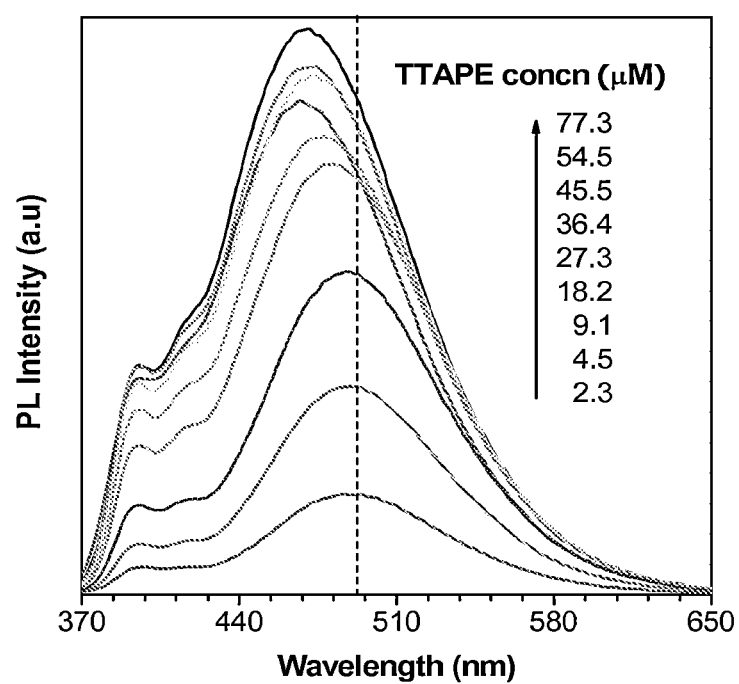
FIG. 57 shows the PL spectra of 9 μM of G-quadruplex DNA (G1 in 150 mM K$^+$) in the presence of different concentrations of TTAPE in 5 mM Tris-HCl buffer (pH=7.5). Excitation wavelength: 350 nm.
Figure 58:
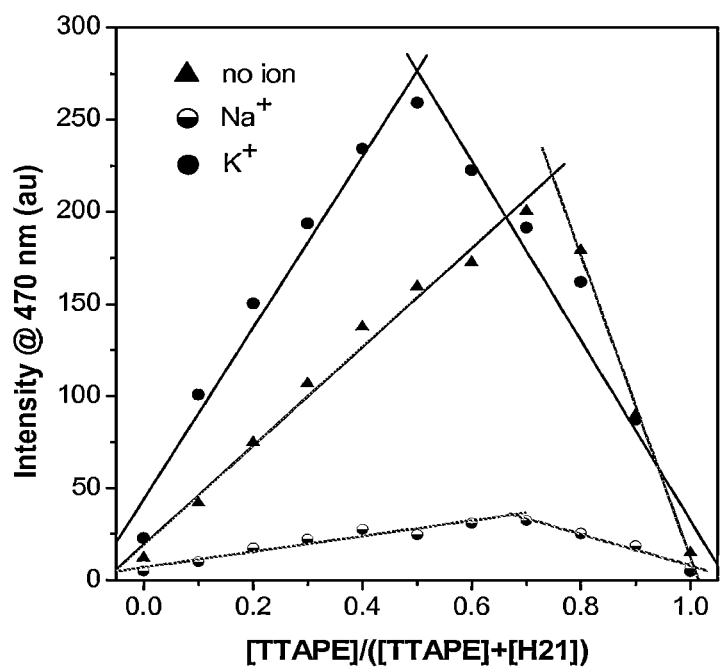
FIG. 58 shows the job plots for the binding of TTAPE to H21 in Tris-HCl (blue), K-Tris (black), or Na-Tris (red) buffer solution (pH=7.50). The sum of TTAPE and DNA concentrations was kept at 10 μM. Fluorescent intensities for the bound TTAPE at 470 nm are normalized to the maximum increase in each case. The y-axis represents the difference in PL intensity for mole fraction of ligand ($\chi_L$) in DNA. Intercept mole fraction values were determined from least-squares fits to the linear data portions, giving $y_{jmi}$ values of 0.50 (1:1 stoichiometry) for H21 in K-Tris, 0.67 (3:1) for H21 in Na-Tris, and 0.75 (4:1) for H21 in Tris-HCl, respectively.
Figure 59:
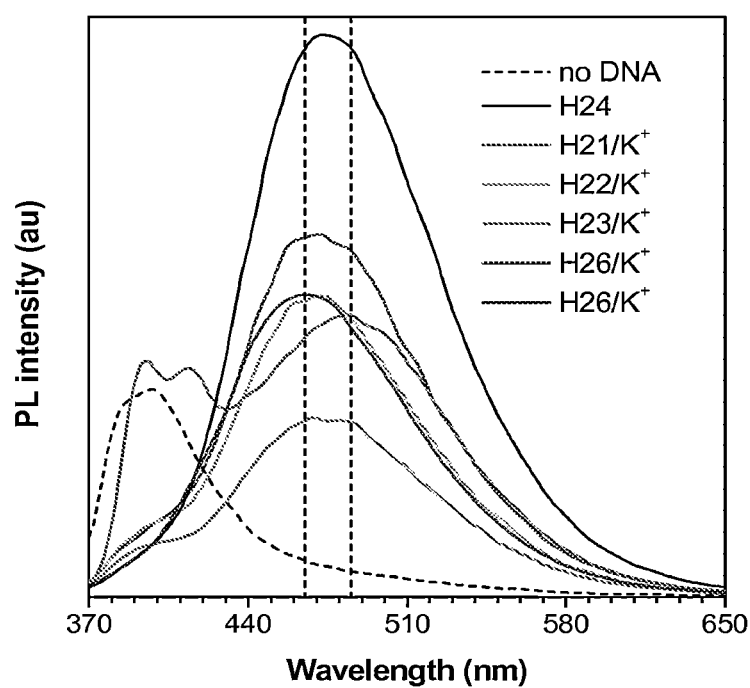
FIG. 59 shows the emission spectra of buffer solutions (pH=7.5) of TTAPE/DNA containing $K^+$. [TTAPE]=4.5 μM, [DNA]=4.5 μM. Excitation wavelength: 350 nm.
Figure 60A:
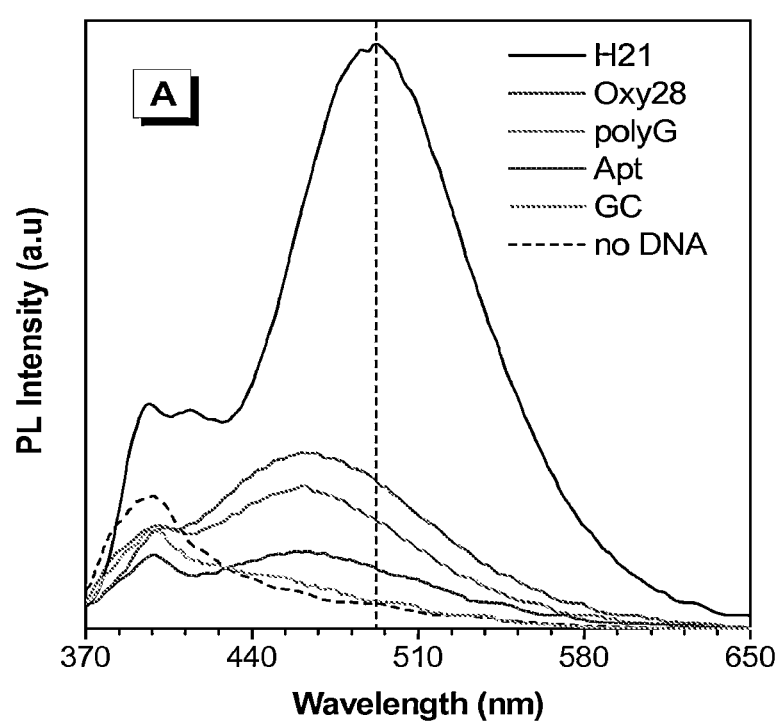
FIG. 60A shows the emission spectra of TTAPE with different G-rich DNA sequences in the presence of $K^+$. [TTAPE]=4.5 μM; [DNA]=9 [$K^+$]=0.5 M. Excitation wavelength: 350 nm.
Figure 60B:
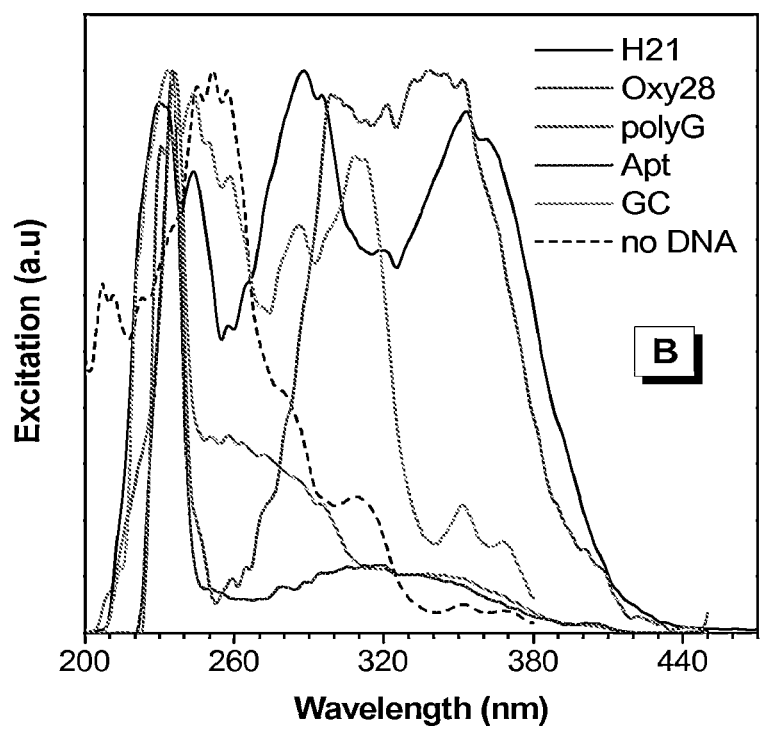
FIG. 60B shows the excitation spectra of TTAPE with different G-rich DNA sequences in the presence of $K^+$. [TTAPE]=4.5 μM; [DNA]=9 μM; [$K^+$]=0.5 M. Excitation wavelength: 350 nm.
Figure 60C:
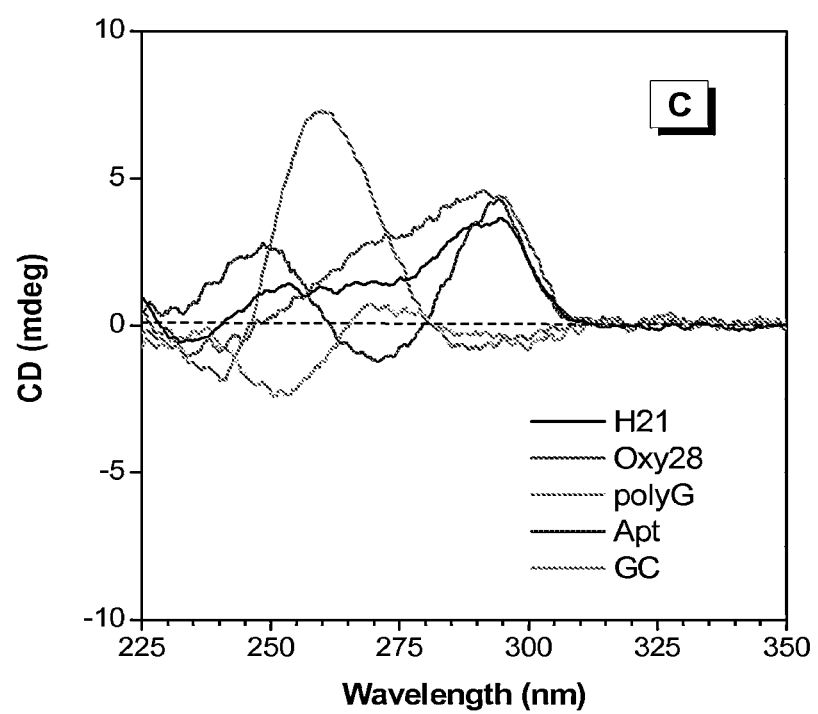
FIG. 60C shows the CD spectra of TTAPE with different G-rich DNA sequences in the presence of $K^+$. [TTAPE]=4.5 μM; [DNA]=9 μM; [$K^+$]=0.5 M. Excitation wavelength: 350 nm.
Figure 61:
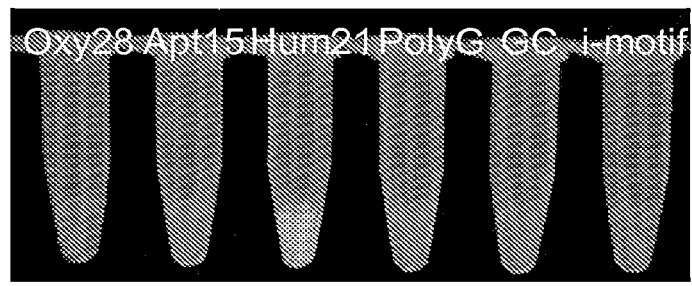
FIG. 61 is a photograph of $K^+$-Tris-HCl buffer solution of TTAPE in the presence of different DNAs under the illumination of a handheld UV lamp. [TTAPE]=4.5 μM; [DNA]=4.5 μM, [$K^+$]=0.5 M.
Figure 63:
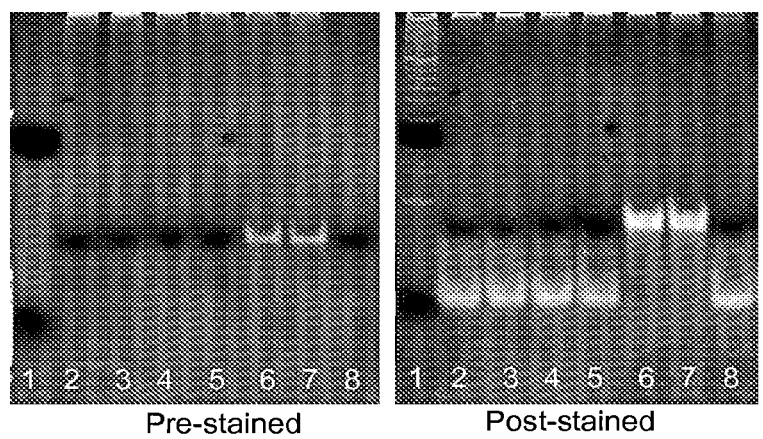
FIG. 63 shows the prestained poly(acrylamide) gels of (1) DNA ladder on the left side; (2) H21/TTAPE; (3) H21/Na$^+$/TTAPE; (4) H21/K$^+$/TTAPE; (5) H21/Ca$^{2+}$/TTAPE; (6) H26/TTAPE; (7) H26/K$^+$/TTAPE; (8) H21. On the right side the figure shows the post-stained gels with either 10 μM TTAPE for 10 min.
Figure 64:
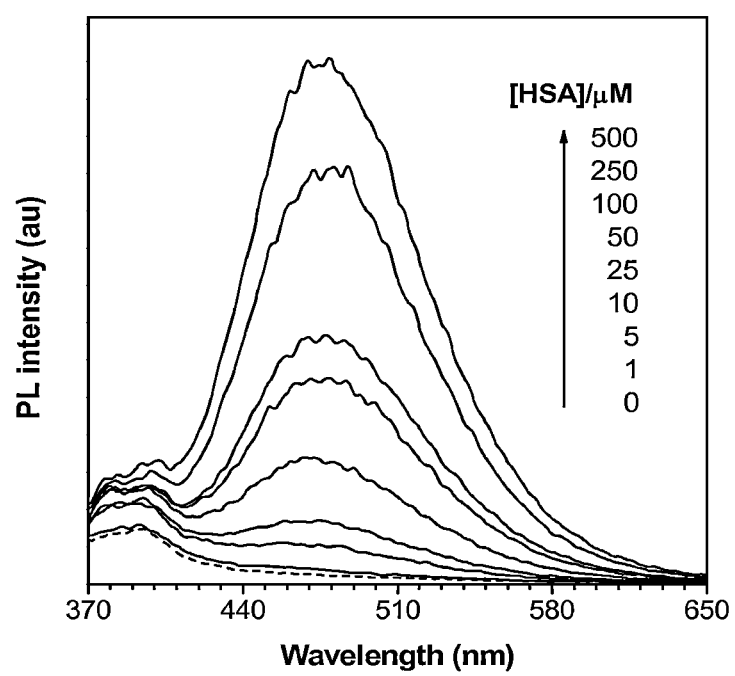
FIG. 64 shows the FL spectrum of SATPE with addition of HSA in artificial urine solution (pH=6.0). [SATPE]=5 μM. Excitation wavelength: 350 nm.
Figure 65:
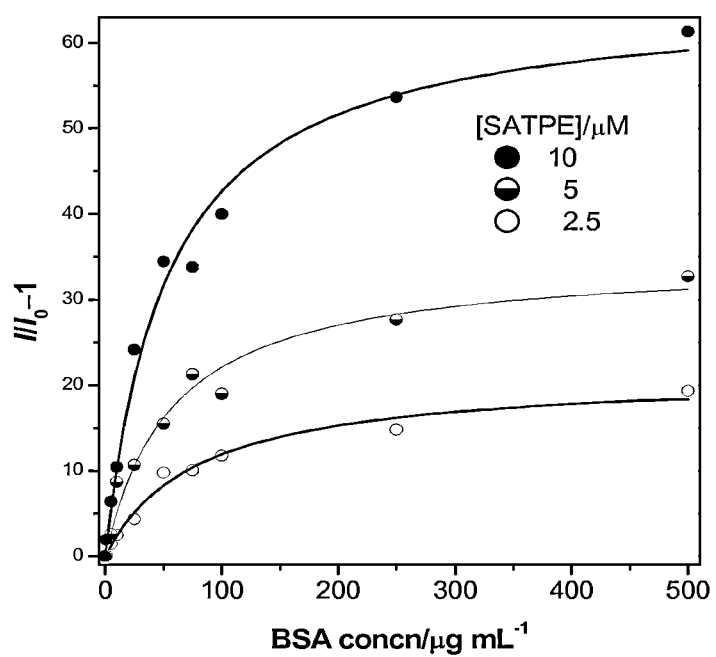
FIG. 65 shows the binding isotherm of BSA to different concentrations of SATPE in artificial urine (plot of FL intensity at 470 nm). Excitation wavelength: 350 nm.

TTAPE was prepared by the synthetic route shown in FIG. 49. Dehydrobromination of 4,4'-dihydroxybenzophenone (DHBP) with 1,2-dibromoethane in the presence of potassium carbonate yields 4,4'-bis(2-bromoethoxy)-benzophenone (BBEBP). McMurry coupling of BBEBP produces 1,1,2,2-tetrakis[4-(2-bromoethoxy}phenyl]ethene (TBEPE), which is quaternized by triethylamine to furnish a salt of TTAPE. The reaction intermediates and final product were fully characterized by spectroscopic methods, from which satisfactory analysis data were obtained. TBEPE is completely soluble in chloroform, acetonitrile (AN) and THF, slightly soluble in ethanol and methanol, but totally insoluble in water. TTAPE, on the other hand, is soluble in water as well as all the organic solvents mentioned above, due to the amphiphilic nature of the ammonium salt.

AIE Effect

Figure 31:
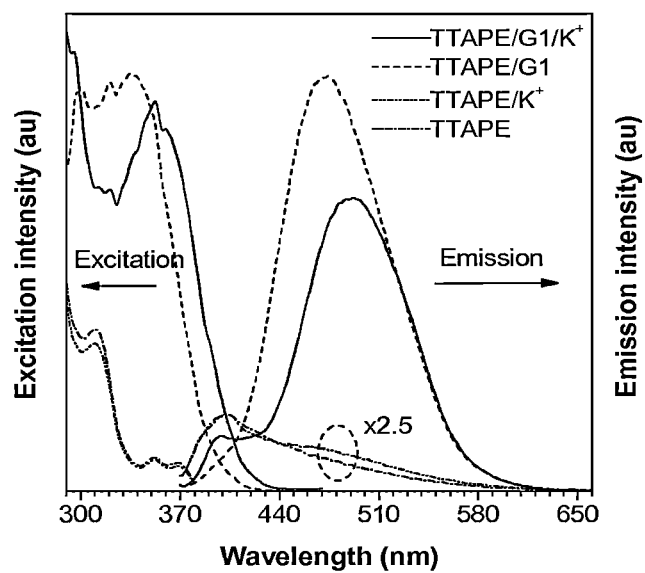
FIG. 31 shows the excitation and emission spectra of TTAPE solutions in a Tris-HCl buffer in the presence or absence of K$^+$ ion and/or G1 [TTAPE]=4.5 μM, [G1]=9 μM, [K$^+$]=0.5 M; $\lambda_{ex}$=350 nm.

When dissolved in its good solvents at molecular level, TBEPE is virtually nonluminescent. Addition of poor solvents into its solutions dramatically boosts its emission efficiency. A dilute AN solution of TBEPE, for example, emits a faint UV light (FIG. 31). When a large amount of water (99 vol %) is added, the resultant mixture shows an intense FL spectrum peaked at 479 nm. Since water is a nonsolvent of TBEPE, its molecules must have aggregated in the aqueous mixture. TBEPE is therefore induced to emit by aggregate formation; in other words, it is AIE active. The mixture is transparent and homogeneous, suggesting that the dye aggregates suspended in the mixture are nanosized. In the dilute AN solution, the phenyl rings of TBEPE can rotate against its central olefinic double bond, which nonradiatively deactivates the excited state and renders the dye non-emissive. The intramolecular rotations are largely restricted in the nanoaggregates in the An/water mixture. This blocks the non-radiative decay channel of the dye and makes it highly luminescent.

Figure 26A:
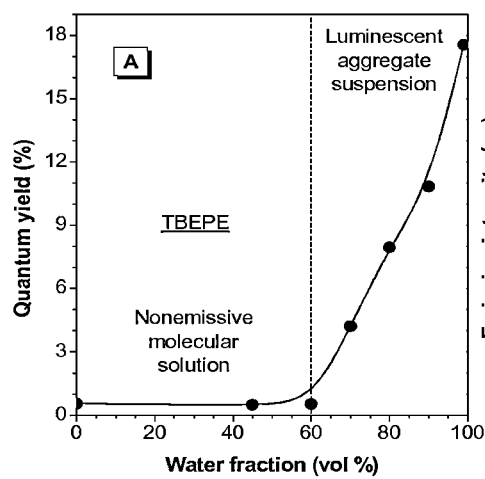
FIG. 26A is a plot of quantum yield of TBEPE vs. composition of AN/water mixture.

Changes in the $\phi_F$ values of TBEPE in the AN/water mixtures with different water contents further confirm its AIE nature. In the AN solution, TBEPE exhibits a negligibly small $\phi_F$ value (~0.5%), which remains almost unchanged till up to ~60% of water is added (FIG. 26A). Afterward the $\phi_F$ value starts to increase swiftly. In the AN/water mixtures with lower water fractions, TBEPE is genuinely dissolved, while in the aqueous mixtures with higher water fractions (>60%), the dye molecules cluster together due to the deterioration in the solvating power of the mixture. When the water fraction is increased to 99 vol %, the $a\phi_F$ value is increased to ~18%, which is ~35-fold higher than that in the pure AN solvent. The absolute $\phi_F$ values of the aggregates should be much higher than the relative ones given in FIG. 26A, if the light scattering caused by the Mie effect of the nanoaggregates is taken into consideration.

Figure 26B:
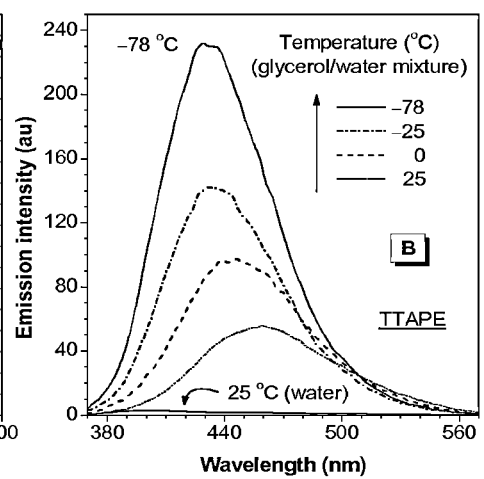
FIG. 26B shows the FL spectra of TTAPE in a glycerol/water mixture (99:1 by volume) at different temperatures; the spectrum of its water solution at 25° C. is shown for comparison. [dye]=5 µM; ex=350 nm.

TTAPE is completely soluble in water. Owing to its amphiphilic nature associated with its quaternary tetraalkylammonium moieties, addition of AN, THF or methanol into its water solution fails to make the dye molecules aggregate. As a result, the emissions from TTAPE in all these mixtures are as weak as that in the pure water solution. However, increasing viscosity and decreasing temperature of the solution of TTAPE can activate its FL process. As can be seen from FIG. 26B, TTAPE in a viscous glycerol/water mixture at 25° C. emits an intense blue light of 464 nm. When the viscous mixture is cooled to ~78 C., its emission intensity is further increased. At the cryogenic temperature, solvent viscosity is increased and molecular motions are further hampered. TTAPE can thus be induced to emit by restricting its intramolecular rotations, which is the exact cause for the AIE effect of its TBEPE cousin (vide supra).

DNA Probing

Figure 27A:
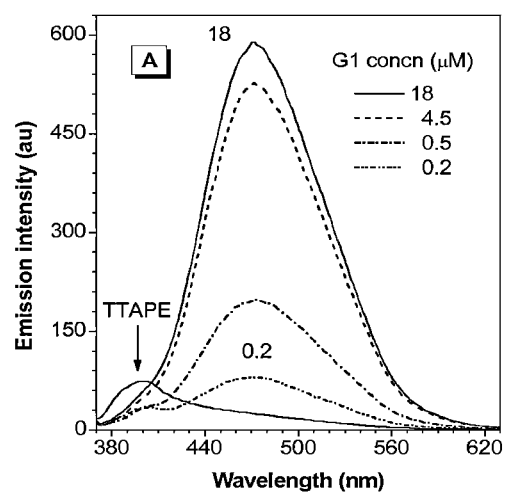
FIG. 27A shows the fluorimetric titration of G1 to an aqueous solution of TTAPE (4.5 µM) in 5 mM Tris-HCl buffer (pH=7.50).
Figure 27B:
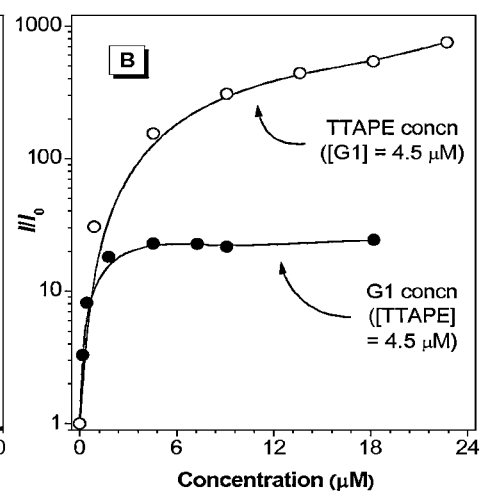
FIG. 27B shows the change in emission intensity (I) at 470 nm with variation in concentration of G1 or TTAPE; $\lambda_{ex}$=350 nm.
Figure 28:
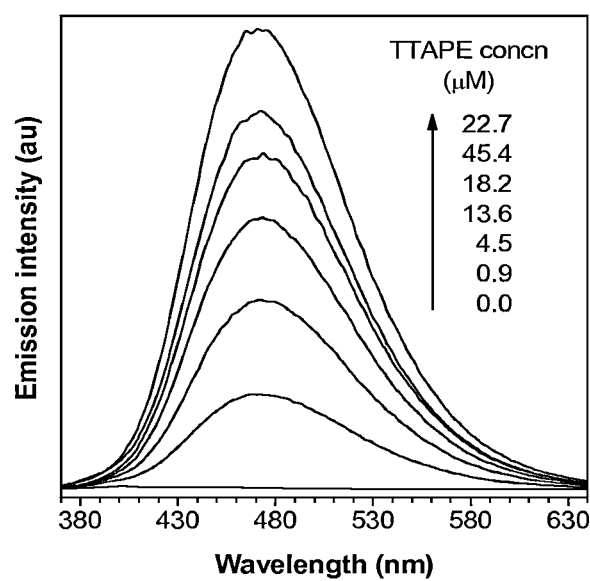
FIG. 28 shows the emission spectra of TTAPE in the presence of a solution of G1 (4.5 µM) in 5 mM Tris-HCl buffer (pH=7.50).

G1 is a 21-mer ssDNA that mimics human telomeric sequence. When the DNA is added into a solution of TTAPE in a Tris-HCl buffer, the solution starts to luminesce (FIG. 27A). Similar FL "lightup" phenomenon has been observed in the thiazole orange system. The $I/I_0$ ratio of TTAPE at 470 nm increases rapidly in a narrow DNA concentration range and reaches its maximum at [G1]=5 μM (FIG. 27B). While conventional FL dyes suffer from self-quenching problems at high dye concentrations, the FL of TTAPE is continuously intensified with increasing its concentration (FIG. 28 and FIG. 27B), thanks to its unique AIE feature. In the aqueous buffer, the cationic dye spontaneously binds to the anionic DNA via electrostatic attraction, resulting in the formation of a TTAPE/G1 complex. Hydrophobic interaction between TTAPE and G1 may have also played a role in the binding process. These intermolecular forces lock conformations of the TTAPE molecules bound to the G1 strands. Consequently, the intramolecular rotations of TTAPE are restricted, which thus blocks its radiationless relaxation pathways and activates its FL process.

The FL "turn-on" switching of TTAPE by binding to G1 strand inspires us to check whether it can be used as a DNA marker in the PAGE assay. Electrophoresis assay of G1 was performed on a Hoefer miniVE system in 1xTBE buffer under nondenaturing conditions using a 20% native poly (acrylamide) gel at 100V for 3 h at 40 C. An AlphaDigiDoc™ system with a DE-500 MultiImage™ II light cabinet and an ML-26 UV transilluminator (Alpha Innotech) was used for data collection and analysis. The gel was poststained with a 10 μM TTAPE solution for 5 min at room temperature, rinsed with distilled water, and photographed under UV light at 290-330 nm by the gel documentation system. EB was used to poststain the gel in parallel for comparison. Concentrations of G1 in the range of 0.5-10.0 μM were used to check the visualizability of the dye-stained DNA in the PAGE assay.

Figure 29:
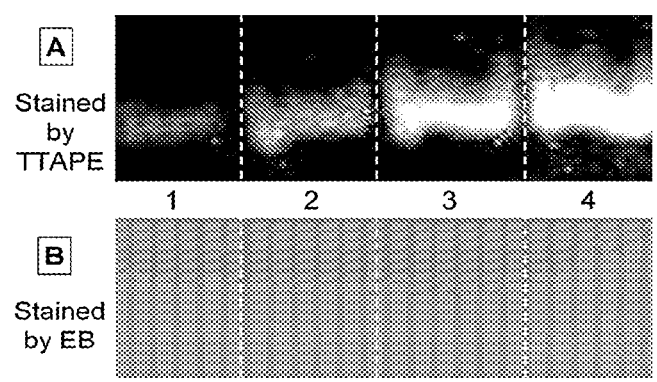
FIG. 29 shows the PAGE assays of G1 at concentrations of 0.5, 1.0, 5.0 and 10.0 µM (lanes 1-4). The gels were post-stained by (A) 10 µM TTAPE and (B) 1.3 µM EB for 5 min.

After running PAGE of G1 in a Tris-borate-ethylene-diaminetetraacetic acid (TBE) buffer, the gel is stained by a TTAPE solution for 5 min. Upon UV illumination, the stained gel shows FL bands at various G1 concentrations (FIG. 29A). Ethidium bromide (EB) is a widely used visualization agent for PAGE assay. The gel stained by EB exhibits bright background emissions (FIG. 29B), although a much lower EB concentration has been used. The G1 bands are not visualized until the gel has been stained by EB for as long as 30 min. Band visualization by EB is usually realized by its intercalation into the hydrophobic region of DNA, which makes the staining a slow process. On the other hand, the FL of TTAPE is activated by its spontaneous electrostatic interaction with charged surface of DNA, which can be achieved in a short time. Sensitivity test reveals that TTAPE can detect ~0.5 μM of G1. The detection limit can be further lowered by increasing tile dye concentration, as suggested by tile solution $I/I_0$ data (c.f., FIG. 27B). The present subject matter thus has the advantages of fast response and high sensitivity, in addition to its excellent miscibility with aqueous media.

Effects of Cationic Species

Among the cationic species, $Na^+$ and $NH_4^+$ are known to be able to induce quadruplex formation but the TTAPE emission is still diminished by these cations. It is known that the conformation of G-quadruplex is highly dependent on the type of cationic species. In the presence of $Na^+$, G1 exhibits a CD spectrum with positively and negatively signed Cotton effects at 295 and 265 nm, respectively (cf., FIG. 30). This suggests the formation of a G-quadruplex with an antiparallel strand alignment, which differs from the G-quadruplex with mixed parallel/antiparallel strand arrangements fanned in the presence of $K^+$. The difference in the geometric conformation may account for the observed difference in the emission behavior. This offers an attractive possibility of using TTAPE as a bioprobe to discriminate between quadruplexes with different conformations.

Figure 36:
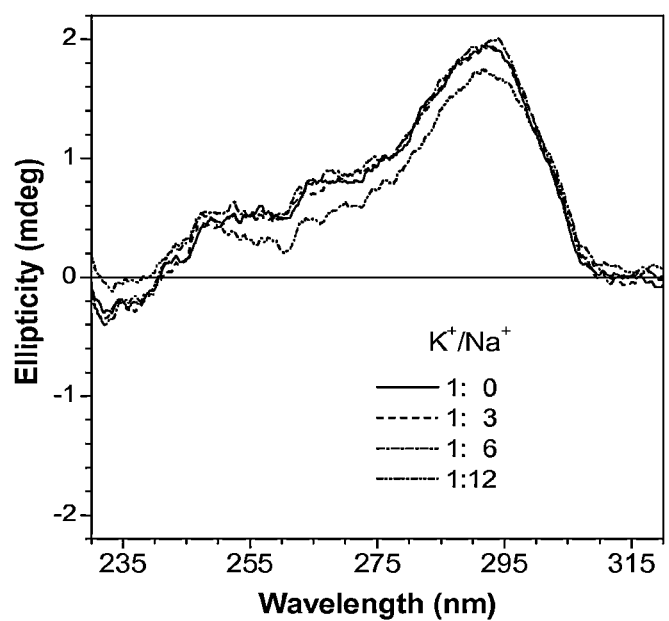
FIG. 36 is a CD spectra of the G1/TTAPE/K$^+$ solutions in a Tris-HCl buffer titrated by different amounts of Na$^+$ ions. [G1]=9 μM, [TTAPE]=4.5 μM, [K$^+$]=100 mM; $\lambda_{ex}$=350 nm.

Various electrolytes exist in the biological systems and excess or absence of one or two of these ionic species can cause biomolecules to undergo conformational transitions, resulting in either favorable biological effect or undesirable dysfunction. As can be seen from FIG. 34B, addition of $Na^+$ into TTAPE/G1/$K^+$ gradually decreases the intensity of the quadruplex-specific emission at 492 nm. The large amount of $Na^+$ ions drives the dye molecules chemisorbed on the G-quadruplex surface into the aqueous media, resulting in the observed emission attenuation. The spectral profile, however, remains unchanged, even when the amount of the added $Na^+$ ions is 12-fold higher than that of $K^+$, indicating that the G-quadruplex has maintained its structural integrity. This is further proved by the CD data: the CD spectrum of the G-quadruplex formed in the presence of $K^+$ is unaffected by the perturbations from the excess amount of externally added $Na^+$ ions (FIG. 36). This suggests that the $K^+$-containing quadruplex is more stable than the $Na^+$ one or that $K^+$ is superior to $Na^+$ in inducing/stabilizing the quadruplex structure.

It is clear that TTAPE is highly affinitive to $K^+$-containing G-quadruplex but not its $Na^+$ cousin. Isothermal titration calorimetry (ITC) measurements are performed, in an effort to understand the thermodynamic basis for the binding affinity difference. ITC is a sensitive technique for the studies of bimolecular processes and can provide direct information about binding affinities and associated thermodynamic parameters. A calorimetric titration experiment was performed at 25.00±0.01° C. on a MicroCal VP-ITC apparatus. G1 solutions for the ITC experiments were prepared in all-potassium (K-Tris: 5 mM Tris-HCl and 150 mM KCl) or all-sodium (Na-Tris: 5 mM Tris-HCl and 150 mM NaCl) buffer at pH 7.50, as required. The buffer solution of G1 was heated to 85° C. and cooled slowly to ensure the folding of the DNA into G-quadruplex structure. For a typical titration, a series of 10 μL aliquots of TTAPE solution were injected into the G1/M$^+$ solution at a 240 s interval. The heat for each injection was determined by the integration of the peak area in the thermogram with respect to time. Blank titration was conducted by injecting TTAPE into the sample cell containing only buffer under the same condition. The interaction heat was corrected by subtracting the blank heat from that for the TTAPE/G1 titration. The $k_b$ values were derived by fitting the isotherm curves with Origin 5.0 software.

Figures 37A, 37B:
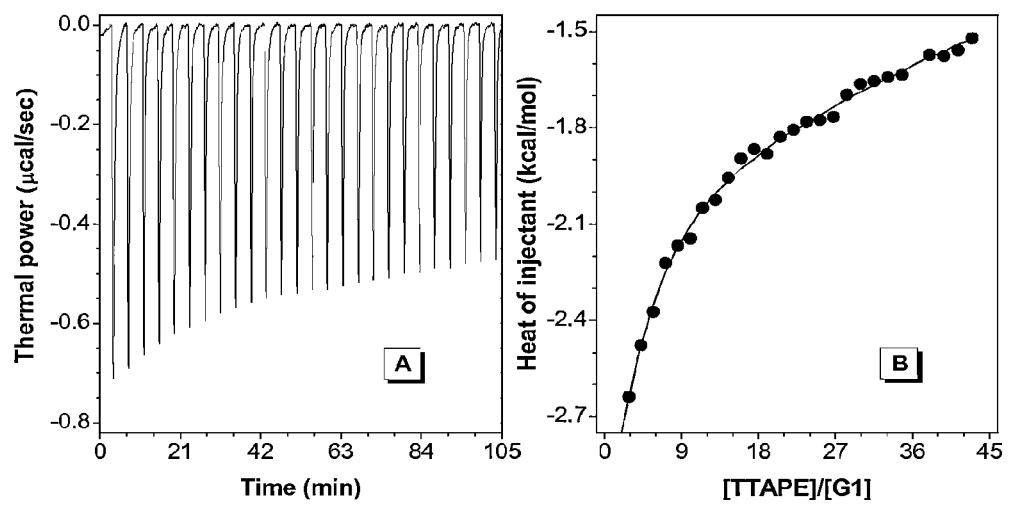
FIG. 37A shows the calorimetric curves for titration of G1 in a K-Tris buffer with serial injections of TTAPE at 25° C.
FIG. 37B shows the binding isotherm as a function of [TTAPE]/[G1] molar ratio in the buffer solution.

As can be seen from FIG. 37A, injection of a tiny aliquot (10 μL) of a TTAPE solution into a G1/K$^+$ buffer yields a large exothermic peak. Fitting the data of integrated heat generated per injection in the binding isotherm (FIG. 37B) gives a binding constant ($K_b$) of $2.4 \times 10^5$ M$^{-1}$, from which a Gibbs energy ($\Delta G°$) of $-7.3$ kcal mol$^{-1}$ is obtained. However, in the case of the Na$^+$ titration, the binding constant is too small to be determined accurately from the ITC data.

Biosensing Processes

Figure 45:
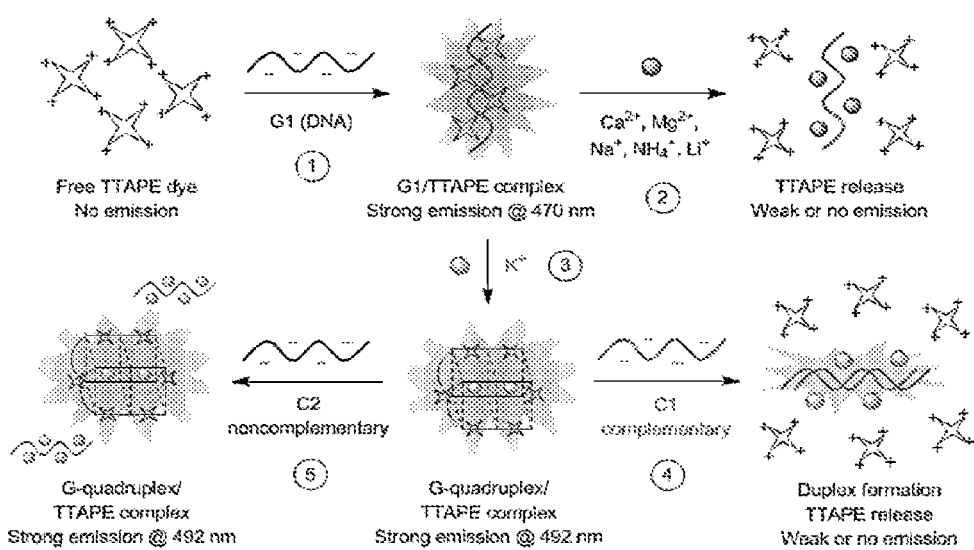
FIG. 45 shows the fluorescent bioprobing processes of TTAPE.

It has now become clear that TTAPE is a fluorescent marker that can perform multiple functions, including DNA probing, G-quadruplex recognition, and potassium-ion sensing (FIG. 45). The non-emissive TTAPE molecules dissolved in the aqueous buffer become highly luminescent upon binding to G1 via mainly electrostatic attraction, as the DNA binding restricts their intramolecular rotations (Process 1 of FIG. 45). Addition of competitive cations such as Li$^+$, Na$^+$, NH$_4^+$, Mg$^{2+}$ and Ca$^{2+}$ weakens or quenches the emission, because the cations drive the bound dye molecules back to solution (Process 2 of FIG. 45). Addition of K$^+$, however, induces G1 to fold into a G-quadruplex structure, resulting in a red shift in the emission spectrum (Process 3 of FIG. 45). Hybridization with a complementary ssDNA (C1) unfolds the G-quadruplex and affords a duplex. The K$^+$ ions in the solution compete with the TTAPE molecules for binding with the dsDNA. The dye molecules are released back to the solution and the emission is thus diminished (Process 4 of FIG. 45). On the other hand, a noncomplementary ssDNA strand (C2) does not disassemble the G-quadruplex structure. As a result, the characteristic emission of the quadruplex/TTAPE complex at 492 nm is preserved (Process 5 of FIG. 45).

TTAPE can function as a "light-up" bioprobe for DNA detection, G-quadruplex identification, and potassium-ion sensing. TTAPE can be utilized as an external fluorescent marker to study conformational structures, to monitor folding processes of label-free oligonucleotides with G-rich strand sequences, and to visualize DNA bands in PAGE assay. The spectral red-shift diagnostically signals the presence of quadruplex structure, allowing a visual distinguishment of G-quadruplex from other DNA conformations. Accordingly, TTAPE has application in biomedicine studies, especially for high-throughput quadruplex-targeting anticancer drug screening.

Anti-Cancer Therapy

Not only does TTAPE behave as a fluorescence marker, which enables the detection of G-quadruplex DNA structure, TTAPE also has an effect in inducing G-quadruplex structure formation. Specifically, TTAPE promotes formation of G-quadruplex at about 250° C. or higher. Incubating the DNA sample with TTAPE (TPE-1) at 25° C. results in a spectral profile similar to the DNA sample incubated with K$^+$ ions at the same temperature (FIG. 77), while incubating the DNA sample with other TPE derivatives (labeled as TPE-2, TPE-3 and TPE-4 in FIG. 77) show a similar spectral profile as the control (i.e., DNA alone). This G-quadruplex formation ability of TTAPE at about 25° C. or higher indicates its application as a lead compound of quadruplex targeting drugs for anti-cancer therapy. In order to be a lead compound in quadruplex-targeting anti-cancer drugs, TTAPE is chemically modified by substituting one or more of the triethylamine groups with other positively charged groups including piperidine, pyrazole, piperazine and imidazole. Such chemical modification does not substantially affect the G-quadruplex-inducing property of TTAPE at the above specified temperature. Furthermore, through subsequent structural screening and modification, such as conjugation of the substituted TTAPE to a G-quadruplex targeting motif, an efficient anti-cancer pharmaceutical composition based on targeting a specific G-rich sequence and/or G-quadruplex can be developed.

Detection of Amyloid Fibril Formation

Figures 66A, 66B:
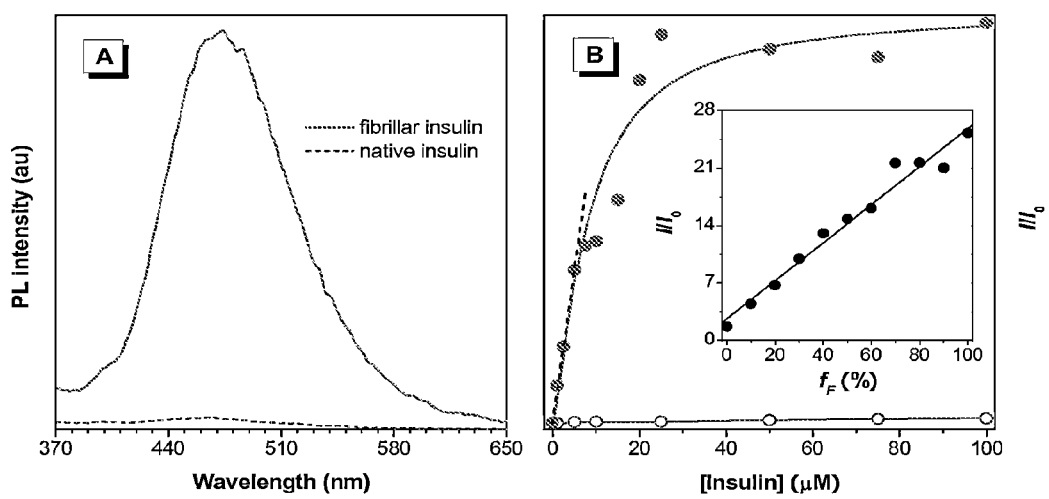
FIG. 66A shows FL spectra of TPE-SO3 in the presence of native and fibrillar states of bovine insulin.
FIG. 66B shows the change in FL intensity of TPE-SO3 at 470 nm with different concentration of fibrillar (solid circle) and native insulin (open circle).

TPE-SO3 was synthesized according to synthesis scheme 1 herein. The AIE effect of TPE-SO3 is highly specific and sensitive. As seen in FIG. 66A, the TPE-SO3 solution is non-emissive in the absence of proteins. The solution remains faintly luminescent at ca. 470 nm upon addition of native bovine insulin (fainted line in FIG. 66A). Native insulin is a 51-residue hormone and adopts a primarily helical structure. On the other hand, insulin can favorably form amyloid fibrils in vitro under certain conditions such as elevated temperature and low pH. Therefore, when the native insulin is heated at high temperature (e.g., 65° C.) and low pH (e.g. pH 1.6), fibrillar insulin is gradually formed and the TPE-SO3 solution becomes luminescent (solid line in FIG. 66A). Its emission intensity is enhanced progressively with an increase in concentration of fibrillar insulin. Close inspection of the binding isotherm reveals a linear relationship at low insulin concentration range (0-5 μM) (FIG. 66B). The fluorescence of TPE-SO3 remains negligible even when the concentration of native insulin is varied from 0 to 100 μM. Further, the fluorescence emission of TPE-SO3 to fibrillar insulin is demonstrated to be unaffected in the presence of native insulin (FIG. 66B inset). The emission of TPE-SO3 increases monotonically with a linear increase of fibrillar insulin fraction.

Figure 67:
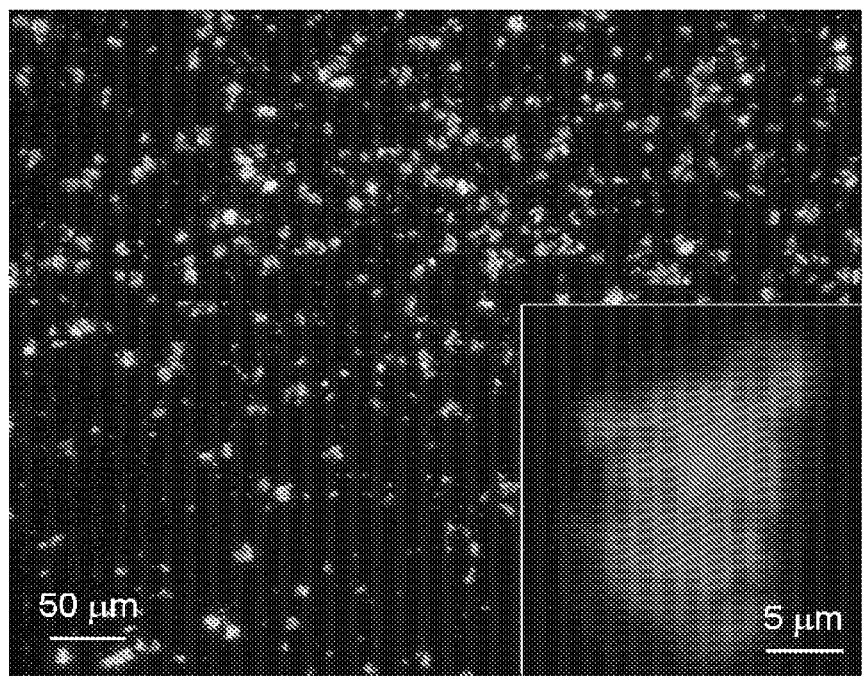
FIG. 67 shows fluorescence micrographs of insulin fibrils stained by TPE-SO3 solution.

TPE-SO3 of the present subject matter has excellent water solubility due to its sulfonate groups. As a result, TPE-SO3 solutions can be used as detection tools to stain amyloid fibrils and the stained amyloid fibrils can be visualized under fluorescence microscope with minimal background fluorescence noise (FIG. 67).

The distinct FL behaviors of TPE-SO3 toward native and fibrillar insulin as well as the highly solubility thereof clearly demonstrate its usefulness as an external indicator for monitoring the kinetic of amyloid fibril formation.

Retardation Effect on Amyloid Fibril Formation

Figure 70:
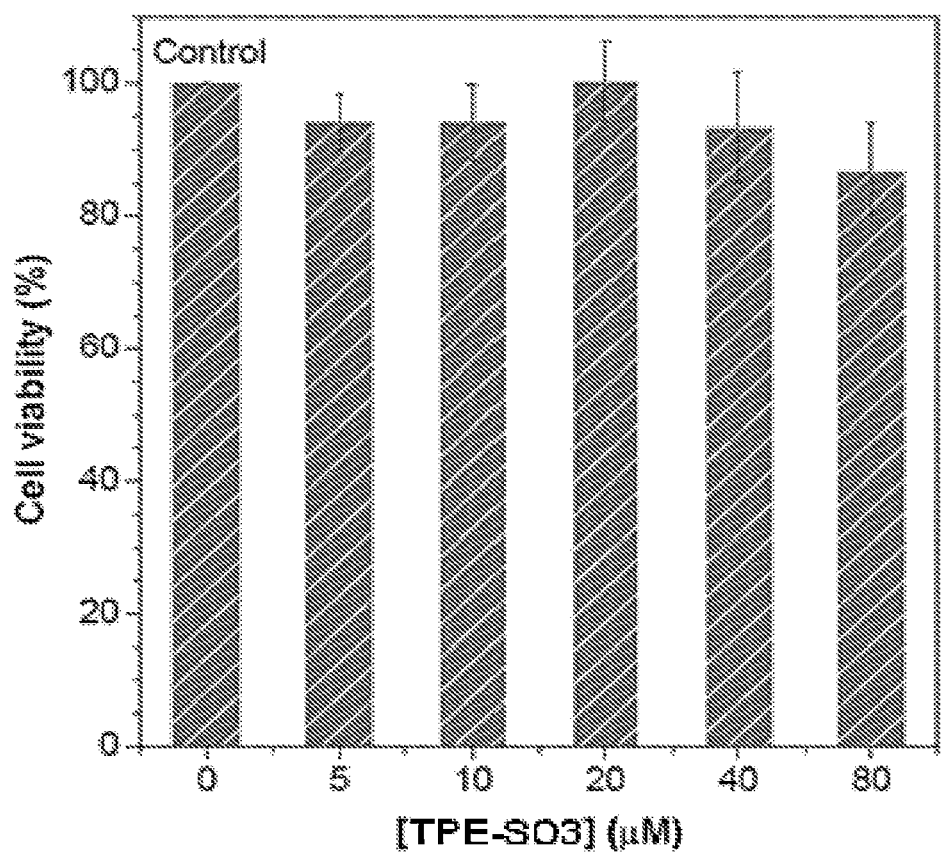
FIG. 70 shows MIT toxicity test for TPE-SO3.

TPE-SO3 is surprisingly found to have a retardation effect on amyloid fibril formation. In situ incubation of TPE-SO3 with insulin solution has shown to lengthen the lag phase of fibrillation and decelerate the elongation rate of the growth phase in a concentration dependent manner (FIGS. 69A and 69B). The growth rate of insulin fibrillation is also decreased exponentially against the concentration of TPE-SO3 (FIG. 69C). These results indicate that TPE-SO3 may interfere with the denaturation of native insulin as well as the intermolecular interactions between the insulin molecules. Further studies on the retardation effect of TPE-SO3 on insulin fibril formation shows that the effect is more significant at the early stage in the time course of the insulin fibril formation (FIG. 75). TPE-SO3 is also shown to be non-toxic; cell viability is unaffected or hardly influenced in the presence of TPE-SO3 (FIG. 70). TPE-SO3 is safe for administration in combination with pharmaceuticals, thus non-toxic TPE-SO3 is useful as an amyloid protein stabilizer, such as for use in long-term storage and delivery of therapeutic insulin in diabetes treatment.

Figure 71:
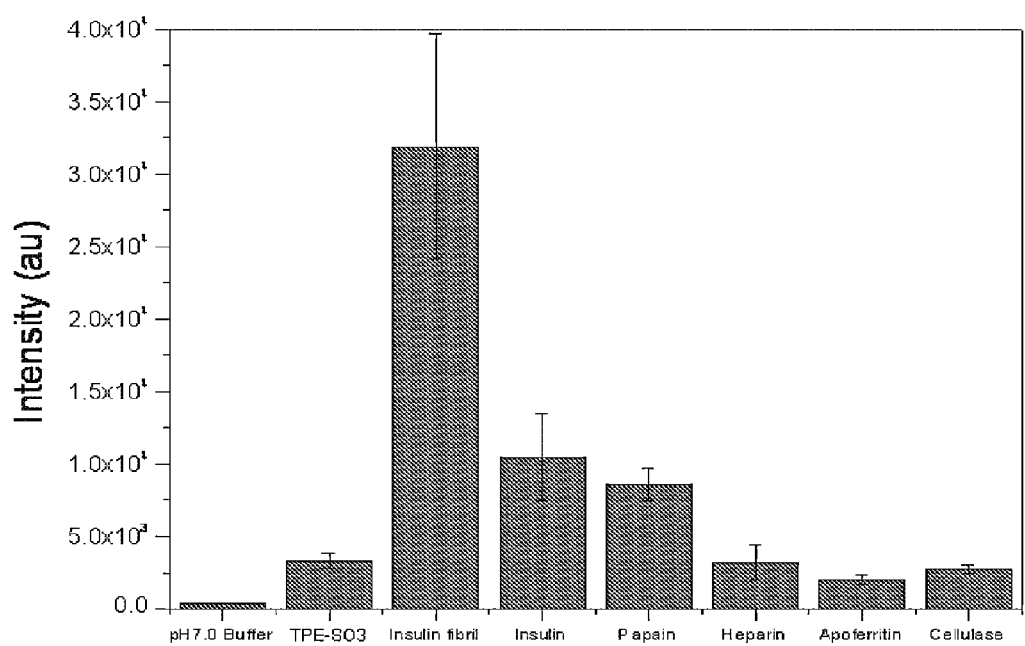
FIG. 71 demonstrates the fluorescence behaviour of TPE-SO3 against various proteins.
Figure 72:
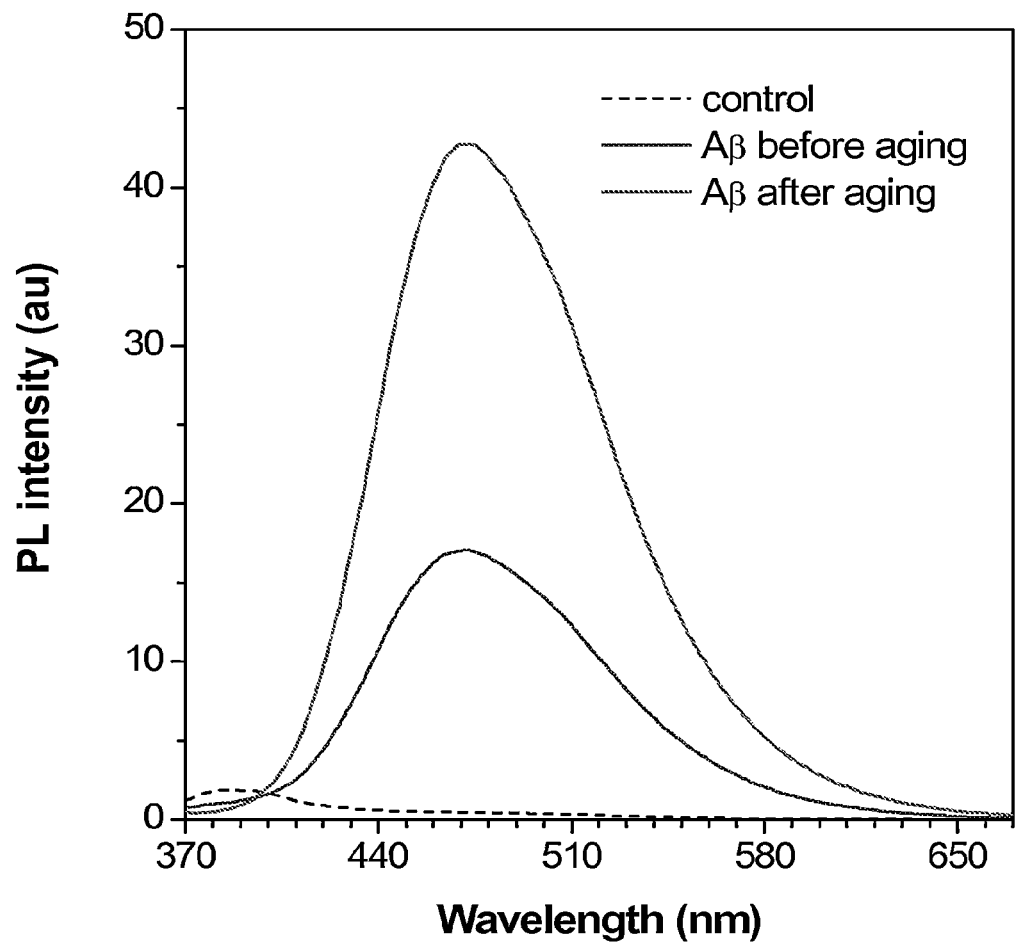
FIG. 72 shows the emission of TPE-SO3 with amyloid-beta-peptide before and after aging.
Figure 73:
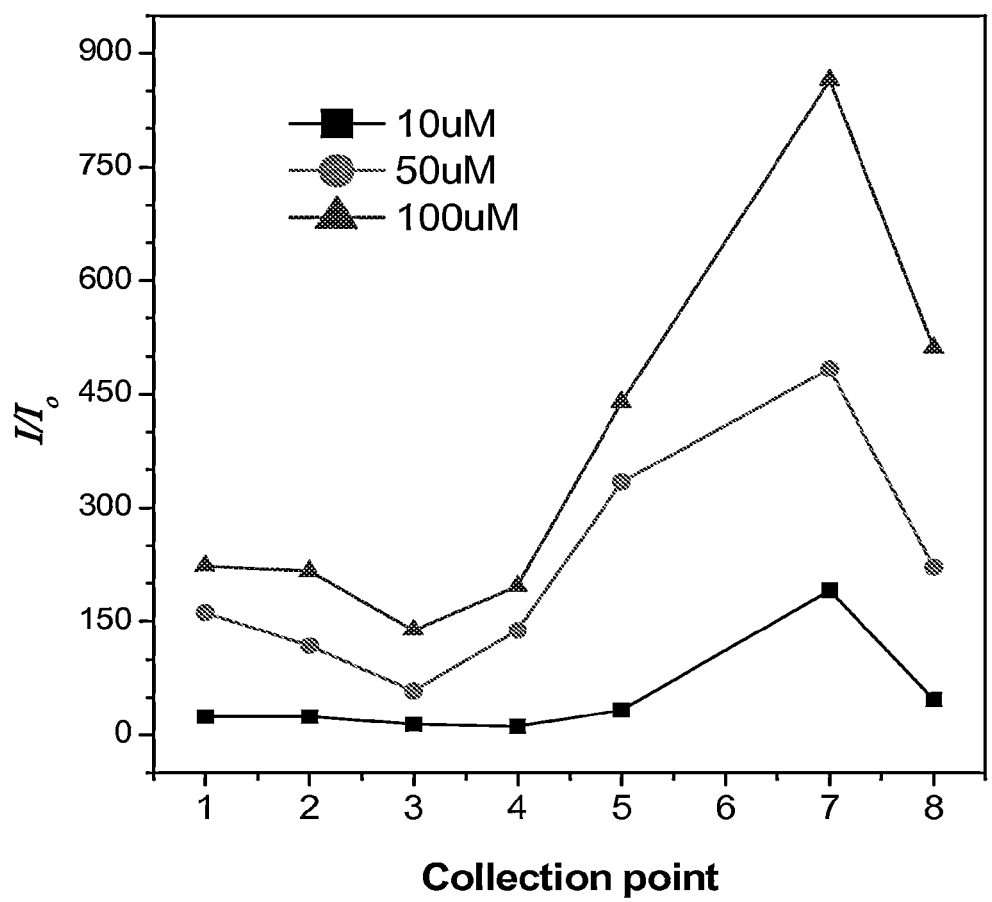
FIG. 73 shows the rate of fluorescence enhancement of different concentrations of TPE-SO3 during lysozyme fibrillation.

A comparative study of PL (photoluminescence) intensity of TPE-SO3 in different amyloid proteins (FIG. 71) shows that TPE-SO3 has the highest selectivity towards insulin fibril over the native insulin and among other protein monomers. Different forms of amyloid-beta (Aβ) peptide are also tested with TPE-SO3 (FIG. 72) and the result shows that TPE-SO3 is more specific to Aβ peptide after aging than before aging. Formation of Aβ fibril is a marker of certain neurodegenerative diseases such as Alzheimer's disease and Parkinson's disease. Another amyloid protein candidate, lysozyme, which also tends to form fibril under similar physiological conditions to insulin is also tested with different TPE-SO3 concentrations in a time course manner (FIG. 73). The result demonstrates that the rate of fluorescence enhancement of TPE-SO3 at different concentrations is significantly higher at later stage of lysozyme fibril formation reflecting the exponential growth rate of fibrils. The result also demonstrates that the rate of fluorescence enhancement at each time point increases in a concentration-dependent manner.

EXAMPLES

The following examples are illustrative of the presently described subject matter and are not intended to be limitations thereon.

Example 1

1,2-Bis(4-hydroxyphenyl)-1,2-diphenylethylene (TPE-OH)

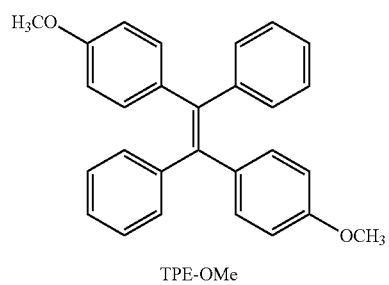

TPE-OMe

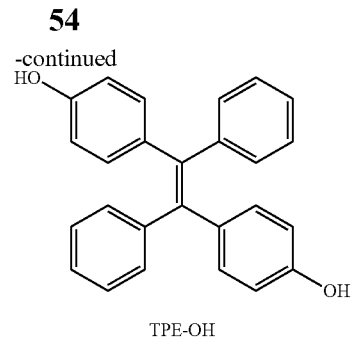

TPE-OH

A suspension of p-methoxybenzophenone (1.06 g, 5.0 mmol), 1.34 equiv of $TiCl_3/AlCl_3$ (5.81 g, 6.7 mmol), and 25 equiv of Zn dust (8.01 g, 122.0 mmol) in 100 ml of dry THF was refluxed for 20 h. The reaction mixture was cooled to room temperature and filtered. The filtrates were evaporated and the crude product was purified by a silica gel column using hexane as eluent. 1,2-Bis(4-methoxyphenyl)-1,2diphenylethene (TPE-OMe) was isolated in 91% yield.

TPE-OMe (1.40 g, 3.56 mmol) was dissolved in 20 ml of dichloromethane (DCM) in a 100 ml flask, and the flask was placed in an acetone-dry ice bath at −78° C. A solution of 3.59 g (14.3 mmol) of boron tribromide in 10 ml of DCM was added carefully to the mixture under stirring. The resultant mixture was allowed to warm to room temperature overnight under stirring. The reaction product was hydrolyzed by careful shaking with 20 ml of water. The organic phase was separated and concentrated by a rotary evaporator. The crude product was purified by recrystallization from THF/methanol to afford a white solid in 97% yield.

Characterization data of TPE-OMe: $^1$H NMR ($CDCl_3$, 300 MHz) δ (ppm): 7.10-7.06 (m, 10H), 6.93 (t, 4H), 6.64 (t, 4H), 3.74 (s, 6H). $^{13}$C NMR ($CDCl_3$, 75 MHz) δ (ppm): 158.0, 144.4, 139.7, 136.5, 132.6, 131.5, 127.8, 126.3, 113.2, 55.2. MS (TOF) m/e: 392.1 (M+, calcd. 392.2).

TPE-OH: $^1$H NMR ($CDCl_3$, 300 MHz) δ (ppm): 7.11-7.02 (m, 10H), 6.88 (t, 4H), 6.56 (d, 4H). $^{13}$C NMR ($CDCl_3$, 75 MHz) δ (ppm): 154.1, 144.2, 139.7, 135.5, 132.8, 131.5, 127.8, 126.3, 114.7. MS (TOF) m/e: 363.1 [(M−H)+, calcd: 363.1].

Example 2

1,2-Diphenyl-1,2-bis(4,4'-(3-sulfonato)propoxyl) phenylethylene (TPE-SO3/BSPOTPE)

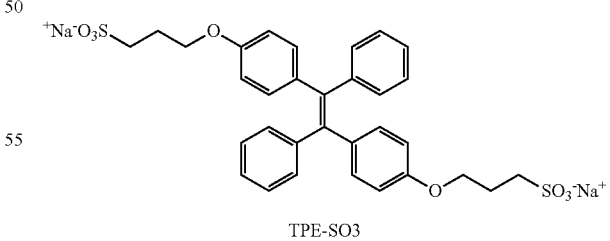

TPE-SO3

Into a 100 m round-bottom flask were added TPE-OH (0.5 g, 1.37 mmol) and 20 m of anhydrous ethanol under nitrogen. The mixture was stirred until all solids disappeared. A mixture of NaOEt (0.20 g, 3.0 mmol) in 20 ml ethanol was added dropwise and stirred for 1 h, causing the colorless solution to turn orange-red. Into the solution was added 0.35 g of 1,3-propanesultone (2.88 mmol) in 20 m of ethanol. The mixture was vigorously stirred for 12 h and a white product precipitated out from the solution. The product was collected by filtration and washed with ethanol and acetone twice to give a white solid in 61% yield.

Characterization data of BSPOTPE: $^1$H NMR (DMSO-d6, 300 MHz) δ (ppm): 7.25-7.13 (m, 6H), 7.08-7.02 (m, 4H), 6.95-6.90 (m, 4H), 6.81-6.73 (m, 4H), 4.09-4.02 (m, 4H), 2.66-2.58 (m, 4H), 2.08-2.02 (m, 4H). $^{13}$C NMR (DMSO-d6, 75 MHz) δ (ppm): 157.0, 143.9, 139.2, 135.5, 131.9, 130.8, 127.8, 126.2, 113.8, 66.4, 47.9, 25.3. MS (TOF) m/e: 631.1 [(M+2H)+-Na, calcd. 631.1], 609.2 [(M+3H)+2Na, calcd. 609.1].

Example 3

N,N'-[1,2-Diphenyl-1,2-bis(1,4-phenoxyethyl)vinyl]bis(triethylammonium bromide) (TPE-C2N+)

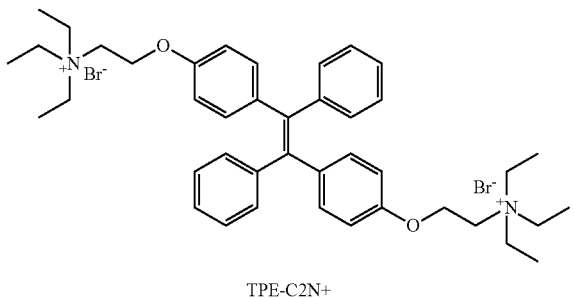 [SMILES: CC[N+](CC)(CC)CCOc1ccc(/C(=C(\c2ccccc2)c2ccc(OCC[N+](CC)(CC)CC)cc2)c2ccccc2)cc1 ; [Br-] ; [Br-]]

TPE-C2N+

To a mixture of sodium hydride (84 mg) and 1,2-bis(4-hydroxyphenyl)-1,2-diphenylethene (0.50 g) in dry dioxane (20 ml), 1,2-dibromoethane (1.50 g) was added at room temperature. The mixture was heated to reflux and stirred for 24 h. After filtration and concentration, the product was isolated and purified by silica gel chromatography using chloroform/hexane (1:1 v/v) as elute. 1,2-Bis[4-(2-bromoethoxy)phenyl]-1,2-diphenylethene (TPE-C2Br) was obtained in 32% yield.

A 250 ml flask with a magnetic spin bar was charged with TPE-C2Br (100 mg) dissolved in 100 ml of THF. To this solution was added triethylamine (5 ml). The mixture was heated to reflux and stirred for 3 days. During this period, 10 ml of water was added at several intervals. THF and extra triethylamine were evaporated. The water solution was washed by chloroform three times. After solvent evaporation, the residue was washed with chloroform and acetone and then dried overnight in vacuum at 50° C. TPE-C2N+ was isolated in 56% yield.

Characterization data of TPE-C2Br: $^1$H NMR (300 MHz, CDCl3), δ (ppm): 7.10-7.02 (m, 10H), 6.95-6.92 (m, 4H), 6.65-6.59 (m, 4H), 4.15-4.11 (m, 4H), 3.55-3.49 (m, 4H). $^{13}$C NMR (75 MHz, CDCl$_3$), δ (ppm): 156.6, 144.1, 139.8, 137.2, 132.7, 131.5, 127.8, 126.4, 114.0, 67.8, 29.3. MS (TOF), m/e: 578.03 ([M]+, calcd. 578.03).

TPE-C2N+: $^1$H NMR (300 MHz, CDCl$_3$), δ (ppm): 7.09-7.00 (m, 10H), 6.97-6.87 (m, 4H), 6.61-6.54 (m, 4H), 3.90-3.84 (m, 4H), 3.45-3.40 (m, 4H), 2.00-1.97 (m, 4H), 1.88-1.84 (m, 4H). $^{13}$C NMR (75 MHz, CDCl$_3$), δ (ppm): 157.9, 144.9, 140.3, 137.2, 133.2, 132.1, 128.3, 126.9, 114.2, 67.3, 34.2, 30.2, 28.6. MS (TOF), m/e: 634.09 ([M]+, calcd. 634.09).

Example 4

N,N'-[1,2-Diphenyl-1,2-bis(1,4-phenoxybutyl)vinyl]bis(triethylammonium bromide) (TPE-C4N+)

The synthesis of the below compound was carried out according to Example 3 by using the corresponding dibromobutane.

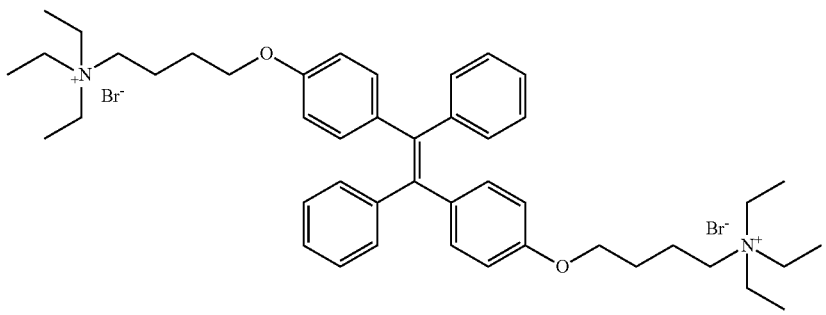

TPE-C4N+

Characterization data of TPE-C4Br: $^1$H NMR (300 MHz, CDCl$_3$), δ (ppm): 7.09-7.00 (m, 10H), 6.97-6.87 (m, 4H), 6.61-6.54 (m, 4H), 3.90-3.84 (m, 4H), 3.45-3.40 (m, 4H), 2.00-1.97 (m, 4H), 1.88-1.84 (m, 4H). $^{13}$C NMR (75 MHz, CDCl$_3$), δ (ppm): 157.9, 144.9, 140.3, 137.2, 133.2, 132.1, 128.3, 126.9, 114.2, 67.3, 34.2, 30.2, 28.6. MS (TOF), m/e: 634.09 ([M]+, calcd. 634.09).

TPE-C4N+: $^1$H NMR (300 MHz, d-DMSO), δ (ppm): 7.25-7.19 (m, 6H), 7.07-6.92 (m, 8H), 6.83-6.77 (m, 4H), 4.04-4.02 (m, 4H), 3.36-3.29 (m, 16H), 1.86-1.81 (m, 8H), 1.34-1.11 (m, 18H). $^{13}$C NMR (75 MHz, d-DMSO), δ (ppm): 156.9, 143.8, 139.3, 135.7, 132.0, 130.7, 127.9, 126.4, 113.7, 66.5, 55.6, 52.0, 25.5, 18.0, 7.2. MS (TOF), m/e: 789.50 ([M.2H$_2$O—HBr]+, calcd. 789.44).

Example 5

1,1,2,2-tetrakis(4-hydroxyphenyl)ethylene (DHTPE)

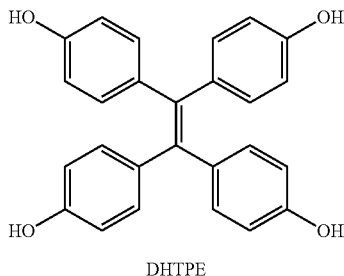 [SMILES: Oc1ccc(C(=C(c2ccc(O)cc2)c2ccc(O)cc2)c2ccc(O)cc2)cc1]

DHTPE

A suspension of 4,4'-dihydroxybenzophenone (3.0 g, 14.0 mmol), 1 equiv of TiCl$_4$ (1.54 ml, 14.0 mmol), and 2 equiv of Zn dust (1.83 g, 28.0 mmol) in 100 ml of dry THF was refluxed for 20 h. The reaction mixture was cooled to room temperature and filtered. The filtrates were evaporated and the crude product was purified by a silica gel column using ethyl acetate (EA) as eluent. DHTPE was obtained as slight yellow powder of 83% yield.

Characterization data of DHTPE: $^1$H NMR (300 MHz, d-DMSO), δ (ppm): 9.24-8.94 (br), 7.07-7.04 (d, 4H), 6.95-6.95 (d, 4H), 6.70-6.56 (m, 4H), 6.47-6042 (t, 4H). $^{13}$C NMR (75 MHz, CDCl$_3$), δ (ppm): MS (FAB), m/e: 391.2 ([M−4H]+, calcd. 392.1).

Example 6

1,2-Bis[4-(3-triphenylphosphonium)phenyl]-1,2-diphenylethene bromide (TPE-MitoB)

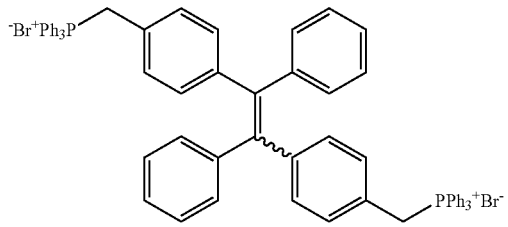

A suspension of 4-methylbenzophenone (1, 3.6 g, 10.0 mmol), TiCl$_4$ (1.9 g, 10.0 mmol), and Zn dust (1.3 g, 20.0 mmol) in dry THF (100 mL) was refluxed for 20 g. Afterward, the reaction mixture was cooled to room temperature and filtered. The filtrate was evaporated and the crude product was purified on a silica-gel column using DCM as eluent. 1,2-Bis(4-methylphenyl)-1,2-diphenylethene was isolated as white solid in 94% yield. $^1$H NMR (300 MHz, CDCl$_3$), δ (TMS, ppm): 7.11-7.00 (m, 10H), 6.91 (d, 8H), 2.26 (d, 6H). δ (75 MHz, CDCl$_3$) 144.8, 141.6, 141.1, 136.6, 132.0, 131.9, 129.0, 128.2, 126.9, 21.9. m/z (FAB) 360.2 [M$^+$]; calc. 360.2.

To a mixture of 1,2-Bis(4-methylphenyl)-1,2-diphenylethene (1.8 g, 5.0 mmol) and NBS (1.7 g, 10.0 mmol) in CCl$_4$ was added catalytic amount of BPO at room temperature. The mixture was stirred and heated to reflux for 8 h. After filtration and solvent evaporation, the product was purified by silica gel chromatography using DCM/hexane (1:4 v/v) as eluent. 1,2-Bis[4-(bromomethyl)phenyl]-1,2-diphenylethene was isolated as pale yellow solid in 43% yield. $^1$H NMR (300 MHz, CDCl$_3$), δ (TMS, ppm): 7.14-7.07 (m, 10H), 7.02-6.96 (m, 8H), 4.41 (d, 4H). $^{13}$C NMR (75 MHz, CDCl$_3$), δ (TMS, ppm): 144.4, 143.9, 141.5, 136.6, 132.3, 132.0, 129.2, 128.5, 127.4, 34.3. m/z (FAB) 518.0 [M$^+$]; calc. 518.2.

Triphenylphosphonium salt, TPE-TPP, was prepared from 1,2-Bis[4-(bromomethyl)phenyl]-1,2-diphenylethene (0.5 g, 1.0 mmol) and triphenylphosphine (1.0 g, 4.0 mmol) in DMF at 100° C. After stirring for 24 h, the solution was poured into large amount of toluene. The white precipitate was collected in 80% yield to obtain Bis(Triphenylphosphonium)Tetraphenylethene (TPE-MitoB). $^1$H NMR (400 MHz, DMSO-d$_6$), δ (TMS, ppm): 7.90-7.55 (m, 30H), 7.16-6.66 (m, 18H), 5.039 (d, 4H). $^{13}$C NMR (100 MHz, CDCl$_3$), δ (TMS, ppm): 135.25, 135.05, 134.35, 134.31, 134.26, 134.21, 131.06, 130.91, 130.31, 130.18, 130.05, 127.72, 126.82, 118.02, 117.17, 34.69. m/z 882.5 [(M−2Br)$^+$]; calc. 882.4.

Example 7

1-[4-(1-methyl-4-pyridine)ethene]-1,2,3-triphenylethene hexafluorophosphate (TPE-MitoY)

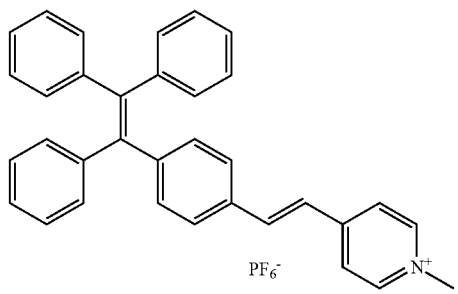

1,4-dimethylpyridinium iodide. 1H NMR (400 MHz, CDCl3), δ (TMS, ppm): 8.73 (d, J=6.4 Hz, 2H), 7.92 (d, J=6.0 Hz, 2H), 4.36 (s, 3H), 2.68 (s, 3H). HRMS (MALDI-TOF): m/z 107.7845 [(M-I)$^+$, calcd 108.0813]

4-(1,2,2-Triphenylvinyl)benzaldehyde. 1H NMR (400 MHz, CDCl3), δ (TMS, ppm): 9.90 (s, 1H), 7.61 (d, J=8.2 Hz, 2H), 7.19 (d, J=8.2 Hz, 2H), 7.11 (m, 9H), 7.02 (m, 6H). HRMS (MALDI-TOF): m/z 361.1588 [(M+1)$^+$, calcd 360.1514]

A solution of 4-(1,2,2-Triphenylvinyl)benzaldehyde (200 mg, 0.55 mmol) and iodide salt of 1,4-dimethylpyridinium iodide (130 mg, 0.55 mmol) in dry ethanol (15 mL) was refluxed under nitrogen for 48 h. After the reaction mixture was cooled to ambient temperature, the solvent was evaporated under reduced pressure. The solid was dissolved in acetone (5 mL) and a saturated aqueous solution of KPF$_6$ (5 mL) was then added. After stirring for 30 min, the solution was evaporated to dryness. The residue was purified by a silica gel column chromatography using dichloromethane/acetone mixture (5:1 v/v) as eluent to give a yellow product in 53% yield to obtain 4-{2-[4-(1,2,2-triphenylvinyl)phenyl]vinyl}-1-methylpyridiniumhexafluorophosphate (TPE-MitoY). $^1$H NMR (400 MHz, CDCl3), δ (TMS, ppm): 8.40 (d, J=6.4 Hz, 2H), 7.80 (d, J=5.6 Hz, 2H), 7.51 (d, J=16 Hz, 1H), 7.31 (d, J=8 Hz, 2H), 7.13 (m, 19H), 6.95 (d, J=16 Hz, 1H), 4.27 (s, 3H). $^{13}$C NMR (100 MHz, DMSO-d6), δ (ppm): 152.36, 145.45, 145.01, 142.84, 142.68, 141.55, 140.06, 139.87, 133.22, 131.37, 130.65, 130.55, 127.91, 127.79, 127.58, 126.80, 126.73, 123.37, 123.11, 46.83. HRMS (MALDI-TOF): m/z 450.2123[(M-PF$_6$)$^+$, calcd 450.2222].

Example 8

1-[4-(1,2-dimethyl-5-benzothiazole)]-1,2,3-triphenylethene iodide (TPE-ThT)

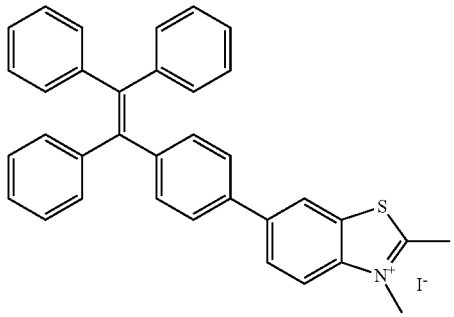 [SMILES: Cc1sc2cc(-c3ccc(C(=C(c4ccccc4)c4ccccc4)c4ccccc4)cc3)ccc2[n+]1C ; [I-]]

A solution of 6-bromo-2-methylbenzothiazole (0.5 mmol, 114 mg), (4-dihydroxyboron-phenyl)-1,2,3-triphenylethene (0.6 mmol, 225.8 mg), sodium carbonate (5 mmol, 530 mg) and Tetrakis(triphenylphosphine)palladium (0.03 mmol, 34.7 mg) in THF/H$_2$O (4:1, v/v) mixture was refluxed for 12 h. Afterward, the resulting mixture was cooled to room temperature and THF was evaporated under reduced pressure. The obtained residue was extracted with CH$_2$Cl$_2$ three times and the combined organic layer was dried over MgSO4, filtered and the solvent was evaporated under reduced pressure. The crude product was purified by silica gel chromatography with hexane/dichloromethane (7:3) as eluent to afford the desired product (215 mg, 0.45 mmol) as yellow solid. Yield=90%. $^1$H NMR (400 MHz, CDCl$_3$), δ (TMS, ppm): 7.98-7.94 (m, 2H), 7.65-7.62 (d, 1H), 7.40-7.38 (d, 2H), 7.14-7.04 (m, 17H), 2.85 (s, 3H). HRMS (MALDI-TOF), m/z calcd. for C$_{34}$H$_{25}$NS: 479.1708. Found 479.11712 (M$^+$).

To a solution of this product (0.5 mmol, 240 mg) in dry acetonitrile, iodomethane (0.8 mmol, 114 mg) was added dropwise. The reaction mixture was refluxed for 12 h and cooled to room temperature. The dark solution was concentrated under reduced pressure and precipitated in excess of diethyl ether. The precipitates were collected and washed by diethyl ether several times to obtain the desired product (0.23 mmol, 140 mg) as faint yellow solid. Yield: 45%. $^1$H NMR (400 MHz, CDCl$_3$), δ (TMS, ppm): 8.18 (s, 1H), 7.97 (d, 1H), 7.90 (d, 1H), 7.33-7.31 (d, 2H), 7.16-7.03 (m, 17H), 4.46 (s, 3H), 3.43 (s, 3H). HRMS (MALDI-TOF), m/z calcd. for (C$_{35}$H$_{28}$NS)$^+$ I$^-$: 494.1937. Found 494.1948 (M$^+$).

Example 9

1-[4-(1-ethyl-2-benzothiazole)ethene]-1,2,3-triphenylethene hexafluorophosphate (TPEBe)

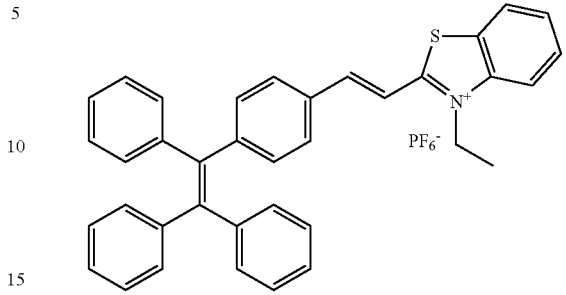

3-Ethyl-2-methyl-1,3-benzothiazol-3-ium iodide. $^1$H NMR (400 MHz, CD3OD), δ (TMS, ppm): 8.33 (d, J=7.8 Hz, 2H), 8.30 (d, J=8.4 Hz, 2H), 7.92 (dd, J1=7.8 Hz, J2=8.4 Hz, 2H), 7.81 (dd, J1=7.8 Hz, J2=8.4 Hz, 2H), 4.85 (q, J=7.5 Hz, 4H), 3.27 (s, 3H), 1.60 (t, 6H, J=7.5 Hz, 6H). HRMS (MALDI-TOF): m/z 178.0660 [(M+1)$^+$, calcd 178.0690]

4-(1,2,2-Triphenylvinyl)benzaldehyde. $^1$H NMR (400 MHz, CDCl3), δ (TMS, ppm): 9.90 (s, 1H), 7.61 (d, J=8.2 Hz, 2H), 7.19 (d, J=8.2 Hz, 2H), 7.11 (m, 9H), 7.02 (m, 6H). HRMS (MALDI-TOF): m/z 361.1588 [(M+1)$^+$, calcd 360.1514]

A solution of 4-(1,2,2-Triphenylvinyl)benzaldehyde (200 mg, 0.55 mmol) and iodide salt of 3-Ethyl-2-methyl-1,3-benzothiazol-3-ium iodide (169 mg, 0.55 mmol) in dry EtOH (15 mL) was refluxed under nitrogen for 48 h. After cool to ambient temperature, the solvent was evaporated under reduced pressure. The solid was dissolved in acetone (5 mL) and a saturated aqueous solution of KPF$_6$ (5 mL) was then added. After stirring for 30 min, the solution was evaporated to dryness. The residue was purified by a silica gel column chromatography using dichloromethane and acetone mixture (5:1 v/v) as eluent to give a yellow product in 62% yield to obtain 3-{2-[4-(1,2,2-triphenylvinly)phenyl]vinyl}-2-methyl-1,3-benzothiazol-3-ium hexafluorophosphate (TPEBe). NMR (400 MHz, DMSO-d$_6$), δ (ppm): 8.41 (d, J=8.0 Hz, 1H), 8.27 (d, J=8.4 Hz, 1H), 8.13 (d, J=15.6 Hz, 1H), 7.94 (d, J=16 Hz 1H), 7.75-7.88 (m 4H), 7.02-7.15 (m 11H), 6.96-7.00 (m 6H), 4.91 (q, 2H), 1.42 (t, J=7.2 Hz, 3H). $^{13}$C NMR (100 MHz, DMSO-d6): δ (ppm): 171.4, 148.4, 147.5, 142.6, 142.4, 142.0, 140.8, 139.6, 131.3, 130.6, 130.5, 130.4, 129.5, 129.3, 128.2, 127.8, 127.7, 126.9, 126.7, 124.3, 116.5, 112.9, 44.4, 14.0. HRMS (MALDI-TOF): m/z 520.2281 [(M-PF$_6$)$^+$, calcd 520.2099]. Anal. Calcd for C$_{37}$H$_{30}$F$_6$NPS: C, 66.76; H, 4.54; N, 2.10. Found: C, 67.26; H, 4.45; N, 2.18.

Example 10

N,N',N'',N'''-[1,2-Tetrakis(1,4-phenoxybutyl)vinyl]tetrakis(triethylammonium bromide) (N+C4-TPE-C4N+)

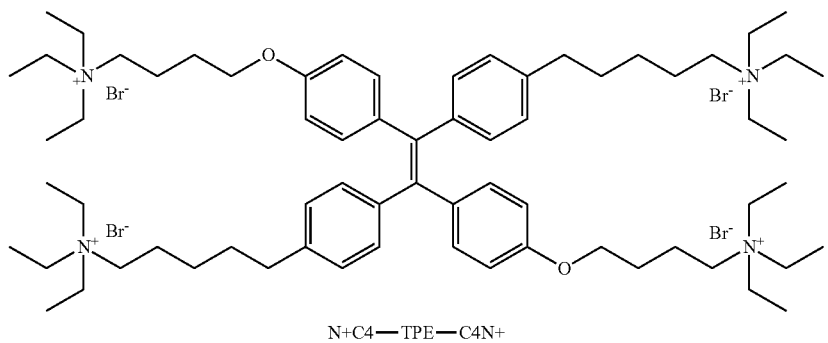

N+C4—TPE—C4N+

To a mixture of DHTPE (0.4 g, 20 mmol) and potassium carbonate in acetone, 1,4-dibromobutane (3 ml) was added and the mixture was heated to reflux and stirred for 24 h. After filtration and concentration, the product was isolated and purified by silica gel chromatography using chloroform/hexane (1:1 v/v) as eluent. The product 1,1,2,2-tetrakis(4-(4-bromobutoxy)phenyl)ethane (BrC4-TPE-C4Br) was obtained as white powder in 21% yield.

Characterization data of BrC4-TPE-C4Br: $^1$H NMR (300 MHz, CDCl$_3$), δ (ppm): 7.08-6.99 (m, 8H), 6.81-6.60 (m, 8H), 3.94-6.86 (m, 8H), 3.49-3.42 (m, 8H), 2.07-2.00 (m, 8H), 1.92-1.85 (m, 8H). $^{13}$C NMR (75 MHz, CDCl$_3$), δ (ppm): 157.2, 136.6, 132.7, 129.5, 114.3, 66.9, 33.9, 29.9, 28.3. MS (FAB), m/e: 937.0 ([M]+, calcd. 936.4).

N+C4-TPE-C4N+: $^1$H NMR (300 MHz, d-DMSO), δ (ppm): 7.29-7.27 (d, 1H), 7.10-7.08 (d, 1H), 6.83-6.80 (d, 7H), 6.83-6.80 (m, 7H), 3.91-3.83 (m, 8H), 3.23-3.18 (m, 16H), 2.89-2.84 (m, 8H), 1.70-1.65 (m, 20H), 1.17-1.06 (m, 40H). $^{13}$C NMR (75 MHz, d-DMSO), δ (ppm): 157.3, 135.6, 132.6, 130.6, 114.4, 67.2, 56.5, 52.9, 46.5, 26.4, 18.9, 8.0. MS (TOF), m/e: 933.6 ([M−4Br-3CH$_2$CH$_3$]+, calcd. 933.7).

Example 11

N,N',N'',N'''-[1,2-Tetrakis(1,4-phenoxyethyl)vinyl] tetrakis(triethylammonium bromide) (N+C2-TPE-C2N+)

The synthesis of the below compound was carried out according to Example 6 by using the corresponding dibromoethane.

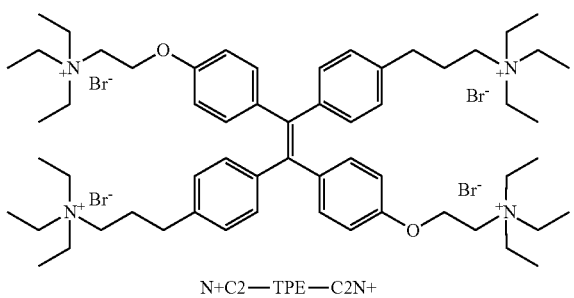

N+C2—TPE—C2N+

Characterization data of BrC2-TPE-C2Br: $^1$H NMR (300 MHz, CDCl$_3$), δ (ppm): 7.71-7.70 (m, 1H), 7.54-7.53 (m, 1H), 7.10-7.07 (d, 4H), 6.93-6.90 (d, 3H), 6.84-6.82 (d, 4H), 6.65-6.63 (d, 3H), 4.28-4.22 (m, 8H), 3.63-3.60 (m, 8H). $^{13}$C NMR (75 MHz, CDCl$_3$), δ (ppm): 156.7, 132.8, 130.0, 115.0, 114.1, 68.0, 29.6. MS (TOF), m/e: 823.9 ([M]+, calcd. 824.2).

N+C2-TPE-C2N+: $^1$H NMR (400 MHz, D$_2$O), δ (ppm): 6.94-6.89 (m, 8H), 6.67-6.65 (m, 4H), 4.24-4.23 (m, 8H), 3.54-3.45 (m, 8H), 3.30-3.25 (m, 16H), 3.10-3.05 (m, 8H), 1.20-1.13 (m, 36H). $^{13}$C NMR (100 MHz, D$_2$O), δ (ppm): 156.2, 138.2, 133.1, 114.5, 98.0, 61.9, 56.0, 54.2, 54.1, 47.4, 9.1, 7.6. MS (TOF), m/e: 1222.5 ([M−2H]+, calcd. 1224.4).

Example 12

N,N',N'',N'''-[1,2-Tetrakis(1,4-phenoxyethyl)vinyl] tetrakis(trimethylammonium bromide) (TTAPE-Me)

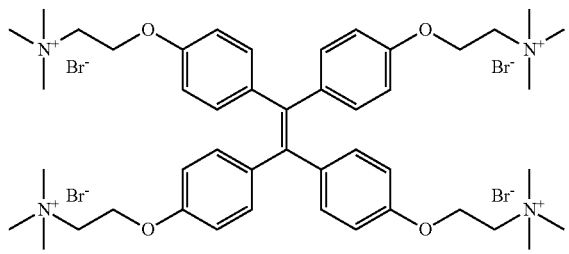

To a mixture of 4,4'-dihydroxybenzophenone (1.0 g, 4.7 mmol) and potassium carbonate (1.3 g, 9.3 mmol) in acetone (50 mL) was added 1,8-dibromooctane (3.8 g, 14.0 mmol). The mixture was refluxed under stirring for 12 h. After filtration and solvent evaporation, the crude product was purified by a silica gel column using chloroform as eluent. 4,4'-bis(8-bromooctyloxy)benzophenone was obtained as white powder in 66% yield (3.10 g). R$_f$=0.5 (chloroform). NMR (400 MHz, CDCl$_3$), δ (ppm): 7.78 (d, 4H), 6.94 (d, 4H), 4.05 (t, 4H), 3.42 (t, 4H), 1.89□1.80 (m, 8H), 1.48-1.39 (m, 16H). $^{13}$C NMR (100 MHz, CDCl$_3$), δ (ppm): 193.9, 161.8, 131.6, 129.9, 113.3, 67.5, 33.3, 32.1, 28.5, 28.4, 28.0, 27.4, 25.3.

In a suspension of 4,4'-bis(8-bromooctyloxy)benzophenone (1.0 g, 1.7 mmol) in 50 mL of THF were added TiCl$_4$ (0.19 mL, 1.7 mmol) and Zn dust (0.22 g, 3.4 mmol). After refluxing for 20 h, the reaction mixture was cooled to room temperature and filtered. The solvent was evaporated under vacuum and the crude product was purified by a silica gel column using a chloroform/hexane (1:1 v/v) mixture as eluent. 1,1,2,2-tetrakis[4-(8-bromooctyloxy)phenyl]-ethene was obtained as yellow viscous liquid in 62% yield (0.6 g). R$_f$=0.5 (chloroform/hexane=1:1). $^1$H NMR (400 MHz, CDCl$_3$), δ (ppm): 6.99-6.90 (m, 8H), 6.63-6.60 (m, 8H), 3.87-3.80 (m, 8H), 3.41-3.39 (m, 8H), 1.86-1.70 (m, 16H), 1.34-1.26 (m, 32H). $^{13}$C NMR (100 MHz, CDCl$_3$), δ (ppm): 157.9, 137.5, 133.2, 129.9, 114.2, 68.3, 55.6, 34.7, 33.4, 29.9, 29.3, 28.7, 26.6.

1,1,2,2-tetrakis[4-(2-trimethylammonioethoxy)-phenyl] ethene tetrabromide (TTAPE-Me was made by quaternization of 1,1,2,2-tetrakis[4-(8-bromooctyloxy)phenyl]-ethene with an excess amount of trimethylamine. Pale yellow powder; 85% yield. $^1$H NMR (400 MHz, D$_2$O), δ (ppm): 7.09 (d, 8H), 6.83 (d, 8H), 4.46 (t, 8H), 3.80 (t, 8H), 3.25 (s, 36H). $^{13}$C NMR (100 MHz, D$_2$O), δ (ppm): 155.4, 139.2, 137.4, 132.3, 113.7, 64.8, 61.6, 53.7. MS (TOF), m/e 855.6561 ([M−2Br-3CH$_3$]$^+$, calcd. 855.6725).

Example 13

4,4'-(1,2-diphenylvinyl)di(phenylboronic acid) (TPE-BA)

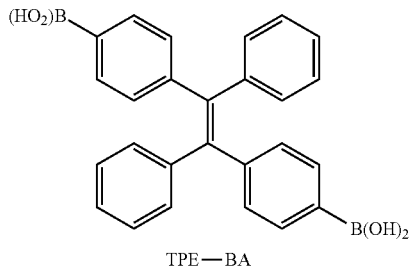

1,2-bis(4-bromophenyl)-1,2-diphenylethene (0.4 g, 0.82 mmol) was dissolved in 20 ml of distilled tetrahydrofuran (THF) in a 100 ml flask, and the flask was placed in an acetone-dry ice bath at –78 C. A solution of 1.0 ml (2.6 mmol) of n-butyllithium (2.5 M in hexane) was added carefully to the mixture under stirring. After 1 h, 0.46 ml (4.0 mmol) of trimethyl borate was added to the solution and allowed to react for 45 min. The mixture was warmed to room temperature and overnight. Then dilute HCl was used to quench the reaction. After filtration and drying, the product was purified by silica gel column with ethyl acetate as eluent. The product was obtained as yellow solid in 54% yield.

Characterization data of TPE-BA: $^1$H NMR (d-MeOH, 300 MHz) δ (ppm): 7.26-7.17 (m, 10H), 7.01-6.94 (m, 4H), 6.73-6.65 (m, 4H); $^{13}$C NMR (d-MeOH, 75 MHz), δ (TMS, ppm): 157.2, 146.2, 141.4, 137.0, 133.9, 132.7, 128.9, 127.4, 115.7; MS (TOF) m/e: 422.2 ([M−2H]+ calcd: 420.1).

Example 14

4,4'-(1,2-diphenylvinyl)di(phenylcarboxylic acid) (TPE-CA)

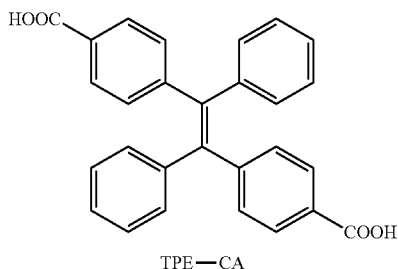

1,2-bis(4-bromophenyl)-1,2-diphenylethene (1 g, 2.04 mmol) was dissolved in 20 ml of distilled tetrahydrofuran (THF) in a 100 ml flask, and the flask was placed in an acetone-dry ice bath at –78° C. A solution of 0.56 ml (6.12 mmol) of n-butyllithium (2.5 M in hexane) was added carefully to the mixture under stirring. The solution was transferred to a 500 ml flask with dry ice in it. The resultant mixture was stirred overnight under nitrogen at room temperature. After evaporation of THF, potassium hydroxide solution was added and the aqueous solution was washed by diethyl ether for several times. 3M hydrochloric acid was used to acidify the aqueous solution. Ethyl acetate was used to extract the product. And the organic layer was dried with MgSO$_4$ to give the product with the yield of 24%.

Characterization data of TPE-CA: $^1$H NMR (d-Acetone, 300 MHz) δ (ppm): 7.99-7.93 (m, 3H), 7.50-7.46 (m, 1H), 7.35-7.28 (m, 9H), 7.25-7.16 (m, 4H), 7.15-7.10 (m, 1H); $^{13}$C NMR (d-Acetone, 75 MHz), δ (TMS, ppm): 166.1, 147.8, 142.4, 142.3, 141.1, 132.6, 130.7, 130.5, 128.8, 128.4, 127.6, 127.3, 126.7, 126.3, 120.0; MS (TOF) m/e: 403.14 ([M-OH]+ calcd: 403.14).

Example 15

1,2-di[4-(aminomethyl)phenyl]-1,2-diphenylethylene (TPE-MA)

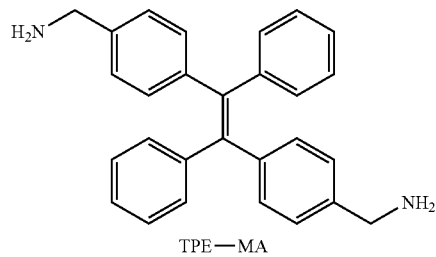

A mixture of 1,2-diphenyl-1,2-dip-tolylethene (TPE-Me, 2 g, 5.6 mmol), NBS (2 g, 11.1 mmol) and a catalyst amount of benzoyl peroxide in carbon tetrachloride (50 ml) was gently refluxed for 8 h in a 150 ml round-bottom flask. After filtration and concentration, the product was isolated and purified by silica gel chromatography using chloroform/hexane (1:4 v/v) as eluent. 1,2-bis(4-(bromomethyl)phenyl)-1,2-diphenylethene (TPE-MB) was obtained as light yellow powder in 45% yield.

A mixture of TPE-MB (0.8 g, 1.5 mmol) and NaN$_3$ (0.1 g, 1.5 mmol) in DMSO (30 ml) was stirred under N$_2$ at room temperature for 18 h. The reaction mixture was added to water (200 ml) slowly, and then extracted with dichloromethane. The combined organic layers were dried with MgSO$_4$ and evaporated to dryness. The crude product was purified by silica gel chromatography eluting with 1:1 chloroform/hexane to give 1,2-bis(4-(azidomethyl)phenyl)-1,2diphenylethene (TPE-MN3) as a white-off solid in 73% yield.

The azido-substituted TPE (TPE-MN3) (0.3 g, 0.7 mmol) was dissolved in dry THF (60 ml) and LiAlH$_4$ (0.15 g, 4.1 mmol) was added slowly at room temperature with constant stirring under nitrogen. Following the addition, the mixture was heated at reflux for 8 h. Water (5 ml-10 ml) was added slowly to decompose the excess LiAlH$_4$. The solution was then filtered and THF was used to wash the solid residue. After evaporation of the organic filtrate, dilute hydrochloric acid was added and the aqueous solution was washed by diethyl ether for several times. Ammonium hydroxide was used to basify the aqueous solution, following the extraction by diethyl ether. The organic layer was dried with Na$_2$SO$_4$ and evaporated to dryness. TPE-MA was obtained as light yellow powder in 87% yield.

Characterization data of TPE-MB: $^1$H NMR (CDCl$_3$, 300 MHz) δ (ppm): 7.14-7.07 (m, 10H), 7.02-6.96 (m, 8H), 4.42-4.40 (d, 4H); $^{13}$C NMR (COCl$_3$, 75 MHz), δ (TMS, ppm): 144.4, 143.9, 141.5, 126.6, 132.3, 132.0, 129.2, 128.5, 127.4, 34.3; MS (TOF) ink: 518.0 ([M]+ calcd: 518.2).

TPE-MN3: $^1$H NMR (CDCl$_3$, 300 MHz) δ (ppm): 7.12-7.07 (m, 6H), 7.04-6.99 (m, 12H), 4.24 (s, 4H); $^{13}$C NMR (CDCl$_3$, 75 MHz), δ (TMS, ppm): 144.4, 143.9, 141.5, 134.1, 132.4, 131.9, 128.5, 128.4, 127.3, 55.2; MS (TOF) m/e: 400.15 ([M−3N]+ calcd: 400.14).

TPE-MA: $^1$H NMR (d-MeOH, 300 MHz) δ (ppm): 7.10-7.06 (m, 10H), 7.00-6.93 (m, 8H), 3.75-3.70 (hr, 4H); $^{13}$C NMR (CDCl$_3$, 75 MHz), δ (TMS, ppm): 143.9, 142.4, 140.7, 131.6, 131.4, 127.8, 127.7, 126.5, 126.4, 30.4; MS (TOF) m/e: 374.1 ([M-NH$_2$]+ calcd: 374.2)

Example 16

1,1'-Bis-[4-(N,N-diethylaminomethyl)phenyl]-2,3,4,5-tetraphenylsilole (A$_2$-HPS) and N,N'-[1,1'-bis(1,4-benzylene)-2,3,4,5-tetraphenylsilolyl)bis(triethylammonium bromide) (HPS-(C1N+)2

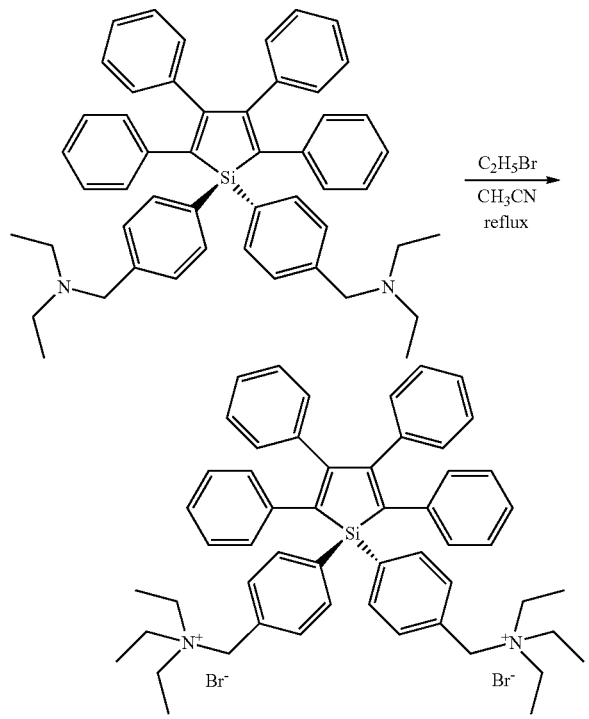

Into a 500 ml round-bottomed flask were added 150 ml THF, 5 ml water, 2.2 g potassium carbonate, 6 ml diethyl amine, and 5 g p-bromobenzyl bromide. The resultant mixture was refluxed for 12 h. The mixture was then cooled to room temperature, into which 6 ml concentrated HCl was added, followed by the addition of 150 ml water. The mixture was extracted with 100 ml diethyl ether for three times. The diethyl ether solution was dried with anhydrous magnesium sulfate over night and then the magnesium sulfate was removed by filtration. Diethyl ether was evaporated and the raw product was purified by a silica gel column using hexane/chloroform mixture (1:1 by volume) as the eluent. (p-bromobenzyl)diethyl amine (BBDA) was obtained in 74% yield (3.6 g).

Into a solution of tolan (5 g, 28 mmol) in THF (25 ml) was added under dry nitrogen lithium shaving (0.214 mg, 31 mmol). The mixture was stirred for 12 h at room temperature and the resultant green-blue colored THF solution was added dropwise to a solution of tetrachlorosilane (1.61 ml, 14 mmol) in 125 ml THF. The reaction mixture was stirred for 2 h at room temperature and then refluxed for 5 h.

Into another flask were added BBDA (6.8 g, 28 mmol) and 80 ml THF. The mixture was cooled to –78° C., into which 10 ml n-BuLi (2.5 M in hexane) was added. After stirring for 1.5 h, the mixture was transferred dropwise at –78° C. to the solution of chlorosilole (preparation shown in previous patent). The reaction mixture was allowed to warm to room temperature and was then stirred overnight at that temperature. Then THF was removed by evaporation, and the crude product was dissolved in diethyl ether. The solution was washed three times by water. The crude product was purified by a silica gel column using chloroform as the eluent at first and changed to ethyl acetate when no by product came out. The product A$_2$-HPS was obtained in 28% yield after recrystallization from acetone/ethanol mixture.

Characterization data of BBDA: $^1$H NMR (CDCl$_3$, 300 MHz) δ (ppm): 7.40 (d, 2H), 7.23 (d, 2H), 3.51 (5.2H), 2.50 (m, 4H), 1.04 (m, 6H).

A$_2$-HPS: $^1$H NMR (CDCl$_3$, 300 MHz) δ (ppm): 7.56 (d, 2H), 7.32 (d, 2H), 7.05-6.75 (m, hr, 20H), 3.55 (s, 4H), 2.54 (m, 8H), 1.04 (m, 12H). $^{13}$C NMR (75 MHz, CDCl$_3$), δ (TMS, ppm): 156.6, 142.3, 140.0, 139.9, 139.0, 136.2, 130.2, 129.8, 129.0, 127.9, 127.6, 126.5, 125.7, 57.8, 47.2, 12.1. MS (CI): m/e calcd. For C$_{50}$H$_{52}$N$_2$Si, 708.4. found 709.4 (M+). UV (THF, 4.0×10$^{-5}$ mol/L), λ$_{max}$ (nm): 364. Melting point: 119-120° C.

HPS-(C1N+)$_2$ was obtained by refluxing A$_2$-HPS together with bromoethane in acetonitrile.

Example 17

1,1'-methyl-2,5-bis[4-(1-sulfonatopropyl-2-isoindole)ethenephenyl]-3,4-bisphenyl silole (Cy2Silole)

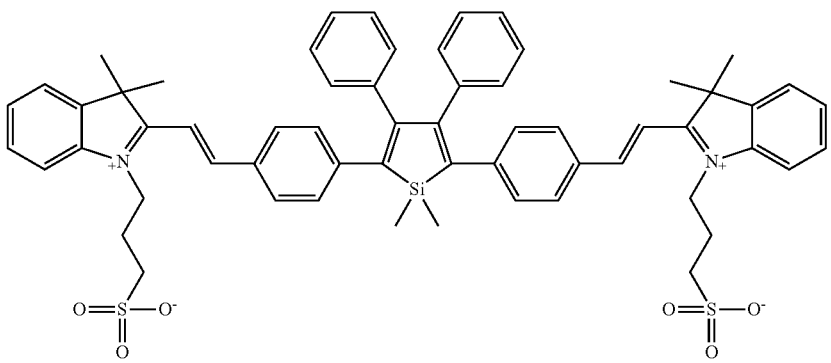

Cy$_2$Silole

To a THF solution of phenylacetylene (4.0 mL, 36.4 mmol) was added n-BuLi (25.0 mL, 40.1 mmol, 1.6 M solution in hexane) at −78° C. After stirring at −78° C. for 4 h, dichlorodimethylsilane (2.2 mL, 18.2 mmol) was added. The mixture was warmed to room temperature and stirred overnight. The solvent was removed under reduced pressure. The mixture was dissolved in DCM and washed with brine and water. The organic layer was dried over magnesium sulfate. The crude product was purified by a silica-gel column using hexane as eluent. A colorless solid was obtained in 86.1% yield. $^1$H NMR (400 MHz, CDCl$_3$), (δ (ppm): 7.57 (m, 4H), 7.36 (m, 6H), 0.55 (s, 6H). $^{13}$C NMR (100 MHz, CDCl$_3$), δ (ppm): 132.1, 128.9, 128.2, 122.6, 105.9, 90.6, 0.45. HRMS (MALDI-TOF), m/z 260.1013 (M$^+$, calcd 260.1021).

A mixture of lithium (0.056 g, 8 mmol) and naphthalene (1.04 g, 8 mmol) in 8 mL of THF was stirred at room temperature under nitrogen for 3 h to form a deep dark green solution of LiNaph. The viscous solution was then added dropwise to a solution of the above product (0.52 g, 2 mmol) in 5 mL of THF over 4 min at room temperature. After stirring for 1 h, the mixture was cooled to 0° C. and then diluted with 25 mL THF. A black suspension was formed upon addition of ZnCl$_2$·TMEDA (2 g, 8 mmol). After stirring for an additional hour at room temperature, a solution of 4-bromobenzaldehyde (0.78 g, 4.2 mmol) and PdCl$_2$(PPh$_3$)$_2$ (0.08 g, 0.1 mmol) in 25 mL of THF was added. The mixture was refluxed overnight. After cooled to room temperature, 100 mL of H$_2$O was added and the mixture was extracted with DCM. The combined organic layer was washed with brine and water and then dried over magnesium sulfate. After solvent evaporation under reduced pressure, the residue was purified by a silica-gel column using gradient DCM/hexane (50:50 to 100:0 v/v) as eluent. The product was obtained as a yellow solid in 65.4% yield (0.62 g, 1.3 mmol). $^1$H NMR (400 MHz, CDCl$_3$), δ (TMS, ppm): 9.89 (s, 2H), 7.65 (d, 4H), 7.10-6.98 (m, 10H), 6.78 (d, 4H), 0.51 (s, 6H). $^{13}$C NMR (100 MHz, CDCl$_3$), δ (TMS, ppm): 191.7, 155.8, 146.6, 142.2, 137.6, 133.7, 129.7, 129.6, 129.1, 127.6, 126.9, −4.1. HRMS (MALDI-TOF): m/z 470.1750 (M$^+$, calcd 470.1702).

The above compound (0.23 g, 0.48 mmol) was dissolved and refluxed in 25 mL of anhydrous ethanol under nitrogen. After it was completely dissolved, 0.53 mL (5.8 mmol) of aniline was added and further refluxed overnight. After cooled by ice water, a lot of precipitates were formed and filtered out. The residue was washed twice by cold ethanol and vacuum-dried without further purification. The product was obtained as a yellow solid in 80.5% yield (0.24 g, 0.39 mmol). $^1$H NMR (400 MHz, CDCl$_3$), δ (TMS, ppm): 8.36 (s, 2H), 7.67 (d, 4H), 7.37 (t, 4H), 7.21 (t, 2H), 7.17 (d, 4H), 7.08-6.99 (m, 10H), 6.83 (d, 4H), 0.51 (s, 6H). $^{13}$C NMR (100 MHz, CDCl$_3$), δ (TMS, ppm): 160.1, 155.1, 152.2, 143.4, 142.0, 138.3, 133.6, 129.9, 129.2, 129.1, 128.6, 127.6, 126.6, 125.8, 120.8, −3.9. HRMS (MALDI-TOF): m/z 621.2725 ([M+H]$^+$, calcd 621.2726).

The previous compounds (0.16 g, 0.25 mmol) and (0.18 g, 0.6 mmol) were vacuum-dried and refilled with nitrogen for three times. Afterwards, 25 mL freshly distilled THF and 5 mL of Ac$_2$O were injected to the mixture and refluxed for overnight. After cooled to room temperature, the solvents were evaporated under reduced pressure. The residues were extracted by chloroform and water. The organic layer was further washed with brine and water and dried over magnesium sulfate. After solvent evaporation, the crude product was purified by a silica-gel column using gradient chloroform/methanol (v/v from 90:10 to 0:100) mixture as eluent. Red solids Silo-Cy and Silo-2Cy were obtained in 57.9% and 34.5% yields, respectively.

Characterization Data of Cy$_2$Silo.

$^1$H NMR (400 MHz, CD$_3$OD), δ (TMS, ppm): 8.38+8.35 (s+d, 2H), 7.90 (d, 4H), 7.87 (m, 2H), 7.75 (m, 2H), 7.68-7.58 (m, 6H), 7.16 (d, 4H), 7.10-7.00 (m, 6H), 6.85 (dd, 4H), 4.68 (t, 4H), 2.91 (t, 4H), 2.15 (p, 4H), 1.98 (p, 4H), 1.83 (s, 12H), 0.55 (s, 6H). $^{13}$C NMR (100 MHz, CD$_3$OD), δ (TMS, ppm): 183.6, 158.0, 156.2, 147.5, 145.2, 144.0, 142.2, 139.5, 133.5, 131.8, 131.0, 130.9, 130.6, 128.9, 128.1, 124.1, 116.2, 112.5, 53.9, 51.2, 47.8, 28.2, 26.7, 23.3, −4.0. HRMS (MALDI-TOF): m/z 1026.4275 ([M+2H]$^+$, calcd 1026.4132); 1048.4103 ([M+H+Na]$^+$, calcd 1048.3951).

Example 18

Fluorimetric titration of biomacromolecules to polyenes Bovine serum albumin (BSA) and calf *thymus* DNA (ctDNA) were selected as model proteins and DNA. BSA was dissolved in a pH 7.0 phosphate buffer solution (1.0 mg/ml). DNA was dissolved in deionized water (1.0 mg/ml) and filtered through a 0.45 μm filter. The actual concentration (in nucleic base) was determined by UV photometry using the extinction coefficient $\epsilon_{260}$=6600 M$^{-1}$ cm$^{-1}$.

Stock solutions of polyenes were 5×10$^{-4}$ M in water. Fluorescence titration was carried out by sequentially adding 100 μl aliquots of DNA or BSA solutions to a 100 μl stock solution of polyenes, followed by adding an aqueous phosphate buffer (10 mM, pH 7) to acquire a 10.00 ml solution. The mixtures were stirred for half an hour prior to taking their spectra. See FIGS. 1-10 and Table 1 below.

TABLE 1

Photophysical Properties of TPEs in Solution (soln),[a] Aggregate (aggr),[b] and Binding (bind)[c] States

| TPE | $\lambda_{ab}$, nm[d] | | $\lambda_{ex}$, nm ($\Phi_F$, %)[e] | | |
|---|---|---|---|---|---|
| | soln | aggr | soln | aggr | bind |
| TPE-OMe | 311 | 330 | 394 (0.11) | 477 (15.30) | |
| TPE-OH | 312 | 316 | 393 (0.57) | 439 (8.90) | 467 (35.7) |
| TPE-SO3 | 312 | 320 | 398 (0.37) | 442 (17.47) | 472 (58.2) |

[a]In acetonitrile for TPE-OMe and TPE-OH (10 μM); in water for TPE-SO3 (5 μM).
[b]In 99% water/AN mixture for TPE-OMe and TPE-OH; in 99% AN/water mixture for TPE-SO3.
[c]In BSA solution of TPE-OH·Na$_2$ or TPE-SO3 in an aqueous phosphate buffer with pH = 7.0.
[d]Absorption maximum.
[e]Emission maximum (quantum yield given in the parentheses); excitation wavelength: 350 nm.

Example 19

Comparison of water soluble and non-water soluble tetraphenylethylene derivatives in this example, a group of AIE-active TPE derivatives, i.e., derivatives 1-4 below, were synthesized and water-soluble cationic salts 3 and 4 were evaluated for their utility as bioprobes. In aqueous buffer solutions, these non-emissive fluorophores become highly emissive upon binding to protein and DNA molecules through noncovalent, such as hydrophobic and electrostatic, interactions.

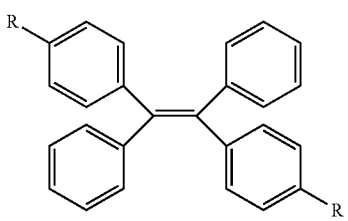

Derivative 1: R is —O(CH$_2$)$_2$Br
Derivative 2: R is —O(CH$_2$)$_4$Br
Derivative 3: R is —O(CH$_2$)$_2$N$^+$(C$_2$H$_5$)$_3$Br$^-$
Derivative 4: R is —O(CH$_2$)$_4$N+(C$_2$H$_5$)$_3$Br$^-$ The TPE derivatives were prepared by the synthetic route as described herein. Reactions of 1,2-bis(4-hydroxyphenyl)-1,2-diphenylethene with α,ω-dibromoalkanes in the presence of sodium hydride yielded TPEs 1 and 2, whose quaternizations by Net$_3$ gave salts 3 and 4, respectively. Molecular structures of the TPEs were characterized by spectroscopic techniques, from which satisfactory analysis data were obtained. Dyes 1 and 2 are soluble in common organic solvents such as acetonitrile (AN), chloroform and THF but insoluble in water. Salts 3 and 4, on the other hand, are soluble in water as well as in DMF and DMSO.

Figure 11A:
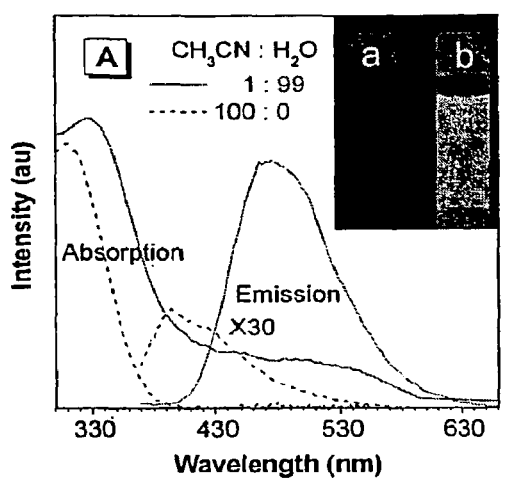
FIG. 11A illustrates the absorption and emission spectra of solutions of derivative 1 (10 µM) in AN and AN-water mixture (1:99 v/v). The inset is photographs of solutions of derivative 1 in (a) AN and (b) the AN-water mixture taken under illumination of a UV lamp.

Dilute solutions of TPEs 1 and 2 in AN are practically non-luminescent. Addition of non-solvent water into the AN solutions can turn on the emissions of the dyes. From the molecular solution in AN to the aggregate suspension in an AN-water mixture (1:99 by volume), the fluorescent intensity of TPE 1 at 476 nm is increased by ~240 fold (FIG. 11A). Its absorption maximum shifts from 310 nm in the solution to 330 nm in the suspension. The excitation maximum of TPE 1 locates at 330 nm, coinciding well with its absorption maximum. The formation of nanoscopic aggregates of TPE 1 is suggested by the level-off tail in the visible region of its absorption spectrum due to the Mie effect of the nanoparticles. Evidently, the emission of TPE 1 is induced by the aggregate formation, or in other words, TPE 1 is AIE-active.

Figure 11B:
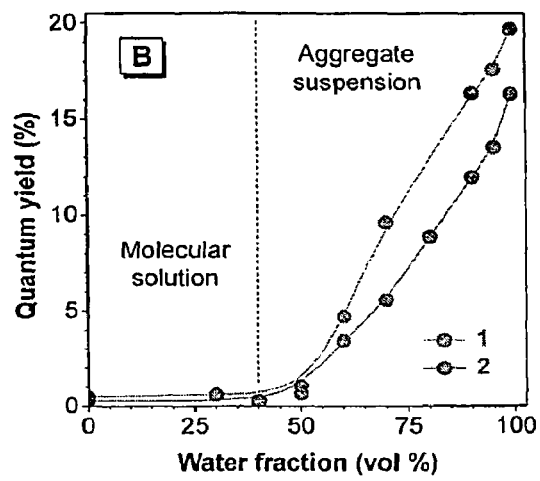
FIG. 11B illustrates the dependence of fluorescence quantum yields of solutions of derivatives 1 and 2 on the solvent composition of AN-water mixture $\lambda_{ex}$=350 nm.

The change of $\Phi_F$ value of TPE 1 with water fraction in the AN-water mixture further reveals its AIE characteristics (FIG. 11B). In the mixtures with water fractions below ~40%, TPE 1 exhibits negligibly small $\Phi_F$ values (~0.5%) because the dye molecules are actually dissolved in the mixtures. The $\Phi_F$ value of TPE 1 starts to increase when the water fraction is increased to ~50%, at which the solvating power of the mixture is decreased to such an extent that the dye molecules begin to aggregate. The $\Phi_F$ value reaches ~20% at a water content of 99%, which is ~40-fold higher than that of its AN solution. The absolute $\Phi_F$ values of the aggregates should be much higher than the relative $\Phi_F$ values given in FIG. 11B, because the determination of the latter did not take into consideration the strong absorption caused by the Mie effect of the aggregates. TPE 2 exhibits similar AIE behavior. TPE Salts 3 and 4 are soluble in water. Addition of methanol, AN, THF and dioxane to their water solutions do not cause the salts to aggregate, possibly due to their amphiphilic nature. Their emissions in the mixtures remain as faint as those in the water solutions. However, increasing the concentrations of the salts can increase their $\Phi_F$ values, indicating that the salts are also AIE-active.

Complexation of the water-soluble AIE TPEs 3 and 4 with calf *thymus* DNA (ctDNA) and bovine serum albumin (BSA) were investigated by spectrometric titrations in aqueous phosphate buffer (pH=7.0) at 25 C. Stock solutions of TPEs 3 and 4 (0.25 mM) were prepared. The mixture of 100 μl stock solution of 3 with 9.9 ml buffer emits faintly at 395 nm with a side band at 462 nm. Its absorption maximum locates at 311 nm, with a molar absorptivity of 12400M$^-$1 cm$^-$1. Upon addition of the DNA, FL intensity of TPE 3 increased by 5.4 fold. Meanwhile its emission maximum shifted to ~462 nm, giving a Stokes shift as large as 134 nm. In the DNA concentration range of 0-100 μg/ml$^{-1}$, the plot of the FL intensity (1) at 462 nm as a function of DNA concentration (c) is a linear line with a correlation coefficient of 0.996. Addition of BSA to a buffer solution of TPE 3 induced a similar effect. The linear range of the I/I$_O$–1 vs. c plot in this case is 0-50 μg/ml$^{-1}$. The excitation maximums of the solutions of TPE3 containing BSA and ctDNA both locate at 328 nm.

The effects of the biopolymers on the FL properties of TPE 4 are much more pronounced. As can be seen from FIG. 12, I/I$_o$ values as high as 16.3 and 23.8 are achieved when 300 μg/ml$^{-1}$ ct DNA and 500 μg/ml$^{-1}$ BSA are added into solutions of TPE 4, respectively. Clearly TPE 4 is a more sensitive bioprobe. The excitation maximum of TPE 4 is at 328 nm and the Stokes shift is ~135 nm. The linear ranges of TPE 4 are narrower: 0-20 μg/ml$^{-1}$ for DNA and 0-40 μg/ml$^{-1}$ for BSA. It is clear that the AIE salts TPEs 3 and 4 can be used as light-up bioprobes for DNA and protein detection. The probing sensitivity and linear range can be tuned by modifying their structures.

Regarding the origin of the emission induced by the addition of the biomacromolecules, the correlation with the AIE nature of the dyes must be considered. In both cases, similar shifts in the fluorescent maximums (from 390-399 nm to 463-478 nm) are observed. The excitation spectra of the biopolymer-induced emissions are also similar to those of the AIEs for the TPE derivatives. These facts lead to a natural conclusion that the strong blue emissions are from the same excited species.

It appears that the restriction of intramolecular rotations in the aggregates of AIE dyes may have blocked their nonradiative channels, thus making them highly emissive. If the AIE process of the TPE dyes follows the same mechanism, they should become emissive in the solutions with high viscosities at low temperatures, because under these conditions their intramolecular rotations would be hampered. The fluorescent behaviors of TPE 4 were thus investigated in a highly viscous glycerol-water (99:1 by volume) mixture at different temperatures. At 25° C., the glycerol-water solution of TPE 4 emits a strong blue light of 467 nm with a Stokes shift of 147 nm (FIG. 13), demonstrating that the high viscosity indeed helps. As the solution temperature is decreased from 25 to –5° C., the FL intensity of TPE4 is increased as expected. Its excitation maximum locates at 328 nm, close to those of its nanoscopic aggregates and its complexes with the biopolymers.

Dynamic NMR experiments of a dichloromethane solution of 1 reveals that its resonance peaks are broadened with a decrease in temperature. The plot of $\delta_{fwhm}$ vs. 1/T gives a linear line, indicating a single mechanism for the peak broadening. All these results confirm that the restriction of intramolecular rotations plays a crucial role in the AIE process. The emissions of the TPE salts can thus be turned on by the addition of the biomacromolecules. In the buffer solutions containing the DNA and BSA, the cationic amphiphilic dyes bind to the biomacromolecules via noncovalent interactions, such as electrostatic attraction (especially for the negative-charged DNA) and hydrophobic effect (particularly for the protein with hydrophobic pockets in its native folding structure). When docked on the surfaces of the biopolymers and in the cavities of their folding structures, the dye molecules aggregate with the aid of strong electronic and hydrophobic interactions between their aryl rings. This suppresses intramolecular rotations of the dye molecules, which in turn impedes their radiationless transitions and activates their fluorescent processes. Thanks to the AIE nature, the emissions of the TPE-biopolymer complexes are greatly intensified with increasing concentration, for the TPE 4-BSA complex. This is truly remarkable, because conventional fluorescent probes suffer from the ACQ problem at high dye concentrations. In summary, in this example, AIE active, water-soluble, conjugated polyene compounds (cationic dyes) have been developed herein for protein and DNA detection in aqueous media for the first time. The nonemissive dye solutions become emissive upon addition of the biomacromolecule, for example, DNA and/or BSA. These AIE compounds exhibit large molar absorptivities, high quantum yields and wide Stokes shifts and are thus ideal "turn-on" fluorescent bioprobes. The restriction of their intramolecular rotations plays a critical role in their AIE processes. Accordingly, any molecule whose electronic conjugation is affected by the twisting of multiple pendants around its core due to involved steric effects can be AIE active. This example demonstrates that AIE luminophors can be utilized as fluorescent probes in the area of biological research.

Example 20

Synthesis of 4,4'-(1,2-diphenylvinyl)di(phenylcarboxylic acid) (TPE-COOH)

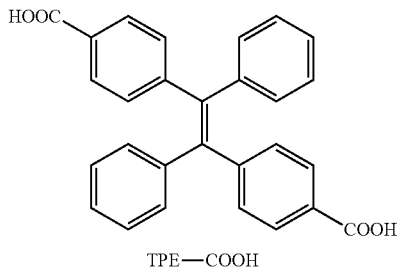

TPE—COOH

The scheme of the synthesis of TPE-COOH is shown in Scheme 1 above. 1,2-bis(4-bromophenyl)-1,2-diphenylethene (1 g, 2.04 mmol) was dissolved in 20 ml of distilled tetrahydrofuran (THF) in a 100 ml flask, and the flask was placed in an acetone/dry ice bath at −78 C. A solution of 0.56 ml (6.12 mmol) of n-butyllithium (2.5 M in hexane) was added carefully to the mixture under stirring. The solution was transferred to a 500 ml flask with dry ice in it. The resultant mixture was stirred overnight under nitrogen at room temperature. After evaporation of THF, potassium hydroxide solution was added and the aqueous solution was washed by diethyl ether for several times. 3 M hydrochloric acid was used to acidify the aqueous solution. Ethyl acetate was used to extract the product. And the organic layer was dried with $MgSO_4$ to give the product with the yield of 24%.

Characterization data of TPE-COOH: $^1$H NMR (d-Acetone, 300 MHz) δ (ppm): 7.99-7.93 (m, 3H), 7.50-7.46 (m, 1H), 7.35-7.28 (m, 9H), 7.25-7.16 (m, 4H), 7.15-7.10 (m, 1H); $^{13}$C NMR (d-Acetone, 75 MHz), δ (TMS, ppm): 166.1, 147.8, 142.4, 142.3, 141.1, 132.6, 130.7, 130.5, 128.8, 128.4, 127.6, 127.3, 126.7, 126.3, 120.0; MS (TOF) m/e: 403.14 ([M-OH]+ calcd: 403.14).

Figure 14:
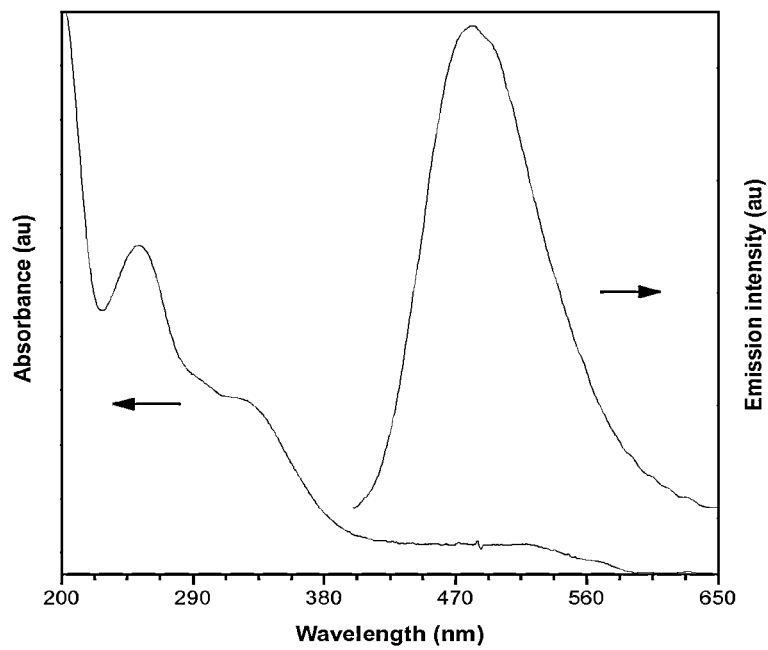
FIG. 14 illustrates the absorption and photoluminescence spectra of TPE-COOH in acetonitrile/water mixture (1:99 v/v). TPE-COOH concentration: 10 µM; excitation wavelength: 346 nm.

The absorption and photoluminescence spectra of the dye in acetonitrile/water mixture (1:99 v/v) are shown in FIG. 14. When it is molecularly dissolved in acetonitrile, it is practically nonfluorescent. However, when large amount of water (insoluble to TPE-COOH yet miscible with acetonitrile) is added, bright cyan light (~480 nm) is observed. The emission becomes stronger with an increase in water content, suggesting that TPE-COOH is AIE-active.

Example 21

Synthesis of 1,2-Bis(4-hydroxyphenyl)-1,2-diphenylethylene (TPE-OH)

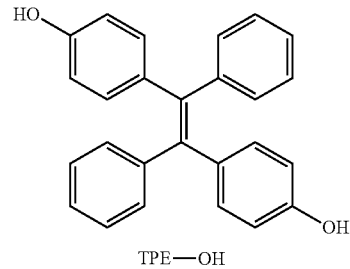

TPE—OH

A suspension of p-methoxybenzophenone (1.06 g, 5.0 mmol), 1.34 equiv of $TiCl_3/AlCl_3$ (5.81 g, 6.7 mmol), and 25 equiv of Zn dust (8.01 g, 122.0 mmol) in 100 ml of dry THF was refluxed for 20 h. The reaction mixture was cooled to room temperature and filtered. The filtrates were evaporated and the crude product was purified by a silica gel column using hexane as eluent. 1,2-Bis(4-methoxyphenyl)-1,2diphenylethene (TPE-OMe) was isolated in 91% yield.

TPE-OMe (1.40 g, 3.56 mmol) was dissolved in 20 ml of dichloromethane (OCM) in a 100 ml flask, and the flask was placed in an acetone-dry ice bath at −78° C. A solution of 3.59 g (14.3 mmol) of boron tribromide in 10 ml of DCM was added carefully to the mixture under stirring. The resultant mixture was allowed to warm to room temperature overnight under stirring. The reaction product was hydrolyzed by careful shaking with 20 ml of water. The organic phase was separated and concentrated by a rotary evaporator. The crude product was purified by recrystallization from THF/methanol to afford a white solid in 97% yield.

Characterization data of TPE-OMe: $^1$H NMR ($CDCl_3$, 300 MHz) δ (ppm): 7.10-7.06 (m, 10H), 6.93 (t, 4H), 6.64 (t, 4H), 3.74 (s, 6H). $^{13}$C NMR ($CDCl_3$, 75 MHz) δ (ppm): 158.0, 144.4, 139.7, 136.5, 132.6, 131.5, 127.8, 126.3, 113.2, 55.2. MS (TOF) m/e: 392.1 (M+, calcd. 392.2).

Characterization data of TPE-OH: $^1$H NMR ($COCl_3$, 300 MHz) δ (ppm): 7.11-7.02 (m, 10H), 6.88 (t, 411), 6.56 (d, 4H). $^{13}$C NMR ($CDCl_3$, 75 MHz) δ (ppm): 154.1, 144.2, 139.7, 135.5, 132.8, 131.5, 127.8, 126.3, 114.7. MS (TOF) m/e: 363.1 [(M−H)+, calcd: 363.1].

Example 22

N,N',N'',N'''-[1,2-Tetrakis(1,4-phenoxyethyl)vinyl] tetrakis(triethylammonium bromide) (N+C2-TPE-C2N+)

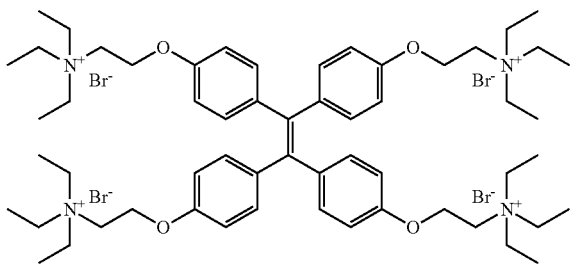 [SMILES: CC[N+](CC)(CC)CCOc1ccc(C(=C(c2ccc(OCC[N+](CC)(CC)CC)cc2)c2ccc(OCC[N+](CC)(CC)CC)cc2)c2ccc(OCC[N+](CC)(CC)CC)cc2)cc1 ; [Br-] ; [Br-] ; [Br-] ; [Br-]]

THF (Labscan) was purified by distillation from sodium benzophenone ketyl under nitrogen immediately prior to use. DHBP, titanium(IV) chloride, zinc dust, 1,2-dibromoethane, potassium carbonate, acetone, triethylamine, and other reagents were all purchased from Aldrich and used as received.

$^1$H and $^{13}$C NMR spectra were measured on a Bruker ARX 300 spectrometer with tetramethyl 1silane (TMS; δ=0) as the internal standard. Mass spectra were recorded on a Finnigan TSQ 7000 triple quadrupole spectrometer operating in a MALDI-TOF mode. UV spectra were measured on a Milton Roy Spectronic 3000 Array spectrophotometer and FL spectra were recorded on a Perkin-Elmer LS 55 spectrofluorometer with a Xenon discharge lamp excitation. Time dependent FL signals were measured using a FluostarOptima multifunctional microplate reader (BMG Labtechnologies) with excitation/emission wavelengths set at 350/470 nm. CD spectra were recorded on a Jasco J-810 spectropolarimeter in 1 mm quartz cuvette using a step resolution of 0.2 nm, a scan speed of 100 nm/min, a sensitivity of 0.1°, and a response time of 0.5 s. Each spectrum was the average of three scans.

The synthetic route to TTAPE is shown in FIG. 49. McMurry coupling of BBEBP yields TBEPE, quaternization of which by triethylamine generates TTAPE. Detailed experimental procedures for the dye synthesis are given below.

To a mixture of DHBP (3.0 g, 14.0 mmol) and potassium carbonate (5.0 g, 36.2 mmol) in acetone (50 ml) was added 1,2-dibromoethane (4 ml, 46.4 mmol). The mixture was refluxed under stirring for 24 h. After filtration and solvent evaporation, the crude product was purified by a silica gel column using chloroform as eluent. BBEBP was obtained as white powder in 70% yield (4.20 g). $R_f$=0.6 (chloroform); $^1$H NMR (300 MHz, CDCl$_3$, 25° C., TMS): δ8=3.68 (t, 4H; BrCH$_2$), 4.38 (t, 4H; OCH$_2$), 6.97 (d, 4H, J=9.0 Hz; Ar), 7.78 ppm (d, 4H, J=9.0 Hz; Ar); $^{13}$C NMR (75 MHz, CDCl$_3$, 25° C., TMS): δ=29.3, 68.6, 114.8, 115.8, 131.9, 133.0, 162.0 ppm.

In a suspension of BBEBP (1.0 g, 2.3 mmol) in 50 ml of THF were added TiCl$_4$ (0.26 ml, 2.3 mmol) and Zn dust (0.31 g, 4.6 mmol). After refluxing for 20 h, the reaction mixture was cooled to room temperature and filtered. The solvent was evaporated under vacuum and the crude product was purified by a silica gel column using a chloroform/hexane (1:4 v/v) mixture as eluent. TBEPE was obtained as white solid in 63% yield (0.606 g). $R_f$=0.7 (chloroform/hexane=1:4); NMR (300 MHz, CDCl$_3$, 25° C., TMS): δ=3.63 (t, 8H; BrCH$_2$), 4.23 (t, 8H; OCH$_2$), 6.66 (d, 8H, J=8.7 HZ; Ar); 6.93 ppm (d, 4H, J=8.7 Hz; Ar); $^{13}$C NMR (75 MHz, CDCl$_3$, 25° C., TMS): δ=29.8, 68.3, 114.5, 133.3, 138.0, 139.1, 157.0 ppm; MALDI-TOF-MS m/z: calcd for $C_{34}H_{32}Br_4O_4^+$: 823.8993. found 823.8688 ([M]+).

In a 250 ml flask with a magnetic stirrer was dissolved TBEPE (100 mg, 0.12 mmol) in THF (100 ml). After adding an excess amount of triethylamine (5 ml, 35.6 mmol), the solution was refluxed for 3 days. During the period, 10 ml of water was added at several intervals. The organic solvents were evaporated under reduced pressure and the aqueous solution was washed with chloroform three times. After solvent evaporation and drying overnight in vacuo at 50° C., TTAPE was isolated as yellow viscous liquid in 56% yield (0.089 g). $^1$H NMR (400 MHz, D$_2$O, 25° C., TMS): δ=1.13-1.20 (m, 36H; NCH$_2$CH$_3$), 3.25-3.30 (m, 24H; NCH$_2$CH$_3$), 3.45-3.54 (m, 8H; OCH$_2$CH$_2$N), 4.23-4.24 (m, 8H; OCH$_2$CH$_2$N), 6.65-6.67 (m, 8H; Ar), 6.89-6.94 ppm (m, 8H; Ar); $^{13}$C NMR (75 MHz, D$_2$O, 25° C., TMS): δ=7.4, 47.2, 54.2, 61.8, 114.5, 133.0, 138.0, 139.5, 156.2 ppm; MALDITOF-MS m/z: calcd for $C_{58}H_{92}Br_4N_4O_4^+$ [M−2Br]$^+$: 1066.5485. found 1066.5359 ([M−2Br]$^+$).

Example 23

Sodium 1,2-bis[4-(3-sulfonatopropoxyl)phenyl]-1,2-dicyanoethene (3)

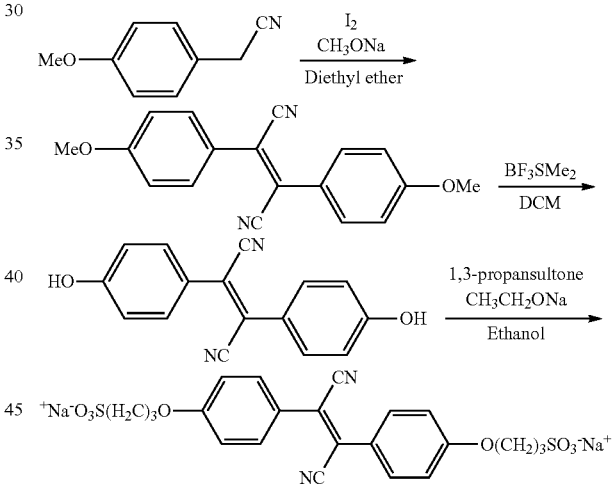

To prepare 2,3-bis(4-methoxyphenyl)fumaronitrile (1), 4-methoxyphenylacetonitrile (3.679 g, 25 mmol) and iodine (6.345 g, 25 mmol) were dissolved in 100 mL diethyl ether under nitrogen atmosphere in a 250 mL three-necked round bottom flask. The solution mixture was cooled to −78° C. Sodium methoxide (2.836 g, 52.5 mmol) in 30 mL methanol was added into the solution mixture dropwise over half an hour. The resulting mixture was warmed to 0° C. for 4 hrs and quenched by 75 mL 3% v/v HCl solution. The precipitate was filtered and washed with water, sodium meta bisulfite, water and ethanol respectively. The crude product was purified by recrystallization by DCM and ethanol to yield greenish yellow crystal. $^1$H NMR (CDCl$_3$, 300 MHz), (TMS, ppm): 3.885 (s, 6H), 6.988-7.039 (d, 4H), 7.770-7.820 (d, 4H). $^{13}$C NMR (CDCl$_3$, 75 MHz), (TMS, ppm): 56.2, 115.3, 118.0, 123.4, 125.3, 131.1, 162.7.

To prepare sodium 1,2-bis[4-(3-sulfonatopropoxyl)phenyl]-1,2-dicyanoethene (3), (1) (0.2903 g, 1 mmol) was dissolved in 10 mL distilled DCM under $N_2$ atmosphere in a 50 mL two-valves round bottom flask. Boron trifluoride methyl sulfide complex (5.26 mL, 50 mmol) was added into the solution slowly. The resulting mixture was stirred at ambient temperature overnight. The solution was concentrated under a stream of $N_2$ and partitioned between 1 M HCl and ethyl acetate. The combined organic later were washed with $H_2O$ and brine, dried over $Na_2SO_4$ and concentrated to give 2,3-bis(4-hydroxyphenyl)fumaronitrile (2) without further purification.

Freshly prepared (2) was then dissolved in 20 mL anhydrous ethanol under $N_2$ atmosphere in a 100 mL three necked round bottom flask. A solution of sodium ethanoxide (0.2 g, 3.0 mmol) in 20 mL ethanol was added into the mixture dropwise over half an hour. The orange red solution was stirred for 1 hr at room temperature. 1,3 propansultone (0.35 g, 2.9 mmol) in 20 mL ethanol was added into the mixture and stirred 12 hrs. The precipitate was filtered and washed with ethanol. The crude product was purified by recrystallization using water and acetone. $^1H$ NMR (D20, 300 MHz), (TMS, ppm): 2.15-2.25 (m, 4H), 2.94-3.07 (m, 4H), 4.10-4.14 (m, 4H), 7.02-7.04 (d, 4H), 7.67-7.76 (d, 4H). $^{13}C$ NMR ($D_2O$, 75 MHz), (TMS, ppm): 24.2, 47.8, 66.7, 115.2, 117.4, 122.8, 124.5, 130.5, 160.8.

Example 24

Preparation of Fluorescent Polymer Particles

Into a 50 ml dropping funnel was dissolved 0.1 wt % TPE-COOH in a monomer mixture of methyl methacrylate, butyl acrylate and 2-hydroxyethylmethacrylate, with the volume ratio of 4:5:1. The solution was purged with nitrogen for 20 min and then added dropwise into the deionized water containing the emulsifier sodium dodecyl sulfate (0.2 wt %). The emulsion copolymerization proceeds at 75° C. under 400 rpm agitation for 6-10 h then stops by cooling.

Figure 15:
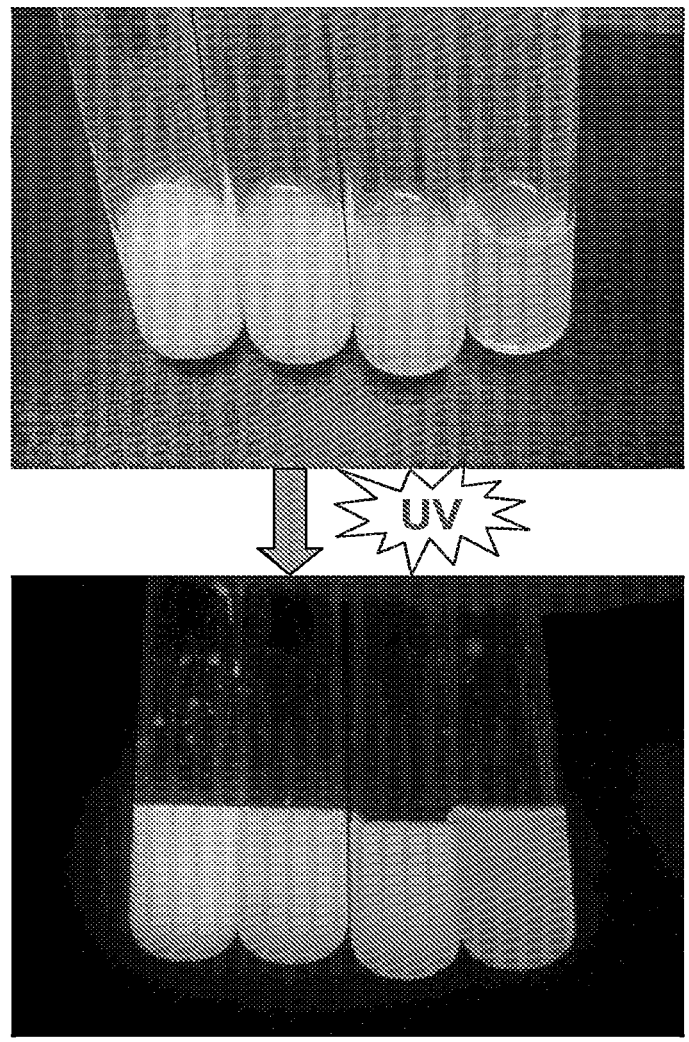
FIG. 15 illustrates the light emission of the fluorescent polymer particle dispersion of Example 24 with various dilutions: 100%, 20%, 5%, 1% (from left to right).

The polymer particle dispersion prepared is quite uniform and stable. The particle dispersion is highly emissive under UV irradiation, even in very dilute state (FIG. 15). It is worthy of noting that the emission of emulsion does not fade even when it is stored for several months under ambient temperature without any protection from light and air. This is due to the high stability of TPE molecules, which is distinctly different from other dye molecules that are prone to be bleached under room illumination.

Example 25

Preparation of Fluorescent Polymer Particles

The procedures are just the same as in Example 24, except that the ratio of TPE-COOH decreases to 0.05 wt % relative to the monomer mixture of methyl methacrylate, butyl acrylate and 2-hydroxyethyl methacrylate (4:5:1 in volume).

Figure 16:
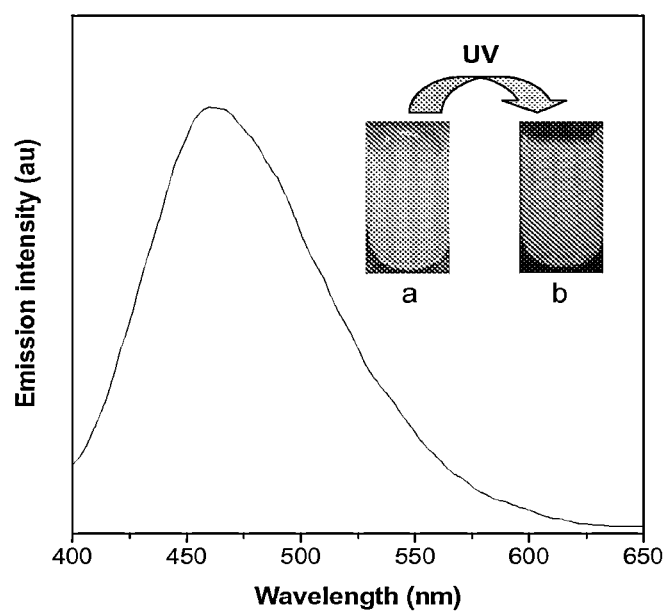
FIG. 16A illustrates the photoluminescence spectrum of the polymer particle dispersion of Example 25 containing TPE-COOH fluorophores. Concentration of the polymer in emulsion: 0.5 wt %; ratio of TPE-COOH to polymer: 0.1%; excitation wavelength: 346 nm.
FIG. 16B illustrates photographs of the polymer nanoparticle emulsion of Example 25 under normal room illumination (a) and 365 nm irradiation from a UV lamp (b).
Figure 17:
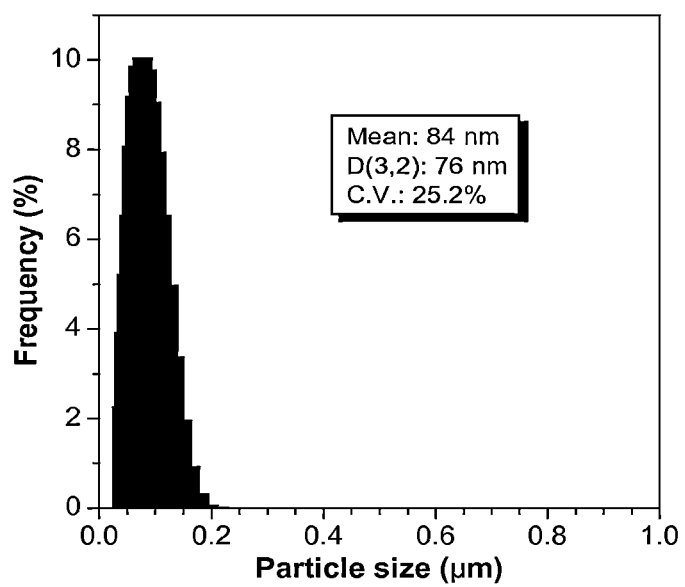
FIG. 17 illustrates the particle size and size distribution of the fluorescent polymer particles of Example 26. The inset shows the number-average diameter (Mean), weight-average diameter (D(3,2)), and coefficient of variation (C.V.) for the particles.

The polymer particle dispersion prepared is quite uniform and stable. The particle dispersion is highly emissive under UV irradiation, even in very dilute state. The photoluminescence spectrum of the dispersion is shown in FIG. 16. The emission peak is found at 458 nm, which is somewhat blue shifted compared to the pure TPE-COOH.

Example 26

Preparation of Fluorescent Polymer Particles

The procedures are just the same as in Example 25, except that the ratio of methyl methacrylate, butyl acrylate and 2-hydroxyethyl methacrylate changes to 5:4:1 in volume.

The polymer particle dispersion prepared is quite uniform and stable. The particle dispersion is highly emissive under UV irradiation, even in very dilute state. The particle size distribution of the polymer nanoparticles in the emulsion was shown in FIG. 18. The diameter of the polymer nanoparticles is on the average of ~80 nm, and the size distribution is narrow.

Example 27

Preparation of Fluorescent Polymer Particle

The procedures are just the same as in Example 25, except that the emulsifier concentration decreases to 0, that is, the emulsion polymerization proceeds in the absence of emulsifier.

Figure 18A:
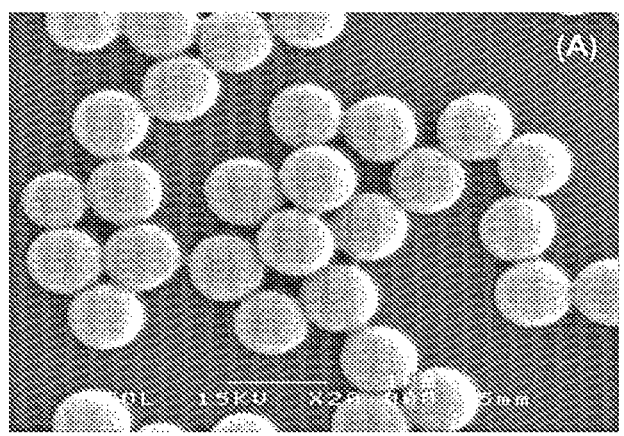
FIG. 18A is a scanning electron micrograph image of the fluorescent polymer particles of Example 27 prepared at a surfactant concentration of 0.

The polymer particle dispersion prepared is quite uniform. The particles tend to precipitate, however, they are readily be redispersed upon agitation. The particle dispersion is highly emissive under UV irradiation, even in very dilute state. The SEM image of the fluorescent polymer particles are shown in FIG. 18A, indicating a 760 nm particle size.

Example 28

Preparation of Fluorescent Polymer Particles

The procedures are just the same as in Example 25, except that the emulsifier concentration decreases to 0.02 wt %.

Figure 18B:
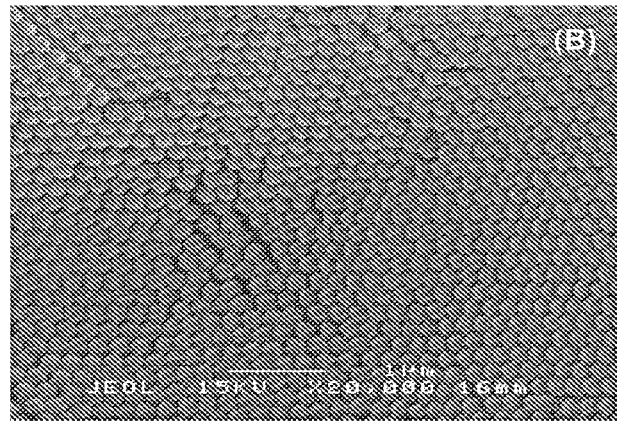
FIG. 18B is a scanning electron micrograph image of the fluorescent polymer particles of Example 28 prepared at a surfactant concentration of 0.02 wt %.

The polymer particle dispersion prepared is quite uniform and stable. The particle dispersion is highly emissive under UV irradiation, even in very dilute state. The SEM image of the fluorescent polymer particles are shown in FIG. 18B, indicating a 250 nm particle size.

Example 29

Preparation of Fluorescent Polymer Particles

The procedures are just the same as in Example 25, except that the emulsifier concentration decreases to 0.04 wt %.

Figure 18C:
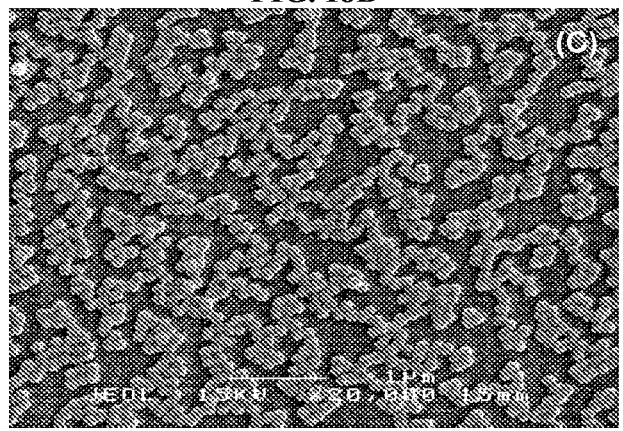
FIG. 18C is a scanning electron micrograph image of the fluorescent polymer particles of Example 29 prepared at a surfactant concentration of 0.04 wt %.

The polymer particle dispersion prepared is quite uniform and stable. The particle dispersion is highly emissive under UV irradiation, even in very dilute state. The SEM image of the fluorescent polymer particles are shown in FIG. 18C, indicating a 120 nm particle size.

Example 30

Preparation of Fluorescent Polymer Particles

The procedures are just the same as in Example 25, except that 2-hydroxyethyl methacrylate is replace by acrylic acid.

The polymer particle dispersion prepared is quite uniform and stable. The particle dispersion is highly emissive under UV irradiation, even in very dilute state. The fluorescent particles have carboxyl functional groups on the surface, which is favorable to the bioconjugation.

Example 31

Preparation of Fluorescent Polymer Particles

The procedures are just the same as in Example 26, except that 2-hydroxyethyl methacrylate is replace by acrylamide.

The polymer particle dispersion prepared is quite uniform and stable. The particle dispersion is highly emissive under UV irradiation, even in very dilute state. The fluorescent particles have amine functional groups on the surface, which is favorable to the bioconjugation.

Example 32

Preparation of Fluorescent Polymer Coating

The procedures for preparation of fluorescent dispersion are just the same as in Example 24. The particle dispersion is highly emissive under UV irradiation, even in very dilute state. The size of the fluorescent particle is less than 100 nm and the glass transition temperature is below room temperature. The dispersion prepared is suitable for film formation, and the fluorescent coating film is shown in FIG. 19A. The coating film formed by control dispersion is nonluminescent while that formed by the fluorescent particle dispersion is highly emissive under UV irradiation.

Example 33

Preparation of Fluorescent, Free-Standing, Flexible Polymer Film

The procedures for preparation of fluorescent dispersion are just the same as that in Example 24. The particle dispersion is highly emissive under UV irradiation, even in very dilute state. The size of the fluorescent particle is less than 100 nm and the glass transition temperature is below room temperature. The dispersion prepared is suitable for film formation. With a PTFE mold, a free-standing flexible film can be facilely fabricated, and the fluorescent film is shown in FIG. 19B. The coating film fanned by control dispersion is nonluminescent while that formed by the fluorescent particle dispersion is highly emissive under UV irradiation. Such fluorescent free-standing flexible polymer film can be used as flexible organic optoelectronic devices.

Example 34

The fluorescent polymer nanoparticles with amino groups were prepared with the method demonstrated in Example 30. The nanoparticle suspension was diluted 10 times by minimum essential media. Then 10 mg of transferrin (Tf) was added into this mixture and gently stirred at room temperature for 2 hours to allow the protein to covalently bond to the particle surface. The human cancer cell lines HeLa was cultured in Dulbecco minimum essential media with 10% fetal bovine serum (FBS), 1% penicillin, and 1% amphotericin B. The day before treatment, cells were seeded in 35 mm culture dishes at a confluency of 70-80%. On the treatment day, the cells in serum-supplemented media were treated with the Tf-conjugated nanoparticles for 2 hours at 37 C. Afterwards, the cells were washed three times with PBS and directly imaged using a fluorescent microscope.

Figure 20A:
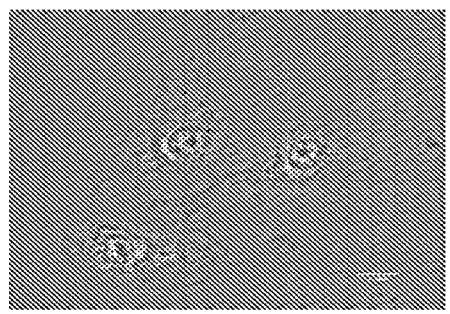
FIG. 20A is a transmission electron micrograph image of HeLa cell treated with the fluorescent polymer nanoparticles of Example 34.
Figure 20B:
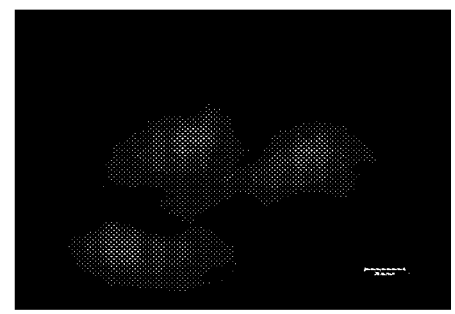
FIG. 20B is a transmission electron micrograph image of HeLa cells treated with the fluorescent polymer nanoparticles of Example 34 upon excitation of 365 nm UV light.

The results are shown in FIG. 20. From the microscopic fluorescence images, it can be seen that the whole cells are bright, indicating that the fluorescent nanoparticles have migrated into the cells. In other words, they are labeled.

Results on cell labeling using the fluorescent polymer nanoparticles have been obtained. As shown below, 48 nm fluorescent polymer nanoparticles were first prepared with amino groups on the surface, and then bioconjugation of transferring, a known protein that tends to target HeLa cells, was carried out. Subsequently, the HeLa cells in serum-supplemented media were treated with the particle-transferrin conjugates. As a result, transferring-conjugated nanoparticles were transported into the cells through the transferrin receptor mediated endocytosis pathway. Since transferrin receptors are minimally distributed in normal cells, transferrin serves as an excellent ligand for preferentially targeting cancerous cells in vitro and in vivo. From the microscopic fluorescence image (FIG. 20), it can be seen that the whole cells are bright, indicating that the fluorescent nanoparticles have migrated into the cells. In other words, they are labeled.

Example 35

Figure 21:
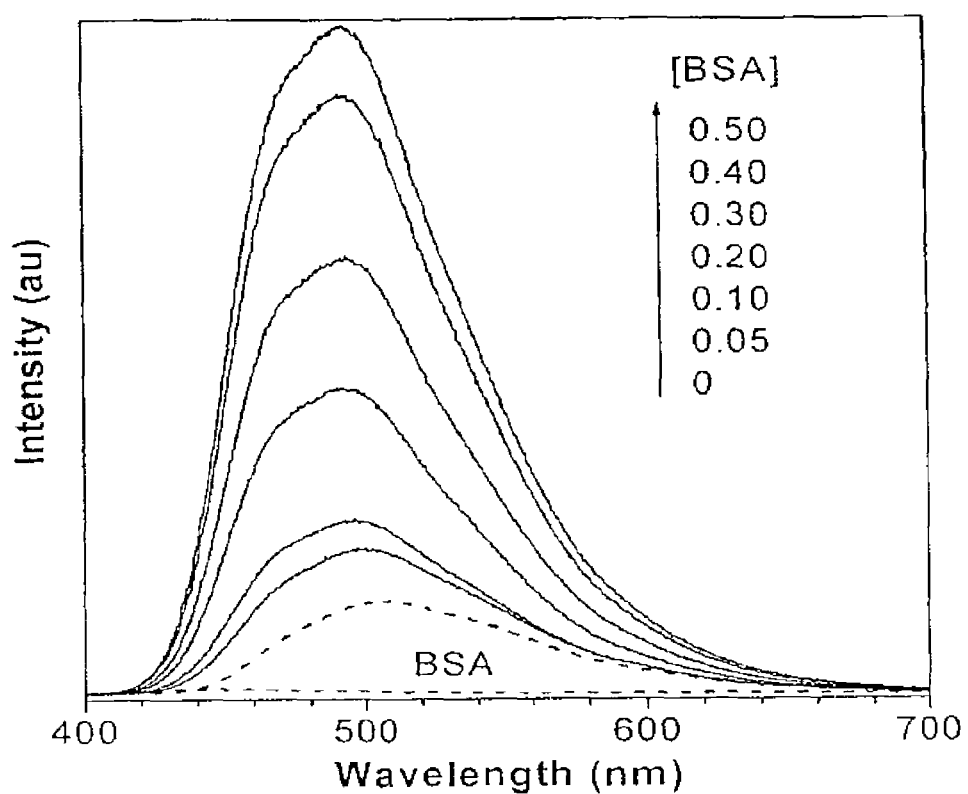
FIG. 21 is PL spectra of the water/methanol (6:4) solutions of a PPS-OH ($5.7 \times 10^{-5}$ M) in the presence of KOH ($8.4 \times 10^{-4}$ M) and BSA (at concentrations given in the figure), as described in Example 35.
Figure 22:
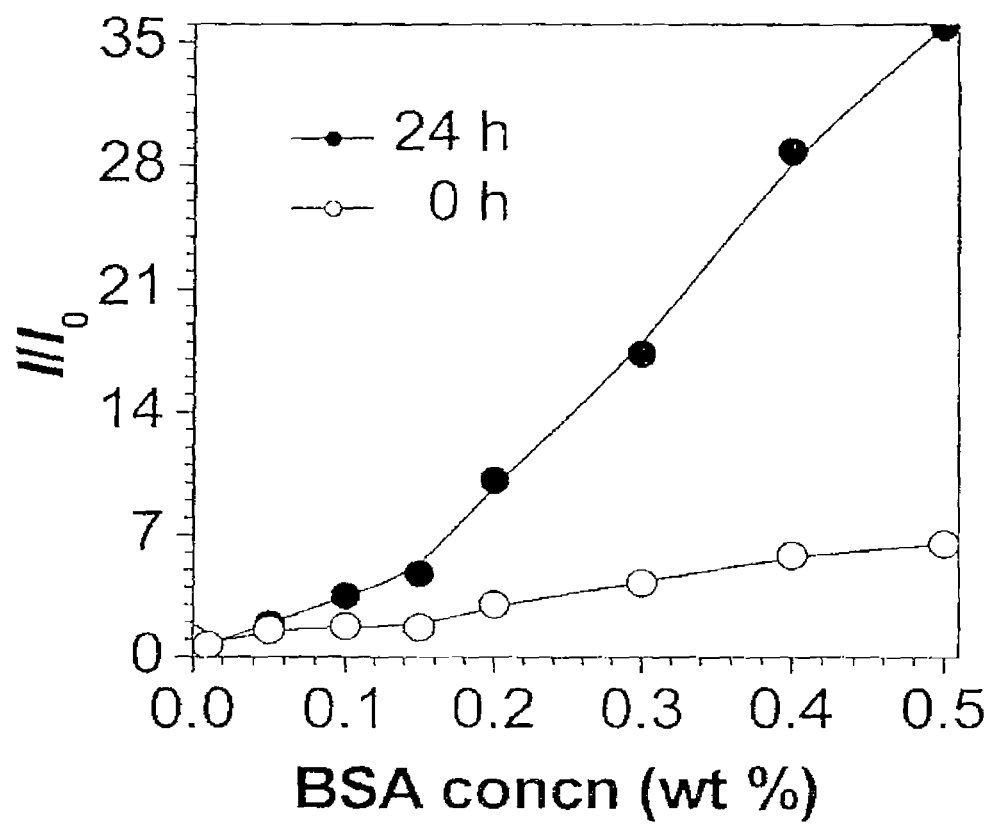
FIG. 22 shows the dependency of fluorescence intensity of PPS-OH on BSA concentration as described in Example 35.

In order to utilize the dye molecules as biosensors in aqueous solutions, we prepared PPS-OH and tested its ability to detect bovine serum albumin (BSA). FIG. 21 depicts the PL spectra of the water/methanol (6:4) solutions of a PPS-OH in the presence of KOH and BSA at different concentrations. Clearly, with increasing amounts of BSA the PL intensity increases significantly. Upon prolonged standing the PL intensity enhances further, probably due to the more complete interaction of PPS-OH with BSA (FIG. 22).

Example 36

Quadruplex Recognition

A complex of ssDNA and TTAPE was prepared by mixing 10 μL G 1 (0.1 mM) and 50 μL TTAPE (0.01 mM) in 5 mM Tris-HCl buffer in a 1.5 ml Eppendorf cup. The solution was incubated at 4° C. for 30 min. G-quadruplex formation was induced by adding 10 μl of a 1.0 M KCl solution into the Eppendorf cup. The final concentrations of TTAPE and G1 were kept at 4.5 and 9.0 μM, respectively. For other cationic species, the same amounts of corresponding salts were used. Kinetic experiment was conducted immediately after the injection of the cationic solution, while other spectral measurements were performed after an incubation period of 30 min.

Figure 30:
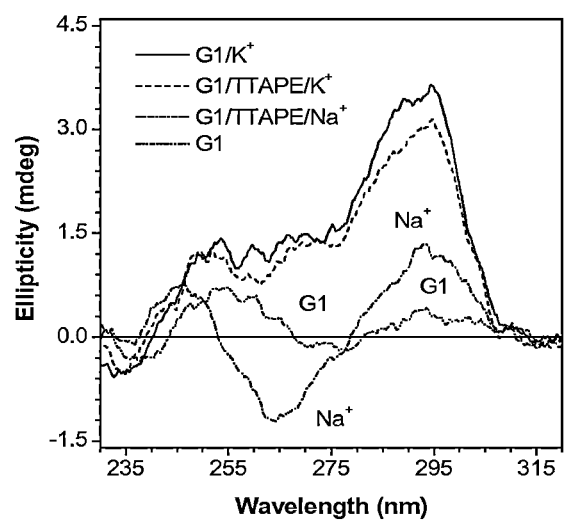
FIG. 30 is a CD spectra of G1 in a Tris-HCl buffer in the presence or absence of a metal ion and/or TTAPE at 20° C. [G1]=9 µM, [ion]=0.5 M, [TTAPE]=4.5 µM.

In the aqueous buffer solution, G1 takes a random coil conformation and shows a weak circular dichroism (CD) curve (FIG. 30). Adding $K^+$ into the G1 solution (G1/$K^+$) promotes G-quadruplex formation, which brings about a change in the CD spectral profile as well as an increase in the ellipticity. The $G_1$/TTAPE/$K^+$ system shows a CD curve with a similar profile and ellipticity, implying that the dye does not affect the quadruplex conformation. The quadruplex formation induces ~20 nm red-shift in both excitation and emission spectra of TTAPE (FIG. 31). A serial titration experiment using $K^+$ as titrate reveals that the spectral red-shift starts from [$K^+$]~10 mM and completes at [$K^+$]~100 mM (FIG. 32). The FL intensity at 470 nm, on the other hand, is monotonically decreased with increasing the $K^+$ concentration. Closer inspection of the data finds that the spectrum at high [$K^+$] contains a shoulder band at ~0.400 nm. This shoulder is probably associated with the emission of the TTAPE molecules that are still bound to the quadruplex but via only one or two of its four ammonium arms. These partially bound dye molecules may undergo partial intramolecular rotations and thus emit weak light in the blue spectral region.

Figures 33A, 33B:
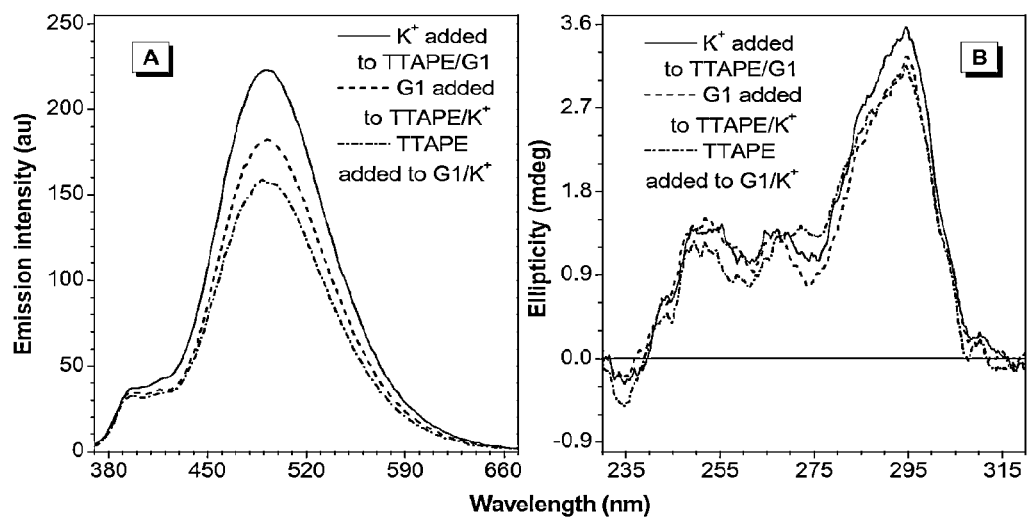
FIG. 33A shows the effects of addition sequence on FL spectra of K$^+$/TTAPE/G1 complex in 5 mM Tris-HCl buffer solutions. [K$^+$]=0.5 M, [TTAPE]=4.5 μM, [G1]=9 μM; $\lambda_{ex}$=350 nm.
FIG. 33B shows the effects of addition sequence on CD spectra of K$^+$/TTAPE/G1 complex in 5 mM Tris-HCl buffer solutions. [K$^+$]=0.5 M, [TTAPE]=4.5 μM, [G1]=9 μM; $\lambda_{ex}$=350 nm.

The addition sequence is systematically investigated to see how it affects the FL and CD spectra of the TTAPE/quadruplex structure. As can be seen from the data summarized in Table 2 and FIGS. 33A and 33B, the FL/CD intensities vary in the order of following addition sequence: $K^+$→TTAPE/G1>G1→TTAPE/$K^+$>TTAPE→G1/$K^+$. Comparison of the data in entries 1 and 2 (Table 2) suggests that some TTAPE molecules pre-round to the G1 strands have been incorporated into the G-quadruplex structure during the $K^+$-induced structural transformation. When TTAPE is added after the G-quadruplex has been formed (entry 3), the dye molecules are difficult to bind to the quadruplex surrounded by numerous K$^+$ ions, hence the observed lowest FL and CD intensities. The profiles of the CD spectra for all the G-quadruplexes formed in the three entries are almost identical (FIG. 33B), confirming that TTAPE does not appreciably distort the G-quadruplex structure.

TABLE 2

Effect of addition sequence on FL and CD intensities of TTAPE/quadruplex complexes at room temperature[a]

| Entry | Mixture[b] | Additive | FL intensity[c] | CD intensity[d] |
|---|---|---|---|---|
| 1[e] | TTAPE/G1 | K$^+$ | 1.00 | 1.00 |
| 2 | TTAPE/K$^+$ | G1 | 0.82 | 0.92 |
| 3 | G1/K$^+$ | TTAPE | 0.70 | 0.88 |

[a]For comparison final concentrations of the three components in all the mixtures were adjusted to be the same.
[b]Incubated at 4° C. for 30 min.
[c]Relative intensity at 492 nm.
[d]Relative intensity at 295 nm.
[e]Data corresponding to those given in FIGS. s 30 and 31.

Example 37

Figure 34A:
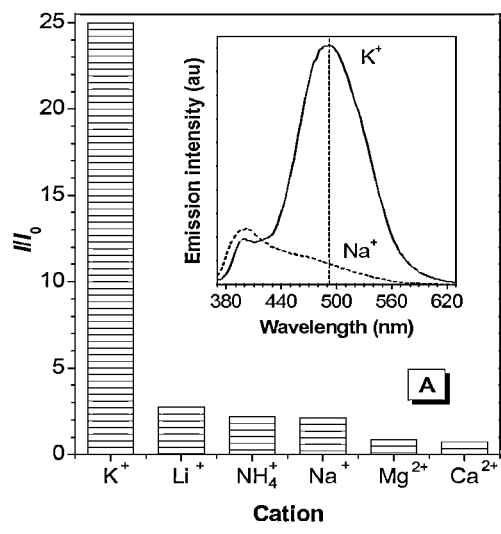
FIG. 34A shows the dependence of FL intensity of TTAPE at 492 nm on cationic species ([ion]=500 mM). FL spectra of TTAPE in the buffer solutions containing G1 and K$^+$ or Na$^+$ ion.
Figure 34B:
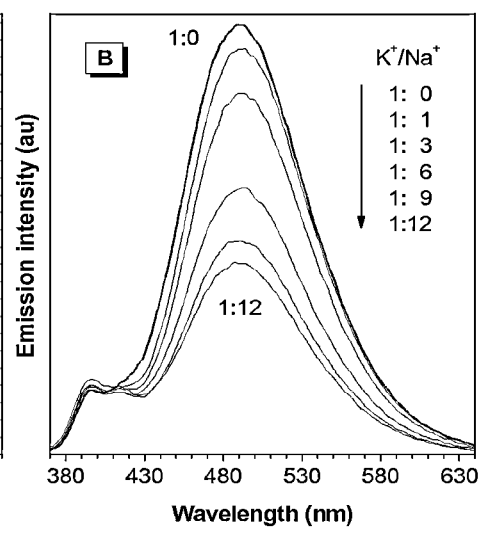
FIG. 34B shows the variation in the FL spectrum of TTAPE/G1/K$^+$ solution with addition of Na$^+$ ion. [TTAPE]=4.5 μM, [G1]=9 μM, [K$^+$]=100 mM; $\lambda_{ex}$=350 nm.
Figures 35A, 35B:
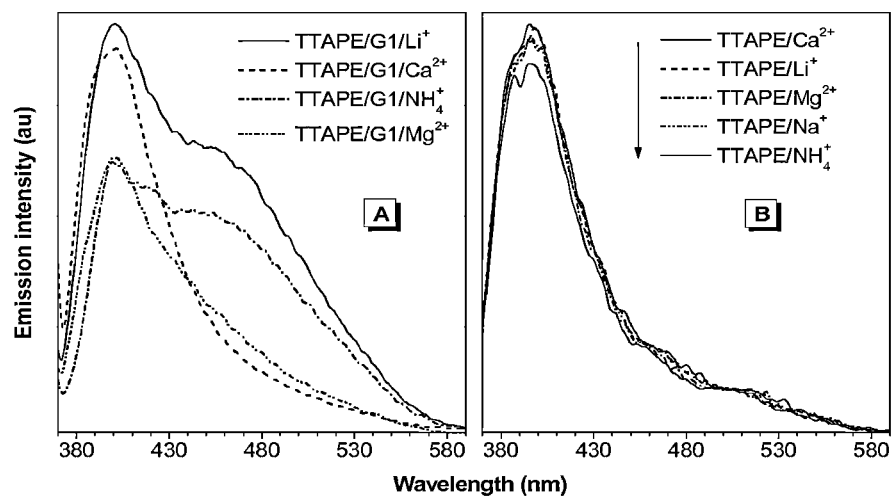
FIG. 35A shows the FL spectra of TTAPE/G1 in a Tris-HCl buffer in the presence of cationic species. [TTAPE]=4.5 μM, [G1]=9 μM, [ion]=0.5 M; $\lambda_{ex}$=350 nm.
FIG. 35B shows the FL spectra of TTAPE in a Tris-HCl buffer in the presence of cationic species. [TTAPE]=4.5 μM, [G1]=9 μM, [ion]=0.5 M; $\lambda_{ex}$=350 nm.

As stated above, addition of K$^+$ into TTAPE/G1 results in a quadruplex-specific emission peak at 492 nm. Addition of Na$^+$ into TTAPE/G1, however, quenches this band (FIG. 34A). Similarly, other cationic species including Li$^+$, NH$_4^+$, Mg$^{2+}$ and CA$^{2+}$ all attenuate this emission band (FIGS. 35A and 35B). After adding into TTAPE/G1, these cation species competes with TTAPE for binding with G1. The externally added cation species prevails because its amount is >10$^4$-fold higher than that of TTAPE. Once the dye molecules are stripped from the DNA strand, their intramolecular rotations are no longer restricted and the AIE band is thus turned off. The FL spectrum of TTAPE/G1 in the presence of K$^+$ is clearly different from, and its peak intensity is outstandingly higher than, those in the presence of other cations, suggesting the potential utility of TTAPE/G1 as a K$^+$ biosensor.

Example 38

Effects of DNA Strands

DNA samples of G1, C1 and C2 were obtained from Operon in desalt purity and used without further purification. G1 was chosen as a model ssDNA mimicking the human telomeric repeat sequence d(T$_2$AG$_3$), which is capable of forming intramolecular G-quadruplex. Concentrations of the DNA strands were determined by measuring their absorptivity (E) values at 260 nm in a 100 μL quartz cuvette [ε(×10$^5$ M$^{-1}$ cm$^{-1}$): 2.14 (G1), 1.85 (C1), 1.85 (C2)]. Water was purified by a Millipore filtration system. Buffer solution was prepared by titrating 5 mM Tris with HCl until its pH value reached 7.50. All experiments were performed at room temperature unless otherwise specified.

Figures 38A, 38B:
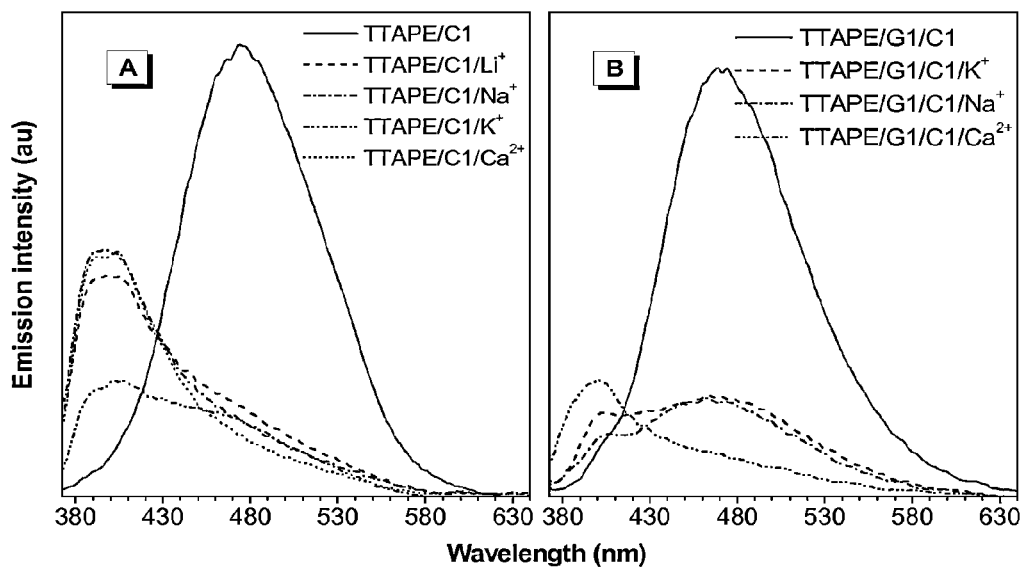
FIG. 38A shows the emission spectra of buffer solutions (pH=7.50) of TTAPE/C1 in the absence and presence of metal ions. [TTAPE]=4.5 μM, [ion]=0.5 M; $\lambda_{ex}$=350 nm; [C1]=9 μM.
FIG. 38B shows the emission spectra of buffer solutions (pH=7.50) of (A) TTAPE/C1 and (B) TTAPE/G1/C1 in the absence and presence of metal ions. [TTAPE]=4.5 μM, [ion]=0.5 M; $\lambda_{ex}$=350 nm; [G1]=[C1]=4.5 μM.

If a DNA contains no G unit, its TTAPE complex ceases to show the quadruplex-specific response to C1 is also a 21-mer ssDNA, but unlike G1, it possesses no G-rich repeat sequence. When C1 is admixed with TTAPE, a blue emission at 474 nm is resulted (FIG. 38A). This emission is, however, quenched upon addition of other cations including K$^+$. Different from G1, C1 cannot fold into G-quadruplex structure in the presence of K$^+$. The K$^+$ ions here just compete with the TTAPE molecules for DNA binding, thus resulting in the expulsion of the dye molecules from the C1 strand and the quenching of the light emission.

Figure 39:
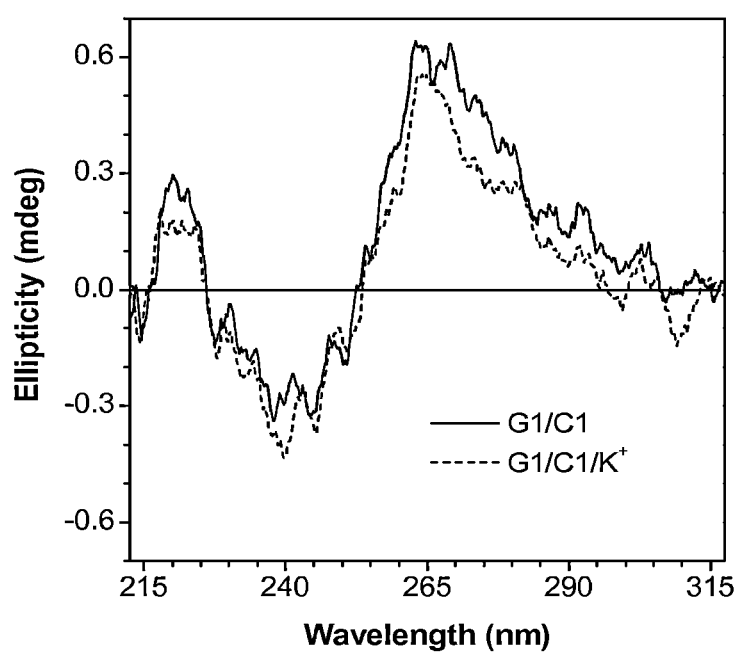
FIG. 39 shows the CD spectra of G1/C1 in the absence or presence of K$^+$ after hybridization in a Tris-HCl buffer (pH=7.50). [G1]=[C1]=4.5 μM, [K$^+$]=0.5 M; $\lambda_{ex}$=350 nm.
Figure 40:
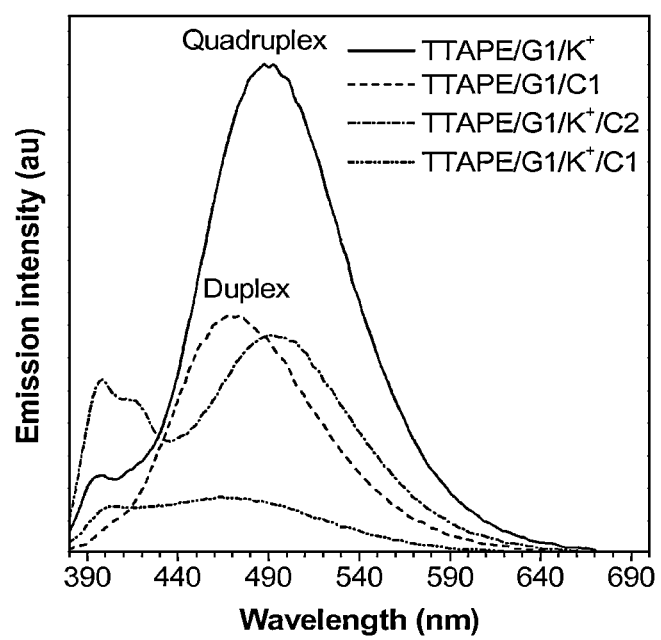
FIG. 40 shows the emission spectra of TTAPE/G1 in a Tris-HCl buffer in the presence of K$^+$ and/or C1 or C2. [TTAPE]=4.5 μM, [K$^+$]=0.5 M; $\lambda_{ex}$=350 nm; [G1]=9 μM (in the absence of Ci), [G1]=[C1]=4.5 μM (in the presence of Ci).
Figure 41:
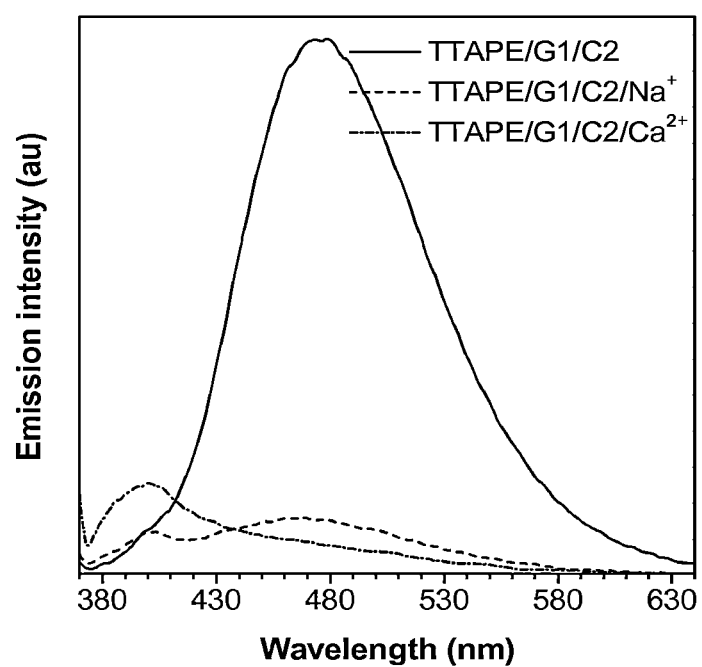
FIG. 41 shows the emission spectra of buffer solutions of TTAPE/C2 in the absence and presence of metal ions. [TTAPE]=4.5 μM, [G1]=[C2]=4.5 μM, [ion]=0.5 M; $\lambda_{ex}$=350 nm.

To be qualified as a specific probe for G-quadruplex recognition, the dye must be able to distinguish the quadruplex from other DNA conformations, especially the double-stranded (ds) one, which is the most ubiquitous conformation for DNAs in living organisms. C1 is a complimentary strand of G1: the two DNA strands hybridize to form a duplex (FIG. 39). The dsDNA induces TTAPE to emit at 470 nm, which is different from the dye emission in the presence of the G-quadruplex ($\lambda_{em}$=492 nm; FIG. 40). The interaction of TTAPE with dsDNA is again electrostatic in nature: when large amounts of other cations are added into G1/C1 solutions, the bound dye molecules are replaced by the externally added cations and the AIE emission band is accordingly attenuated (FIG. 41).

For comparison, the quadrulplex/TTAPE complex is mixed with equal molar amounts of its complementary and noncomplementary strands C1 and C2, respectively. The resultant TTAPE/G1/K$^+$/Ci mixtures are annealed at ~58° C., a temperature ~2° C. below the melting points of the DNAs (~60° C.) for 15 min, followed by a slow cooling to 25° C. to allow double-helix formation. The hybridization of G1 with C1 unfolds the G-quadruplex structure and yields a duplex (dsDNA). As a result, the quadruplex-specific emission at 492 nm is quenched (FIG. 40). The duplex is saturated by the prevailingly large amount of K$^+$ ions and leaves little room for TTAPE molecules to bind, hence making the solution non-emissive. Similar results are obtained for other cationic species (FIG. 38B).

Since C2 is noncomplementary to G1, the G-quadruplex remains unperturbed and the emission at 492 nm is preserved. Intriguingly, however, the emission in the bluer region (at ~400 nm) is increased upon admixing with C2. Although the whole strand of C2 is non-complementary to G1, partial hybridization of some base units of C2 with those of the G-quadruplex of G1, especially those on its surface, via GC and/or AT base pairing is possible. Such pairing replaces some, although not all, of the ammonium groups of a TTAPE bound to the G-quadruplex. The dye molecules hanging on the quadruplex via one or two ammonium arms can undergo partial intramolecular rotations and thus emit in the bluer spectral region. Addition of large amounts of other cationic species into the TTAPE/G1/C2 solutions drives all the dye molecules out of touch with the DNA strands. As a result, the solutions become non-emissive (FIG. 41).

Example 39

Time-Dependent FL

Time-dependent FL was measured on a FluostarOptima multifunctional microplate reader (BMG Labtechnologies) with $\lambda_{ex}/\lambda_{em}$ set at 350/470 nm. To gain insight into dynamics of the folding process of G1, time-dependent FL measurements are performed. Solutions containing TTAPE and G1 are first incubated for 30 min to ensure complete dye/DNA complexation and transferred to a 96-well microtiter plate after incubation. Appropriate amounts of metal ions were added by an automatic injection mode. Kinetic measurements were performed at 20° C. and the FL data were recorded in every 4 s. The change in the emission intensity (1) of the solution after the addition of K$^+$ can be fitted by a second-order exponential curve:

$$I = A_1 e^{-t/\tau 1} + A_2 e^{-t/\tau 2} + c \qquad \text{Eq. (1)}$$

where t is the time, $\tau_1$ and $\tau_2$ are the time constants of FL recovery, $A^1$ and $A^2$ are the respective amplitudes (the folding process is characterized by negative A values), and c is the FL intensity at t=infinity. Mean time constant ($\langle\tau\rangle$) was calculated according to eq. 2:

$$\langle\tau\rangle = \frac{A_1\tau_1 + A_2\tau_2}{A_1 + A_2}. \qquad \text{Eq. (2)}$$

Figure 42:
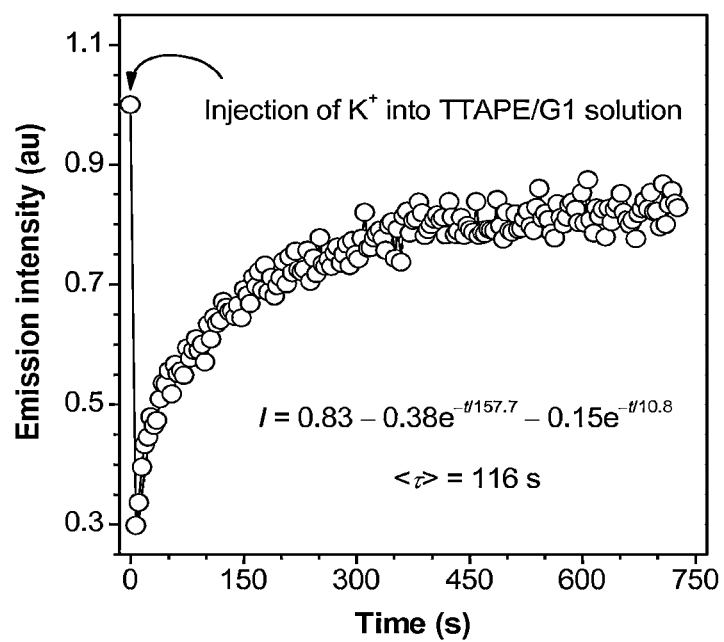
FIG. 42 is the time course of evolution of emission intensity at 470 nm of TTAPE/G1 in a Tris-HCl buffer after injection of a K$^+$ solution. [TTAPE]=4.5 μM, [G1]=9 μM, [K$^+$]=0.5 M; $\lambda_{ex}$=350 nm.

In one embodiment, a solution of potassium chloride is then injected at time t=0 (automatic injection mode) and the emission intensity at 470 nm is monitored. The emission drops abruptly to ~30% of its original intensity at the beginning but starts to recover after ~8 s and finally reaches a plateau at ~320 s (FIG. 42). This suggests a very fast ion-exchange process between $K^+$ and TTAPE with G1 at the beginning. Because of its smaller size and higher concentration, $K^+$ outperforms TTAPE in the DNA binding, leading to the initial quick drop in the FL intensity. The G1 strand then starts to fold into quadruplex with the aid of $K^+$, during which the TTAPE molecules are attracted to bind with the quadruplex, as manifested by the recovery of the FL signal after ~8 s. The complete folding of G1 into the quadruplex conformation takes only ~5 min. This result is consistent with the observations in the previous studies on the DNA folding processes using the surface plasmon resonance and electrospray mass spectrometry techniques.

Figures 43A, 43B:
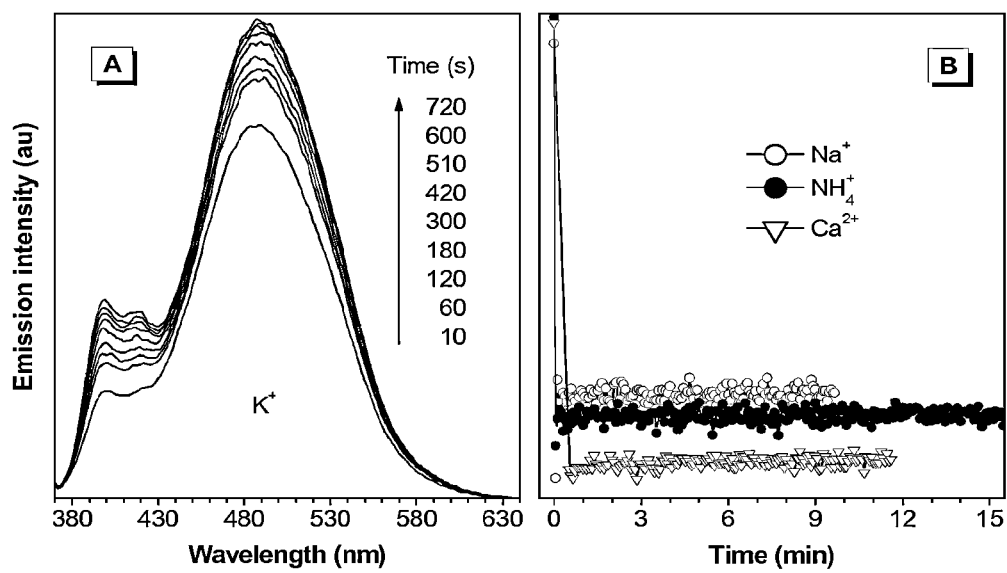
FIG. 43A is the time courses of evolution of emission intensities of buffer solutions of TTAPE/G1 after addition of cationic species. [TTAPE]=4.5 [G1]=9 μM; $\lambda_{ex}$=350 nm; [K$^+$]=0.5 M.
FIG. 43B is the time courses of evolution of emission intensities of buffer solutions of TTAPE/G1 after addition of cationic species. [TTAPE]=4.5 μM, [G1]=9 μM; $\lambda_{ex}$=350 nm; [Na$^+$]=[NH$_4^+$]=0.5 M, [Ca$^{2+}$]=0.25 M.
Figure 44A:
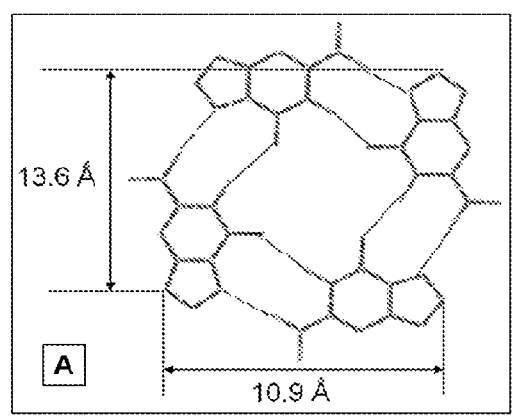
FIG. 44A shows the selected crystal structure of G-quadruplex of a human telomeric DNA (data taken from RSCB Protein Data Bank; ID No. 1KF1).
Figure 44B:
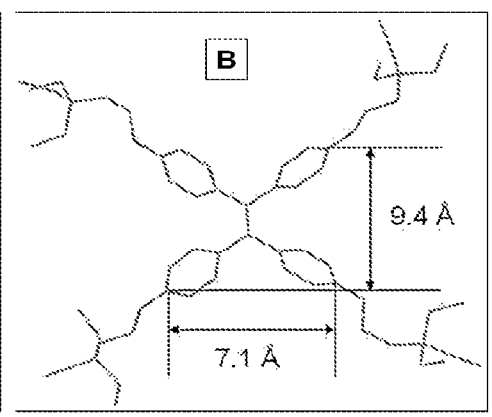
FIG. 44B shows the molecular structure of TTAPE with minimized energy, simulated by molecular mechanics MM2 program installed in Chem3D Ultra 8.0.

The FL recovery process can be fitted by a double-exponential curve, giving a weighted mean time constant ($\langle\tau\rangle$) of 116 s. The inverse of $\langle\tau\rangle$ can be viewed as a rate constant, allowing one to have a kinetic picture of the folding process of the DNA. Control experiments using other cationic species such as $Na^+$, $NH_4^+$ and $Ca^{2+}$ reveal similar FL decreases (FIG. 43), suggesting that the same ion-exchange mechanism is involved in the dye detachment processes. The emission intensities, however, fail to recover from the low values even after a time period as long as 1000 s. For $Na^+$ and $NH_4^+$, it is probably due to the geometric unfitness of TTAPE with the G-quadruplexes formed in the presence of these two cationic species. For $Ca^{2+}$, it is simply because this ion cannot induce the formation of a G-quadruplex structure.

Example 40

Urinary Protein Detection

Urine is an easily accessible body fluid and contains a complex mixture of proteins and peptides, which makes it a reliable source of biomarkers for diagnostics and clinical studies. Determination of urinary protein composition is of major clinical importance because it readily reflects serum composition and kidney functionality. The synthesis route of TPE-SO3 is described in Example 2 above.

Figure 46A:
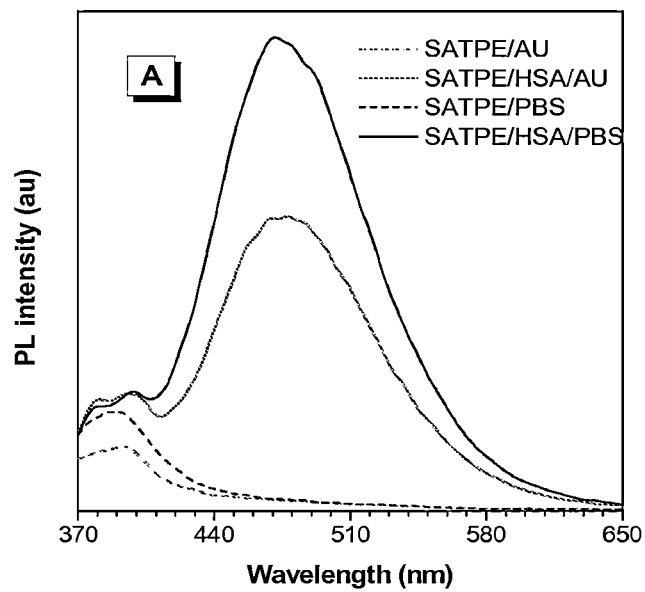
FIG. 46A shows the PL spectra of SATPE with/without HSA in the medium of artificial urine (AU) (pH=6.0)/PBS (pH=7.0). [SATPE]=5 μM; [HSA]=10 μg/ml.
Figure 46B:
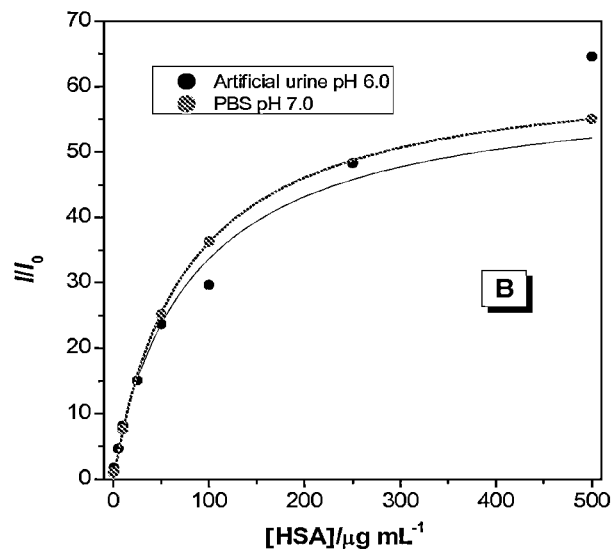
FIG. 46B shows the binding isotherm of HSA to SATPE in artificial urine pH=6.0 (black) (plot of FL intensity at 470 nm). The one in PBS pH=7.0 (red) is for comparison. [SATPE]=5 μM; excitation wavelength: 350 nm.

The water-soluble salt TPE-SO3 is expected to be suitable for protein detection and quantification as an FL bioprobe. A stock solution of TPE-SO3 (0.5 mM) was prepared by directly dissolving it in a pH 7.0 phosphate buffer. The dye solution in the absence of HSA, a model protein, is almost non-emissive (FIG. 46A). Its emission is switched on instantly by the addition of HSA. Its intensity increase (up to ~55-fold, FIG. 46B) and linear range (0-100 ug/ml). In order to determine whether TPE-SO3 can be used in the medium of urine or not, experiments were performed in artificial urine solution (pH 6.0). An artificial urine solution was prepared according to the recipe provided by Brooks and Keevil (T. Brooks, C. W. Keevil, *Lett. Appl. Microbial.* 1997, 24, 20 3-997. The artificial urine solution was 1.1 mm lactic acid, 2.0 min citric acid, 25 mm sodium bicarbonate, 170 mm urea, 2.5 mm calcium chloride, 90 mm sodium chloride, 2.0 mm magnesium sulfate, 10 mm sodium sulfate, 7.0 mm potassium dihydrogen phosphate, 7.0 mm dipotassium hydrogen phosphate, and 25 mm ammonium chloride all mixed in Millipore water. The pH of the solution was adjusted to 6.0 through the addition of 1.0 m hydrochloric acid.

Figure 48:
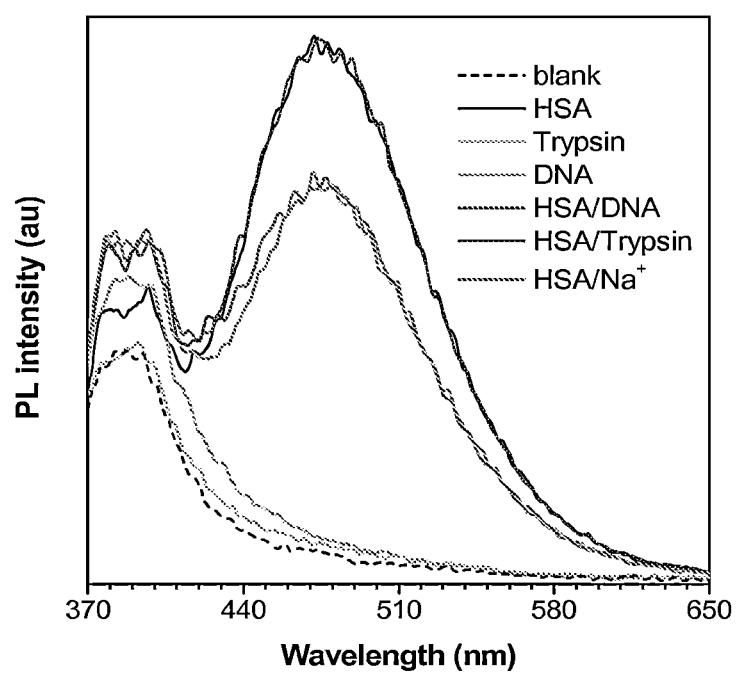
FIG. 48 shows the FL spectrum of SATPE with addition of different proteins in artificial urine (pH=6.0). [SATPE]=5 μM, [protein]=50 μg/ml. Excitation wavelength: 350 nm.

The results show that the presence of high concentration of urea and salts do not interfere with the function of TPE-SO3. The detection limit and linear range can be tuned by adjusting the dye concentration. Intriguingly, TPE-SO3 displays high affinity to albumin over any other proteins (FIGS. 47A and 47B). Albumin proteins, such as HSA, may have a large hydrophobic cavity, which may attract the dyes to stay in it, leading to strong binding interaction. On the other hand, other kinds of protein, such as trypsin, papain, pepsin, and IgG can only adsorb the dyes on the surface of the protein by electrostatic interaction. Thus, in the medium with high ionic strength may mitigate their interaction, resulting in weak or no FL signals. Cross-contaminant experiments were also performed (FIG. 48). The results show that the interaction of TPE-SO3 with HSA can hardly be affected in the presence of other species.

Figure 25:
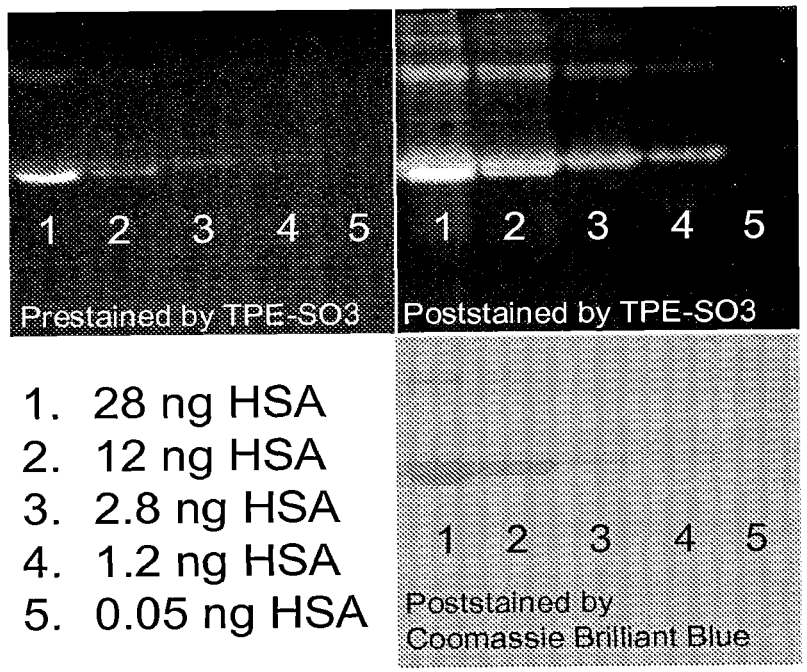
FIG. 25 shows the 12% Native-PAGE of HSA pre/post-stained by TPE-SO3. The gel is poststained by Coomassie Brilliant Blue for comparison.

Similar to TTAPE, TPE-SO3 can also be used in PAGE assays for detecting proteins in biological samples. In a prestaining process samples are mixed with TPE-SO3 prior to being loaded into the gel. The results of the prestaining process with TPE-SO3 can be seen in top left portion of FIG. 25. In addition, a poststaining process was performed where after electrophoresis, the gel was immersed into TPE-SO3 solution for 5 mins before taking an image. The results of the poststaining process with TPE-SO3 can be seen in the top right portion of FIG. 25.

Coomassie Brilliant Blue is a blue dye that can bind to the proteins of a within the PAGE assay and allow you to directly visualize them. After Coomassie staining and destaining, the proteins will appear as blue bands as shown in the lower right portion of FIG. 25. Coomassie Brilliant Blue staining requires long reaction time (normally soaked more than 6 hours), destaining step (immersed in acid solution to dissolve the unbound dyes), and low sensitivity (colorimetric-based method) (see U.S. Pat. No. 5,922,186). In contrast, TPE-SO3 offers an easy and sensitive way to do this same job. Gels only need to be exposed to TPE-SO3 for 3-5 minutes to make the protein bands visible. The use of TPE-SO3 requires no destaining step. The sensitivity of TPE-SO3 is much higher than that of Coomassie Brilliant Blue. It is clear that the use of TPE-SO3 as a stain for PAGE assays is a faster method with fewer steps that provides greater sensitivity than conventional staining methods for protein detection.

Example 41

TTAPE Also Acts as a G-Quadruplex Inducer

Figure 77:
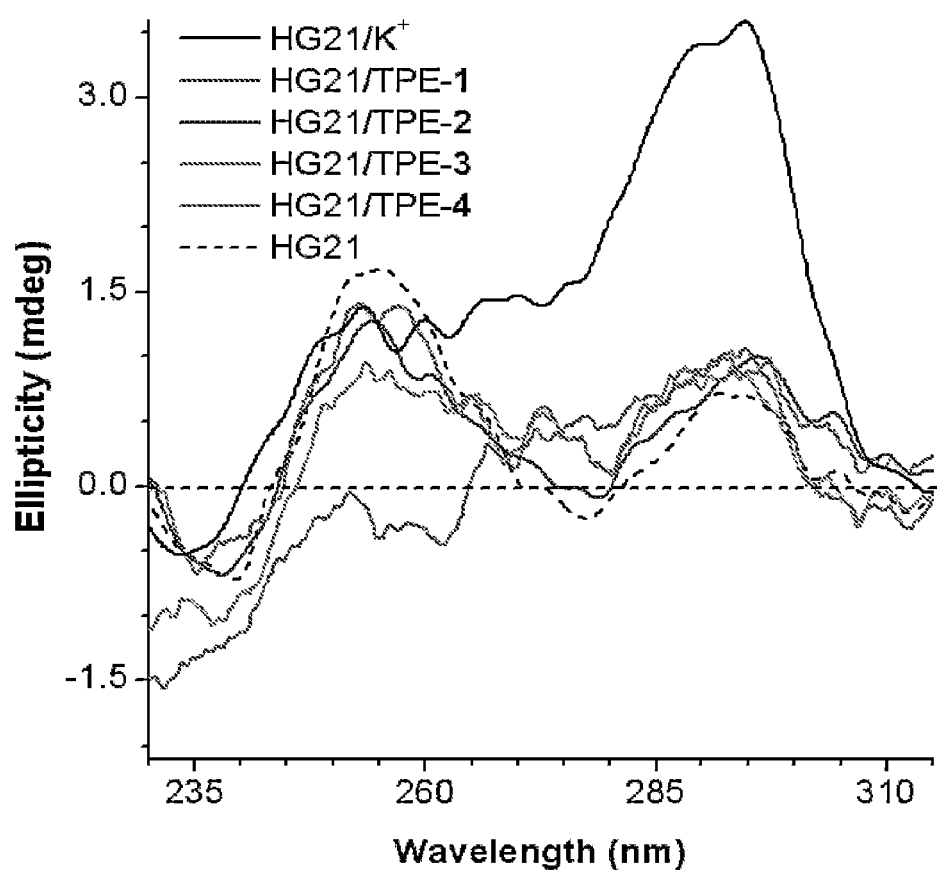
FIG. 77 shows CD spectra of HG21 in Tris-HCl buffer solutions incubated in the presence of different TPE-derivatives, $K^+$ ion or alone at 25° C. [TPE]=4.5 μM; [HG21]=9 μM and [$K^+$]=0.5 M.
Figure 78A:
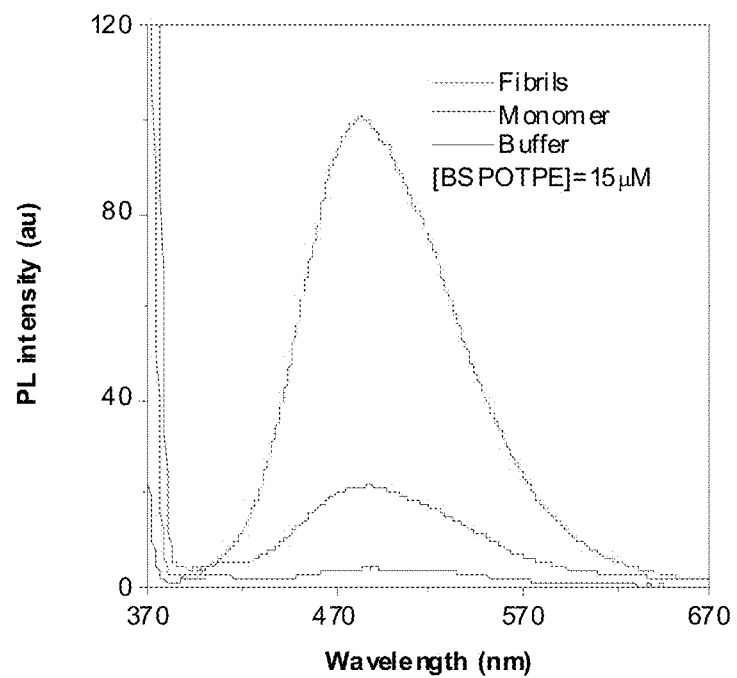
FIGS. 78A, 78B, 78C, 78D, 78E, and 78F show emission spectra of (A) BSPOTPE, (B) TPE-MitoB, (C) TPE-MitoY, (D) TTAPE-Me, (E) Cy$_2$Silo, and (F) TPE-ThT, (15 μM) dyed α-syn (5 μM) monomer and fibrils.
Figure 78B:
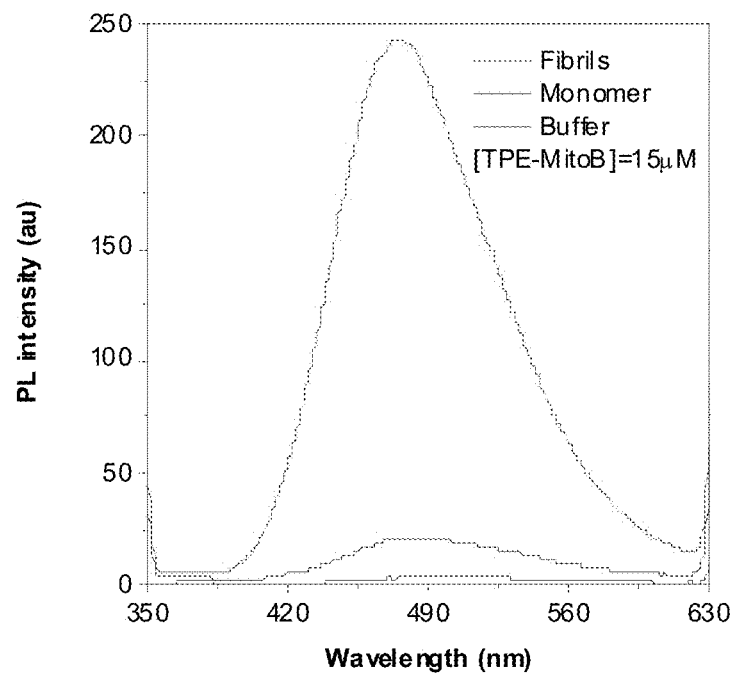
Figure 78C:
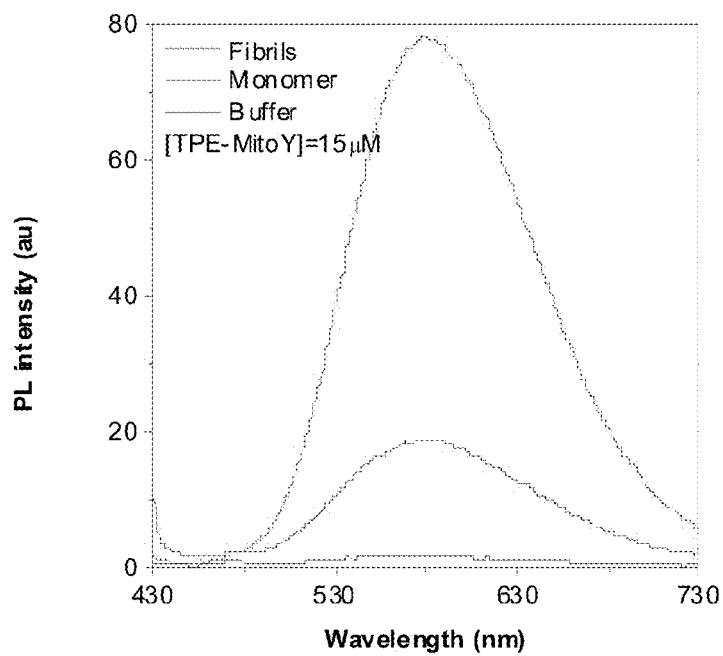
Figure 78D:
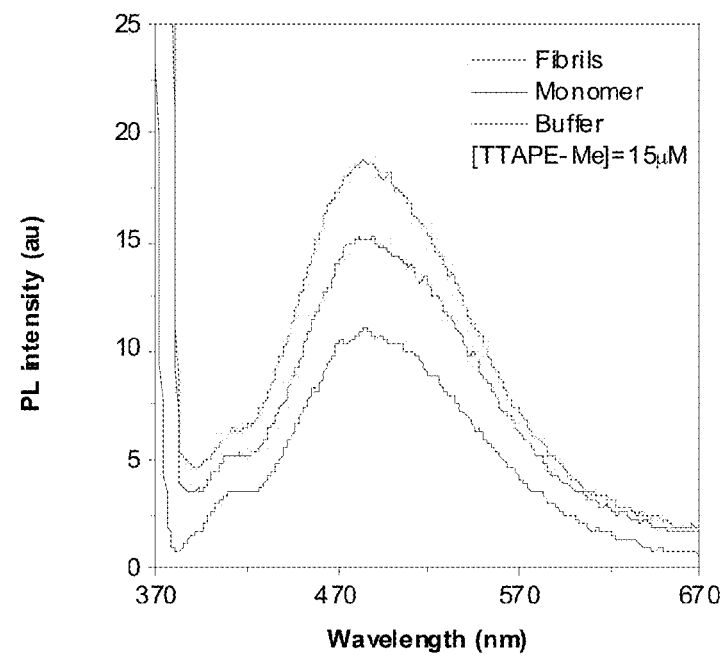
Figure 78E:
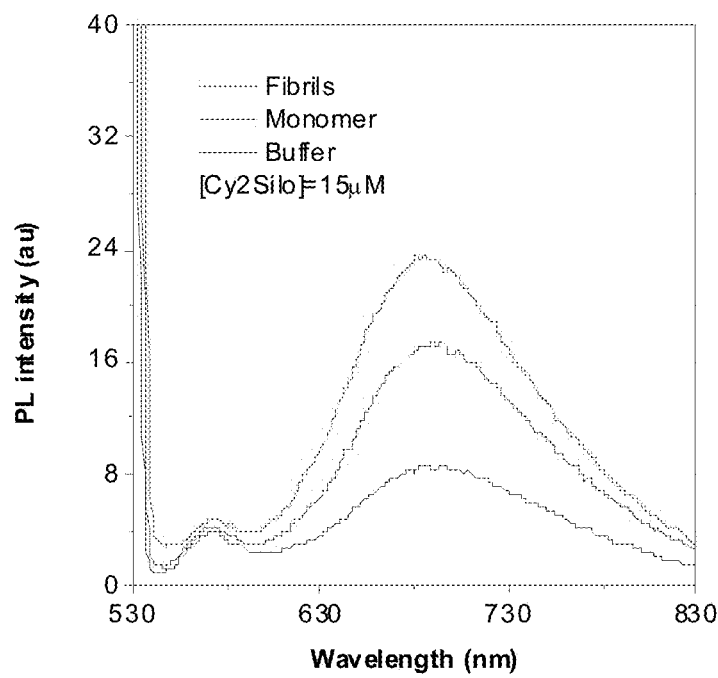
Figure 78F:
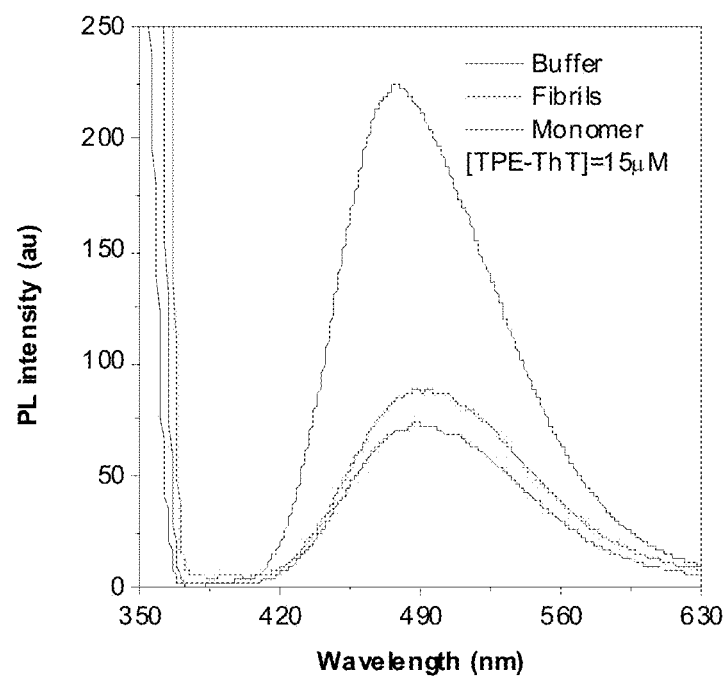
Figure 79:
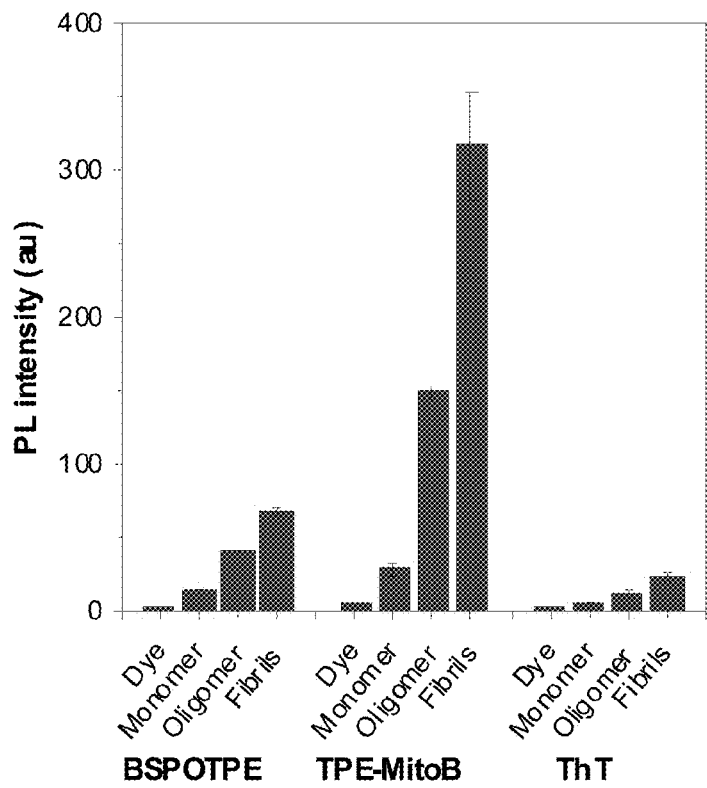
FIG. 79 shows peak intensity of BSPOTPE, TPE-MitoB, and TPE-ThT dyed α-syn (5 μM) monomer, oligomer, and fibrils at 470 nm, 480 nm, and 490 nm, respectively.
Figure 80:
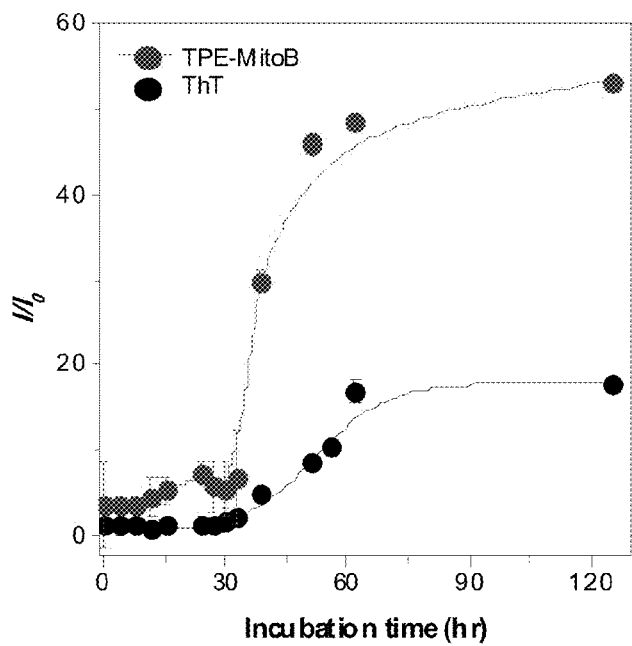
FIG. 80 shows a plot of $I/I_0$ α-syn (5 μM) fibrillation monitored by TPE-MitoB (15 μM) and TPE-ThT (15 μM).

CD spectral profiles of 9 μM DNA in 5 mM Tris-HCl buffer solutions (pH 7.5) incubated under 25° C. with four different TPE derivatives at 4.5 μM or with 0.5M $K^+$ ions are studied (FIG. 77). TPE derivatives 1-4 are TTAPE (Example 6), TPE-2 (chemical structure is not shown herein), TPE-3 (chemical structure is not shown herein) and TPE-C2N+ (Example 3), respectively. Results reveal that TPE-2, TPE-3 and TPE-4 result in spectral profile comparable to the negative control, where DNA incubated with neither TPE derivatives nor $IC^+$ ions. On the other hand, DNA incubated with TTAPE or the known quadruplex inducer; $K^+$ ions have very similar spectral profiles, while the ellipticities of DNA/TTAPE are somehow weaker than DNA/$K^+$. This study leads to the surprisingly founding that TTAPE acts as an internal quadruplex inducer under 25° C., making it useful as a quadruplex-targeting drug for anti-cancer therapy.

Example 42

TPE-SO3 is Highly Sensitive and Specific to Amyloid Fibrils

Bovine insulin powder was dissolved in 25 mM NaCl/HCl solution (pH 1.6 at 65° C.). The solution was passed through a 0.45 μm filter and the concentration was determined by measuring its absorbance at 278 nm. Stock solution of TPE-SO3 with a concentration of 1.0 mM was prepared by dissolving appropriate amount of dye in PBS solution (pH 7.0). Insulin fibrils were prepared by incubating the protein (320 μM) in buffer solution (pH 1.6) at 65° C. for 20 h.

The TPE-SO3 solution alone in phosphate buffered saline (PBS) where no protein is present is non-emissive. The solution remains faintly luminescent at ca. 470 nm upon addition of native bovine insulin. The TPE-SO3 solution becomes luminescent in the presence of small amount of fibrillar insulin (FIG. 66A). The emission intensity is proportional to concentration of fibrillar insulin as seen by the progressively enhancement of intensity with an increase in the concentration of fibrillar insulin. The rate of fluorescence enhancement ($I/I_0$) is fast at low fibrillar insulin concentration and becomes nearly constant at fibrillar insulin concentration greater than 20 μM. The fluorescence of TPE-SO3 remains negligible even when the concentration of native insulin is up to 100 μM (FIG. 66B). To further evaluate the specificity of TPE-SO3 towards fibrillar insulin, the rate of FL intensity enhancement of TPE-SO3 in insulin mixture with different molar fractions of fibrillar insulin (ti) are measured where the total protein concentration is kept at 5 μM. Results (FIG. 66B inset) shows that emission of TPE-SO3 increases monotonically with an increase in the fibrillar insulin fraction in a linear manner, indicating that the fluorescence of TPE-SO3 in detecting insulin fibrils is independent on the presence of native insulin.

Figures 68A, 68B:
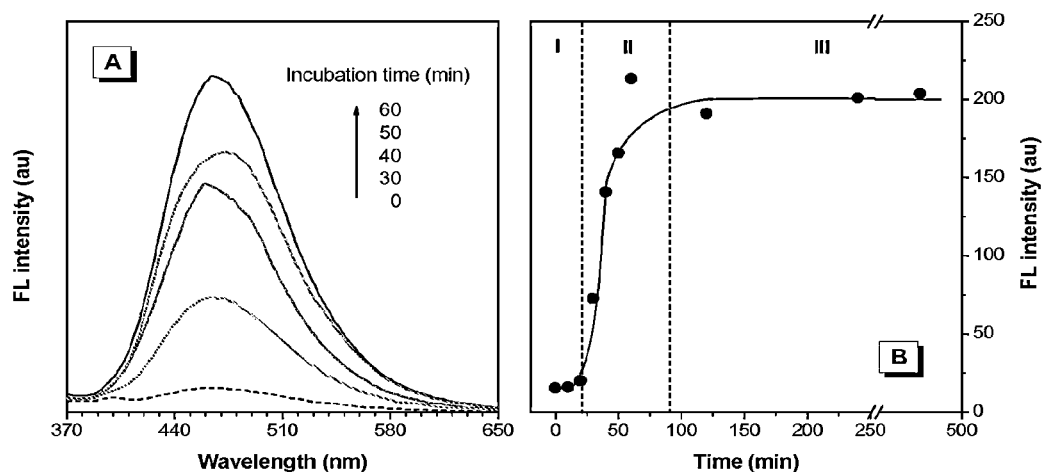
FIG. 68A demonstrates TPE-SO3 FL spectra of insulin incubated at different period of times in buffer solutions (pH 1.6) at 65° C.
FIG. 68B shows TPE-SO3 FL intensity of insulin at 470 nm recorded at different incubation time interval.

The distinct native insulin independent fluorescence emission characteristic of TPE-SO3 to fibrillar insulin enables the compound to be used as an indicator for monitoring the kinetics of insulin fibrillation. As shown in FIG. 68A, insulin solution dissolved in HCl/NaCl (pH 1.6) is incubated at 65° C., such elevated temperature and low pH conditions favor the growth of amyloid fibrils of insulin. FL measurement is carried out at regular time intervals up to 60 mins, where an aliquot of insulin is taken out and diluted with PBS (pH 7.0) at room temperature and an aliquot of TPE-SO3 is added to the protein solution before spectral measurement. All FL measurements are conducted in a PBS buffer (pH=7.0); [TPE-SO3]=15 μM; [Insulin]=5 μM and $\lambda_{ex}$=350 nm.

Results shows that no FL signal is recorded when insulin has been incubated for less than 20 mins. The solution becomes emissive at an incubation time from 30 mins and emission increases rapidly and reaches maximum at 60 mins incubation time. The change in fluorescence intensity at different incubation times corresponds to insulin fibrillation. The changes in FL intensity recorded at 470 nm at different time intervals reveals the duration of (I) lag phase, (II) growth phase and (III) equilibrium phase during fibrillation can be seen in FIG. 68B.

Example 43

TPE-SO3 is an In-Situ Inhibitor of Insulin Fibrillation

In the study of TPE-SO3 perturbation on insulin fibril formation, different concentrations of TPE-SO3 are admixed with insulin solution in buffer solution (pH 1.6) prior to incubation at 65° C. and the fluorescence of TPE-SO3 during the time course of fibrillation is determined. It is surprisingly shown that prior incubation of TPE-SO3 influences the kinetics of insulin fibril formation (FIG. 69A). TPE-SO3 lengthens the lag phase and decelerates the elongation rate of growth phase during fibrillation. The lag phase which associates with a constant low FL signal is extended from 30 mins to 2 h when insulin is premixed with 10 μM TPE-SO3. The exponential growth phase is also prolonged from 30 to 90 mins. It takes more than 3 h in order to reach to the equilibrium phase, while it takes only 1 h in the absence of TPE-SO 3.

Figure 81A:
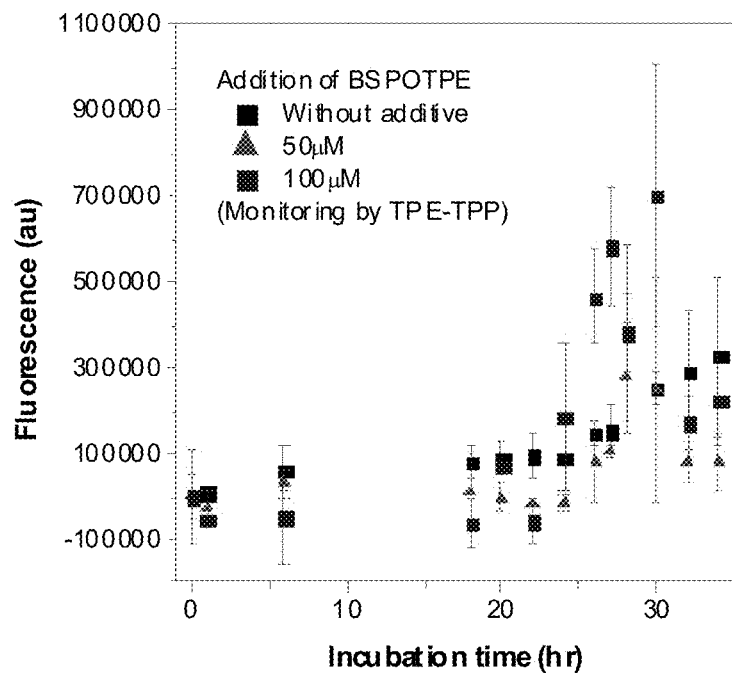
FIGS. 81A and 81B show the retardation effect of BSPOTPE (50 and 100 μM) on α-syn (5 μM) fibrillation as monitored by 15 μM of TPE-TPP and TPE-ThT, respectively.
Figure 81B:
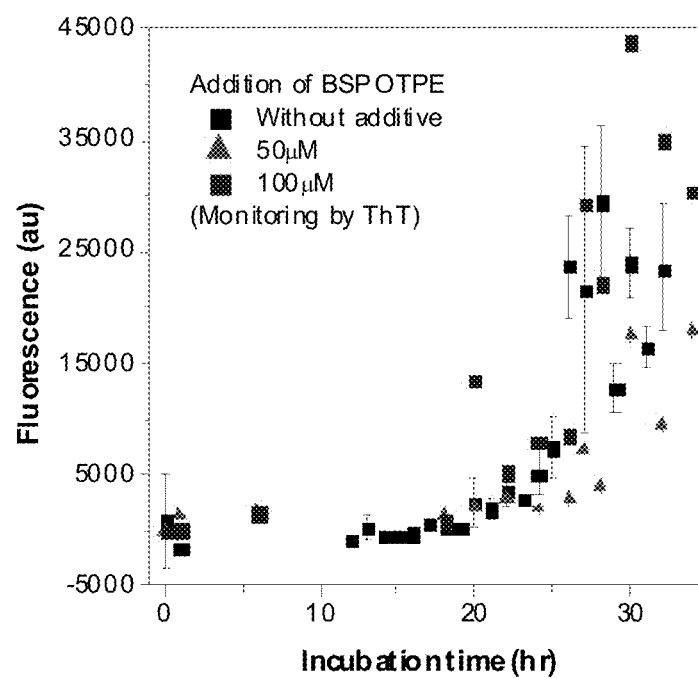

The retardation effect of each of TPE-SO3 and BSPOTPE on amyloid fibril formation strengthens with a higher concentration of TPE-SO3. FIG. 69B shows the correlation between the lag time defined as the duration of lag phase, and the TPE-SO3 concentration incubated with insulin solution. The lag time is shown to extend linearly with an increase in TPE-SO3 concentration. At 25 and 50 μM TPE-SO3, the lag time is extended to 3 and 6 h, respectively. Further increment of TPE-SO3 concentration (100 μM) suppress the formation of fibrils, as revealed by no enhancement in FL signal even after incubation for 20 h. The retardation effect of TPE-SO3 is further confirmed by the exponential decrease of insulin fibrillation growth rate as the concentration of TPE-SO3 becomes higher (FIG. 69C). TPE-SO3 behaves as an internal inhibitor of amyloid fibrillation is clearly seen. Similar effects are seen for BSPOTPE in FIGS. 81A and 81B.

Figure 74:
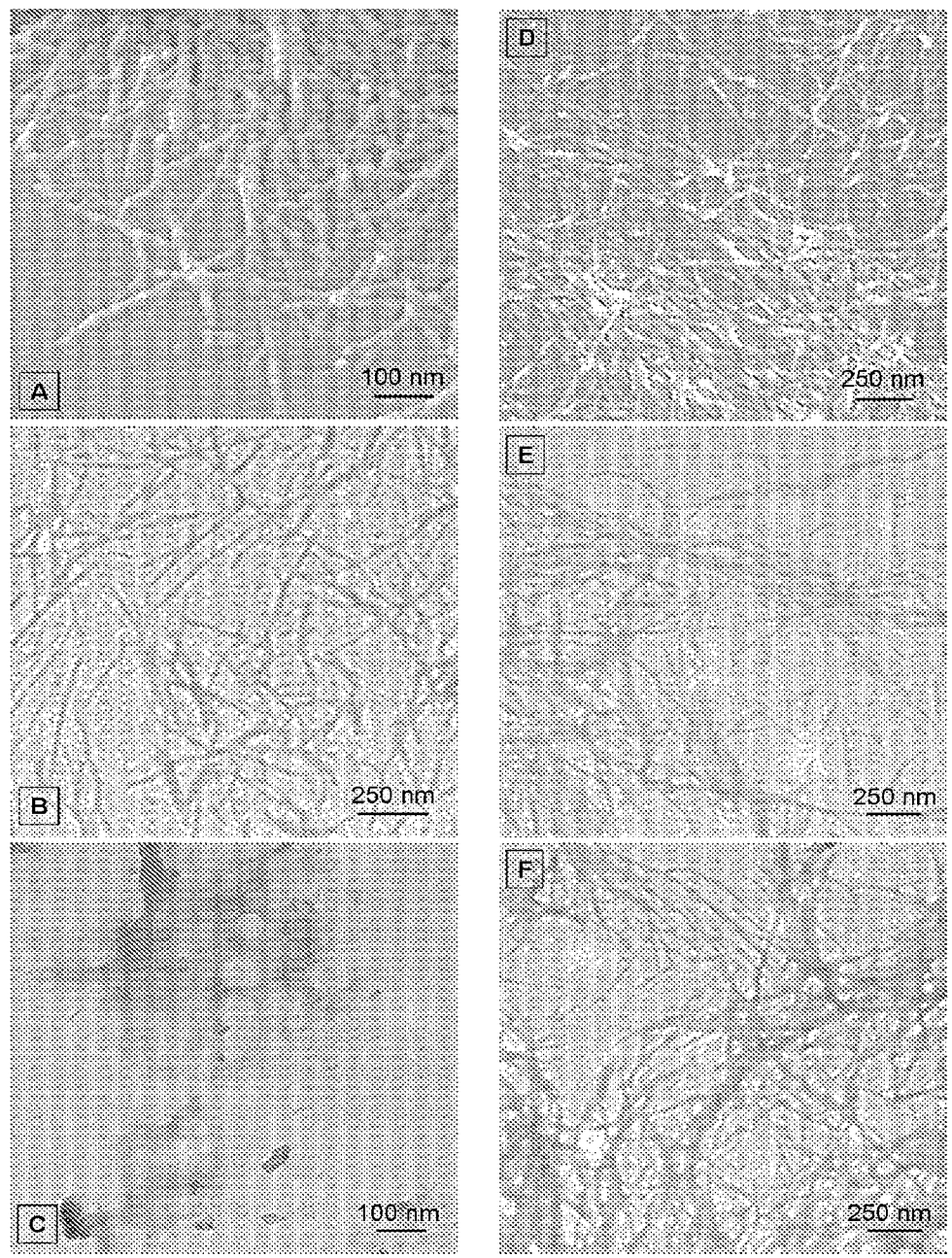
FIG. 74 illustrates formation of insulin fibrils under different conditions: A and D are SEM images and B, C, E and F are TEM images showing insulin after being incubated in the absence (A, B, D and E) and presence (C and F) of TPE-SO3 in pH 1.6 at 65° C. for 1 hour (A-C) and 7 hours (D-F).

Images from scanning electron microscopy (SEM) and transmission electron microscopy (TEM) further confirm the above observation. In the absence of TPE-SO3, amyloid fibrils with diameters of ~20 nm are observed in solution after 1 h incubation (FIGS. 74A and 74B). No fibril-like structure is, however, found under the same condition in the presence of TPE-SO3 (FIG. 74C), indicating that the fibrillation is still in the lag phase after 1 h. After 7 h incubation, mature amyloid fibrils are observed in incubated insulin solutions with and without TPE-SO3 (FIG. 74D-F).

Example 44

TPE-SO3 does not Affect Fibrillation Once Fibril Starts to Grow

Figure 75A:
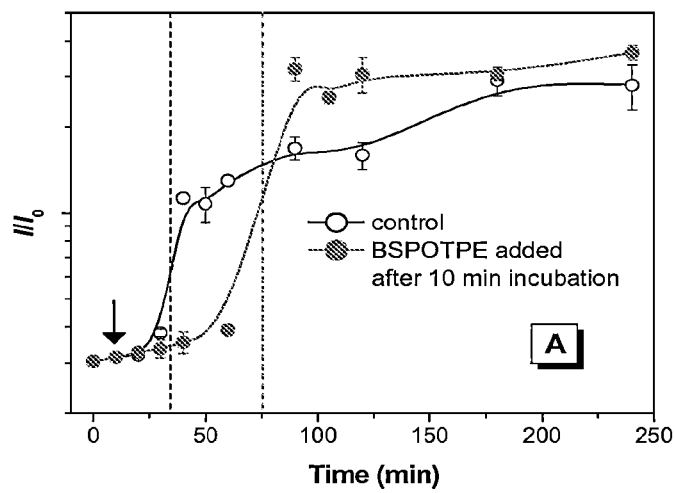
FIG. 75 shows effect of TPE-SO3 on fibrillation kinetics of insulin, where TPE-SO3 is added at different time intervals 10 mins (A), 20 mins (B) and 30 mins (C). The dash lines represent the estimated halftimes of insulin fibrillation.
Figure 75B:
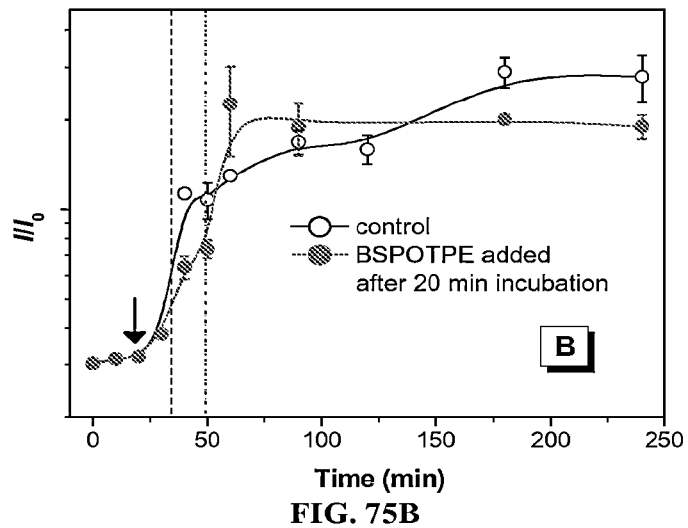
Figure 75C:
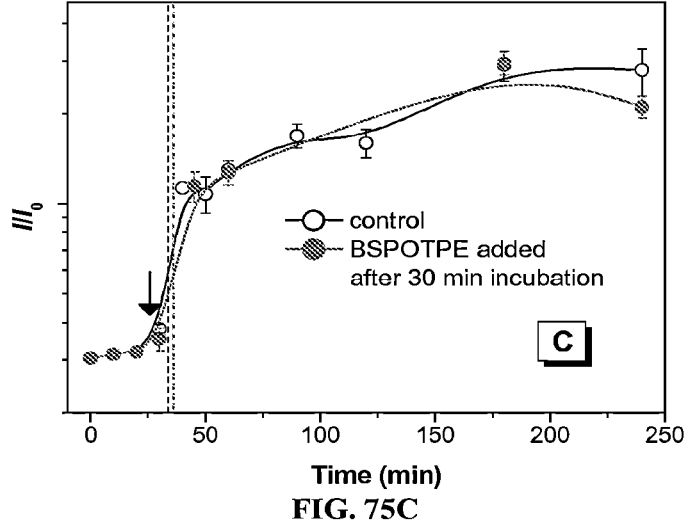

TPE-SO3 is added at different time points of incubation under fibril formation favorable condition at pH 1.6 and 65° C. TPE-SO3 is added to the insulin solution to afford a final concentration of 10 μM. FIG. 73 shows the resultant time-course curve where TPE-SO3 is added at different time intervals as compared to the fibrillation in the absence of TPE-SO3. Addition of TPE-SO3 after 10 mins incubation induces a significant retardation effect on the insulin fibrillation (FIG. 75A). When TPE-SO3 is added at 20 mins, only slight retardation effect can be observed (FIG. 75B). No effect is observed at all when the dye molecule is added after 30 mins of incubation (FIG. 75C). The results indicate that the lag phase where the fibril-competent nucleation occurs is the rate-determining step for the insulin fibrillation. On condition that TPE-SO3 is added before the formation of fibril-competent nucleus, the fibrillation can be inhibited as reflected by extension of the lag phase. At short incubation time such as 10 min, partially unfolded insulin monomers are formed in the solution. The presence of TPE-SO3 will interact with these unfolding intermediates and slow down further nucleation evolvement and subsequent oligomer formation. At a longer incubation time of 30 min, critical nuclei are formed from partially unfolded intermediates. The elongation is so favorable that the addition of TPE-SO3 has no impact on the kinetic of the fibril formation. Once the fibrils start to grow, the presence of TPE-SO3 will not terminate fibrillation or dissociate the fibrils.

Example 45

Emission of TPE-SO3 is pH Dependent

Figure 76:
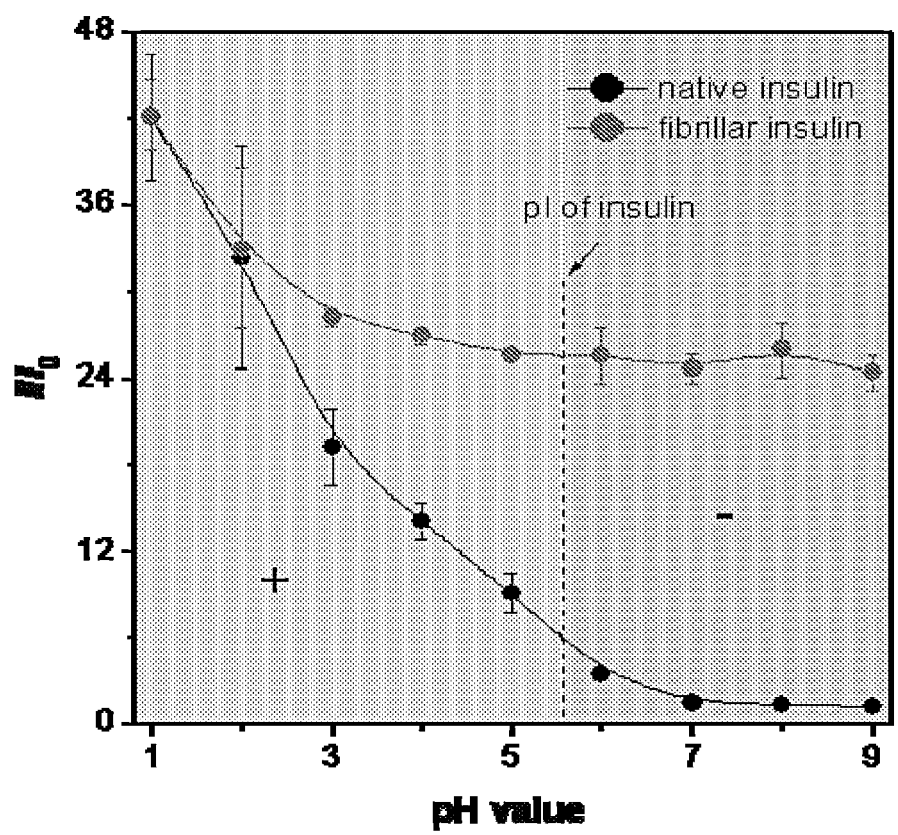
FIG. 76 shows changes in FL intensity of TPE-SO3 with native or fibrillar insulin at different pH environments. Dash lines indicate pI of insulin (pH 5.6).

To understand the effect of pH in TPE-SO3 fluorescence, the FL emissions of TPE-SO3 to native and fibrillar forms of insulin at different pH conditions are determined (FIG. 76). The emission of TPE-SO3 with insulin increases gradually as the pH of surrounding condition lowers, indicating that electrostatic attraction is an indispensable driving force for the binding of TPE-SO3 to insulin. Owning to the low pKa of sulfonate groups, TPE-SO3 has a net negative charge under a wide range of pH conditions. The isoelectric point (pI) of bovine insulin is pH 5.6; therefore at pH lower than pH 5.6, insulin carries a net positive charge. Accordingly, the negatively charged TPE-SO3 can bind strongly with insulin via electrostatic attraction, leading to the strong fluorescence emission.

Example 46

Amyloid Fibril Imaging Using TPE-SO3

Figure 82A:
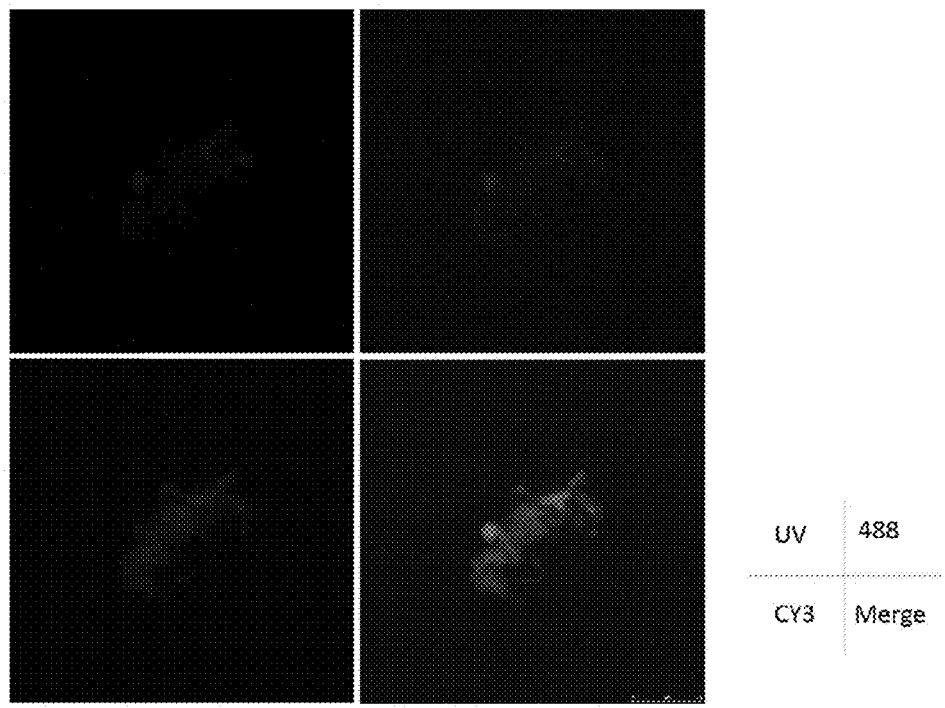
FIGS. 82A, 82B, and 82C show fluorescence imaging of α-synuclein fibrils stained by (A) Cy$_2$Silo, (B) TPEBe, or (C) TPE-MitoY and Cyanine dye (Cy3).
Figure 82B:
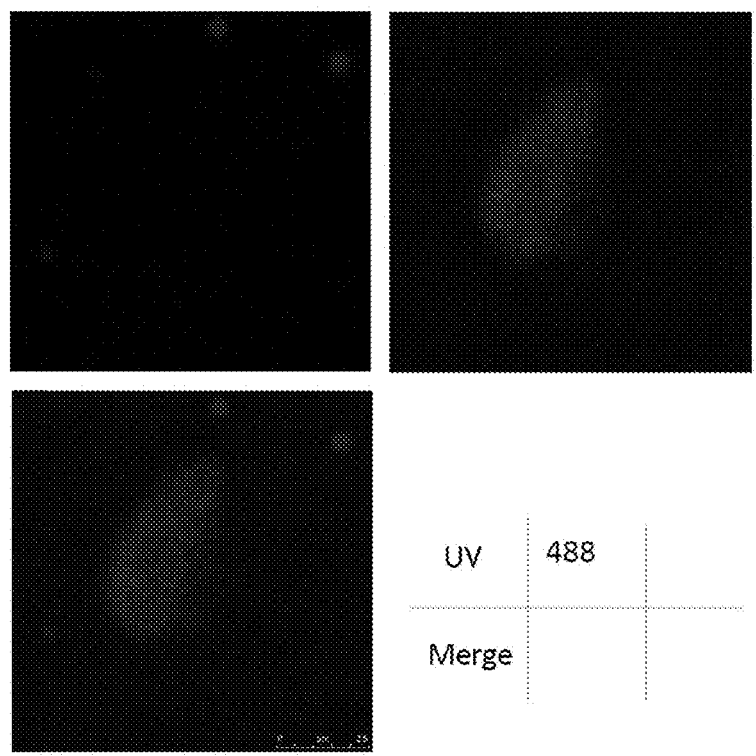
Figure 82C:
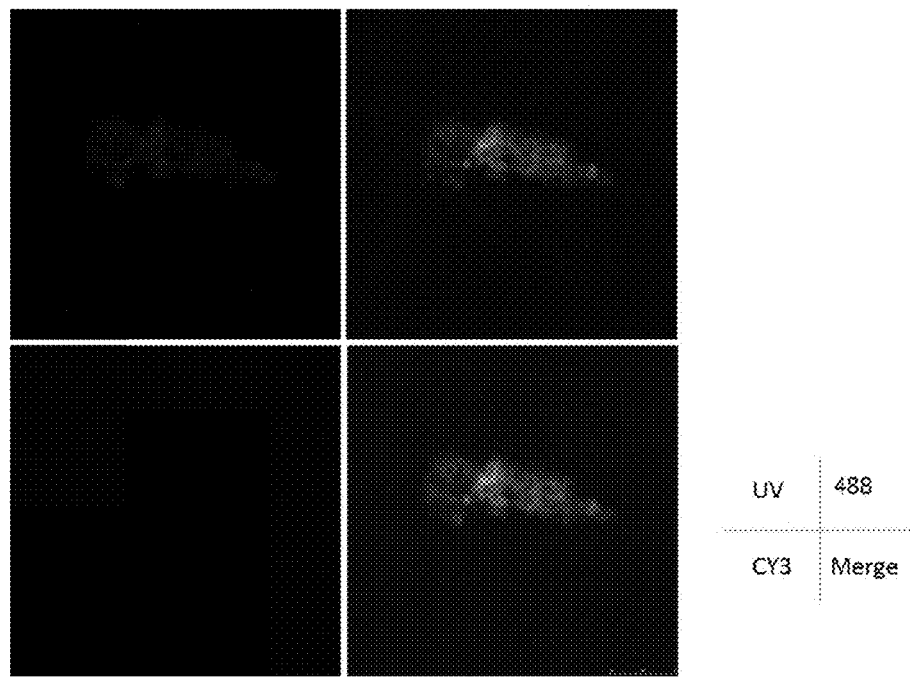
Figure 83:
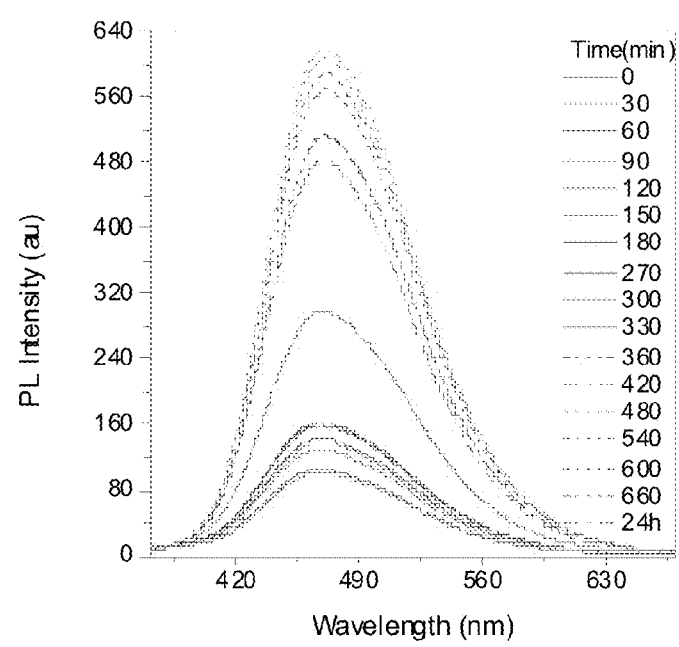
FIG. 83 shows emission spectra of BSPOTPE (50 μM) monitoring the fibrillation of hIAPP (0.1 mM), $\lambda_{ex}$=350 nm.
Figure 84:
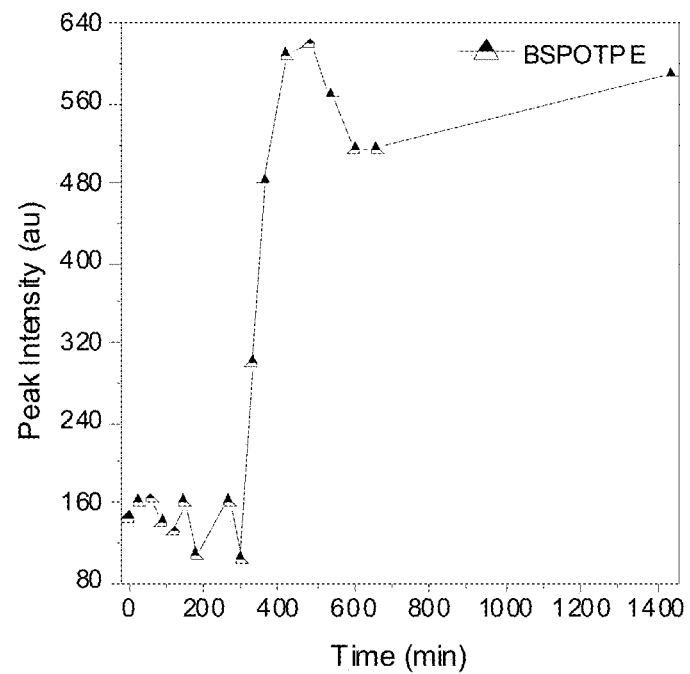
Figure 85:
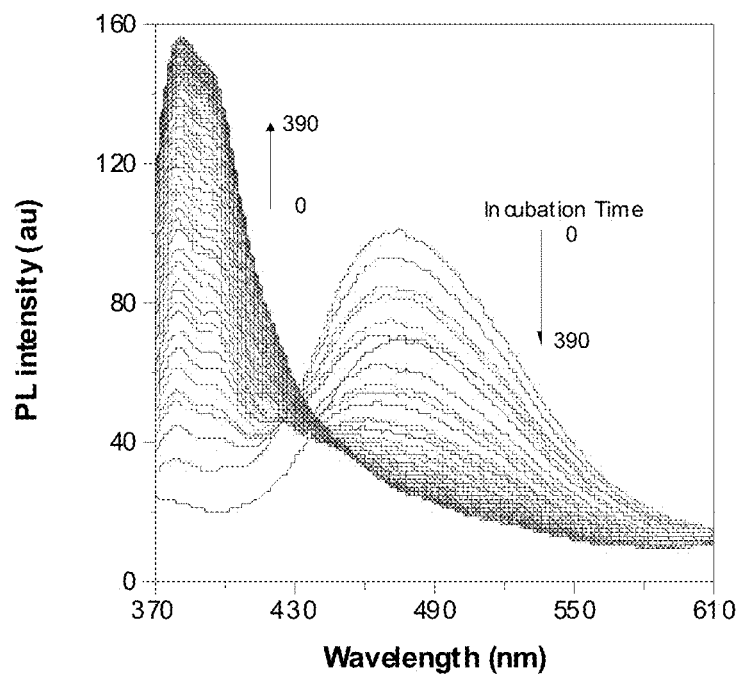
Figure 88:
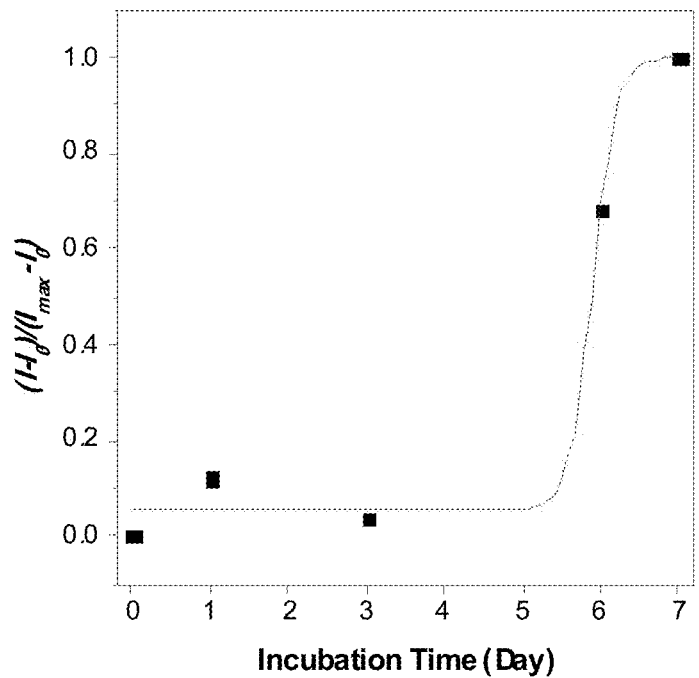
Figure 89:
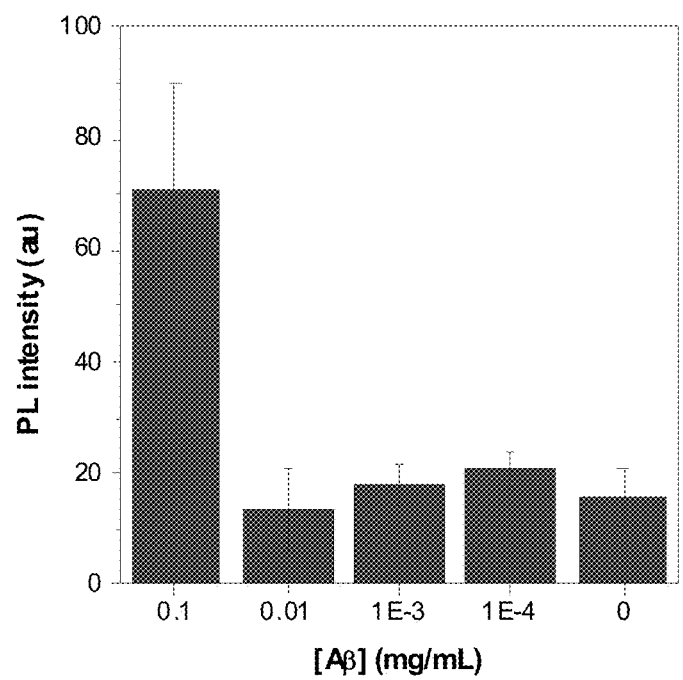
Figure 92:
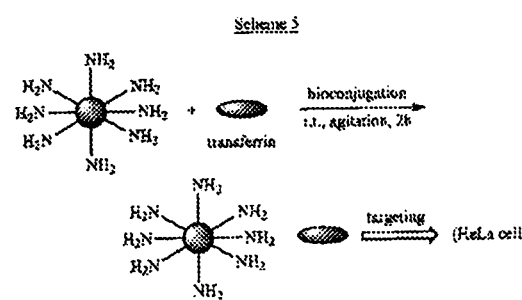

Amyloid fibrils stained with TPE-SO3 solution can be visualized under fluorescence microscope. Microaggregates of insulin fibrils are easily identified as bright greenish-blue emission from TPE-SO3 (FIG. 67). Owing to the excellent water solubility of TPE-SO3, fluorescence background can be ignored and fibril-like structures can be discerned at high magnification (FIG. 67 inset). These results confirm the utilization of TPE-SO3 as a FL stain for protein aggregates from tissue sections ex vivo. Similar results are seen for $Cy_2Silo$ (FIG. 82), TPEBe (FIG. 84), and TPE-MitoY (FIG. 85), indicating that these can all be utilized as FL stains for protein aggregates from tissue sections ex vivo as well.

Example 47

TPE-SO3 is Highly Specific to Fibrillar Amyloid Proteins

To evaluate the specificity of TPE-SO3 fluorescence characteristic to fibrillar proteins, fluorescence intensities of TPE-SO3 against other protein monomers are tested. A stock solution of TPE-SO3 with a concentration of 50/1 is mixed with different protein monomer solutions at 1.0 mg/mL. The fluorescence intensities of the different TPE-SO3-protein mixtures are measured. PBS buffer at pH 7.0 and solution of TPE-SO3 are used as negative controls. Results (FIG. 77) shows that FL of TPE-SO3 with heparin, apoferritin and cellulose is comparable to TPE-SO3 solution alone; FL with papain is comparable to native insulin monomer and fibrillar insulin is significantly higher than other cellular proteins tested.

Not only does TPE-SO3 fluoresce against fibrillar insulin, but other fibrillar amyloid proteins. To illustrate, the emission of TPE-SO3 at 500/1 is measured at $\lambda_{ex}=350$ nm with 0.1 mg/mL amyloid-β-peptide before and after aging. It is shown that the emission of TPE-SO3 increases dramatically upon the formation of amyloid-β-peptide fibrils (i.e., after aging) (FIG. 72). Moreover, the rate of fluorescence enhancement of TPE-SO3 (10 μM, 50 μM and 100 μM) at different time points during lysozyme fibril formation over 4 days (two collections each day) are determined (FIG. 73). As seen in FIG. 73, TPE-SO3 produces fluorescence profile corresponding to lysozyme fibrillation verifying its usefulness as an external indicator for monitoring amyloid protein fibrillation.

Example 48

TPE-SO3 is Non-Toxic and Stable

The toxicity of TPE-SO3 is evaluated using methyl thiazolyl tetrazolium (MTT) assay. $5 \times 10^3$ cells per 0.1 ml per well of HeLa cells are treated with different concentrations of TPE-SO3 (5, 10, 20, 40, and 80 μM) in a 96-well plate for 48 hr at 37° C. 20 ml of PBS containing 3-(4,5-dimethylthiazol-2-yl)-2,5-diphenyltetrazolium bromide (MTT; 5 mgmL$^{-1}$) is added to each well and subject to further incubation at 37° C. for 2-4 h. To dissolve intracellular formazan produced by active mitochondria in HeLa cells, detergent solution (10% w/v sodium dodecyl sulfate in 10 mm HCl; 100 mL per well) is added to each well and incubated overnight in the dark at room temperature. To determine the relative cell viability, absorbance at 595 nm is measured using a spectrophotometric plate reader. It is demonstrated that the toxicity of TPE-SO3 is negligible (FIG. 70).

Furthermore, it is observed that the TPE-SO3 compound is stable under ambient condition for more than one year and aqueous solution thereof remain unchanged at 4° C. refrigeration for more than six months. In addition to TPE-SO3's internal retardation effect on amyloid protein monomer to aggregate, the stability and non-toxicity characteristics thereof confirm the usefulness of compound TPE-SO3 to be used as antiamyloid agent in storing and delivery therapeutic amyloids, such as insulin.

Based on the above examples, while amyloid protein is used as an example, it is to be understood that the external ALE effect and internal retardation effect of the subject water-soluble conjugated polyene compounds are also applicable to other protein aggregates.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter, which are obvious to those skilled in chemistry, biochemistry, or related fields are intended to be within the scope of the following claims.

We claim:

1. A method of monitoring amyloid protein fibrillation in a biological sample comprising contacting a water-soluble conjugated polyene compound that exhibits aggregation induced emission with the biological sample containing an amyloid protein; and detecting fluorescence emitted by said water-soluble conjugated polyene compound and the fluorescence emitted is induced by aggregation of said water-soluble conjugated polyene compound when contacting with said biological sample, wherein said water-soluble conjugated polyene compound is selected from the group consisting of:
   1,2-Bis[4-(3-sulfonatopropoxy)phenyl]-1,2-diphenylethene sodium;
   1,2-Bis[4-(3-triphenylphosphonium)phenyl]-1,2-diphenylethene bromide;
   1-[4-(1-methyl-4-pyridine)ethene]-1,2,3-triphenylethene hexafluorophosphate;
   1-[4-(1,2-dimethyl-5-benzothiazole)]-1,2,3-triphenylethene iodide;
   N,N',N'',N'''-[1,2-tetrakis(1,4-phenoxyethyl)vinyl]tetrakis(trimethylammoniumbromide);
   1-[4-(1-ethyl-2-benzothiazole)ethene]-1,2,3-triphenylethene hexafluorophosphate; and
   1,1'-methyl-2,5-bis[4-(1-sulfonatopropyl-2-isoindole) ethenephenyl]-3,4-bisphenyl silole.

2. The method of claim 1, wherein said amyloid protein is selected from the group consisting of insulin, amyloid betapeptide, tau, alpha-Synuclein, PrP and polyglutamine-containing protein.

3. The method of claim 1, wherein said contacting is carried out at a pH value equal to or lower than 5.6.

4. The method of claim 1, wherein said detecting comprises measuring fluorescence intensity at 470 nm.

5. The method of claim 1, wherein said biological sample is selected from the group consisting of a tissue sample, a cell sample, blood, saliva, spinal fluid, lymph fluid, vaginal fluid, seminal fluid and urine.

6. The method of claim 1, wherein said cation is selected from the group consisting of $K^+$, $Li^+$, $Na^+$, $Mg^2$ $NH_4^+$ and $Ca^{2+}$.

7. A method of retarding fibrillation of an amyloid protein comprising contacting said amyloid protein with a water-soluble conjugated polyene compound to form a stabilized amyloid protein in order to retard fibrillation of the amyloid protein, wherein the water-soluble conjugated polyene compound exhibits aggregation induced emission, wherein said water-soluble conjugated polyene compound is selected from the group consisting of:
   1,2-Bis[4-(3-sulfonatopropoxy)phenyl]-1,2-diphenylethene sodium;
   1,2-Bis[4-(3-triphenylphosphonium)phenyl]-1,2-diphenylethene bromide;
   1-[4-(1-methyl-4-pyridine)ethene]-1,2,3-triphenylethene hexafluorophosphate;
   1-[4-(1,2-dimethyl-5-benzothiazole)]-1,2,3-triphenylethene iodide;
   N,N',N'',N'''-[1,2-tetrakis(1,4-phenoxyethyl)vinyl]tetrakis(trimethylammoniumbromide);
   1-[4-(1-ethyl-2-benzothiazole)ethene]-1,2,3-triphenylethene hexafluorophosphate; and
   1,1'-methyl-2,5-bis[4-(1-sulfonatopropyl-2-isoindole) ethenephenyl]-3,4-bisphenyl silole, and wherein said amyloid protein is selected from the group consisting of insulin, amyloid betapeptide, tau, alpha-Synuclein, PrP and polyglutamine-containing protein.

8. The method of claim 7, further comprising converting said amyloid protein from native form into monomer thereof in an acidic environment prior to said contacting.

9. The method of claim 7, further comprising increasing concentration of said water-soluble conjugated polyene compound to form a partially unfolded amyloid protein associated with said water-soluble conjugated polyene compound.

10. The method of claim 7, wherein said amyloid protein is selected from the group consisting of insulin, amyloid betapeptide, tau, alpha-Synuclein, PrP and polyglutamine-containing protein.

11. The method of claim 7, wherein said cation is selected from the group consisting of $K^+$, $Li^+$, $Na^+$, $Mg^{2+}$, $NH_4^+$ and $Ca^{2+}$.

12. The method of claim 7, wherein said incubating is carried out at a pH value equal to or lower than 5.6.

13. The method of claim 7, wherein said amyloid protein is a pharmaceutical insulin being administered to a subject.

14. The method of claim 13, wherein the subject is in need of treatment for diabetes.

15. A method of storing and delivering an amyloid protein containing pharmaceutical composition for treatment of diseases comprising the method of claim 7, wherein the amyloid protein containing pharmaceutical composition is stored with the water-soluble conjugated polyene compound.

* * * * *

UNITED STATES PATENT AND TRADEMARK OFFICE
CERTIFICATE OF CORRECTION

PATENT NO.         : 9,279,806 B2  
APPLICATION NO.    : 14/171957  
DATED              : March 8, 2016  
INVENTOR(S)        : Benzhong Tang et al.

Page 1 of 1

It is certified that error appears in the above-identified patent and that said Letters Patent is hereby corrected as shown below:

Claims

Claim 6, col. 88, line 44, after "$Na^+$," and before "$NH_4^+$", please replace "$Mg^2$" with "$Mg^{2+}$,"

Signed and Sealed this  
Third Day of May, 2016

Michelle K. Lee  
*Director of the United States Patent and Trademark Office*